US 8,653,021 B2
Feb. 18, 2014

(12) United States Patent
Donald

(10) Patent No.: US 8,653,021 B2
(45) Date of Patent: *Feb. 18, 2014

(54) TARGETING PAX2 FOR THE TREATMENT OF BREAST CANCER

(75) Inventor: Carlton D. Donald, Mount Pleasant, SC (US)

(73) Assignee: Phigenix, Inc., Atlanta, GA (US)

(*) Notice: Subject to any disclaimer, the term of this patent is extended or adjusted under 35 U.S.C. 154(b) by 336 days.

This patent is subject to a terminal disclaimer.

(21) Appl. No.: 13/116,722

(22) Filed: May 26, 2011

(65) Prior Publication Data

US 2011/0318338 A1     Dec. 29, 2011

Related U.S. Application Data

(63) Continuation of application No. 12/708,294, filed on Feb. 18, 2010, now Pat. No. 8,080,534, which is a continuation-in-part of application No. 12/090,191, filed as application No. PCT/US2006/040215 on Oct. 16, 2006, now Pat. No. 7,964,577.

(60) Provisional application No. 60/726,921, filed on Oct. 14, 2005.

(51) Int. Cl.
    *A61K 31/00*          (2006.01)

(52) U.S. Cl.
    USPC .............................................................. 514/1

(58) Field of Classification Search
    None
    See application file for complete search history.

(56) References Cited

U.S. PATENT DOCUMENTS

| | | |
|---|---|---|
| 3,610,795 A | 10/1971 | Antoine et al. |
| 3,687,808 A | 8/1972 | Merigan, Jr. et al. |
| 4,469,863 A | 9/1984 | Ts'o et al. |
| 4,476,301 A | 10/1984 | Imbach et al. |
| 4,587,044 A | 5/1986 | Miller et al. |
| 4,605,735 A | 8/1986 | Miyoshi et al. |
| 4,667,025 A | 5/1987 | Miyoshi et al. |
| 4,762,779 A | 8/1988 | Snitman |
| 4,789,737 A | 12/1988 | Miyoshi et al. |
| 4,824,941 A | 4/1989 | Gordon et al. |
| 4,828,979 A | 5/1989 | Klevan et al. |
| 4,835,263 A | 5/1989 | Nguyen et al. |
| 4,845,205 A | 7/1989 | Huynh Dinh et al. |
| 4,868,116 A | 9/1989 | Morgan et al. |
| 4,876,335 A | 10/1989 | Yamane et al. |
| 4,897,355 A | 1/1990 | Eppstein et al. |
| 4,904,582 A | 2/1990 | Tullis |
| 4,948,882 A | 8/1990 | Ruth |
| 4,958,013 A | 9/1990 | Letsinger |
| 4,980,286 A | 12/1990 | Morgan et al. |
| 4,981,957 A | 1/1991 | Lebleu et al. |
| 5,023,243 A | 6/1991 | Tullis |
| 5,034,506 A | 7/1991 | Summerton et al. |
| 5,082,830 A | 1/1992 | Brakel et al. |
| 5,084,824 A | 1/1992 | Lam et al. |
| 5,109,124 A | 4/1992 | Ramachandran et al. |
| 5,112,963 A | 5/1992 | Pieles et al. |
| 5,118,800 A | 6/1992 | Smith et al. |
| 5,118,802 A | 6/1992 | Smith et al. |
| 5,130,302 A | 7/1992 | Spielvogel et al. |
| 5,134,066 A | 7/1992 | Rogers et al. |
| 5,135,917 A | 8/1992 | Burch |
| 5,138,045 A | 8/1992 | Cook et al. |
| 5,166,315 A | 11/1992 | Summerton et al. |
| 5,168,053 A | 12/1992 | Altman et al. |
| 5,175,273 A | 12/1992 | Bischofberger et al. |
| 5,176,996 A | 1/1993 | Hogan et al. |
| 5,177,196 A | 1/1993 | Meyer, Jr. et al. |
| 5,185,444 A | 2/1993 | Summerton et al. |
| 5,188,897 A | 2/1993 | Suhadolnik et al. |
| 5,214,134 A | 5/1993 | Weis et al. |
| 5,214,136 A | 5/1993 | Lin et al. |
| 5,216,141 A | 6/1993 | Benner |
| 5,218,105 A | 6/1993 | Cook et al. |
| 5,235,033 A | 8/1993 | Summerton et al. |
| 5,245,022 A | 9/1993 | Weis et al. |
| 5,254,469 A | 10/1993 | Warren, III et al. |
| 5,258,506 A | 11/1993 | Urdea et al. |
| 5,262,536 A | 11/1993 | Hobbs, Jr. |
| 5,264,423 A | 11/1993 | Cohen et al. |
| 5,264,562 A | 11/1993 | Matteucci |

(Continued)

FOREIGN PATENT DOCUMENTS

| WO | WO8907136 | 8/1989 |
|---|---|---|
| WO | WO9002806 | 3/1990 |

(Continued)

OTHER PUBLICATIONS

Notification of Transmittal of the International Search Report and the Written Opinion of the International Searching Authority, Application No. PCT/US20101024740, Form PCT/ISA/220, Oct. 27, 2010.
Bose, S.K., et al., "PAX2 oncogene negatively regulates the expression of the host defense peptide human beta defensin-1 prostate cancer", Molecular Immunology 46 (2009), pp. 1140-1148.
Hurtado, A., et al., "Regulation of ERBB2 by oestrogen receptor-PAX2 determines response to tamoxifen", Nature, vol. 456, Dec. 4, 2008, pp. 663-666.
Muratovska, A., et al., "Paired-Box genes are frequently expressed in cancer and often required for cancer cell survival", Oncogene (2003) 22, pp. 7989-7997.
Gibson, W, et al., "Inhibition of PAX2 expression results in alternate cell death pathways in prostate cancer cells differing in p53 status", Cancel Letters 248 (2007), pp. 251-261.

(Continued)

*Primary Examiner* — Tracy Vivlemore
(74) *Attorney, Agent, or Firm* — Ping Wang; Andrews Kurth LLP

(57) ABSTRACT

The present application provides methods of prevention and/or treatment of breast cancer in a subject by inhibiting expression of PAX2. In the cancer treatment methods disclosed, the method of inhibiting expression of PAX2 can be by administration of a nucleic acid encoding an siRNA for PAX2. A method of treating cancer in a subject by administering DEFB1 is also provided. Similarly, provided is a method of treating cancer in a subject by increasing expression of DEFB1 in the subject.

11 Claims, 42 Drawing Sheets
(15 of 42 Drawing Sheet(s) Filed in Color)

(56) References Cited

U.S. PATENT DOCUMENTS

| | | |
|---|---|---|
| 5,264,564 A | 11/1993 | Matteucci |
| 5,272,250 A | 12/1993 | Spielvogel et al. |
| 5,276,019 A | 1/1994 | Cohen et al. |
| 5,278,302 A | 1/1994 | Caruthers et al. |
| 5,286,717 A | 2/1994 | Cohen et al. |
| 5,288,514 A | 2/1994 | Ellman |
| 5,292,873 A | 3/1994 | Rokita et al. |
| 5,294,533 A | 3/1994 | Lupski et al. |
| 5,317,098 A | 5/1994 | Shizuya et al. |
| 5,319,080 A | 6/1994 | Leuman |
| 5,321,131 A | 6/1994 | Agrawal et al. |
| 5,334,711 A | 8/1994 | Sproat et al. |
| 5,359,044 A | 10/1994 | Cook et al. |
| 5,367,066 A | 11/1994 | Urdea et al. |
| 5,371,241 A | 12/1994 | Brush |
| 5,391,723 A | 2/1995 | Priest |
| 5,393,878 A | 2/1995 | Leuman |
| 5,399,676 A | 3/1995 | Froehler |
| 5,405,938 A | 4/1995 | Summerton et al. |
| 5,405,939 A | 4/1995 | Suhadolnik et al. |
| 5,414,077 A | 5/1995 | Lin et al. |
| 5,416,203 A | 5/1995 | Letsinger |
| 5,432,272 A | 7/1995 | Benner |
| 5,434,257 A | 7/1995 | Matteucci et al. |
| 5,436,330 A | 7/1995 | Taira et al. |
| 5,446,137 A | 8/1995 | Maag et al. |
| 5,449,754 A | 9/1995 | Nishioka |
| 5,451,463 A | 9/1995 | Nelson et al. |
| 5,453,496 A | 9/1995 | Caruthers et al. |
| 5,455,233 A | 10/1995 | Spielvogel et al. |
| 5,457,187 A | 10/1995 | Gmeiner et al. |
| 5,459,255 A | 10/1995 | Cook et al. |
| 5,466,677 A | 11/1995 | Baxter et al. |
| 5,466,786 A | 11/1995 | Buhr et al. |
| 5,470,967 A | 11/1995 | Huie et al. |
| 5,476,766 A | 12/1995 | Gold et al. |
| 5,476,925 A | 12/1995 | Letsinger et al. |
| 5,484,908 A | 1/1996 | Froehler et al. |
| 5,486,603 A | 1/1996 | Buhr |
| 5,489,677 A | 2/1996 | Sanghvi et al. |
| 5,502,177 A | 3/1996 | Matteucci et al. |
| 5,503,978 A | 4/1996 | Schneider et al. |
| 5,506,337 A | 4/1996 | Summerton et al. |
| 5,510,475 A | 4/1996 | Agrawal et al. |
| 5,512,439 A | 4/1996 | Hornes et al. |
| 5,512,667 A | 4/1996 | Reed et al. |
| 5,514,785 A | 5/1996 | Van Ness et al. |
| 5,519,126 A | 5/1996 | Hecht |
| 5,519,134 A | 5/1996 | Acevedo et al. |
| 5,525,465 A | 6/1996 | Haralambidis et al. |
| 5,525,711 A | 6/1996 | Hawkins et al. |
| 5,536,821 A | 7/1996 | Agrawal et al. |
| 5,539,082 A | 7/1996 | Nielsen et al. |
| 5,539,083 A | 7/1996 | Cook et al. |
| 5,541,306 A | 7/1996 | Agrawal et al. |
| 5,541,307 A | 7/1996 | Cook et al. |
| 5,541,313 A | 7/1996 | Ruth |
| 5,543,293 A | 8/1996 | Gold et al. |
| 5,545,568 A | 8/1996 | Ellman |
| 5,545,730 A | 8/1996 | Urdea et al. |
| 5,550,111 A | 8/1996 | Suhadolnik et al. |
| 5,552,538 A | 9/1996 | Urdea et al. |
| 5,552,540 A | 9/1996 | Haralambidis |
| 5,556,762 A | 9/1996 | Pinilla et al. |
| 5,561,225 A | 10/1996 | Maddry et al. |
| 5,563,253 A | 10/1996 | Agrawal et al. |
| 5,565,324 A | 10/1996 | Still et al. |
| 5,565,332 A | 10/1996 | Hoogenboom et al. |
| 5,565,552 A | 10/1996 | Magda et al. |
| 5,567,810 A | 10/1996 | Weis et al. |
| 5,567,811 A | 10/1996 | Misiura et al. |
| 5,571,799 A | 11/1996 | Tkachuk et al. |
| 5,573,905 A | 11/1996 | Lerner et al. |
| 5,574,142 A | 11/1996 | Meyer, Jr. et al. |
| 5,576,427 A | 11/1996 | Cook et al. |
| 5,578,717 A | 11/1996 | Urdea et al. |
| 5,578,718 A | 11/1996 | Cook et al. |
| 5,580,731 A | 12/1996 | Chang et al. |
| 5,580,737 A | 12/1996 | Polisky et al. |
| 5,580,967 A | 12/1996 | Joyce |
| 5,585,481 A | 12/1996 | Arnold, Jr. et al. |
| 5,587,361 A | 12/1996 | Cook et al. |
| 5,587,371 A | 12/1996 | Sessler et al. |
| 5,587,469 A | 12/1996 | Cook et al. |
| 5,591,584 A | 1/1997 | Chang et al. |
| 5,591,722 A | 1/1997 | Montgomery et al. |
| 5,594,121 A | 1/1997 | Froehler et al. |
| 5,595,726 A | 1/1997 | Magda et al. |
| 5,595,873 A | 1/1997 | Joyce |
| 5,596,079 A | 1/1997 | Smith et al. |
| 5,596,086 A | 1/1997 | Matteucci et al. |
| 5,596,091 A | 1/1997 | Switzer |
| 5,597,696 A | 1/1997 | Linn et al. |
| 5,597,909 A | 1/1997 | Urdea et al. |
| 5,599,923 A | 2/1997 | Sessler et al. |
| 5,599,928 A | 2/1997 | Hemmi et al. |
| 5,602,240 A | 2/1997 | Demesmaeker et al. |
| 5,608,046 A | 3/1997 | Cook et al. |
| 5,610,289 A | 3/1997 | Cook et al. |
| 5,610,300 A | 3/1997 | Altmann et al. |
| 5,614,617 A | 3/1997 | Cook et al. |
| 5,616,466 A | 4/1997 | Cantor et al. |
| 5,618,704 A | 4/1997 | Sanghvi et al. |
| 5,618,825 A | 4/1997 | Baldwin et al. |
| 5,619,680 A | 4/1997 | Berkovich et al. |
| 5,623,070 A | 4/1997 | Cook et al. |
| 5,624,824 A | 4/1997 | Yuan et al. |
| 5,625,050 A | 4/1997 | Beaton et al. |
| 5,627,053 A | 5/1997 | Usman et al. |
| 5,627,158 A | 5/1997 | Cho-Chung |
| 5,627,210 A | 5/1997 | Valerion et al. |
| 5,631,115 A | 5/1997 | Ohtsuka et al. |
| 5,631,146 A | 5/1997 | Szostak et al. |
| 5,633,133 A | 5/1997 | Long |
| 5,633,360 A | 5/1997 | Bischofberger et al. |
| 5,639,873 A | 6/1997 | Barascut et al. |
| 5,641,754 A | 6/1997 | Iversen |
| 5,645,985 A | 7/1997 | Froehler et al. |
| 5,646,020 A | 7/1997 | Swiggen et al. |
| 5,646,031 A | 7/1997 | DeYoung et al. |
| 5,646,042 A | 7/1997 | Stinchcomb et al. |
| 5,646,265 A | 7/1997 | McGee |
| 5,646,285 A | 7/1997 | Baindur et al. |
| 5,650,316 A | 7/1997 | Aggarwal et al. |
| 5,652,094 A | 7/1997 | Usman et al. |
| 5,652,107 A | 7/1997 | Lizardi et al. |
| 5,658,873 A | 8/1997 | Bertsch-Frank et al. |
| 5,663,046 A | 9/1997 | Baldwin et al. |
| 5,663,312 A | 9/1997 | Chaturvedula |
| 5,670,326 A | 9/1997 | Beutel |
| 5,670,633 A | 9/1997 | Cook et al. |
| 5,677,195 A | 10/1997 | Winkler et al. |
| 5,677,437 A | 10/1997 | Teng et al. |
| 5,677,439 A | 10/1997 | Weis et al. |
| 5,681,941 A | 10/1997 | Cook et al. |
| 5,683,873 A | 11/1997 | George et al. |
| 5,683,874 A | 11/1997 | Kool |
| 5,683,899 A | 11/1997 | Stuart |
| 5,683,902 A | 11/1997 | Hampel et al. |
| 5,688,670 A | 11/1997 | Szostak et al. |
| 5,688,696 A | 11/1997 | Lebl |
| 5,688,941 A | 11/1997 | Cook et al. |
| 5,688,997 A | 11/1997 | Baldwin et al. |
| 5,691,317 A | 11/1997 | Cho-Chung |
| 5,693,535 A | 12/1997 | Draper et al. |
| 5,693,773 A | 12/1997 | Kandimalla et al. |
| 5,698,685 A | 12/1997 | Summerton et al. |
| 5,700,920 A | 12/1997 | Altmann et al. |
| 5,712,146 A | 1/1998 | Khosla et al. |
| 5,712,384 A | 1/1998 | Symonds et al. |
| 5,714,331 A | 2/1998 | Buchardt et al. |
| 5,719,262 A | 2/1998 | Buchardt et al. |
| 5,721,099 A | 2/1998 | Still et al. |
| 5,723,598 A | 3/1998 | Lerner et al. |

(56) References Cited

U.S. PATENT DOCUMENTS

| | | |
|---|---|---|
| 5,728,521 A | 3/1998 | Yuan et al. |
| 5,731,295 A | 3/1998 | Draper et al. |
| 5,731,424 A | 3/1998 | Toothman et al. |
| 5,741,713 A | 4/1998 | Brown et al. |
| 5,770,715 A | 6/1998 | Sugiyama et al. |
| 5,780,228 A | 7/1998 | Parma et al. |
| 5,780,607 A | 7/1998 | Goodnow, Jr. et al. |
| 5,786,138 A | 7/1998 | Swenson |
| 5,786,462 A | 7/1998 | Schneider et al. |
| 5,792,431 A | 8/1998 | Moore et al. |
| 5,792,613 A | 8/1998 | Schmidt et al. |
| 5,795,721 A | 8/1998 | Rabin et al. |
| 5,807,683 A | 9/1998 | Brenner et al. |
| 5,807,718 A | 9/1998 | Joyce et al. |
| 5,807,754 A | 9/1998 | Zambias et al. |
| 5,811,300 A | 9/1998 | Sullivan et al. |
| 5,821,130 A | 10/1998 | Baldwin et al. |
| 5,824,520 A | 10/1998 | Mulligan-Kehoe |
| 5,831,014 A | 11/1998 | Cook et al. |
| 5,834,185 A | 11/1998 | Ts'o et al. |
| 5,834,195 A | 11/1998 | Benkovic et al. |
| 5,834,318 A | 11/1998 | Buettner |
| 5,834,588 A | 11/1998 | Wasserman et al. |
| 5,837,855 A | 11/1998 | Chowrira et al. |
| 5,840,500 A | 11/1998 | Pei et al. |
| 5,846,713 A | 12/1998 | Pagratis et al. |
| 5,847,150 A | 12/1998 | Dorwald |
| 5,849,903 A | 12/1998 | Pietrzkowski et al. |
| 5,856,103 A | 1/1999 | Gray et al. |
| 5,856,107 A | 1/1999 | Ostresh et al. |
| 5,856,188 A | 1/1999 | Hampel et al. |
| 5,856,463 A | 1/1999 | Prydz et al. |
| 5,856,496 A | 1/1999 | Fagnola et al. |
| 5,858,660 A | 1/1999 | Eaton et al. |
| 5,859,190 A | 1/1999 | Meyer et al. |
| 5,861,254 A | 1/1999 | Schneider et al. |
| 5,861,288 A | 1/1999 | Usman et al. |
| 5,864,010 A | 1/1999 | Cook et al. |
| 5,864,026 A | 1/1999 | Jensen et al. |
| 5,866,701 A | 2/1999 | Hampel et al. |
| 5,869,246 A | 2/1999 | Matsuo et al. |
| 5,869,248 A | 2/1999 | Yuan et al. |
| 5,869,253 A | 2/1999 | Draper |
| 5,869,339 A | 2/1999 | Hampel et al. |
| 5,869,641 A | 2/1999 | Jayasena et al. |
| 5,874,443 A | 2/1999 | Kiely et al. |
| 5,874,566 A | 2/1999 | Veerapanane et al. |
| 5,877,021 A | 3/1999 | Stinchcomb et al. |
| 5,877,022 A | 3/1999 | Stinchcomb et al. |
| 5,877,162 A | 3/1999 | Werner et al. |
| 5,877,214 A | 3/1999 | Kim |
| 5,880,972 A | 3/1999 | Horlbeck |
| 5,886,126 A | 3/1999 | Newkome et al. |
| 5,886,127 A | 3/1999 | Newkome et al. |
| 5,891,683 A | 4/1999 | Usman et al. |
| 5,891,684 A | 4/1999 | Usman et al. |
| 5,891,737 A | 4/1999 | Baindur et al. |
| 5,910,408 A | 6/1999 | Szostak et al. |
| 5,916,899 A | 6/1999 | Kiely et al. |
| 5,919,772 A | 7/1999 | Szyf et al. |
| 5,919,955 A | 7/1999 | Fancelli et al. |
| 5,925,527 A | 7/1999 | Hayes et al. |
| 5,939,268 A | 8/1999 | Boger |
| 5,942,387 A | 8/1999 | Holunshead |
| 5,945,070 A | 8/1999 | Kath et al. |
| 5,948,696 A | 9/1999 | Dollee, III et al. |
| 5,955,590 A | 9/1999 | Levina et al. |
| 5,958,691 A | 9/1999 | Pieken et al. |
| 5,958,702 A | 9/1999 | Benner |
| 5,958,792 A | 9/1999 | Desai et al. |
| 5,962,337 A | 10/1999 | Ohlmeyer |
| 5,962,426 A | 10/1999 | Glazer |
| 5,965,719 A | 10/1999 | Hindsgaul |
| 5,972,699 A | 10/1999 | Draper |
| 5,972,704 A | 10/1999 | Draper et al. |
| 5,972,719 A | 10/1999 | Dolle, III et al. |
| 5,976,894 A | 11/1999 | Dolle, III et al. |
| 5,980,704 A | 11/1999 | Cherukuri et al. |
| 5,985,356 A | 11/1999 | Schultz et al. |
| 5,985,621 A | 11/1999 | Usman et al. |
| 5,989,906 A | 11/1999 | Thompson |
| 5,989,908 A | 11/1999 | Scanlon |
| 5,990,088 A | 11/1999 | Ensou et al. |
| 5,994,320 A | 11/1999 | Low et al. |
| 5,998,193 A | 12/1999 | Keese et al. |
| 5,998,203 A | 12/1999 | Matulic-Adamic et al. |
| 5,998,602 A | 12/1999 | Torrence |
| 5,999,086 A | 12/1999 | Ecker |
| 6,001,579 A | 12/1999 | Still et al. |
| 6,001,988 A | 12/1999 | Parma et al. |
| 6,004,617 A | 12/1999 | Schultz et al. |
| 6,005,095 A | 12/1999 | Capaccioli et al. |
| 6,007,995 A | 12/1999 | Baker et al. |
| 6,008,321 A | 12/1999 | Li et al. |
| 6,011,020 A | 1/2000 | Gold et al. |
| 6,013,443 A | 1/2000 | Heilig et al. |
| 6,013,522 A | 1/2000 | Monia et al. |
| 6,017,756 A | 1/2000 | Draper |
| 6,017,768 A | 1/2000 | Baldwin et al. |
| 6,017,898 A | 1/2000 | Pietrzkowski et al. |
| 6,018,042 A | 1/2000 | Mett et al. |
| 6,020,130 A | 2/2000 | Gold et al. |
| 6,022,962 A | 2/2000 | Chowrira et al. |
| 6,025,198 A | 2/2000 | Bennett et al. |
| 6,025,371 A | 2/2000 | Gordeev et al. |
| 6,028,186 A | 2/2000 | Tasset et al. |
| 6,030,776 A | 2/2000 | Eaton et al. |
| 6,030,917 A | 2/2000 | Weinberg et al. |
| 6,031,071 A | 2/2000 | Mandeville et al. |
| 6,033,910 A | 3/2000 | Monia et al. |
| 6,040,193 A | 3/2000 | Winkler et al. |
| 6,040,296 A | 3/2000 | Nyce |
| 6,045,671 A | 4/2000 | Wu et al. |
| 6,045,755 A | 4/2000 | Lebl et al. |
| 6,046,004 A | 4/2000 | Wu et al. |
| 6,046,319 A | 4/2000 | Power et al. |
| 6,051,698 A | 4/2000 | Janjic et al. |
| 6,057,437 A | 5/2000 | Kamiya et al. |
| 6,060,596 A | 5/2000 | Lerer et al. |
| 6,061,636 A | 5/2000 | Horlbeck |
| 6,261,834 B1 | 7/2001 | Srivastava |
| 2002/0142320 A1 | 10/2002 | Ogden et al. |
| 2005/0095257 A1 | 5/2005 | Kwak et al. |

FOREIGN PATENT DOCUMENTS

| | | |
|---|---|---|
| WO | WO9203566 | 3/1992 |
| WO | WO9322434 | 11/1993 |
| WO | WO9524489 | 9/1995 |
| WO | WO9718312 | 5/1997 |
| WO | 98/07833 | 2/1998 |
| WO | WO9858057 | 12/1998 |
| WO | WO9858058 | 12/1998 |
| WO | WO0049175 A1 | 8/2000 |
| WO | WO0146405 A2 | 6/2001 |
| WO | 02/22686 | 3/2002 |
| WO | WO0244321 | 6/2002 |

OTHER PUBLICATIONS

Belgrave, A.K., et al, "Functional analysis of human beta defensin-1 in prostate cancer", Proceedings of the American Association for Cancer Research Annual Meeting, vol. 45, pp. 619 (2004).

European Search Report (Application No. EP 09178274.8, International filed Oct. 16, 2008).

Jemal, A., et al., "Cancer statistics", CA Cancer J. Clin. 2004, vol. 54, No. 1, pp. 8-29 (2004).

Prasad, M.A., et al, "Homozygous and frequent deletion of proximal 8p sequences in human prostate cancers: identification of a potential tumor suppressor gene site", Genes Chromosomes Cancer, vol. 23, No. 3, pp. 255-262 (1998).

McNeel, D. G., et al., "Immune-based therapies for prostate cancer", Immunology Letters, vol. 96, No. 1, pp. 3 (2005).

(56) References Cited

OTHER PUBLICATIONS

Tien, A. H., et al., "Altered immunity accompanies disease progression in a mouse model of prostate dysplasia". Cancer Res., vol. 65, No. 7, pp. 2947-2955 (2005).

Banchereau, J et al., "Immune and clinical responses in patients with metastatic melanoma to CD34+ progenitor-derived dendritic cell vaccine", Cancer Res., vol. 61, No. 17, pp. 6451-6458 (2001).

Fong, L., et al., "Dendritic cell-based Xenoantigen vaccination for prostate cancer immunotherapy", J. Immunol., vol. 167, No. 12, pp. 7150-7156 (2001).

Linzmeier, R., et al., "A 450-kb contig of defensin genes an human chromosome 423", Gene, vol. 233, No. 1-2, pp. 205-211 (1999).

Yang, D. et al., "Multiple roles of antimicrobial defensins, cathelicidins, and eosinophil-derived neurotoxin in host defense", Annual Review of Immunology, vol. 22, No. 1, pp. 181-215 (2004).

Donald, C. D., et al., "Cancer-specific loss of beta-defensin 1 in renal and prostatic carcinomas", Lab Invest., vol. 83, No. 4, pp. 501-505 (2003).

Ganz, T., et al., "Defensins: antimicrobial peptides of vertebrates", C. R. Biol., vol. 327, No. 6, pp. 539-549 (2004).

Mazzucchelli, R., et al., "Molecular mechanisms in prostate cancer", Anal, Quant, Cytol. Histol., vol. 26, No. 3, pp. 127-133 (2004).

Ganz, T., "Defensins and host defense", Science, vol. 286, No. 5439, 420-421 (1999).

Ganz, T., "Immunology, versatile defensins", Science, vol. 298, No. 5595, pp. 977-999 (2002).

Braida, L., et al., "A single-nucleotide polymorphism in the human beta-defensin 1 gene is associated with HIV-1 infection in Italian children", Aids, vol. 18, No. 11, pp. 1598-1600 (2004).

Gropp, R., et al., "Epithelial defensins Impair adenoviral infection: implication for adenovirus-mediated gene therapy", Hum. Gene Then, vol. 10, pp. 6, pp. 957-964 (1999).

Catalano, M. G., et al., "Altered expression of androgen-receptor isoforms in human colon-cancer tissues", Int. J. Cancer, vol. 86, No. 3, pp. 325-330 (2000).

Takeuchi, S. et al., "Differential effects of phthalate esters on transcriptional activities via human estrogen receptors alpha and beta, and androgen receptor", Toxicology, vol. 210, No. 2-3, pp. 223-233 (2005).

Wang, Z., et al., "Analysis of loss of heterozygosity on chromosome 8 in human prostate carcinoma and high grade prostatic interepithelial neoplasia", Zhong Hua Nan Ke Xue, vol. 10, No. 1, pp. 26-28.

Nishimura,M., et al., "Effect of defensin peptides on eukaryotic cells: primary epithelial cells, fibroblasts and squamous cell carcinoma cell lines" Journal of Dermatological Science, vol. 36, No. 2, pp. 87 (2004).

Fromont, G, et al., "Allelic losses in localized prostate cancer: association with prognostic factors". J. Urol., vol. 170, pp. 1394-1397 (2003).

Hugel, A., et al., "Loss of heterozygosity (LOH), malignancy grade and clonality in microdissected prostate cancer", Br. J. Cancer, vol. 79, No. 3-4, pp. 551-557 (1999).

Bockmuhl, U., et al., "Association of 8p23 deletions with poor survival in head and neck cancer", Otolaryngol. Head Neck Surg vol. 124, No. 4, pp. 451-455 (2001).

Macoska, J. A., et al., "Evolution of 8p loss in transformed human prostate epithelial cells", Cancer Genet. Cytogenet., vol. 154, No. 1, pp. 36-43 (2004).

Chaib, H., et al., "Haploinsufficiency and reduced expression of genes localized to the 8p chromosomal region in human prostate tumors", Genes Chromosomes Cancer, vol. 37, No. 3, pp. 306-313 (2003).

Teixeira, M. R., et al., "Genomic analysis of prostate carcinoma specimens obtained via ultrasound-guided needle biopsy may be of use in preoperative decision-making", Cancer, vol. 101, No. 8, pp. 1786-1793 (2004).

Vecchione, A., et al., "FEZ1/LZTS1 is down-regulated in high-grade bladder cancer, and its restoration suppresses tumorigenicity in transitional cell carcinoma cells". Am. J. Pathol., vol. 160, No. 4, pp. 1345-1352 (2002).

Valore, E. V., et al., "Human beta-defensin-1: an antimicrobial peptide of urogenital tissues", J. Clin. Invest., vol. 101 No. 8, pp. 1633-1642 (1998).

Gunther, M., et al., "Specific targets in tumor tissue for the delivery of therapeutic genes", Curr. Med. Chem, Anti-Canc. Agents, vol. 5, No. 2, pp. 157-171 (2005).

Dressler, G. R., "Pax-2, kidney development, and oncogenesis", Med. Pediatr. Oncol., vol. 27, No. 5, pp. 440-444 (1996).

Eccles, M, R., et al., "PAX genes in development and disease: the role of PAX2 in urogenital tract development", Int J. Dev. Biol., vol. 46, No. 4, pp. 535-544 (2002).

Dressler, G. R., "Pax2 in development and renal disease", Int. J. Dev, Biol., vol. 43, No. 5, pp. 463-468 (1999).

Khoubehi, B., et al., "Expression of the developmental and oncogenic PAX2 gene in human prostate cancer", J. Urol. vol. 165, pp. 2115-2120 (2001).

Havik, B., et al., "A novel paired domain DNA recognition motif can mediate Pax2 repression of gene transcription", Biochem. Biophys. Res. Commun., vol. 266, No. 2, pp. 532-541 (1999).

Discenza, M. T., et al., "WT1 is a modifier of the Pax2 mutant phenotype: cooperation and interaction between WT1 and Pax2", Oncogene, vol. 22, No. 50, pp. 8145-8155 (2003).

McConnell, M. J., et al., "Differential regulation of the human Wilms tumour suppressor gene (WT1) promoter by two isoforms of PAX2", Oncogene, vol. 14, No. 22, pp. 2689-2700 (1997).

Yuan, S. S., et al., "Pax-2 interacts with RB and reverses its repression on the promoter of Rig-1, a Robo member", Biochem. Blophys. Res. Commun., vol. 296, No. 4, pp. 1019-1025 (2002).

Stuart, E. T., et al., "Loss of p53 function through PAX-mediated transcriptional repression", EMBO J., vol. 14 No. 22, pp. 5638-5645 (1995).

Michalak,E., et al., "Death squads enlisted by the tumour suppressor p53", Biochem. Biophys. Res. Commun., vol. 331, No. 3, pp. 786-798 (2005).

Tokino, T et al., "The role of p53-target genes in human cancer", Crit. Rev. Oncol. Hematol., vol. 33, No. 1, pp. 1-6, (2000).

Muratovska, A., et al., "Paired-Box genes are frequently expressed in cancer and often required for cancer cell survival", Oncogene, vol. 22, No. 39, pp. 7989-7997 (2003).

Tagge, E. P., et al., "Paired box gene expression in Wilms' tumor", J. Pediatr. Surg., vol. 29, No. 2, pp. 134-141 (1994).

Murer, L., et al., "Expression of nuclear transcription factor PAX2 in renal biopsies of juvenile nephronophthisis", Nephron, vol. 91, No. 4, pp. 588-593 (2002).

Eccles, M. R., et al., "Expression of the PAX2 gene in human fetal kidney and Wilms' tumor", Cell Growth Differ., vol. 3, No. 5, pp. 279-289 (1992).

Ogata, T., et al., "Genetic evidence for a novel gene(s) involved in urogenital development on 10q26", Kidney Int., vol. 58, No. 6, pp. 2281-2290 (2000).

Ostrom, L, et al., "Reduced Pax2 gene dosage increases apoptosis and slows the progression of renal cystic disease", Dev. Biol., vol. 219, No. 2, pp. 250-258 (2000).

Mazal, P. R., et al., "Expression of aquaporins and PAX-2 compared to CD10 and cytokeratin 7 in renal neoplasms: a tissue microarray study", Mod. Pathol., vol. 18, No. 4, pp. 535-540 (2005).

Perfettini, J. L., et al., "Fatal liaisons of p53 with Bax and Bak", Nat. Cell. Biol., vol. 6, No. 5, pp. 386-388 (2004).

Coultas, L, et al., "The role of the Bcl-2 protein family in cancer", Semin. Cancer Biol., vol. 13, No. 2, pp. 115-123 (2003).

Mrgue,C. M., et al., "Transcriptional modulation of the anti-apoptotic protein BCL-XL by the paired box transcription factors PAX3 and PAX3/FKHR", Oncogene, vol. 19, No. 25, pp. 2921-2929 (2000).

Nakamura.Y., "Isolation of p53-target genes and their functional analysis", Cancer Sci., vol. 95, No. 1, pp. 7-11 (2004).

Perfettini, J. L., et al., "Mitochondrial fusion and fission in the control of apoptosis", Trends. Cell Biol., vol. 15, No. 4, pp. 179-183 (2005).

(56) References Cited

OTHER PUBLICATIONS

Orlando, V., et al., "Mapping chromosomal proteins in vivo by formaldehyde-crosslinked- chromatin immunoprecipitation", Trends. Biochem. Sci., vol. 25, pp. 99-104 (2000).
Boyd, K E., et al., "Coexamination of site-specific transcription factor binding and promoter activity in living cells", Mol. Cell Biol., vol. 19, pp. 8393-8399 (1999).
Wells, J., et al., "Characterizing transcription factor binding sites using formaldehyde crosslinking and immunoprecipitation", Methods, vol. 26, pp. 48-56 (2002).
Sikorski, R. S., et al, "A system of shuttle vectors and yeast host strains designed for efficient manipulation of DNA in *Saccharomyces cerevisiae*", Genetics, vol. 122, pp. 19-27 (1989).
Nigro, J. M., et al, "Human p53 and CDC2Hs genes combine to inhibit the proliferation of *Saccharomyces cerevisiae*", Mol Cell. Biol, vol. 12, pp. 1357-1365 (1992).
Wilson, T. E., et al., "Identification of the DNA binding site for NGFI-B by genetic selection in yeast", Science, vol. 252, pp. 1296-1300(1991).
Liu, J., et al, "Identifying DNA-binding sites and analyzing DNA-binding domains using a yeast selection system", METHODS: A companion to Methods in Enzymology, vol. 5, pp. 125-137 (1993).
Jackers, P., et al., "Ets-dependent regulation of target gene expression during megakaryopoiesis", J. Biol. Chem., vol. 279, pp. 52183-52190 (2004).
Fonsato, V., et al, "Expression of PAX2 in human renal tumor-derived endothelial cells sustains apoptosis resistance and angiogenesis", American Journal of Pathology, vol. 168, pp. 706-713 (2006).
Almquist, R. G., et al., "Synthesis and biological activity of a ketomethylene analogue of a tripeptide inhibitor of angiotensin converting enzyme", J. Med. Chem., vol. 23, pp. 1392-1398 (1980).
Askew, B., et al., "Molecular recognition with convergent functional groups. 6. synthetic and structural studies with a model receptor for nucleic acid components", J. Am. Chem. Soc., vol. 111, pp. 1082-1090 (1989).
Bagshawe, K. D., et al., "A cytotoxic agent can be generated selectively at cancer sites", Br. J. Cancer, vol. 58, pp. 700-703 (1988).
Battelli, M. G., et al., "T lymphocyte kiling by a xanthine-oxidase-containing immunotoxin", Cancer Immunology Immunotherapy, vol. 35, pp. 421-425 (1992).
Benner, S. A.,"Expanding the genetic lexicon: incorporatng nonstandard amino acids into proteins by ribosome-based synthesis", TIB Tech., vol. 12, pp. 158-163 (1994).
Berkner, K. L, et al "Abundant expression of polyomavirus middle T antigen and dihydrofolate reductase in an adenovirus recombinant", J. Virology, vol. 61, pp. 1213-1220 (1987).
Bout, A., et al., "Lung gene therapy: In Vivo adenovirus-mediated gene transfer to Rhesus monkey airway epithelium", Human Gene Therapy, vol. 5, pp. 3-10 (1994).
Brigham, K. L., et al., "Expression of a prokaryotic gene in culture lung endothelial cells after lipofection with a plasmid vector", Am. J. Respir. Cell Mol. Biol., vol. 1, pp. 95-100 (1989).
Brown, D. T., et al., "Penetration of host cell membranes by adenovirus 2", J. Virology, vol. 12, pp. 386-396 (1973).
Brown, V. I., et al., "Molecular and cellular mechanisms of receptor-mediacted endocytosis", DNA and Cell Biology, vol. 10, pp. 399-409 (1991).
Cahill, S. J., et al., "Site-specific mutagenesis with unnatural amino acids", TIBs, vol. 14, No. 10, pp. 400-403 (1989).
Caillaud, C, et al, "Adenviral vector as a gene delivery system into cultured rat neuronal and glial cells", Eur. J. Neuroscience, vol. 5, pp. 1287-1291 (1993).
Carrara, G., et al., "Two helices plus a linker: a small model substrate for eukaryotic RNase P", Proc. Natl. Acad. Sci., USA, vol. 92, pp. 2627-2631 (1995).
Chardonnet, Y., et al, "Early events in the interaction of adenoviruses with HeLa cells I. penetration of Type 5 and intracellular release of the DNA genome", Viology, vol. 40, pp. 462-477 (1970).
Check, E., et al, "RNA to the rescue", nature, vol. 425, pp. 10-12 (2003).
Creighton, T. E., "Posttranslational covalent modifications of polypeptide chains", Proteins: Structure and Molecular Properties, W. H. Freeman & Co., San Francisco, pp. 79-86 (1983).
Cohen, B. A., et al., "An artificial cell-cycle inhibitor isolated from a combinatorial library", Proc. Natl. Acad. Sci., USA, vol. 95, p. 14272-17277 (1998).
Cotter, U. A., et al., "Molecular genetic analysis of herpesvirus and their potential use as vectors for gene therapy applications", Current Opinion in Molecular Therapeutics, vol. 1, No. 5, pp. 633-644.
Crooke, S. T., et al., "Pharmacokinetic properties of several novel oligonucleotide analogs in mice", J. Pharmacol. Exp. Ther., vol. 277, pp. 923-937 (1996).
Davidson, D., et al., "Overproduction of polyomavirus middle T antigen in mammalian cells through the use of an adenovirus vector", J. Virology, vol. 61, pp. 1226-1239 (1987).
Davies, J. A., et al., "Development of an siRNA-based method for repressing specific genes in renal organ culture and its use to show that the Wt1 tumour suppressor is required for nephron differentiation", Human Molecular Genetics, vol. 13, pp. 235-246 (2004).
English, U., et al., "Chemically modified oligonucleotides as probes and inhibitors", Angewandte Chemie, International Edition in English, vol. 30, pp. 613-722 (1991).
Felgner, P. L, et al., "Lipofection: a highly efficient, lipid-mediated DNA-transfection procedure", Proc. Natl. Acad. Sci., USA, vol. 84, pp. 7413-7417 (1987).
Fields, S., et al., "A novel genetic system to detect protein-protein interactions", Nature, vol. 340, pp. 245-256 (1989).
Gomez-Foix, A. M., et al., "Adenovirus-mediated transfer of the muscle glycogen phosphorylase gene into hepatocytes confers altered regulation of glycogen metabolishm", J. Biol. Chem., vol. 267, pp. 25129-25134 (1992).
Guzman, R. J., et al., "Efficient gene transfer into myocardium by direct injection of adenovirus vectors", Circulation Research, vol. 73, pp. 1201-1207 (1993).
Hann, M., et al, "On the double bond isostere of the peptide bond: preparation of an enkephaline analogue", J. Chem. Soc. Perkin. Trans., pp. 307-314 (1982).
Haj-Ahmad, Y., et al., "Development of a helper-independent human adenovirus vector and its use in the transfer of herpes simplex virus thymidine kinase gene", J. Virology, vol. 57, pp. 267-274 (1986).
Hammond. S. M., et al., "post-transcriptional gene silencing by double-stranded RNA", Nature Rev. Gen., vol. 2, pp. 110-119 (2001).
Holladay, M. W., et al., "Synthesis of hydroxyethylene and ketornethylene dipeptide isosteres", Tetrahedron Letters, vol. 24, pp. 4401-4404 (1983).
Hruby, V. J., et al., "Conformational restrictions of biologically active peptides via amino acid side chain groups", Life Sciences, vol. 31, pp. 189-199 (1982).
Hudson, D., et al., "Methionine enkephalin and isosteric analogues", Int. J. Peptide Protein Res., vol. 14, pp. 177-185 (1979).
Hueber, P-A., et al., "PAX2 inactivation enhances cisplatin-induced apoptosis in renal carcinoma cells", Kidney International, vol. 89, pp. 1139-1145 (2006).
Hughes, B. J., et al., "Monoclonal antibody targeting of liposomes to mouse lung in vivo", vol. 49, pp. 6214-6220 (1989).
Ibba, M., et al., "Towards engineering proteins by site-directed Incorporation in vivo of non-natural amino acids", Nature Biotechnology, vol. 12, pp. 678-682 (1994).
Ibba, M., et al., "Strategies for in vitro and in vivo translation with non-natural amino acids", Biotechnology & Genetic Engineering Reviews, vol. 13, pp. 197-216 (1995).
Itakura. K., et al., "Synthesis and use of synthetic oligonucleotides", Ann. Rev, Biochem., vol. 53, pp. 323-356 (1984).
Jaeger, J. A., et al., "Predicting optimal and suboptimal secondary structure for RNA", Methods in Enzymology, vol. 183, pp. 281-306 (1989).
Jaeger, J. A., et al., "Improved predictins of secondary structures for RNA", Proc. Natl. Acad. Sci., USA, vol. 86, pp. 7706-7710 (1989).
Jennings-White, C, et al., "Synthesis of ketomethylene analogs of dipeptides", Terahedron Letter, vol. 23, pp. 2533-2534 (1982).
Kabanove, A. V., et al, "A new class of antivirals; antisense oligonucleotides combine with a hydrophobic substituent effectively

(56) References Cited

OTHER PUBLICATIONS inhibit influenza virus reproduction and synthesis of virus-specific proteins in MDCK cells", FEBS letter., vol. 259, pp. 327-330 (1990).

Kirshenbaum, L. A., et al., "Highly efficient gene transfer into adult ventricular myocytes by recombinant adenovirus", J. Clin. Invest., vol. 92, pp. 381-387 (1993).

Kunkel, T. A., et al., "Rapid and efficient site-specific mutagenesis without phenotypic selection", Methods in Enzymology, vol. 154, pp. 367-382 (1987).

Lamins, L. A., et al., "Osmotic control of kdp operon expression in *Escherichia coli*", Proc. Natl. Acad. Sci., USA, vol. 78, pp. 464-468 (1981).

Letsinger, R. L, et al., "Cholesteryl-conjugate oligonudeotides: synthesis, properties, and activity as inhibitors of replciation of human immunodeficiency virus in cell culture", Proc, Natt. Acad. Sci., USA, vol. 86, pp. 6553-6556 (1989).

Lewis, R. A., et al., "Automated site-directed drug design: the conception of spacer skeleton for primary structure generation", Proc. R. Soc. Lond., vol. 236, pp. 125-140 (1989).

Litzinger, D. C, et al., "Biodistribution and immunotargetability of ganglioside-stabilized dioleoylphosphatidylethanofamine liposomes", Biochimica et Biophysica Acta, vol. 1104, pp. 179-187 (1992).

Lusky, M., etal., "Bovine papilioma virus contains an activator of gene expression at the distal end of the early transcription unit", Mol. Cell. Biol., vol. 3, pp. 1108-1122 (1983).

Manoharan, M., et al., "Chemical modifications to improve uptake and bioavailability of antisense oligonucleotides", Ann. N. Y. Acad. Sci., vol. 660, pp. 306-309 (1992).

Manoharan, M., et al., "Introduction of a lipophilic thioether tether in the minor groove of nucleic adds for antisense applications", Bioorganic & Medicinal Chemistry Letters, vol. 3, pp. 2765-2770 (1993).

Manoharan, M., et al., "Cholic acid-oligonucleotide conjugates for antisense applications", Bioorganic & Medicinal Chemistry Letters, vol. 4, pp. 1053-1060 (1994).

Manoharan, M., et al., "Oligonucleotide conjugates: alteration of the pharmacokinetic properties of antisense agents", Nucleotides & Nucleotides, vol. 14, pp. 969-973 (1995).

Manoharan, M., et al., "Lipidic nucleic adds", Tetrahedron Letters, vol. 36, pp. 3651-3654 (1995).

Massie, B., et al., "Construction of a helper-free recombinant adenovirus that expresses polyomavirus large T antigen", Molecular and Cellular Biology, vol. 6, pp. 2872-2883 (1986).

McKinlay, M. A., et al., "Rational design of antiviral agents", Annu. Rev. Pharmacol. Toxical., vol. 29, pp. 111-122 (1989).

Mishra, R. K., et al,, "Improve leishmanicidal effect of phosphorotioate antisense oligonucleotides by LDL-mediated delivery", Biochimica et Biophysica Acta, vol. 1264, pp. 229-237 (1995).

Morley, J. S., "Modulation of the action of regulatory peptides by structural modification", Trends. Pharm. Sci., pp. 463-468 (1980).

Morsy, M. A., et al., "Efficient adenoviral-mediated omithine transcarbamylase expression in deficient mouse and human hepatocytes", J. Clin. Invest., vol. 92, pp. 1580-1586 (1993).

Muratovska, A., et al., "Paired-Box genes are frequently expressed in cancer and often required for cancer cell survival", Oncogene, vol. 22, pp. 7989-7997 (2003).

Narang, S. A., et al., "Chemical synthesis of deoxyoligonucleotides by the modified triester method", Methods in Enzymology, vol. 65, pp. 610-620 (1980).

Needleman, S., B., et al., "A general method applicable to the search for similarities in the amino acid sequence of two proteins", J. Mol. Biol vol. 48, pp. 443-453 (1970).

Nielsen, P. E., et al., "Peptide nucleic acid (PNA). A DNA mimic with a peptide backbone", Bioconjugate Chem., vol. 5, pp. 3-7 (1994).

27 Oberhauser, B., et al., "Effective incorporation of 2-O-methyl-oligoribonucleotides into liposomes and enhanced cell association through modification with thiocholesterol", Nucleic Acids Research, vol. 20, pp. 533-538 (1992).

Osborne, T. F., et al., "Transcription control region within the protein-coding portion of adenovirus E1A genes", Molecular and Cellular Biology, vol. 4, 1293-1305 (1984).

Pearson, W. R., et al., "Improved tools for biological sequence comparison", Proc. Natl. Acad. Sci., USA, vol. 85, pp. 2444-2448 (1988).

Perry, N. C., et al., "The use of 3D modeling databases for identifying structure activity relationships", QSAR: Quantitative Structure-Activity Relationships in Drug Design, pp. 189-193 (1989).

Pietersz, G. A., et al., "Antibody conjugates for the treatment of cancer", Immunological Reviews, vol. 129, pp. 57-80 (1992).

Ragot, T., et al., "Replication-defective recombinant adenovirus expressing the Epstein-Barr virus (EBV) envelop glycoprotein gp340/220 induces protective immunity against EBV-induced lymphomas in the cottontop tamarin", Journal of General Virology, vol. 74, pp. 501-507 (1993).

Ram, Z., et al., "In situ retroviral-mediated gene transfer fro the treatment of brain tumors in rats", Cancer Research, vol. 53, pp. 83-88 (1993).

Remington: The Science and Practice of Pharmacy (19th ed.) A. R. Gennaro, Mack Publishing Company, Easton, PA 1995. (tabel of content).

Rich, D. P., et al., "Development and analysis of recombinant adenovirus for gene therapy for cystic fibrosis", Human Gene Therapy, vol. 4, pp. 461-476 (1993).

Ripka, W., et al., "Computers picture of the perfect drug", New Scientist, pp. 54-57 (Jun. 16, 1988).

Rizo, J., et al., "Constrained peptides; models of bioactive peptides and protein substructures", Annu. Rev. Biochem., vol. 61, pp. 387-418 (1992).

Roberts, R. W., et al., "RNA-peptide fusions for the in vitro selection of peptides and proteins", Proc. Natl. Acad. Sci., USA, vol. 94, pp. 12297-12302 (1997).

Roessler, B. J., et al., "Adenoviral-mediated gene transfer to rabbit synovium in vivo", J. Clin. Invest, vol. 92, pp. 1085-1092 (1993).

Roffler, S. P., et al., "Anti-nelplastic glucuronide prodrug treatment of human tumor cells targeted with a monoclonal antibody-enzyme conjugate", Biochimical Pharmacology, vol. 42, pp. 2062-2065 (1994).

Rouvinen, J., et al, "Computer-aided drug design", Acta Pharmaceutica Fennica, vol. 97, pp. 159-166 (1988).

Saison-Behmoaras, T. et al., Short modified antisense oligonucleotides directed against Ha-ras point mutation induce selective cleavage of the mRNA and inhibit T24 cells proliferation;, The EMBO Journal, vol. 10, pp. 1111-1118 (1991).

Senter, P. D., et al., "Generation of 5-fluorouracil from 5-fluorocytosine by monoclonal antibody-cytosine deaminase conjugates", Biocojugate Chem., vol. 2, 447-451 (1991).

Senter, P. D., et al., "Generation of cytotoxic agents by targeted enzymens", vol. 4, pp. 3-9 (1993).

Seth, P., et al., "Role of a Low-pH environment in adenovirus enhancement of the toxicity of a *Pseudomonas* exotoxin-epidermal growth factor conjugate", J. Virology, vol. 51, pp. 650-655 (1984).

Seth, P., et al., "Evidnece that the penton base of adenovirus is involved in potentiation of toxicity of Pseudomonas exotoxin conjugated to epidermal growth factor", Molecular and Cellular Biology, vol. 4, pp. 1528-1533 (1984).

Sharp, P. A., et al, "RNA interference-2001", Genes & Dev., vol. 15, pp. 485-490 (2001).

Shea, R. G., et al, "Synthesis, hybridization properties and antiviral activity of lipid-oiigodeoxynucleotide conjugates", Nucleic Acids Research, vol. 18, pp. 3777-3783 (1990).

Svensson, U., et al., "Role of vesicles during adenovirus 2 internalization into HeLa cells", J. Virology, vol. 55, pp. 442-149 (1985).

Svinarchuk, F. P., et al., "Inhibition of HIV proliferation in MT-4 cells by antisense oligonucleotide conjugated to lipophilic groups.", Biochimie, vol. 75, pp. 49-54 (1993).

Smith, T. F., et al., "Comparison of biosequences", Advances in Applied Mathematics, vol. 2, pp. 482-489 (1981).

Smith, T. W., et al "Cardiac glycoside-specific antibodies in the treatment of digitalis intoxication", Antibodies in Human Diagnosis and Therapy, edited by Edgar Haber and Richard M. Krause, Raven Press, New York, pp. 365-389 (1977).

(56) References Cited

OTHER PUBLICATIONS

Spatola, A. F., et al., "Structure-activity relationships of enkephalins containing serially replaced thiomethylene amide bond surrogates", Life Sciences, vol. 38, pp. 1243-1249 (1986).

Spatola, A. F., "Peptide backbone modifications: a structure-activity analysis of peptides containing amide bond surrogates conformational constraints, and rela", Chemistry and Biochemistry of Amino acids, Peptides, and Proteins, Marcel Dekker, New York, pp. 267-357 (1983).

Sun, T., et al, "Human artificial episomal chromosomes for cloning large DNA fragments in human cells", Nature genetics, vol. 8, pp. 33-41 (1994).

Szelke, M., et al., "Enzyme inhibitors, European Patent Application, EP 45,665", Chemical Abstracts, vol. 97, pp. 624 (1982).

Szostak, J. W., "In vitro genetics", TIBS, vol. 17, pp. 89 (1992).

Thorson, J. S., et al., "A biosynthetic approach for the incorporation of unnatural amino acids into proteins", Methods in Molecular Biology, vol. 77, pp. 43-73 (1991).

Tolcher, A. W., et al., "A phase I pharmacokinetic and biological correlative study of oblimersen sodium (Genasense, G3139), an Antisense oligonucleotide to the Bcl-2 mRNA, and of docetaxel in patients with hormone-refractory prostate cancer", Clinical Cancer Research, vol. 10, pp. 5048-5057 (2004).

Varga, M. J., et al., "Infectious entry pathway of adenovirus Type 2", J. Virology, vol. 65, pp. 6061-6070 (1991).

Verma, I. M., "Retroviral vectors for gene transfer", Microbiology, pp. 229-232 (1985).

Waterhouse, P. M., et al., "Virus resistance and gene silencing in plants can be induced by simultaneous expression of sense and antisense RNA", Proc. Natl. Acad. Sci., USA, vol. 95, pp. 13959-13964 (1998).

Wickham, T. J., et al., "Ingerins alpha V beta 3 and alpha V beta 5 promote adenovirus internalization but not virus attachment", Cell, vol. 73, pp. 309-319 (1993).

Xu, Q., et al., "Crystal structure of a paired domain-DNA complex at 2.5 A resolution reveals structural basis for Pax developmental mutations", Cell, vol. 80, pp. 639-650 (1995).

Yuan, Y., et al., "Substrate recognition by human RNase P: identification of small, model substrates for the enzyme", The EMBO Journal, vol. 14, pp. 159-168 (1995).

Yuan, Y., et al., "Targeted cleavage of mRNA by human RNase P", Proc. Natl. Acad. Sci., USA, vol. 89, pp. 8006-8010 (1992).

Zabner, J et al., "Adenovirus-mediated gene transfer transiently corrects the chloride transport defect in nasal epithelia of patients with cystic fibrosis", Cell, vol. 75, pp. 207-216 (1993).

Zabner, J., et al., "Safety and efficacy of repetitive adenovirus-mediated transfer of CFTR cDNA to airway epithelia of primates and cotton rats", Nature, vol. 6, pp. 75-83 (1994).

Zucht, H. D., et al., "Human p-defensin-1: a urinary peptide present in variant molecular forms and its putative functional implication", European Journal of Medical Research, vol. 3, pp. 315-323 (1998).

Zoller, U. J., et al., "New recombinant DNA methodology for protein engineering", Current Opinion in Biotechnology, vol. 3, pp. 348-354 (1992).

Banerji, J., et al., "A lymphocyte-specific cellular enhancer is located downstream of the joining region in immunoglobulin heavy chain genes", Cell, vol. 33, pp. 729-740 (1983).

Greenway, P. J. , et al., "Human cytomegalovirus DNA: BamHI, EcoRI and PstI restriction endonuclease cleavage maps", Gene. vol. 18, pp. 355-360 (1982).

Fiers, W., et al., "Complete nucleotide sequence of SV40 DNA", Nature, vol. 273, pp. 113-120 (1978).

Forster, A. C., et al., "External guide sequences for an RNA enzyme", Science, vol. 249, pp. 783-786 (1990).

La Salle, G. L. G., et al., "An adenovirus vector for gene transfer into neurons and glia in the brain", Science, vol. 259, pp. 988-990 (1993).

Mulligan, R., et al., "The basic science of gene therapy", Science, vol. 260, pp. 926-932 (1993).

Nielsen, P. E., et al, "Sequence-selective recognition of DNA by strand displacement with a Thymine-substituted polyamide", Science, vol. 254, pp. 1497-1500 (1991).

Wolff, J. A., et al., "Direct gene transfer into mouse muscle in vivo", Science, vol. 247, pp. 1465-1468 (1990).

Zuker, M., et al., "On finding all suboptimal foldings of an RNA molecule", Science, vol. 244, pp. 48-52 (1989).

Bensch, K., et al., "hBD-1: a novel beta-defensin from human plasma", FEBS Lett., vol. 368, pp. 331-335 (1995).

Bose, S., et al., "PAX2 oncogene negatively regulates the expression of the host defense peptide human beta defensin-1 in prostate cancer", Mol Immunol., vol. 46, pp. 1140-1148 (2009).

Gibson, W., et al., "Inhibition of PAX2 expression results in alternate cell death pathways in prostate cancer cells differing in p53 status", Cancer Letters, vol. 248, pp. 251-261 (2007).

Harder, J., et al., "Isolation and characterization of human beta -defensin-3, a novel human inducible peptide antibiotic", J. Bio. Chem., vol. 276, pp. 5707-5713 (2001).

Harder, J., et al "A peptide antibiotic from human skin", Nature, vol. 387, pp. 861 (1997).

Jia, H-P., et al., "Discovery of new human beta-defensins using a genomics-based approach", Gene, vol. 263, pp. 211-218 (2001).

Morrison, S et al., "Chimeric human antibody molecules: mouse antigen-binding domains with human constant region domains", vol. 81, pp. 6851-6855 (1984).

Book reviews: Sociology and Pharmacy Practice, Am. J. Pharm. Edu., vol. 70, pp. 1-3 (2006).

Wilson, D., "High resolution crystal structure of a paired (PAX) class cooperative homeodomain dimer on DNA", Cell, vol. 82, pp. 709-719 (1995).

Lin, S., et al., "Differentially expressed genes in activity-induced apoptotic LNCaP cells", Biochem. Biophys. Res. Commun. vol. 257, No. 1, pp. 187-192 (1999).

Written Opinion of the International Searching Authority (International Patent Application No. PCT/US2006/040215 filed Oct. 16, 2006).

International Preliminary Report on Patentability (International Patent Application No. PCT/US2006/040215 filed Oct. 16, 2006).

International Search Report (International Patent Application No. PCT/US2006/040215 filed Oct. 16, 2006).

European Search Report (European Application No. 06816925.9 filed Apr. 14, 2008).

Muratovska A., et al., "Paired-Box genes are frequently expressed in cancer and often required for cancer cell survival", Oncogene, vol. 22, No. 39, pp. 7989-7997 (2003).

Hueber P., et al., "PAX2 inactivation enhances cisplatin-induced apoptosis in renal carcinoma cells", Kidney international, vol. 69, No. 7, pp. 1139-1145 (2006).

Gibson W., et al., "Comparison of RNA interference silencing of PAX 2 expression in PC3 and Du145 prostate cancer cell lines", Proceedings of the American Association for Cancer Research Annual Meeting & 96th meeting of the American-Association-for-Cancer-Research, vol. 46, pp. 16 (2005).

Gnarra, J. R., et al., "Expression of Pax-2 in human renal cell carcinoma and growth inhibition by antisense oligonucleotides", Cancer Res., vol. 55, No. 18, pp. 4092-4098 (1995).

Strasser, A., "The role of BH3-only proteins in the immune system", Nat. Rev. Immunol., vol. 5, No. 3, pp. 189-200 (2005).

Buttiglieri, S., et al., "Role of Pax2 in apoptosis resistance and proinvasive phenotype of Kaposi's sarcoma cells", J. Biol. Chem., vol. 279, No. 6, pp. 4136-4143 (2004).

Papo, N., et al., "Host defense peptides as new weapons in cancer treatment", Cell. Mol. Life Sci., vol. 62, pp. 784-790 (2005).

Donald, C., et al., "Cancer-specific loss of beta-defensin 1 in renal and prostatic carcinomas", Laboratory Investigation, vol. 83, pp. 501-505 (2003).

Casey, G., "The BRCA1 and BRCA2 breast cancer genes", Current Opinion in Oncology, vol. 9, pp. 88-93 (1997).

Stuart, E., et al., "Mammalian Pax Genes", Annu. Rev. Genet., vol. 27, pp. 219-236 (1993).

(56) References Cited

OTHER PUBLICATIONS

Jatoi, I., et al., "Breast Cancer Screening", Am. J. Surg., vol. 177, pp. 518-524 (1999).

Marcus, J., et al., "Hereditary Breast Cancer", Cancer, vol. 77, pp. 697-709 (1996).

Miki, Y., et al., "A strong candidate for the breast and ovarian cancer susceptibility gene BRCA1", Science, vol. 266, pp. 66-93 (1994).

Katz, A., et al., "Gene activity during the early phase of androgen-stimulated rat prostate regrowth", Cancer Research, vol. 49, pp. 5889-5894 (1969).

International Preliminary Report on Patentability (International Patent Application No. PCT/US2008/051168 filed Jan. 16, 2008).

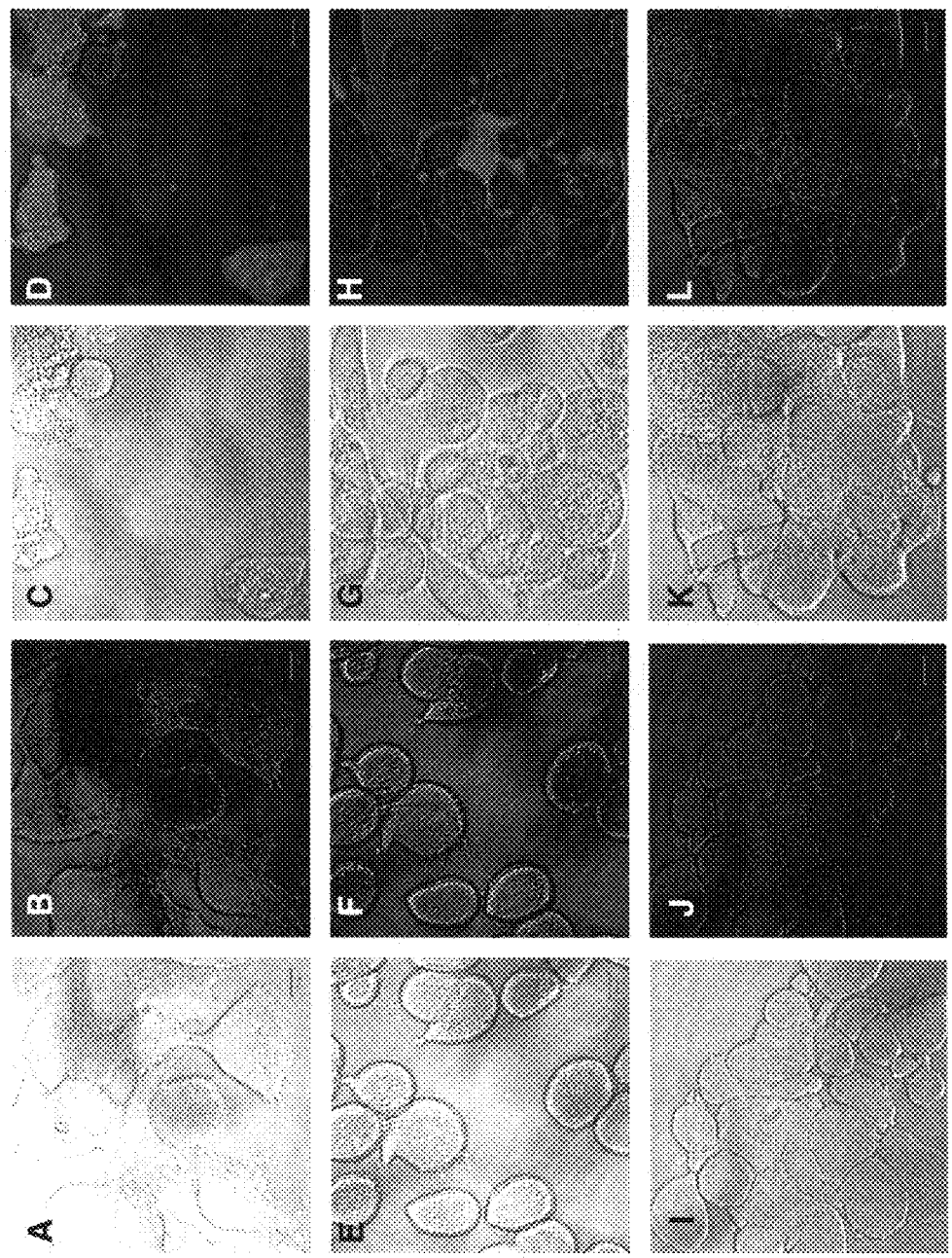
FIG. 5A-L

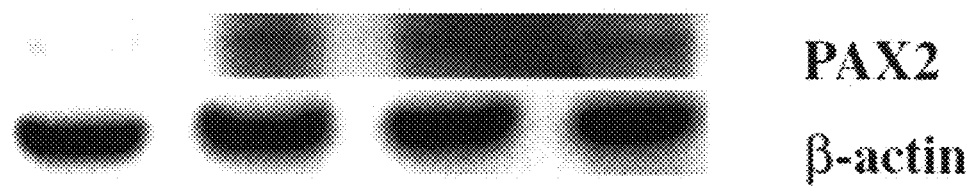
FIG. 38A
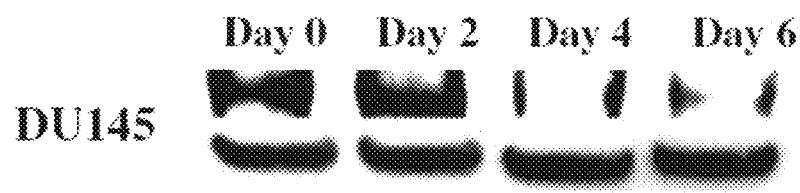
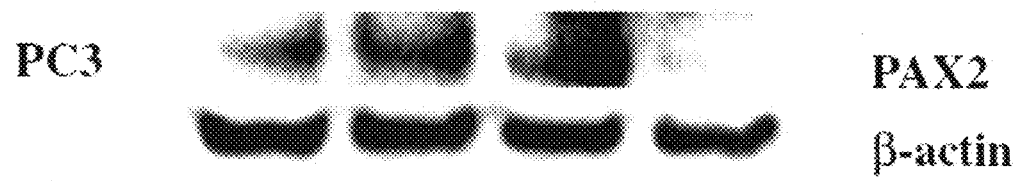
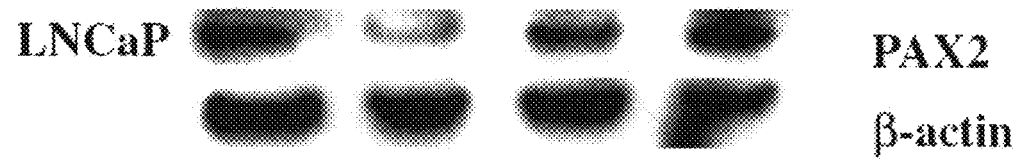
FIG. 38B

TARGETING PAX2 FOR THE TREATMENT OF BREAST CANCER

The present application is a continuation application of U.S. patent application Ser. No. 12/708,294, filed on Feb. 18, 2010, which is a continuation-in-part application of U.S. patent application Ser. No. 12/090,191, filed Sep. 15, 2008 as a national stage application of PCT/US2006/040215 which claims priority to U.S. Patent Application No. 60/726,921, filed Oct. 14, 2005. The entirety of all of the aforementioned applications is incorporated herein by reference.

BACKGROUND

Breast cancer is the most common cause of cancer in women and the second most common cause of cancer death in women in the U.S. While the majority of new breast cancers are diagnosed as a result of an abnormality seen on a mammogram, a lump or change in consistency of the breast tissue can also be a warning sign of the disease. Heightened awareness of breast cancer risk in the past decades has led to an increase in the number of women undergoing mammography for screening, leading to detection of cancers in earlier stages and a resultant improvement in survival rates. Still, breast cancer is the most common cause of death in women between the ages of 45 and 55.

It is known that many types of cancer are caused by genetic aberrations, i.e., mutations. The accumulation of mutations and the loss of cellular control functions cause progressive phenotypic changes from normal histology to early pre-cancer such as intraepithelial neoplasia (IEN) to increasingly severe IEN to superficial cancer and finally to invasive disease. Although this process can be relatively aggressive in some cases, it generally occurs relatively slowly over years and even decades. Oncogene addiction is the physiologic dependence of cancer cells on the continued activation or overexpression of single oncogenes for maintaining the malignant phenotype. This dependence occurs in the milieu of the other changes that mark neoplastic progression.

The long period of progression to invasive cancer provides an opportunity for clinical intervention. Therefore, it is important to identify biomarkers that are indicative of pre-cancerous conditions so that treatment measures can be taken to prevent or delay the development of invasive cancer.

SUMMARY

One aspect of the present invention relates to a method for preventing or treating a breast condition in a subject. The method comprises administering to a breast tissue of the subject, a composition that inhibits PAX2 expression or PAX2 activity.

In one embodiment, the breast condition is breast cancer or mammary intraepithelial neoplasia (MIN).

In another embodiment, the inhibiting expression of PAX2 comprises administering to the breast cancer tissue or MIN tissue in the subject a nucleic acid encoding an siRNA for PAX2.

In a related embodiment, the siRNA comprises a sequence selected from the group consisting of SEQ ID NOS: 3-6 and 11-15.

In another embodiment, the composition comprises an oligonucleotide that inhibits PAX2 binding to the DEFB1 promoter.

In a related embodiment, the oligonucleotide comprises SEQ ID NO:1 in forward or reverse orientation.

In a related embodiment, the oligonucleotide comprises the sequence of X1GGAACX2, wherein X1 and X2 are 0 to 30 nucleotides complementary to nucleotides contiguous to SEQ ID NO:1 in the DEFB1 coding sequence.

In a related embodiment, the oligonucleotide comprises a sequence selected from the group consisting of SEQ ID NOS: 18-21, 25, 26, 28 and 29.

In another embodiment, the composition comprises a blocker of RAS signaling pathway.

In another embodiment, the composition comprises an antagonist selected from the group consisting of antagonists of angiotensin II, antagonists of angiotensin II receptor, antagonists of angiotensin-converting enzyme (ACE), antagonists of mitogen-activated protein kinase (MEK), antagonists of (extracellular signal-regulated kinase) ERK1, 2, and antagonists of signal transducer and activator of transcription 3 (STAT3).

Also disclosed is a method of treating breast cancer or MIN in a subject, comprising enhancing expression of DEFB1 in a breast cancer tissue or MIN tissue in the subject.

In one embodiment, the enhancing expression of DEFB1 comprises administering to the breast cancer tissue or MIN tissue in the subject an efficient amount of DEFB1.

In another embodiment, the enhancing expression of DEFB1 comprises administering to the breast cancer tissue or MIN tissue in the subject an efficient amount of an expression vector encoding DEFB1.

Also disclosed is a method for treating a breast condition in a subject, comprising: (a) determining the PAX2-to-DEFB1 expression ratio in a diseased breast tissue from said subject; (b) determining the ER/PR status of said diseased breast tissue from said subject; and (c) based on the result of (a) and (b), administering to a breast tissue of said subject, a composition that (1) inhibits PAX2 expression or PAX2 activity, (2) expresses DEFB1 or (3) inhibits PAX2 expression or PAX2 activity and expresses DEFB1.

BRIEF DESCRIPTION OF THE DRAWINGS

The file of this patent contains at least one drawing executed in color. Copies of this patent with color drawings will be provided by the Patent and Trademark Office upon request and payment of the necessary fee.

The accompanying drawings illustrate one or more embodiments of the invention and, together with the written description, serve to explain the principles of the invention. Wherever possible, the same reference numbers are used throughout the drawings to refer to the same or like elements of an embodiment.

FIG. 5 shows pan-caspase analysis following DEFB1 induction.

In FIG. 17A, Lane 1 contains a 100 bp molecular weight marker. Lane 2 is a positive control representing 160 bp region of the DEFB1 promoter amplified from DU145 before cross-linking and immunoprecipitation. Lane 3 is a negative control representing PCR performed without DNA. Lanes 4 and 5 are negative controls representing PCR from immunoprecipitations performed with IgG from cross-linked DU145 and PC3, respectively. PCR amplification of 25 pg of DNA (lane 6 and 8) and 50 pg of DNA (lane 7 and 9) immunoprecipitated with anti-PAX2 antibody after crosslinking show 160 bp promoter fragment in DU145 and PC3, respectively. In FIG. 17B, Lane 1 contains a 100 bp molecular weight marker. Lane 2 is a positive control representing 160 bp region of the DEFB1 promoter amplified from DU145 before cross-linking and immunoprecipitation. Lane 3 is a negative control representing PCR performed without DNA. Lane 4 and 5 are negative controls representing PCR from immunoprecipitations performed with IgG from cross-linked DU145 and PC3, respectively. PCR amplification of 25 pg of DNA (lane 6 and 8) and 50 pg of DNA (lane 7 and 9) immunoprecipitated with anti-PAX2 antibody after crosslinking show 160 bp promoter fragment in DU145 and PC3, respectively

FIG. 25A shows treatment of DU145 cells with Losartan suppresses phosphor-ERK 1/2 and PAX2 expression; FIG. 25B shows MEK kinase inhibitors and AICAR suppresses PAX2 protein expression; FIG. 25C shows MEK kinase inhibitors and Losartan suppresses phospho-STAT3 protein expression.

FIG. 34A shows hBD-1 expression levels compared relative to hPrEC cells in prostate cancer cell lines before and after hBD-1 induction. An asterisk represents statistically higher expression levels compared to hPrEC. Double asterisks represent statistically significant levels of expression compared to the cell line before hBD-1 induction (Student's t-test, p<0.05). FIG. 34B shows ectopic hBD-1 expression verified in the prostate cancer cell line DU145 by immunocytochemistry. hPrEC cells were stained for hBD-1 as appositive control (A: DIC and B: fluorescence). DU145 cells were transfected with hBD-1 and induced for 18 hours (C: DIC and D: fluorescence). Sizebar=20 µM.

FIG. 36A shows comparison of hBD-1 expression levels in normal, PIN and tumor sections. FIG. 36B shows comparison of cMYC expression level in normal, PIN and tumor sections.

FIGS. 38A and 38B show silencing of PAX2 protein expression following PAX2 siRNA treatment. FIG. 38A shows PAX2 expression examined by Western blot analysis in HPrEC prostate primary cells (lane 1) and in DU145 (lane 2), PC3 (lane 3) and LNCaP (lane 4) prostate cancer cells. Blots were stripped and re-probed for -actin as an internal control to ensure equal loading. FIG. 38B shows Western blot analysis of DU145, PC3 and LNCaP all confirmed knockdown of PAX2 expression following transfection with PAX2 siRNA duplex. Again, blots were stripped and re-probed for β-actin as an internal control.

DETAILED DESCRIPTION

Figure 1A:
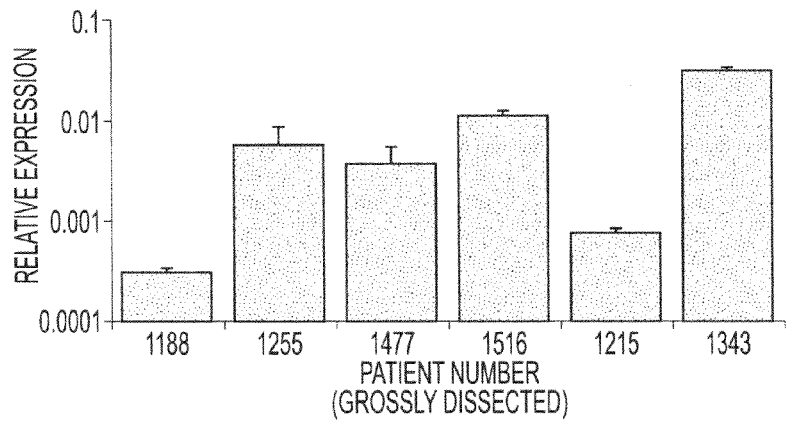
FIGS. 1A-1D show quantitative RT-PCR (QRT-PCR) analysis of beta-defensin-1 (DEFB1) expression.

One aspect of the present invention provides a method of preventing or treating breast cancer in a subject. The method includes administering to the subject a composition comprising an inhibitor of PAX2 expression or PAX2 activity, or an enhancer of DEFB-1 expression or DEFB-1 activity. In one embodiment, the subject is diagnosed with mammary intraepithelial neoplasia (MIN).

In some aspects, PAX2 is upregulated in breast tissue prior to MIN. Thus, also provided is a method of treating or preventing MIN in a subject. The method comprises administering to the subject a composition comprising an inhibitor of PAX2 expression or PAX2 activity, or an enhancer of DEFB-1 expression or DEFB-1 activity.

"Activities" of a protein include, for example, transcription, translation, intracellular translocation, secretion, phosphorylation by kinases, cleavage by proteases, homophilic and heterophilic binding to other proteins, ubiquitination. In some aspects, "PAX2 activity" refers specifically to the binding of PAX2 to the DEFB-1 promoter.

Breast Cancer

The commonly used screening methods for breast cancer include self and clinical breast exams, x-ray mammography, and breast Magnetic Resonance Imaging (MRI). The most recent technology for breast cancer screening is ultrasound computed tomography, which uses sound waves to create a three-dimensional image and detect breast cancer without the use of dangerous radiation used in x-ray mammography. Genetic testing may also be used. Genetic testing for breast cancer typically involves testing for mutations in the BRCA genes. It is not a generally recommended technique except for those at elevated risk for breast cancer.

The incidence of breast cancer, a leading cause of death in women, has been gradually increasing in the United States over the last thirty years. While the pathogenesis of breast cancer is unclear, transformation of normal breast epithelium to a malignant phenotype may be the result of genetic factors, especially in women under 30. The discovery and characterization of BRCA1 and BRCA2 has recently expanded our knowledge of genetic factors which can contribute to familial breast cancer. Germ-line mutations within these two loci are associated with a 50 to 85% lifetime risk of breast and/or ovarian cancer. However, it is likely that other, non-genetic factors also have a significant effect on the etiology of the disease. Regardless of its origin, breast cancer morbidity and mortality increases significantly if it is not detected early in its progression. Thus, considerable effort has focused on the early detection of cellular transformation and tumor formation in breast tissue.

Currently, the principal manner of identifying breast cancer is through detection of the presence of dense tumorous tissue. This may be accomplished to varying degrees of effectiveness by direct examination of the outside of the breast, or through mammography or other X-ray imaging methods. The latter approach is not without considerable cost, however. Every time a mammogram is taken, the patient incurs a small risk of having a breast tumor induced by the ionizing properties of the radiation used during the test. In addition, the process is expensive and the subjective interpretations of a technician can lead to imprecision, e.g., one study showed major clinical disagreements for about one-third of a set of mammograms that were interpreted individually by a surveyed group of radiologists. Moreover, many women find that undergoing a mammogram is a painful experience. Accordingly, the National Cancer Institute has not recommended mammograms for women under fifty years of age, since this group is not as likely to develop breast cancers as are older women. It is compelling to note, however, that while only about 22% of breast cancers occur in women under fifty, data suggests that breast cancer is more aggressive in pre-menopausal women.

PAX2

PAX genes are a family of nine developmental control genes coding for nuclear transcription factors. They play an important role in embryogenesis and are expressed in a very ordered temporal and spatial pattern. They all contain a "paired box" region of 384 base pairs encoding a DNA binding domain which is highly conserved throughout evolution (Stuart, E T, et al. 1994). The influence of Pax genes on developmental processes has been demonstrated by the numerous natural mouse and human syndromes that can be attributed directly to even a heterozygous insufficiency in a Pax gene. A PAX2 sequence is given in Dressler, et al. 1990. The amino acid sequences of the human PAX2 protein and its variants, as well as the DNA sequences encoding the proteins, are listed in SEQ ID NOS: 39-50 (SEQ ID NO:39, amino acid sequence encoded by exon 1 of the human PAX2 gene; SEQ ID NO:40, human PAX2 gene promoter and exon 1; SEQ ID NO:41, amino acid sequence of the human PAX2; SEQ ID NO:42, human PAX2 gene; SEQ ID NO:43, amino acid sequence of the human PAX2 gene variant b; SEQ ID NO:44, human PAX2 gene variant b; SEQ ID NO:45, amino acid sequence of the human PAX2 gene variant c; SEQ ID NO:46, human PAX2 gene variant c; SEQ ID NO:47, amino acid sequence of the human PAX2 gene variant d; SEQ ID NO:48, human PAX2 gene variant d; SEQ ID NO:49, amino acid sequence of the human PAX2 gene variant e; SEQ ID NO:50 human PAX2 gene variant e). It has been reported that PAX2 suppresses DEFB-1 expression by binding to the DEFB-1 promoter (Bose S K et al., Mol Immunol. 2009, 46:1140-8.) at a 5'-CCTTG-3' (SEQ ID NO:1) recognition site immediately adjacent to the DEFB1 TATA box. In some references, the binding site is also referred to as the 3'-GTTCC-5' (SEQ ID NO:1) or 5'-CAAGG-3' (SEQ ID NO:2) recognition site, which is the sequence on the opposite strand. The two sequences both refer to the PAX2 binding site on the DEFB1 promoter. Examples of cancers in which PAX2 expression has been detected are listed in Table 1

TABLE 1

PAX2-expressing cancers

| PAX2 Expressing Cancers | Estimated New Cases in US | Estimated Deaths in US | Estimated New Cases Global | Estimated Deaths Global |
|---|---|---|---|---|
| Prostate | 234,460 | 27,350 | 679,023 | 221,002 |
| Breast | 214,600 | 41,430 | 1,151,298 | 410,712 |
| Ovarian | 20,180 | 15,310 | 204,500 | 124,860 |
| Renal | 38,890 | 12,840 | 208,479 | 101,895 |
| Brain | 12,820 | 18,820 | 189,485 | 141,650 |
| Cervical | 9,710 | 3,700 | 493,243 | 273,505 |
| Bladder | 61,420 | 13,060 | 356,556 | 145,009 |

TABLE 1-continued

PAX2-expressing cancers

| PAX2 Expressing Cancers | Estimated New Cases in US | Estimated Deaths in US | Estimated New Cases Global | Estimated Deaths Global |
|---|---|---|---|---|
| Leukemia | 35,020 | 22,280 | 300,522 | 222,506 |
| Kaposi Sarcoma | Data Not Available | Data Not Available | Data Not Available | Data Not Available |
| TOTAL(approx.) | 627,100 | 154,790 | 3,583,106 | 1,641,139 |

DEFB1

Beta-defensins are cationic peptides with broad-spectrum antimicrobial activity that are products of epithelia and leukocytes. These two exon, single gene products are expressed at epithelial surfaces and secreted at sites including the skin, cornea, tongue, gingiva, salivary glands, esophagus, intestine, kidney, urogenital tract, and the respiratory epithelium. To date, five beta-defensin genes of epithelial origin have been identified and characterized in humans: DEFB1 (Bensch et al., 1995), DEFB2 (Harder et al., 1997), DEFB3 (Harder et al., 2001; Jia et al., 2001), DEFB4, and HE2/EP2. The amino acid sequence of human DEFB1 and the human DEFB1 gene sequences are shown in SEQ ID NOS:63 and 64, respectively.

The primary structure of each beta-defensin gene product is characterized by small size, a six cysteine motif, high cationic charge and exquisite diversity beyond these features. The most characteristic feature of defensin proteins is their six-cysteine motif that forms a network of three disulfide bonds. The three disulfide bonds in the beta-defensin proteins are between C1-C5, C2-C4 and C3-C6. The most common spacing between adjacent cysteine residues is 6, 4, 9, 6, 0. The spacing between the cysteines in the beta-defensin proteins can vary by one or two amino acids except for C5 and C6, located nearest the carboxy terminus. In all known vertebrate beta-defensin genes, these two cysteine residues are adjacent to each other.

A second feature of the beta-defensin proteins is their small size. Each beta-defensin gene encodes a preproprotein that ranges in size from 59 to 80 amino acids with an average size of 65 amino acids. This gene product is then cleaved by an unknown mechanism to create the mature peptide that ranges in size from 36 to 47 amino acids with an average size of 45 amino acids. The exceptions to these ranges are the EP2/HE2 gene products that contain the beta-defensin motif and are expressed in the epididymis.

A third feature of beta-defensin proteins is the high concentration of cationic residues. The number of positively charged residues (arginine, lysine, histidine) in the mature peptide ranges from 6 to 14 with an average of 9.

The final feature of the beta-defensin gene products is their diverse primary structure but apparent conservation of tertiary structure. Beyond the six cysteines, no single amino acid at a given position is conserved in all known members of this protein family. However, there are positions that are conserved that appear to be important for secondary and tertiary structures and function.

Despite the great diversity of the primary amino acid sequence of the beta-defensin proteins, the limited data suggests that the tertiary structure of this protein family is conserved. The structural core is a triple-stranded, antiparallel beta-sheet, as exemplified for the proteins encoded by BNBD-12 and DEFB2. The three beta-strands are connected by a beta-turn, and an alpha-hairpin loop, and the second beta-strand also contains a beta-bulge. When these structures are folded into their proper tertiary structure, the apparently random sequences of cationic and hydrophobic residues are concentrated into two faces of a globular protein. One face is hydrophilic and contains many of the positively charged side chains and the other is hydrophobic. In solution, the HBD-2 protein encoded by the DEFB2 gene exhibited an alpha-helical segment near the N-terminus not previously ascribed to solution structures of alpha-defensins or to the beta-defensin BNBD-12. The amino acids whose side chains are directed toward the surface of the protein are less conserved between beta defensin proteins while the amino acid residues in the three beta-strands of the core beta-sheet are more highly conserved.

Beta-defensin peptides are produced as pre-pro-peptides and then cleaved to release a C-terminal active peptide fragment; however the pathways for the intracellular processing, storage and release of the human beta-defensin peptides in airway epithelia are unknown.

Inhibitors of PAX2 Expression or PAX2 Activity
Functional Nucleic Acids

The inhibitor of the disclosed methods can be a functional nucleic acid that inhibits PAX2 expression. Functional nucleic acids are nucleic acid molecules that have a specific function, such as binding a target molecule or catalyzing a specific reaction. Functional nucleic acid molecules can be divided into the following categories, which are not meant to be limiting. For example, functional nucleic acids include antisense molecules, aptamers, ribozymes, triplex forming molecules, RNAi, and external guide sequences. The functional nucleic acid molecules can act as affectors, inhibitors, modulators, and stimulators of a specific activity possessed by a target molecule, or the functional nucleic acid molecules can possess a de novo activity independent of any other molecules.

Functional nucleic acid molecules can interact with any macromolecule, such as DNA, RNA, polypeptides, or carbohydrate chains. Thus, functional nucleic acids can interact with the mRNA of PAX2 or the genomic DNA of PAX2 or they can interact with the polypeptide PAX2. Often functional nucleic acids are designed to interact with other nucleic acids based on sequence homology between the target molecule and the functional nucleic acid molecule. In other situations, the specific recognition between the functional nucleic acid molecule and the target molecule is not based on sequence homology between the functional nucleic acid molecule and the target molecule, but rather is based on the formation of tertiary structure that allows specific recognition to take place.

Antisense molecules are designed to interact with a target nucleic acid molecule through either canonical or non-canonical base pairing. The interaction of the antisense molecule and the target molecule is designed to promote the destruction of the target molecule through, for example, RNAseH mediated RNA-DNA hybrid degradation. Alternatively the antisense molecule is designed to interrupt a processing function that normally would take place on the target molecule, such as transcription or replication. Antisense molecules can be designed based on the sequence of the target molecule. Numerous methods for optimization of antisense efficiency by finding the most accessible regions of the target molecule exist. Exemplary methods would be in vitro selection experiments and DNA modification studies using DMS and DEPC. It is preferred that antisense molecules bind the target molecule with a dissociation constant (Kd) less than or equal to $10^{-6}$, $10^{-8}$, $10^{-10}$, or $10^{-12}$.

Aptamers are molecules that interact with a target molecule, preferably in a specific way. Typically aptamers are small nucleic acids ranging from 15-50 bases in length that fold into defined secondary and tertiary structures, such as stem-loops or G-quartets. Aptamers can bind small molecules, such as ATP and theophiline, as well as large molecules, such as reverse transcriptase and thrombin. Aptamers can bind very tightly with Kd's from the target molecule of less than $10^{-12}$ M. It is preferred that the aptamers bind the target molecule with a Kd less than $10^{-6}$, $10^{-8}$, $10^{-10}$, or $10^{-12}$. Aptamers can bind the target molecule with a very high degree of specificity. For example, aptamers have been isolated that have greater than a 10,000 fold difference in binding affinities between the target molecule and another molecule that differ at only a single position on the molecule. It is preferred that the aptamer have a Kd with the target molecule at least 10, 100, 1000, 10,000, or 100,000 fold lower than the Kd with a background binding molecule. It is preferred when doing the comparison for a polypeptide for example, that the background molecule be a different polypeptide.

Ribozymes are nucleic acid molecules that are capable of catalyzing a chemical reaction, either intramolecularly or intermolecularly. Ribozymes are thus catalytic nucleic acid. It is preferred that the ribozymes catalyze intermolecular reactions. There are a number of different types of ribozymes that catalyze nuclease or nucleic acid polymerase type reactions which are based on ribozymes found in natural systems, such as hammerhead ribozymes, hairpin ribozymes, and tetrahymena ribozymes. There are also a number of ribozymes that are not found in natural systems, but which have been engineered to catalyze specific reactions de novo. Preferred ribozymes cleave RNA or DNA substrates, and more preferably cleave RNA substrates. Ribozymes typically cleave nucleic acid substrates through recognition and binding of the target substrate with subsequent cleavage. This recognition is often based mostly on canonical or non-canonical base pair interactions. This property makes ribozymes particularly good candidates for target specific cleavage of nucleic acids because recognition of the target substrate is based on the target substrates sequence.

Triplex forming functional nucleic acid molecules are molecules that can interact with either double-stranded or single-stranded nucleic acid. When triplex molecules interact with a target region, a structure called a triplex is formed, in which there are three strands of DNA forming a complex dependant on both Watson-Crick and Hoogsteen base-pairing. Triplex molecules are preferred because they can bind target regions with high affinity and specificity. It is preferred that the triplex forming molecules bind the target molecule with a Kd less than $10^{-6}$, $10^{-10}$, or $10^{-12}$.

External guide sequences (EGSs) are molecules that bind a target nucleic acid molecule forming a complex, and this complex is recognized by RNase P, which cleaves the target molecule. EGSs can be designed to specifically target a RNA molecule of choice. RNAse P aids in processing transfer RNA (tRNA) within a cell. Bacterial RNAse P can be recruited to cleave virtually any RNA sequence by using an EGS that causes the target RNA:EGS complex to mimic the natural tRNA substrate. Similarly, eukaryotic EGS/RNAse P-directed cleavage of RNA can be utilized to cleave desired targets within eukaryotic cells.

Gene expression can also be effectively silenced in a highly specific manner through RNA interference (RNAi). This silencing was originally observed with the addition of double stranded RNA (dsRNA). Once dsRNA enters a cell, it is cleaved by an RNase III-like enzyme, Dicer, into double stranded small interfering RNAs (siRNA) 21-23 nucleotides in length that contains 2 nucleotide overhangs on the 3' ends.

In an ATP dependent step, the siRNAs become integrated into a multi-subunit protein complex, commonly known as the RNAi induced silencing complex (RISC), which guides the siRNAs to the target RNA sequence. At some point the siRNA duplex unwinds, and it appears that the antisense strand remains bound to RISC and directs degradation of the complementary mRNA sequence by a combination of endo and exonucleases. However, the effect of iRNA or siRNA or their use is not limited to any type of mechanism.

Short Interfering RNA (siRNA) is a double-stranded RNA that can induce sequence-specific post-transcriptional gene silencing, thereby decreasing or even inhibiting gene expression. In one example, an siRNA triggers the specific degradation of homologous RNA molecules, such as mRNAs, within the region of sequence identity between both the siRNA and the target RNA. For example, WO 02/44321 discloses siRNAs capable of sequence-specific degradation of target mRNAs when base-paired with 3' overhanging ends, herein incorporated by reference for the method of making these siRNAs. Sequence specific gene silencing can be achieved in mammalian cells using synthetic, short double-stranded RNAs that mimic the siRNAs produced by the enzyme dicer. siRNA can be chemically or in vitro-synthesized or can be the result of short double-stranded hairpin-like RNAs (shRNAs) that are processed into siRNAs inside the cell. Synthetic siRNAs are generally designed using algorithms and a conventional DNA/RNA synthesizer. Suppliers include Ambion (Austin, Tex.), ChemGenes (Ashland, Mass.), Dharmacon (Lafayette, Colo.), Glen Research (Sterling, Va.), MWB Biotech (Esbersberg, Germany), Proligo (Boulder, Colo.), and Qiagen (Vento, The Netherlands). siRNA can also be synthesized in vitro using kits such as Ambion's SILENCER® siRNA Construction Kit. Disclosed herein are any siRNA designed as described above based on the sequences for PAX2.

The production of siRNA from a vector is more commonly done through the transcription of a short hairpin RNAs (shRNAs). Kits for the production of vectors comprising shRNA are available, such as, for example, Imgenex's GENESUPPRESSOR™ Construction Kits and Invitrogen's BLOCK-IT™ inducible RNAi plasmid and lentivirus vectors. Disclosed herein are any shRNA designed as described above based on the sequences for the herein disclosed inflammatory mediators.

In certain embodiments, the functional nucleic acids include siRNAs that inhibit expression of PAX 2 (anti-PAX2 siRNA). Examples of anti-PAX2 siRNAs include, but are not limited to, siRNAs having the sequences of (5' to 3' direction): AUAGACUCGACUUGACUUCUU (SEQ ID NO: 3), AUCUUCAUCACGUUUCCUCUU (SEQ ID NO: 4), GUAUUCAGCAAUCUUGUCCUU (SEQ ID NO: 5), GAUUUGAUGUGCUCUGAUGUU (SEQ ID NO: 6), ACCCGACTATGTTCGCCTGG (SEQ ID NO: 11), AAGCTCTGGATCGAGTCTTTG (SEQ ID NO: 12), ATGTGTCAGGCACACAGACG (SEQ ID NO: 13), GUCGAGUCUAUCUGCAUCCUU (SEQ ID NO: 14), GGAUGCAGAUAGACUCGACUU (SEQ ID NO: 15), and
fragments of at least 10 nucleic acids and conservative variants thereof; and combinations thereof.

In other embodiments, the functional nucleic acids include antisense RNA to PAX2 and oligonucloitdes that interfere with or inhibit the binding of PAX2 to the DEFB1 promoter. The oligonucleotide can be complementary to the sequence of PAX2 that binds to the DEFB1 promoter. Alternatively, the oligonucleotide can interact with the PAX2 in a way that inhibits binding to DEFB1. This interaction can be based on three-dimensional structure rather than primary nucleotide sequence.

PAX proteins are a family of transcription factors conserved during evolution and able to bind specific DNA sequences through a domains called a "paired domain" and a "homeodomain". The paired domain (PD) is a consensus sequence shared by certain PAX proteins (e.g., PAX2 and PAX6). The PD directs DNA binding of amino acids located in the α3-helix forming a DNA-Protein complex. For PAX2, the amino acids in the HD recognize and interact specifically with a CCTTG (SEQ ID NO:1) DNA core sequence. Oligonucleotides include this sequence or its complement are expected to be inhibitors. A critical DNA region in the DEFB1 promoter for PAX2 protein binding has the sequence of AAGTTCACCCTTGACTGTG (SEQ ID NO: 16).

In one embodiment, the oligonucleotide has the sequence of V-CCTTG-W (SEQ ID NO: 17), wherein V and W are nucleotide sequences of 1 to 35 nucleotides. In certain embodiments, V or W or both comprise contiguous nucleotide sequences that normally flank the PAX2 binding site of DEFB1 promoter. Alternatively, the nucleotide sequences of V and/or W may be unrelated to the DEFB1 promoter, and selected randomly to avoid interference with the PAX2 recognition sequence.

Other examples of oligonucleotides that inhibit PAX2 binding to the DEFB1 promoter include, but are not limited to, oligonucleotide having the sequences of (5' to 3' direction):

```
                                        (SEQ ID NO: 18)
CTCCCTTCAGTTCCGTCGAC, (SEQ ID NO: 19)
CTCCCTTCACCTTGGTCGAC, (SEQ ID NO: 20)
ACTGTGGCACCTCCCTTCAGTTCCGTCGACGAGGTTGTGC,
and (SEQ ID NO: 21)
ACTGTGGCACCTCCCTTCACCTTGGTCGACGAGGTTGTGC.
```

Other Inhibitors

Besides functional neucleotides, the inhibitors of PAX2 expression or PAX2 activity can be any small molecule that interferes or inhibits binding of PAX2 to the DEFB1 promoter. The inhibitors of PAX2 expression or PAX2 activity can also be an antagonist of angiotensin II or an antagonist of angiotensin-converting enzyme (ACE). For example, the inhibitor can be enalapril or/and an antagonist of angiotensin II type 1 receptor (AT1R). The inhibitor can be valsartan, olmesartan, or/and telmisartan. The inhibitor can be an antagonist of MEK, an antagonist of ERK1,2 or/and an antagonist of STATS. In some aspects, the disclosed inhibitor of PAX2 expression or activity is not an AT1R receptor antagonist. The term "antagonist" refers to an agent that inhibits the activity of the target.

The antagonists of MEK and/or ERK1,2 include U0126 and PD98059. U0126 is a chemically synthesized organic compound that was initially recognized as a cellular AP-1 antagonist, and found to be a very selective and highly potent inhibitor of Mitogen-Activated Protein Kinase (MAPK) cascade by inhibiting its immediate upstream activators, Mitogen Activated Protein Kinase Kinase 1 and 2 (also known as MEK1 and MEK2, IC50: 70 and 60 nM respectively). U0126 inhibits both active and inactive MEK1,2, unlike PD98059 which only inhibits activation of inactive MEK. Blockade of MEK activation would prevent downstream phosphorylation of a number of factors including p62TCF (Elk-1), an upstream inducer of c-Fos and c-Jun, components of the AP-1 complex. Inhibition of MEK/ERK pathway by U0126 also prevents all effects of oncogenic H-Ras and K-Ras, inhibits part of the effects triggered by growth factors and blocks the production of inflammatory cytokines and matrix metalloproteinases.

PD98059 has been shown to act in vivo as a highly selective inhibitor of MEK1 activation and the MAP kinase cascade. PD98059 binds to the inactive forms of MEK1 and prevents activation by upstream activators such as c-Raf. PD98059 inhibits activation of MEK1 and MEK2 with IC50 values of 4 μM and 50 μM, respectively.

In certain embodiments, the expression of PAX2 is inhibited by administering to the breast cancer tissue or MIN tissue in the subject a blocker of RAS signaling pathway.

In certain other embodiment, the inhibitor of PAX2 expression or PAX2 activity is conjugated to an antibody, a receptor or a ligand to target the tumor tissue.

Enhancer of DEFB-1 Expression or DEFB-1 Activity.

Enhancer of DEFB-1 expression or DEFB-1 activity can be vectors that express DEFB-1 protein. Since PAX2 inhibits DEFB-1 expression, inhibitors of PAX2 expression or PAX2 activity are also enhancers of DEFB-1 expression.

Delivery Systems

There are a number of compositions and methods which can be used to deliver nucleic acids to cells, either in vitro or in vivo. These methods and compositions can largely be broken down into two classes: viral based delivery systems and non-viral based delivery systems. For example, the nucleic acids can be delivered through a number of direct delivery systems such as, electroporation, lipofection, calcium phosphate precipitation, plasmids, viral vectors, viral nucleic acids, phage nucleic acids, phages, cosmids, or via transfer of genetic material in cells or carriers such as cationic liposomes. Such methods are well known in the art and readily adaptable for use with the compositions and methods described herein. In certain cases, the methods will be modified to specifically function with large DNA molecules. Further, these methods can be used to target certain diseases and cell populations by using the targeting characteristics of the carrier.

Nucleic Acid Based Delivery Systems

The inhibitors of PAX2 expression or PAX2 activity and enhancers of DEFB1 expression or DEFB1 activity may be delivered to the target cells using nucleic acid based delivery systems, such as plasmids and viral vectors. As used herein, plasmid or viral vectors are agents that transport the disclosed nucleic acids, such as PAX2 siRNA into the cell without degradation and include a promoter yielding expression of the gene in the cells into which it is delivered. In some embodiments the vectors are derived from either a virus or a retrovirus. Viral vectors are, for example, Adenovirus, Adeno-associated virus, Herpes virus, Vaccinia virus, Polio virus, AIDS virus, neuronal trophic virus, Sindbis and other RNA viruses, including these viruses with the HIV backbone. Also preferred are any viral families which share the properties of these viruses which make them suitable for use as vectors. Retroviruses include Murine Maloney Leukemia virus, MMLV, and retroviruses that express the desirable properties of MMLV as a vector. Retroviral vectors are able to carry a larger genetic payload, i.e., a transgene or marker gene, than other viral vectors, and for this reason are a commonly used vector. However, they are not as useful in non-proliferating cells. Adenovinis vectors are relatively stable and easy to work with, have high titers, and can be delivered in aerosol formulation, and can transfect non-dividing cells. Pox viral vectors are large and have several sites for inserting genes, they are thermostable and can be stored at room temperature. Viral vectors can have higher transaction (ability to introduce genes) abilities than chemical or physical methods to introduce genes into cells. Typically, viral vectors contain, non-structural early genes, structural late genes, an RNA polymerase III transcript, inverted terminal repeats necessary for replication and encapsidation, and promoters to control the transcription and replication of the viral genome. When engineered as vectors, viruses typically have one or more of the early genes removed and a gene or gene/promotor cassette is inserted into the viral genome in place of the removed viral DNA. Constructs of this type can carry up to about 8 kb of foreign genetic material. The necessary functions of the removed early genes are typically supplied by cell lines which have been engineered to express the gene products of the early genes in trans.

The nucleic acids that are delivered to cells typically contain expression controlling systems. For example, the inserted genes in viral and retroviral systems usually contain promoters, and/or enhancers to help control the expression of the desired gene product. A promoter is generally a sequence or sequences of DNA that function when in a relatively fixed location in regard to the transcription start site. A promoter contains core elements required for basic interaction of RNA polymerase and transcription factors, and may contain upstream elements and response elements.

Preferred promoters controlling transcription from vectors in mammalian host cells may be obtained from various sources, for example, the genomes of viruses such as: polyoma, Simian Virus 40 (SV40), adenovirus, retroviruses, hepatitis-B virus and most preferably cytomegalovirus, or from heterologous mammalian promoters, e.g. beta actin promoter.

Enhancer generally refers to a sequence of DNA that functions at no fixed distance from the transcription start site and can be either 5' or 3' to the transcription unit. Furthermore, enhancers can be within an intron as well as within the coding sequence. They are usually between 10 and 300 bp in length, and they function in cis. Enhancers function to increase transcription from nearby promoters. Enhancers also often contain response elements that mediate the regulation of transcription. Promoters can also contain response elements that mediate the regulation of transcription. Enhancers often determine the regulation of expression of a gene. While many enhancer sequences are now known from mammalian genes (globin, elastase, albumin, -fetoprotein and insulin), typically one will use an enhancer from a eukaryotic cell virus for general expression. Preferred examples are the SV40 enhancer on the late side of the replication origin (bp 100-270), the cytomegalovirus early promoter enhancer, the polyoma enhancer on the late side of the replication origin, and adenovirus enhancers.

The promotor and/or enhancer may be specifically activated either by light or specific chemical events which trigger their function. Systems can be regulated by reagents such as tetracycline and dexamethasone. There are also ways to enhance viral vector gene expression by exposure to irradiation, such as gamma irradiation, or alkylating chemotherapy drugs.

In certain embodiments the promoter and/or enhancer region can act as a constitutive promoter and/or enhancer to maximize expression of the region of the transcription unit to be transcribed. In certain constructs the promoter and/or enhancer region be active in all eukaryotic cell types, even if it is only expressed in a particular type of cell at a particular time. A preferred promoter of this type is the CMV promoter (650 bases). Other preferred promoters are SV40 promoters, cytomegalovirus (full length promoter), and retroviral vector LTR.

It has been shown that all specific regulatory elements can be cloned and used to construct expression vectors that are selectively expressed in specific cell types such as melanoma cells. The glial fibrillary acetic protein (GFAP) promoter has been used to selectively express genes in cells of glial origin.

Expression vectors used in eukaryotic host cells (yeast, fungi, insect, plant, animal, human or nucleated cells) may also contain sequences necessary for the termination of transcription which may affect mRNA expression. These regions are transcribed as polyadenylated segments in the untranslated portion of the mRNA encoding tissue factor protein. The 3' untranslated regions also include transcription termination sites. It is preferred that the transcription unit also contain a polyadenylation region. One benefit of this region is that it increases the likelihood that the transcribed unit will be processed and transported like mRNA. The identification and use of polyadenylation signals in expression constructs is well established. It is preferred that homologous polyadenylation signals be used in the transgene constructs. In certain transcription units, the polyadenylation region is derived from the SV40 early polyadenylation signal and consists of about 400 bases. It is also preferred that the transcribed units contain other standard sequences alone or in combination with the above sequences improve expression from, or stability of, the construct.

The viral vectors may include nucleic acid sequence encoding a marker product. This marker product is used to determine if the gene has been delivered to the cell and once delivered is being expressed. Preferred marker genes are the E. Coli lacZ gene, which encodes β-galactosidase, and green fluorescent protein.

In some embodiments the marker may be a selectable marker. Examples of suitable selectable markers for mammalian cells are dihydrofolate reductase (DHFR), thymidine kinase, neomycin, neomycin analog G418, hydromycin, and puromycin. When such selectable markers are successfully transferred into a mammalian host cell, the transformed mammalian host cell can survive if placed under selective pressure. There are two widely used distinct categories of selective regimes. The first category is based on a cell's metabolism and the use of a mutant cell line which lacks the ability to grow independent of a supplemented media. Two examples are: CHO DHFR-cells and mouse LTK-cells. These cells lack the ability to grow without the addition of such nutrients as thymidine or hypoxanthine. Because these cells lack certain genes necessary for a complete nucleotide synthesis pathway, they cannot survive unless the missing nucleotides are provided in a supplemented media. An alternative to supplementing the media is to introduce an intact DHFR or TK gene into cells lacking the respective genes, thus altering their growth requirements. Individual cells which were not transformed with the DHFR or TK gene will not be capable of survival in non-supplemented media.

The second category is dominant selection which refers to a selection scheme used in any cell type and does not require the use of a mutant cell line. These schemes typically use a drug to arrest growth of a host cell. Those cells which have a novel gene would express a protein conveying drug resistance and would survive the selection. Examples of such dominant selection use the drugs neomycin, mycophenolic acid, or hygromycin. The three examples employ bacterial genes under eukaryotic control to convey resistance to the appropriate drug G418 or neomycin (geneticin), xgpt (mycophenolic acid) or hygromycin, respectively. Others include the neomycin analog G418 and puromycin.

Non-Nucleic Acid Based Systems

The inhibitors of PAX2 expression or PAX2 activity and enhancers of DEFB1 expression or DEFB1 activity may also be delivered to the target cells in a variety of ways. For example, the compositions can be delivered through electroporation, or through lipofection, or through calcium phosphate precipitation. The delivery mechanism chosen will depend in part on the type of cell targeted and whether the delivery is occurring for example in vivo or in vitro.

Thus, the compositions can comprise lipids such as liposomes, such as cationic liposomes (e.g., DOTMA, DOPE, DC-cholesterol) or anionic liposomes. Liposomes can further comprise proteins to facilitate targeting a particular cell, if desired. Administration of a composition comprising a compound and a cationic liposome can be administered to the blood afferent to a target organ or inhaled into the respiratory tract to target cells of the respiratory tract. Furthermore, the compound can be administered as a component of a microcapsule that can be targeted to specific cell types, such as macrophages, or where the diffusion of the compound or delivery of the compound from the microcapsule is designed for a specific rate or dosage.

In the methods described above which include the administration and uptake of exogenous DNA into the cells of a subject (i.e., gene transduction or transfection), delivery of the compositions to cells can be via a variety of mechanisms. As one example, delivery can be via a liposome, using commercially available liposome preparations such as LIPOFECTIN, LIPOFECTAMINE (GIBCO-BRL, Inc., Gaithersburg, Md.), SUPERFECT (Qiagen, Inc. Hilden, Germany) and TRANSFECTAM (Promega Biotec, Inc., Madison, Wis.), as well as other liposomes developed according to procedures standard in the art. In addition, the disclosed nucleic acid or vector can be delivered in vivo by electroporation, the technology for which is available from Genetronics, Inc. (San Diego, Calif.) as well as by means of a SONOPORATION machine (ImaRx Pharmaceutical Corp., Tucson, Ariz.).

The materials may be in solution, suspension (for example, incorporated into microparticles, liposomes, or cells). These may be targeted to a particular cell type via antibodies, receptors, or receptor ligands. Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration.

Nucleic acids that are delivered to cells which are to be integrated into the host cell genome, typically contain integration sequences. These sequences are often viral related sequences, particularly when viral based systems are used. These viral integration systems can also be incorporated into nucleic acids which are to be delivered using a non-nucleic acid based system of deliver, such as a liposome, so that the nucleic acid contained in the delivery system can be come integrated into the host genome.

Other general techniques for integration into the host genome include, for example, systems designed to promote homologous recombination with the host genome. These systems typically rely on sequence flanking the nucleic acid to be expressed that has enough homology with a target sequence within the host cell genome that recombination between the vector nucleic acid and the target nucleic acid takes place, causing the delivered nucleic acid to be integrated into the host genome. These systems and the methods necessary to promote homologous recombination are known to those of skill in the art.

The inhibitors of PAX2 expression or PAX2 activity and enhancers of DEFB1 expression or DEFB1 activity can be delivered to the target cells in a variety of ways. can be administered in a pharmaceutically acceptable carrier and can be delivered to the subjects cells in vivo and/or ex vivo by a variety of mechanisms well known in the art (e.g., uptake of naked DNA, liposome fusion, intramuscular injection of DNA via a gene gun, endocytosis and the like).

If ex vivo methods are employed, cells or tissues can be removed and maintained outside the body according to standard protocols well known in the art. The compositions can be introduced into the cells via any gene transfer mechanism, such as, for example, calcium phosphate mediated gene delivery, electroporation, microinjection or proteoliposomes. The transduced cells can then be infused (e.g., in a pharmaceutically acceptable carrier) or homotopically transplanted back into the subject per standard methods for the cell or tissue type. Standard methods are known for transplantation or infusion of various cells into a subject.

Composition and Kits

Another aspect of the present invention relates to compositions and kits for treating or preventing cancer. The composition includes an inhibitor of PAX2 expression or PAX2 activity, and/or an enhancer of DEFB-1 expression or DEFB-1 activity, and a pharmaceutically acceptable carrier.

By "pharmaceutically acceptable" is meant a material that is not biologically or otherwise undesirable, i.e., the material may be administered to a subject, along with the nucleic acid or vector, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

Suitable carriers and their formulations are described in Remington: The Science and Practice of Pharmacy (19th ed.) ed. A. R. Gennaro, Mack Publishing Company, Easton, Pa. 1995. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of composition being administered.

Pharmaceutical carriers are known to those skilled in the art. These most typically would be standard carriers for administration of drugs to humans, including solutions such as sterile water, saline, and buffered solutions at physiological pH. The compositions can be administered intramuscularly or subcutaneously. Other compounds will be administered according to standard procedures used by those skilled in the art.

Pharmaceutical compositions may include carriers, thickeners, diluents, buffers, preservatives, surface active agents and the like in addition to the molecule of choice. Pharmaceutical compositions may also include one or more active ingredients such as antimicrobial agents, anti-inflammatory agents, anesthetics, and the like.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids or binders may be desirable.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

The materials may be in solution, suspension (for example, incorporated into microparticles, liposomes, or cells). These may be targeted to a particular cell type via antibodies, receptors, or receptor ligands. Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes.

The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration.

The materials described above as well as other materials can be packaged together in any suitable combination as a kit useful for performing, or aiding in the performance of, the disclosed method. It is useful if the kit components in a given kit are designed and adapted for use together in the disclosed method. For example disclosed are kits for detecting, treating, or preventing prostate cancer, PIN, breast cancer, and MIN. The kit comprising an inhibitor of PAX2 expression or PAX2 activity, and/or an enhancer of DEFB1expression or DEFB1 activity. In one embodiment, the kit contains a peptide or an antibody that specifically bind PAX2 or DEFB1.

A composition disclosed herein may be administered in a number of ways depending on whether local or systemic treatment is desired, and on the area to be treated. For example, the compositions may be administered orally, parenterally (e.g., intravenous, subcutaneous, intraperitoneal, or intramuscular injection), by inhalation, extracorporeally, topically (including transdermally, ophthalmically, vaginally, rectally, intranasally) or the like.

As used herein, "topical intranasal administration" means delivery of the compositions into the nose and nasal passages through one or both of the nares and can comprise delivery by a spraying mechanism or droplet mechanism, or through aerosolization of the nucleic acid or vector. Administration of the compositions by inhalant can be through the nose or mouth via delivery by a spraying or droplet mechanism. Delivery can also be directly to any area of the respiratory system (e.g., lungs) via intubation.

Parenteral administration of the composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained.

The exact amount of the compositions required will vary from subject to subject, depending on the species, age, weight and general condition of the subject, the severity of the allergic disorder being treated, the particular nucleic acid or vector used, its mode of administration and the like. An appropriate amount can be determined by one of ordinary skill in the art using only routine experimentation given the teachings herein. Thus, effective dosages and schedules for administering the compositions may be determined empirically, and making such determinations is within the skill in the art. The dosage ranges for the administration of the compositions are those large enough to produce the desired effect in which the symptoms disorders are affected. The dosage should not be so large as to cause adverse side effects, such as unwanted cross-reactions, anaphylactic reactions, and the like. Generally, the dosage will vary with the age, condition, sex and extent of the disease in the patient, route of administration, or whether other drugs are included in the regimen, and can be determined by one of skill in the art. The dosage can be adjusted by the individual physician in the event of any counter indications. Dosage can vary, and can be administered in one or more dose administrations daily, for one or several days.

Guidance can be found in the literature for appropriate dosages for given classes of pharmaceutical products.

For example, a typical daily dosage of the disclosed composition used alone might range from about 1 μg/kg to up to 100 mg/kg of body weight or more per day, depending on the factors mentioned above. In certain embodiments, the treatment method is tailored based on the PAX2-to-DEFB1 expression ratio (P/D ratio) and estrogen-receptor (ER)/progesterone-receptor (PR) status of the diseased tissue. Table 2 shows the treatment options based on the P/D ratio and ER/PR status. There is a positive correlation between PAX2 status and ER status in normal breast tissue, MIN and low grade breast carcinoma. PAX2 also regulates ERBB2 expression and subsequently Her2/neu expression via the oestogen receptor. Conversely, there is an inverse relationship between PAX2 expression and high grade (or invasive) breast carcinoma. Therefore monitoring PAX2 expression levels can be used to predict drug response or resistance, as well as identify patients who may be candidates for DEFB1 or anti-PAX2 therapy. The term "anti-PAX2 therapy" refers to methods for inhibiting PAX2 expression or PAX2 activity. The term "DEFB1 therapy" refers to methods for increasing DEFB1 expression. The term "DEFB1 therapy" does not include methods for inhibiting PAX2 expression or PAX2 activity, although such methods also result in increase of DEFB1 expression.

As shown in Table 2, anti-PAX2 therapy and/or DFB1 therapy may be used in conjunction with one or more other treatments for breast cancer, such as anti-hormone treatment (e.g., Tamoxifen), anti-ERBB2 treatment (e.g., Herceptin), anti-Her2 treatment (e.g., Trastuzumab), and anti-AIB-1/SRC-3 treatment.

determined by determining the levels of PAX2 and DEFB1 in a cell or cells obtained directly from the breast tissue.

The "PAX2-to-DEFB1 expression ratio" can be determined directly at protein level or indirectly at the RNA level. The protein levels may be measured with protein arrays, immunoassays and enzyme assays. The RNA levels may be measured, for example, with DNA arrays, RT-PCR and Northern Blotting. In certain embodiments, the PAX2-to-DEFB1 expression ratio is determined by determining the expression level of PAX2 gene relative to the expression level of a control gene, determining the expression level of DEFB1 gene relative to the expression level of the same control gene, and calculating the PAX2-to-DEFB1 expression ratio based on the expression levels of PAX2 and DEFB1. In one embodiment, the control gene is the glyceraldehyde 3-phosphate dehydrogenase (GAPDH) gene.

Immunoassays

Immunoassays, in their most simple and direct sense, are binding assays involving binding between antibodies and antigen. Many types and formats of immunoassays are known and all are suitable for detecting the disclosed biomarkers. Examples of immunoassays are enzyme linked immunosorbent assays (ELISAs), radioimmunoassays (RIA), radioimmune precipitation assays (RIPA), immunobead capture assays, Western blotting, dot blotting, gel-shift assays, Flow cytometry, protein arrays, multiplexed bead arrays, magnetic capture, in vivo imaging, fluorescence resonance energy transfer (FRET), and fluorescence recovery/localization after photobleaching (FRAP/FLAP).

TABLE 2

Using PAX2-to-DEFB1 Ratio to Treat Breast Conditions

| Tissue Type | Change in PAX2/DEFB1 Ratio* | ER/PR Status | DEFB1 Therapy | Anti-PAX2 Therapy | Adjuvant Therapy |
|---|---|---|---|---|---|
| MIN | ↑ | ER+/PR+ | No | Yes | No |
| Low Grade Cancer | | ER+/PR+ | Yes | Yes | Anti-ERBB2 (eg. Herceptin) Anti-Her2 (eg. Trastuzumab) Anti-AIB-1/SRC-3 |
| Low Grade Cancer | ↑ | ER+/PR− | Yes | Yes | Anti-ERBB2 (eg. Herceptin) Anti-Her2 (eg. Trastuzumab) Anti-AIB-1/SRC-3 |
| High Grade Cancer | ↑ | ER+/PR+ | Yes | No | Anti-hormone (eg. Tamoxifen) Anti-ERBB2 (eg. Herceptin) Anti-Her2 (eg. Trastuzumab) Anti-AIB-1/SRC-3 |
| High Grade Cancer | ↓ | ER+/PR− | Yes | No | Anti-hormone (eg. Tamoxifen) Anti-ERBB2 (eg. Herceptin) Anti-Her2 (eg. Trastuzumab) Anti-AIB-1/SRC-3 |
| High Grade Cancer | ↓ | ER−/PR+ | Yes | No | Anti-ERBB2 (eg. Herceptin) Anti-Her2 (eg. Trastuzumab) |
| High Grade Cancer | ↓ | ER−/PR− | Yes | No | Anti-ERBB2 (eg. Herceptin) Anti-Her2 (eg. Trastuzumab) |

*Compared to the PAX2/DEFB1 ratio in normal breast epithelium

PAX2-To-DEFB1 Expression Ratio

As used hereinafter, the term "PAX2-to-DEFB1 expression ratio" refers to the ratio between the amount of functional PAX2 protein or its variant and the amount of functional DEFB1 protein or its variant in a given cell or tissue. Levels of PAX2 and DEFB1 expression in a cell or tissue can be measured any method known in the art. In certain embodiments, the levels of PAX2 and DEFB1 expression in breast tissue are In general, immunoassays involve contacting a sample suspected of containing a molecule of interest (such as the disclosed biomarkers) with an antibody to the molecule of interest or contacting an antibody to a molecule of interest (such as antibodies to the disclosed biomarkers) with a molecule that can be bound by the antibody, as the case may be, under conditions effective to allow the formation of immunocomplexes. In many forms of immunoassay, the sample-antibody composition, such as a tissue section, ELISA plate, dot blot or Western blot, can then be washed to remove any non-specifically bound antibody species, allowing only those antibodies specifically bound within the primary immune complexes to be detected.

Radioimmune Precipitation Assay (RIPA) is a sensitive assay using radiolabeled antigens to detect specific antibodies in serum. The antigens are allowed to react with the serum and then precipitated using a special reagent such as, for example, protein A sepharose beads. The bound radiolabeled immunoprecipitate is then commonly analyzed by gel electrophoresis. Radioimmunoprecipitation assay (RIPA) is often used as a confirmatory test for diagnosing the presence of HIV antibodies. RIPA is also referred to in the art as Farr Assay, Precipitin Assay, Radioimmune Precipitin Assay; Radioimmunoprecipitation Analysis; Radioimmunoprecipitation Analysis, and Radioimmunoprecipitation Analysis.

Also contemplated are immunoassays wherein the protein or antibody specific for the protein is bound to a solid support (e.g., tube, well, bead, or cell) to capture the antibody or protein of interest, respectively, from a sample, combined with a method of detecting the protein or antibody specific for the protein on the support. Examples of such immunoassays include Radioimmunoassay (RIA), Enzyme-Linked Immunosorbent Assay (ELISA), Flow cytometry, protein array, multiplexed bead assay, and magnetic capture.

Protein arrays are solid-phase ligand binding assay systems using immobilized proteins on surfaces which include glass, membranes, microtiter wells, mass spectrometer plates, and beads or other particles. The assays are highly parallel (multiplexed) and often miniaturized (microarrays, protein chips). Their advantages include being rapid and automatable, capable of high sensitivity, economical on reagents, and giving an abundance of data for a single experiment. Bioinformatics support is important; the data handling demands sophisticated software and data comparison analysis. However, the software can be adapted from that used for DNA arrays, as can much of the hardware and detection systems.

Capture arrays form the basis of diagnostic chips and arrays for expression profiling. They employ high affinity capture reagents, such as conventional antibodies, single domains, engineered scaffolds, peptides or nucleic acid aptamers, to bind and detect specific target ligands in high throughput manner. Antibody arrays are available commercially. In addition to the conventional antibodies, Fab and scFv fragments, single V-domains from camelids or engineered human equivalents (Domantis, Waltham, Mass.) may also be useful in arrays.

Nonprotein capture molecules, notably the single-stranded nucleic acid aptamers which bind protein ligands with high specificity and affinity, are also used in arrays (SomaLogic, Boulder, Colo.). Aptamers are selected from libraries of oligonucleotides by the Selex™ procedure and their interaction with protein can be enhanced by covalent attachment, through incorporation of brominated deoxyuridine and UV-activated crosslinking (photoaptamers). Photocrosslinking to ligand reduces the crossreactivity of aptamers due to the specific steric requirements. Aptamers have the advantages of ease of production by automated oligonucleotide synthesis and the stability and robustness of DNA; on photoaptamer arrays, universal fluorescent protein stains can be used to detect binding.

An alternative to an array of capture molecules is one made through 'molecular imprinting' technology, in which peptides (e.g., from the C-terminal regions of proteins) are used as templates to generate structurally complementary, sequence-specific cavities in a polymerizable matrix; the cavities can then specifically capture (denatured) proteins that have the appropriate primary amino acid sequence (ProteinPrint™, Aspira Biosystems, Burlingame, Calif.).

Another methodology which can be used diagnostically and in expression profiling is the ProteinChip® array (Ciphergen, Fremont, Calif.), in which solid phase chromatographic surfaces bind proteins with similar characteristics of charge or hydrophobicity from mixtures such as plasma or tumor extracts, and SELDI-TOF mass spectrometry is used to detection the retained proteins.

Other useful methodology includes large-scale functional chips constructed by immobilizing large numbers of purified proteins on a chip, and multiplexed bead assays.

Antibodies

The term "antibodies" is used herein in a broad sense and includes both polyclonal and monoclonal antibodies. In addition to intact immunoglobulin molecules, also included in the term "antibodies" are fragments or polymers of those immunoglobulin molecules, and human or humanized versions of immunoglobulin molecules or fragments thereof, as long as they are chosen for their ability to interact with, for example, PAX2 or DEFB1, such that PAX2 is inhibited from interacting with DEFB1. Antibodies that bind the disclosed regions of PAX2 or DEFB1 involved in the interaction between PAX2 and DEFB1 are also disclosed. The antibodies can be tested for their desired activity using the in vitro assays described herein, or by analogous methods, after which their in vivo therapeutic and/or prophylactic activities are tested according to known clinical testing methods.

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, as long as they exhibit the desired antagonistic activity (See, U.S. Pat. No. 4,816,567 and Morrison et al., Proc. Natl. Acad. Sci. USA, 81:6851-6855 (1984)).

As used herein, the term "antibody" or "antibodies" can also refer to a human antibody and/or a humanized antibody. Many non-human antibodies (e.g., those derived from mice, rats, or rabbits) are naturally antigenic in humans, and thus can give rise to undesirable immune responses when administered to humans. Therefore, the use of human or humanized antibodies in the methods serves to lessen the chance that an antibody administered to a human will evoke an undesirable immune response. Methods for humanizing non-human antibodies are well known in the art.

DNA Arrays

A DNA or oligonucleotide microarray consists of an arrayed series of a plurality of microscopic spots of oligonucleotides, called features, each containing a small amount (typically in the range of picomoles) of a specific oligonucleotide sequence. The specific oligonucleotide sequence can be a short section of a gene or other oligonucleotide element that are used as probes to hybridize a cDNA or cRNA sample under high-stringency conditions. Probe-target hybridization is usually detected and quantified by fluorescence-based detection of fluorophore-labeled targets to determine relative abundance of nucleic acid sequences in the target.

The probes are typically attached to a solid surface by a covalent bond to a chemical matrix (via epoxy-silane, amino-silane, lysine, polyacrylamide or others). The solid surface can be glass or a silicon chip or microscopic beads. Oligonucleotide arrays are different from other types of microarray only in that they either measure nucleotides or use oligonucleotide as part of its detection system.

To detect gene expression in target tissue or cells using an oligonucleotide array, nucleic acid of interest is purified from the target tissue or cells. The nucleotide can be all RNA for expression profiling, DNA for comparative hybridization, or DNA/RNA bound to a particular protein which is immunoprecipitated (ChIP-on-chip) for epigenetic or regulation studies.

In one embodiment, total RNA is isolated (total as it is nuclear and cytoplasmic) by guanidinium thiocyanate-phenol-chloroform extraction (e.g. Trizol). The purified RNA may be analyzed for quality (e.g., by capillary electrophoresis) and quantity (e.g., by using a nanodrop spectrometer. The total RNA is RNA is reverse transcribed into DNA with either polyT primers or random primers. The DNA products may be optionally amplified by PCR. A label is added to the amplification product either in the RT step or in an additional step after amplification if present. The label can be a fluorescent label or radioactive labels. The labeled DNA products are then hybridized to the microarray. The microarray is then washed and scanned. The expression level of the gene of interest is determined based on the hybridization result using method well known in the art.

Pharmacogenomics

In another embodiment, the PAX2 and/or DEFB1 expression profiles are used for determine pharmacogenomics of breast cancer. Pharmacogenomics refers to the relationship between an individual's genotype and that individual's response to a foreign compound or drug. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer an anti-cancer drug, as well as tailoring the dosage and/or therapeutic regimen of treatment with the anti-cancer drug.

Pharmacogenomics deals with clinically significant hereditary variations in the response to drugs due to altered drug disposition and abnormal action in affected persons. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally-occurring polymorphisms. For example, glucose-6-phosphate dehydrogenase deficiency (G6PD) is a common inherited enzymopathy in which the main clinical complication is hemolysis after ingestion of oxidant drugs (anti-malarials, sulfonamides, analgesics, nitrofurans) and consumption of fava beans.

One pharmacogenomics approach to identifying genes that predict drug response, known as "a genome-wide association," relies primarily on a high-resolution map of the human genome consisting of already known gene-related sites (e.g., a "bi-allelic" gene marker map which consists of 60,000-100,000 polymorphic or variable sites on the human genome, each of which has two variants). Such a high-resolution genetic map can be compared to a map of the genome of each of a statistically substantial number of subjects taking part in a Phase II/III drug trial to identify genes associated with a particular observed drug response or side effect. Alternatively, such a high resolution map can be generated from a combination of some ten-million known single nucleotide polymorphisms (SNPs) in the human genome. As used herein, an "SNP" is a common alteration that occurs in a single nucleotide base in a stretch of DNA. For example, an SNP may occur once per every 1,000 bases of DNA. An SNP may be involved in a disease process. However, the vast majority of SNPs may not be disease associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals. Thus, mapping of the PAX2 and/or DEFB1 to SNP maps of breast patients may allow easier identification of these genes according to the genetic methods described herein.

Alternatively, a method termed the "candidate gene approach," can be utilized to identify genes that predict drug response. According to this method, if a gene that encodes a drug target is known, all common variants of that gene can be fairly easily identified in the population and it can be determined if having one version of the gene versus another is associated with a particular drug response.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYPZC19) has provided an explanation as to why some subjects do not obtain the expected drug effects or show exaggerated drug response and serious toxicity after taking the standard and safe dose of a drug. These polymorphisms are expressed in two phenotypes in the population, the extensive metabolizer and poor metabolizer. The prevalence of poor metabolizer phenotypes is different among different populations. For example, the gene coding for CYP2D6 is highly polymorphic and several mutations have been identified in poor metabolizers, which all lead to the absence of functional CYP2D6. Poor metabolizers of CYP2D6 and CYP2C19 quite frequently experience exaggerated drug response and side effects when they receive standard doses. If a metabolite is the active therapeutic moiety, poor metabolizers show no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification.

Alternatively, a method termed the "gene expression profiling" can be utilized to identify genes that predict drug response. For example, the gene expression of an animal dosed with a drug can give an indication whether gene pathways related to toxicity have been turned on.

Information generated from more than one of the above pharmacogenomics approaches can be used to determine appropriate dosage and treatment regimens for prophylactic or therapeutic treatment an individual. This knowledge, when applied to dosing or drug selection, can avoid adverse reactions or therapeutic failure and thus enhance therapeutic or prophylactic efficiency when treating a subject with a breast condition.

In one embodiment, the PAX2 and/or DEFB1 expression profiles, as well as the ER/PR status, in a subject are used to determine the appropriate treatment regimens for an individual with a breast condition.

In another embodiment, the PAX2 expression level (typically determine in reference to a control gene as actin gene or GAPDH gene) is used in patients with triple negative breast cancer (i.e., oestrogen receptor (ER) negative, progesterone receptor (PR) negative, human epidermal growth factor receptor 2 (HER2) negative) to measure of the effectiveness of cancer therapy, to determine treatment course, or to monitor cancer recurrence.

The present invention is further illustrated by the following examples which should not be construed as limiting. The contents of all references, patents and published patent applications cited throughout this application, as well as the Figures and Tables are incorporated herein by reference.

EXAMPLE 1

Human Beta Defensin-1 is Cytotoxic to Late-Stage Prostate Cancer and Plays a Role in Prostate Cancer Tumor Immunity In this example, DEFB1 was cloned into an inducible expression system to examine what effect it had on normal prostate epithelial cells, as well as androgen receptor positive (AR+) and androgen receptor negative (AR−) prostate cancer cell lines. Induction of DEFB1 expression resulted in a decrease in cellular growth in AR− cells DU145 and PC3, but had no effect on the growth of the AR+ prostate cancer cells LNCaP. DEFB1 also caused rapid induction of caspase-mediated apoptosis. Data presented here are the first to provide evidence of its role in innate tumor immunity and indicate that its loss contributes to tumor progression in prostate cancer.

Materials and Methods

Cell Lines:

The cell lines DU145 were cultured in DMEM medium, PC3 were grown in F12 medium, and LNCaP were grown in RPMI medium (Life Technologies, Inc., Grand Island, N.Y.). Growth media for all three lines was supplemented with 10% (v/v) fetal bovine serum (Life Technologies). The hPrEC cells were cultured in prostate epithelium basal media (Cambrex Bio Science, Inc., Walkersville, Md.). All cell lines were maintained at 37° C. and 5% CO2.

Tissue Samples and Laser Capture Microdissection:

Prostate tissues obtained from consented patients that underwent radical prostatectomy were acquired through the Hollings Cancer Center tumor bank in accordance with an Institutional Review Board-approved protocol. This included guidelines for the processing, sectioning, histological characterization, RNA purification and PCR amplification of samples. Following pathologic examination of frozen tissue sections, laser capture microdissection (LCM) was performed to ensure that the tissue samples assayed consisted of pure populations of benign prostate cells. For each tissue section analyzed, LCM was performed at three different regions containing benign tissue and the cells collected were then pooled.

Prostate tissues were obtained from patients who provided informed consent prior to undergoing radical prostatectomy. Samples were acquired through the Hollings Cancer Center tumor bank in accordance with an Institutional Review Board-approved protocol. This included guidelines for the processing, sectioning, histological characterization, RNA purification and PCR amplification of samples. Prostate specimens received from the surgeons and pathologists were immediately frozen in OCT compound. Each OCT block was cut to produce serial sections which were stained and examined. Areas containing benign cells, prostatic intraepithelial neoplasia (PIN), and cancer were identified and used to guide our selection of regions from unstained slides using the Arcturus PixCell II System (Sunnyvale, Calif.). Caps containing captured material were exposed to 20 µl of lysate from the Arcturus Pico Pure RNA Isolation Kit and processed immediately. RNA quantity and quality was evaluated using sets of primers that produce 5' amplicons. The sets include those for the ribosomal protein L32 (the 3' amplicon and the 5' amplicon are 298 bases apart), for the glucose phosphate isomerase (391 bases apart), and for the glucose phosphate isomerase (842 bases apart). Ratios of 0.95 to 0.80 were routinely obtained for these primer sets using samples from a variety of prepared tissues. Additional tumor and normal samples were grossly dissected by pathologists, snap frozen in liquid nitrogen and evaluated for hBD-1 and cMYC expression.

Cloning of DEFB1 Gene:

DEFB1 cDNA was generated from RNA by reverse transcription-PCR. The PCR primers were designed to contain ClaI and KpnI restriction sites. DEFB1 PCR products were restriction digested with ClaI and KpnI and ligated into a TA cloning vector. The TA/DEFB1 vector was then transfected into *E. coli* by heat shock and individual clones were selected and expanded. Plasmids were isolated by Cell Culture DNA Midiprep (Qiagen, Valencia, Calif.) and sequence integrity verified by automated sequencing. The DEFB1 gene fragment was then ligated into the pTRE2 digested with ClaI and KpnI, which served as an intermediate vector for orientation purposes. Then the pTRE2/DEFB1 construct was digested with ApaI and KpnI to excise the DEFB1 insert, which was ligated into pIND vector of the Ecdysone Inducible Expression System (Invitrogen, Carlsbad, Calif.) also double digested with ApaI and KpnI. The construct was again transfected into *E. coli* and individual clones were selected and expanded. Plasmids were isolated and sequence integrity of pIND/DEFB1 was again verified by automated sequencing.

Transfection:

Cells ($1 \times 10^6$) were seeded onto 100-mm Petri dishes and grown overnight. Then the cells were co-transfected using Lipofectamine 2000 (Invitrogen, Carlsbad, Calif.) with 1 µg of pVgRXR plasmid, which expresses the heterodimeric ecdysone receptor, and 1 µg of the pIND/DEFB1 vector construct or empty pIND control vector in Opti-MEM media (Life Technologies, Inc., Grand Island, N.Y.).

RNA Isolation and Quantitative RT-PCR:

In order to verify DEFB1 protein expression in the cells transfected with DEFB1 construct, RNA was collected after a 24 hour induction period with Ponasterone A (Pon A). Briefly, total RNA was isolated using the SV Total RNA Isolation System (Promega, Madison, Wis.) from approximately $1 \times 10^6$ cells harvested by trypsinizing. Here, cells were lysed and total RNA was isolated by centrifugation through spin columns. For cells collected by LCM, total RNA was isolated using the PicoPure RNA Isolation Kit (Arcturus Biosciences, Mt. View, Calif.) following the manufacturer's protocol. Total RNA (0.5 µg per reaction) from both sources was reverse transcribed into cDNA utilizing random primers (Promega). AMV Reverse Transcriptase II enzyme (500 units per reaction; Promega) was used for first strand synthesis and Tfl DNA Polymerase for second strand synthesis (500 units per reaction; Promega) as per the manufacturer's protocol. In each case, 50 pg of cDNA was used per ensuing PCR reaction. Two-step QRT-PCR was performed on cDNA generated using the MultiScribe Reverse Transcripatase from the TaqMan Reverse Transcription System and the SYBR® Green PCR Master Mix (Applied Biosystems).

The primer pair for DEFB1 was generated from the published DEFB1 sequence (GenBank Accession No. U50930). The primer sequences are:

```
Sense (5'-3')
β-actin
                                        SEQ ID NO: 51
5'-CCTGGCACCCAGCACAAT-3'

SEQ ID NO: 53
DEFB1
5'-GTTGCCTGCCAGTCGCCATGAGAACTTCCTAC-3'

Antisense (5'-3')
β-actin
                                        SEQ ID NO: 52
5'-GCCGATCCACACGGAGTACT-3'

SEQ ID NO: 54
DEFB1
5'-TGGCCTTCCCTCTGTAACAGGTGCCTTGAATT-3'
```

Forty cycles of PCR were performed under standard conditions using an annealing temperature of 56° C. In addition, β-actin (Table 2) was amplified as a housekeeping gene to normalize the initial content of total cDNA. DEFB1 expression was calculated as the relative expression ratio between DEFB1 and β-actin and was compared in cells lines induced and uninduced for DEFB1 expression, as well as LCM benign prostatic tissue. As a negative control, QRT-PCR reactions without cDNA template were also performed. All reactions were run three times in triplicate.

MTT Cell Viability Assay:

To examine the effects of DEFB1 on cell growth, metabolic 3-[4,5-dimethylthiazol-2yl]-2,5 diphenyl tetrazolium bromide (MTT) assays were performed. PC3, DU145 and LNCaP cells co-transfected with pVgRXR plasmid and pIND/DEFB1 construct or empty pIND vector were seeded onto a 96-well plate at $1-5\times10^3$ cells per well. Twenty-four hours after seeding, fresh growth medium was added containing 10 μM Ponasterone A daily to induce DEFB1 expression for 24-, 48- and 72 hours after which the MTT assay was performed according to the manufacturer's instructions (Promega). Reactions were performed three times in triplicate.

Flow Cytometry:

PC3 and DU145 cells co-transfected with the DEFB1 expression system were grown in 60-mm dishes and induced for 12, 24, and 48 hours with 10 μM Ponasterone A. Following each incubation period, the medium was collected from the plates (to retain any detached cells) and combined with PBS used to wash the plates. The remaining attached cells were harvested by trypsinization and combined with the detached cells and PBS. The cells were then pelleted at 4° C. (500×g) for 5 min, washed twice in PBS, and resuspended in 100 μl of 1× Annexin binding buffer (0.1 M Hepes/NaOH at pH 7.4, 1.4 M NaCl, 25 mM $CaCl_2$) containing 5 μl of Annexin V-FITC and 5 μl of PI. The cells were incubated at RT for 15 min in the dark, then diluted with 400 μl of 1× Annexin binding buffer and analyzed by FACscan (Becton Dickinson, San Jose, Calif.). All reactions were performed three times.

Microscopic Analysis:

Cell morphology was analyzed by phase contrast microscopy. DU145, PC3 and LNCaP cells containing no vector, empty plasmid or DEFB1 plasmid were seeded onto 6 well culture plates (BD Falcon, USA). The following day plasmid-containing cells were induced for a period of 48 h with media containing 10 μM Ponasterone A, while control cells received fresh media. The cells were then viewed under an inverted Zeiss IM 35 microscope (Carl Zeiss, Germany). Phase contrast pictures of a field of cells were obtained using the SPOT Insight Mosaic 4.2 camera (Diagnostic Instruments, USA). Cells were examined by phase contrast microscopy under 32× magnification and digital images were stored as uncompressed TIFF files and exported into Photoshop CS software (Adobe Systems, San Jose, Calif.) for image processing and hard copy presentation.

Caspase Detection:

Detection of caspase activity in the prostate cancer cell lines was performed using APO LOGIX™ Carboxyfluorescin Caspase detection kit (Cell Technology, Mountain View, Calif.). Active caspases were detected through the use of a FAM-VAD-FMK inhibitor that irreversibly binds to active caspases. Briefly, DU145 and PC3 cells ($1.5-3\times10^5$) containing the DEFB1 expression system were plated in 35 mm glass bottom microwell dishes (Matek, Ashland, Mass.) and treated for 24 hours with media only or with media containing PonA as previously described. Next, 10 μl of a 30× working dilution of carboxyfluorescein labeled peptide fluoromethyl ketone (FAM-VAD-FMK) was added to 300 μl of media and added to each 35 mm dish. Cells were then incubated for 1 hour at 37° C. under 5% CO2. Then, the medium was aspirated and the cells were washed twice with 2 ml of a 1× Working dilution Wash Buffer. Cells were viewed under differential interference contrast (DIC) or under laser excitation at 488 nm. The fluorescent signal was analyzed using a confocal microscope (Zeiss LSM 5 Pascal) and a 63× DIC oil lens with a Vario 2 RGB Laser Scanning Module.

Statistical Analysis:

Statistical differences were evaluated using the Student's t-test for unpaired values. P values were determined by a two-sided calculation, and a P value of less than 0.05 was considered statistically significant.

Results

Figure 1B:
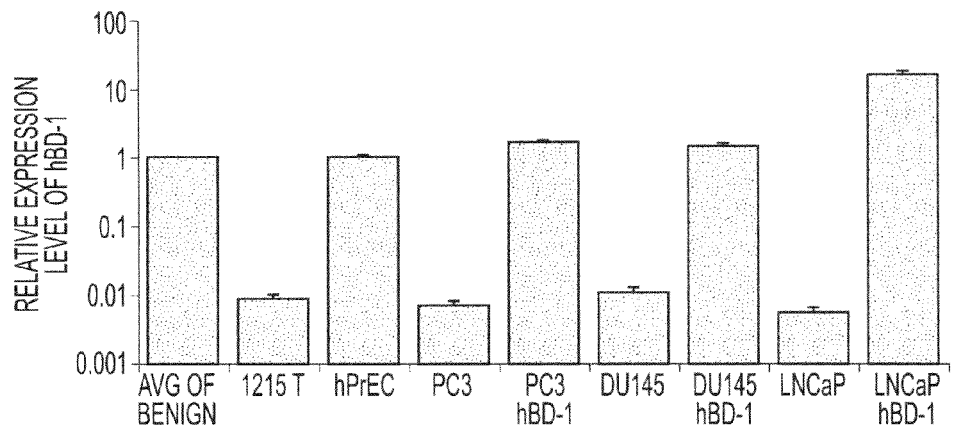

DEFB1 Expression in Prostate Tissue and Cell Lines: DEFB1 expression levels were measured by QRT-PCR in benign and malignant prostatic tissue, hPrEC prostate epithelial cells and DU145, PC3 and LNCaP prostate cancer cells. DEFB1 expression was detected in all of the benign clinical samples. The average amount of DEFB1 relative expression was 0.0073. In addition, DEFB1 relative expression in hPrEC cells was 0.0089. There was no statistical difference in DEFB1 expression detected in the benign prostatic tissue samples and hPrEC (FIG. 1A). Analysis of the relative DEFB1 expression levels in the prostate cancer cell lines revealed significantly lower levels in DU145, PC3 and LNCaP. As a further point of reference, relative DEFB1 expression was measured in the adjacent malignant section of prostatic tissue from patient #1215. There were no significant differences in the level of DEFB1 expression observed in the three prostate cancer lines compared to malignant prostatic tissue from patient #1215 (FIG. 1B). In addition, expression levels in all four samples were close to the no template negative controls which confirmed little to no endogenous DEFB1 expression (data not shown). QRT-PCR was also performed on the prostate cancer cell lines transfected with the DEFB1 expression system. Following a 24 hour induction period, relative expression levels were 0.01360 in DU145, 0.01503 in PC3 and 0.138 in LNCaP. Amplification products were verified by gel electrophoresis.

Figure 1C:
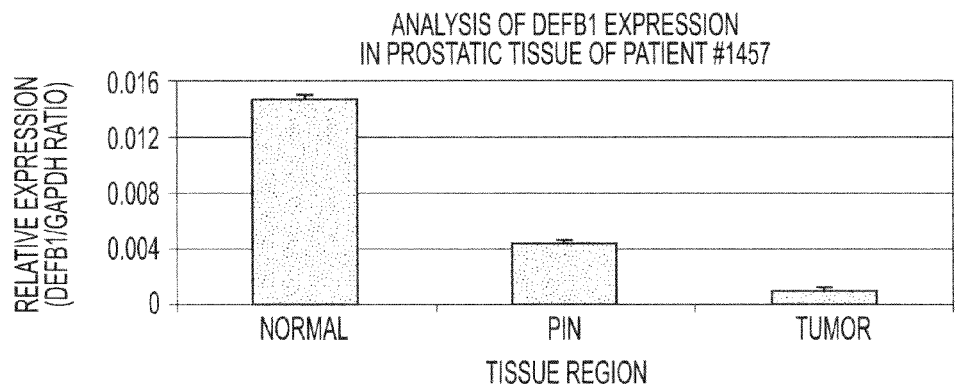
Figure 1D:
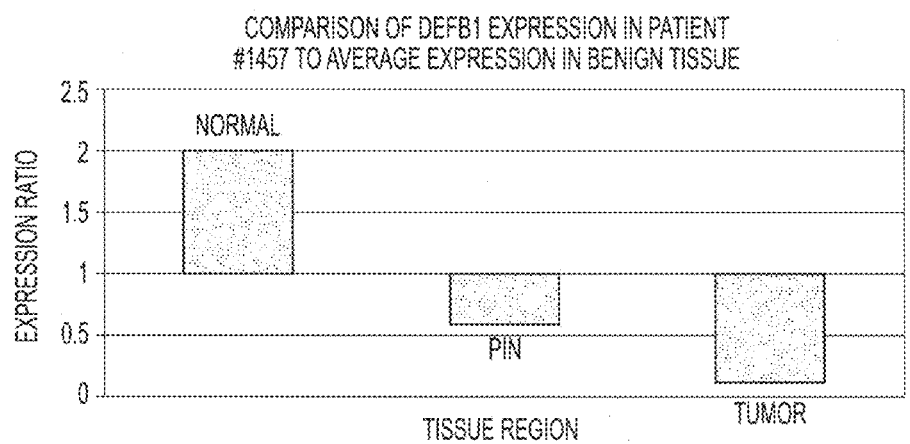

QRT-PCR was performed on LCM tissues regions containing benign, PIN and cancer. DEFB1 relative expression was 0.0146 in the benign region compared to 0.0009 in the malignant region (FIG. 1C). This represents a 94% decrease which again demonstrates a significant down-regulation of expression. Furthermore, analysis of PIN revealed that DEFB1 expression level was 0.044 which was a 70% decrease. Comparing expression in patient #1457 to the average expression level found in benign regions of six other patients (FIG. 1A) revealed a ratio of 1.997 representing almost twice as much expression (FIG. 1D). However, the expression ratio was 0.0595 in PIN and was 0.125 in malignant tissue compared to average expression levels in benign tissue.

Figure 2:
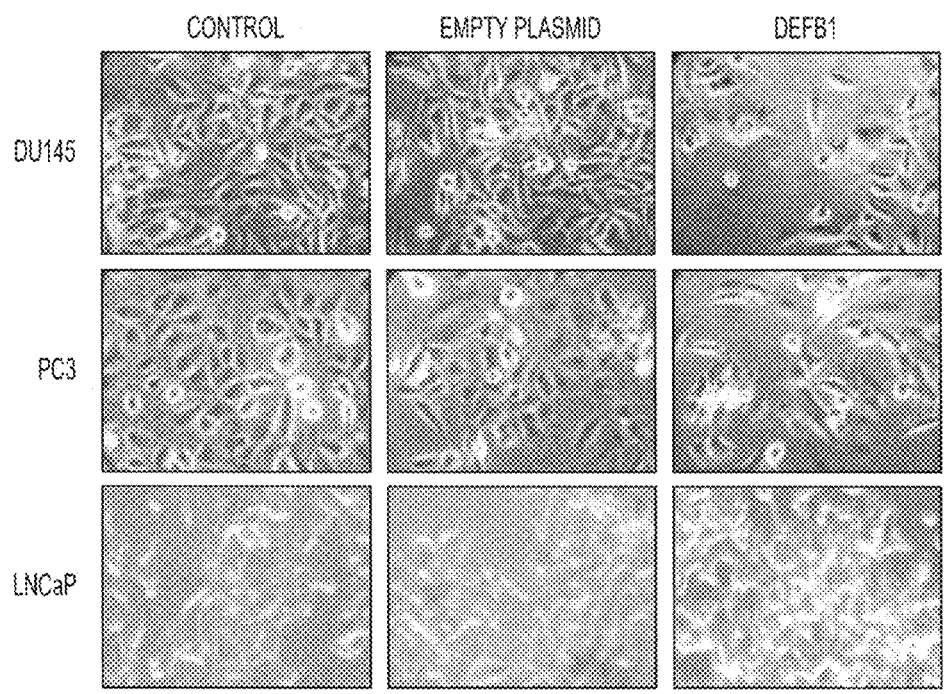
FIG. 2 shows microscopic analysis of DEFB1 induced changes in membrane integrity and cell morphology. Membrane ruffling is indicated by black arrows and apoptotic bodies are indicated white arrows.

DEFB1 Causes Cell Membrane Permeability and Ruffling: Induction of DEFB1 in the prostate cancer cell lines resulted in a significant reduction in cell number in DU145 and PC3, but had no effect on cell proliferation in LNCaP (FIG. 2). As a negative control, cell proliferation was monitored in all three lines containing empty plasmid. There were no observable changes in cell morphology in DU145, PC3 or LNCaP cells following the addition of PonA. In addition, DEFB1 induction resulted in morphological changes in both DU145 and PC3. Here cells appeared more rounded and exhibited membrane ruffling indicative of cell death. Apoptotic bodies were also present in both lines.

Figure 3:
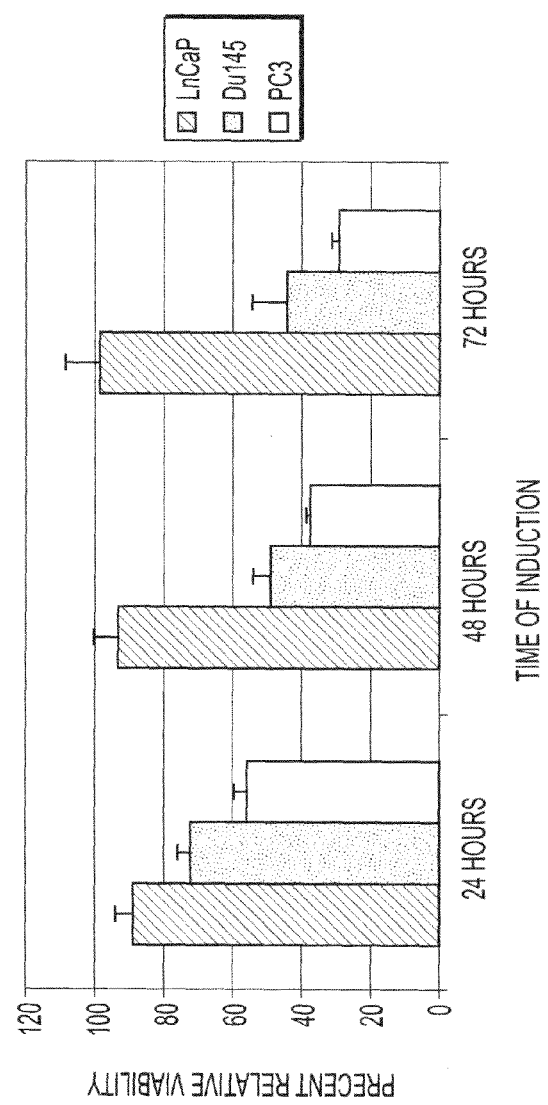
FIG. 3 shows analysis of DEFB1 Cytotoxicity in Prostate Cancer Cells. The prostate cell lines DU145, PC3 and LNCaP were treated with PonA to induce DEFB1 expression for 1-3 days after which MTT assay was performed to determine cell viability. Results represent mean±s.d., n=9.

Expression of DEFB1 Results in Decreased Cell Viability: The MTT assay showed a reduction in cell viability by DEFB1 in PC3 and DU145 cells, but no significant effect on LNCaP cells (FIG. 3). After 24 hours, relative cell viability was 72% in DU145 and 56% in PC3. Analysis 48 hours after induction revealed 49% cell viability in DU145 and 37% cell viability in PC3. After 72 hours of DEFB1 expression resulted in 44% and 29% relative cell viability in DU145 and PC3 cells, respectively.

Figure 4A:
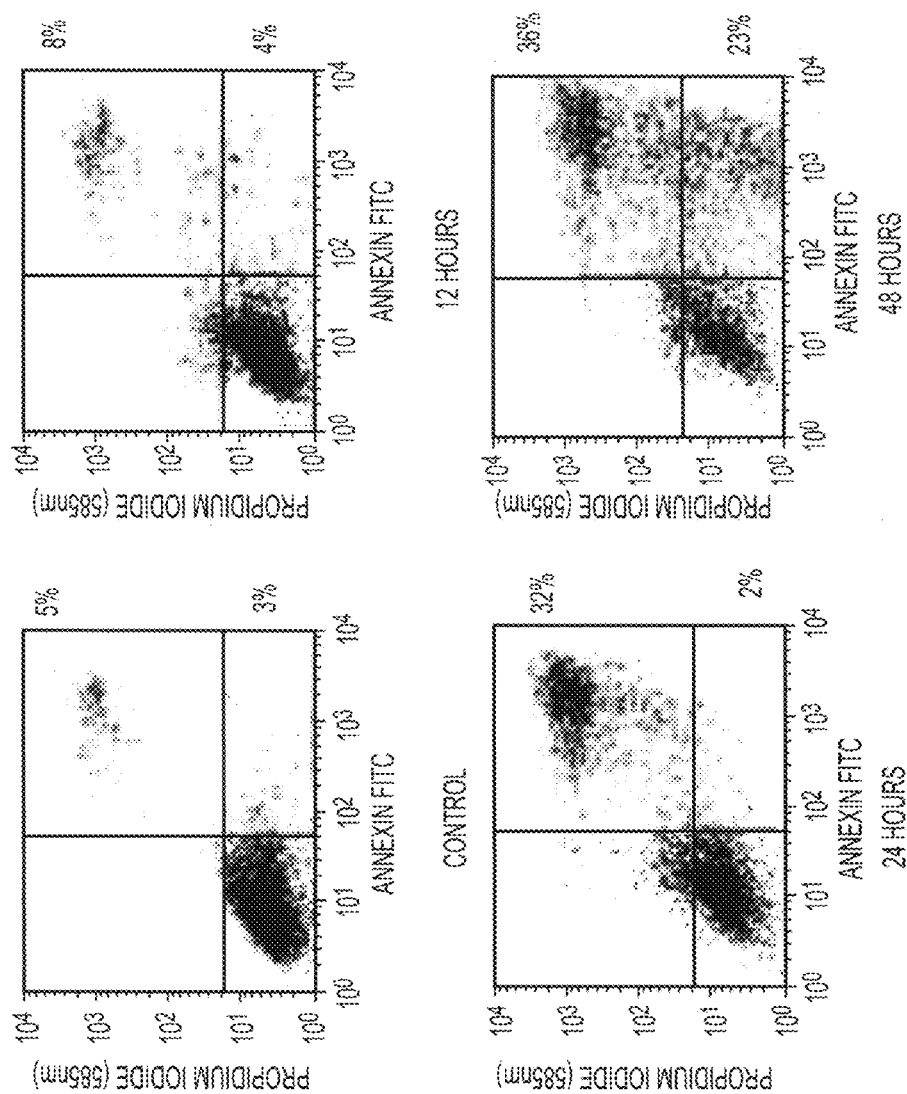
FIGS. 4A and 4B show induction of cell death in DU145 and PC3 cells by DEFB1.
Figure 4B:
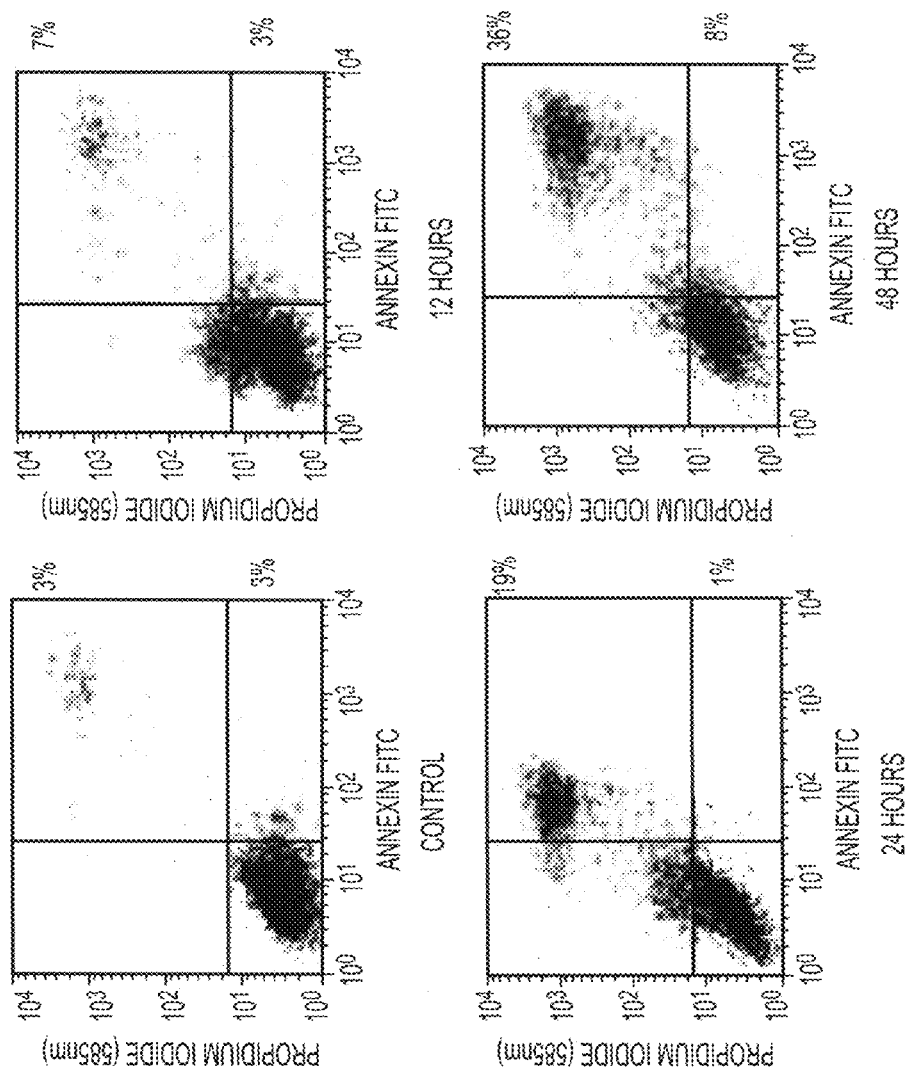

DEFB1 Causes Rapid Caspase-mediated Apoptosis in Late-stage Prostate Cancer Cells: In order to determine whether the effects of DEFB1 on PC3 and DU145 were cytostatic or cytotoxic, FACS analysis was performed. Under normal growth conditions, more than 90% of PC3 and DU145 cultures were viable and non-apoptotic (lower left quadrant) and did not stain with annexin V or PI. After inducing DEFB1 expression in PC3 cells, the number of apoptotic cells (lower and upper right quadrants) totaled 10% at 12 hours, 20% at 24 hours, and 44% at 48 hours (FIG. 4B). For DU145 cells, the number of apoptotic cells totaled 12% after 12 hours, 34% at 24 hours, and 59% after 48 hours of induction (FIG. 4A). There was no increase in apoptosis observed in cells containing empty plasmid following induction with PonA (data not shown).

Caspase activity was determined by confocal laser microscopic analysis (FIG. 5). DU145 and PC3 cell were induced for DEFB1 expression and activity was monitored based on the binding of green fluorescing FAM-VAD-FMK to caspases in cells actively undergoing apoptosis. Analysis of cells under DIC showed the presence of viable control DU145 (panel A), PC3 (panel E) and LNCaP (panel I) cells at 0 hours. Excitation by the confocal laser at 488 nm produced no detectable green staining which indicates no caspase activity in DU145 (panel B), PC3 (panel F) or LNCaP (panel J). Following induction for 24 hours, DU145 (panel C), PC3 (panel G) and LNCaP (panel K) cells were again visible under DIC. Confocal analysis under fluorescence revealed green staining in DU145 (panel D) and PC3 (panel H) cell indicating caspase activity. However, there was no green staining in LNCaP (panel L), indicating no induction of apoptosis by DEFB1.

In conclusion, this study provides the functional role of DEFB1 in prostate cancer. Furthermore, these findings show that DEFB1 is part of an innate immune system involved in tumor immunity. Data presented here demonstrate that DEFB1 expressed at physiological levels is cytotoxic to AR− hormone refractory prostate cancer cells, but not to AR+ hormone sensitive prostate cancer cell nor to normal prostate epithelial cells. Given that DEFB1 is constitutively expressed in normal prostate cells without cytotoxicity, it may be that late-stage AR− prostate cancer cells possess distinct phenotypic characteristics that render them sensitive to DEFB1 cytotoxicity. Thus, DEFB1 is a viable therapeutic agent for the treatment of late-stage prostate cancer, and potentially other cancers as well.

EXAMPLE 2 siRNA Mediated Knockdown of PAX2 Expression Results in Prostate Cancer Cell Death Independent of P53 Status This example examines the effects of inhibiting PAX2 expression by RNA interference in prostate cancer cells which differ in p53 gene status. The results demonstrate that the inhibition of PAX2 results in cell death irrespective of p53 status, indicating that there are additional tumor suppressor genes or cell death pathways inhibited by PAX2 in prostate cancer.

Materials and Methods siRNA Silencing of PAX2:

In order to achieve efficient gene silencing, a pool of four complementary short interfering ribonucleotides (siRNAs) targeting human PAX2 mRNA (Accession No. NM_003989.1), were synthesized (Dharmacon Research, Lafayette, Colo., USA). A second pool of four siRNAs were used as an internal control to test for the specificity of PAX2 siRNAs. Two of the sequences synthesized target the GL2 luciferase mRNA (Accession No. X65324), and two were non-sequence-specific (Table 3). For annealing of siRNAs, 35 M of single strands were incubated in annealing buffer (100 mM potassium acetate, 30 mM HEPES-KOH at pH 7.4, 2 mM magnesium acetate) for 1 min at 90° C. followed by 1 h incubation at 37° C.

TABLE 3

PAX2 siRNA Sequences.
A pool of four siRNA was utilized to
inhibit PAX2 protein expression.

| Sense (5'-3') | | |
|---|---|---|
| Sequence A | 5'-GAAGUCAAGUCGAGUCUAUUU-3' | SEQ ID NO: 7 |
| Sequence B | 5'-GAGGAAACGUGAUGAAGAUUU-3' | SEQ ID NO: 8 |
| Sequence C | 5'-GGACAAGAUUGCUGAAUACUU-3' | SEQ ID NO: 9 |
| Sequence D | 5'-CAUCAGAGCACAUCAAAUCUU-3' | SEQ ID NO: 10 |
| Antisense (5'-3') | | |
| Sequence A | 5'-AUAGACUCGACUUGACUUCUU-3' | SEQ ID NO: 3 |
| Sequence B | 5'-AUCUUCAUCACGUUUCCUCUU-3' | SEQ ID NO: 4 |
| Sequence C | 5'-GUAUUCAGCAAUCUUGUCCUU-3' | SEQ ID NO: 5 |
| Sequence D | 5'-GAUUUGAUGUGCUCUGAUGUU-3' | SEQ ID NO: 6 |

Western Analysis:

Briefly, cells were harvested by trypsinization and washed twice with PBS. Lysis buffer was prepared according to the manufacturer's instructions (Sigma), and was then added to the cells. Following a 15 minute incubation period at 4° C. on an orbital shaker, cell lysate were then collected and centrifuged for 10 minutes at 12000×g to pellet cellular debris. The protein-containing supernatant were then collected and quantitated. Next, 25 µg protein extract was loaded onto an 8-16% gradient SDS-PAGE (Novex). Following electrophoresis, proteins were transferred to PVDF membranes, and then blocked with 5% nonfat dry milk in TTBS (0.05% Tween 20 and 100 mM Tris-Cl) for 1 hour. Blots were then probed with rabbit anti-PAX2 primary antibody (Zymed, San Francisco, Calif.) at a 1:2000 dilution. After washing, the membranes were incubated with anti-rabbit antibody conjugated to horseradish peroxidase (HRP) (dilution 1:5000; Sigma), and signal detection was visualized using chemilluminescence reagents (Pierce) on an Alpha Innotech Fluorchem 8900. As a control, blots were stripped and reprobed with mouse anti-β-actin primary antibody (1:5000; Sigma-Aldrich) and HRP-conjugated anti-mouse secondary antibody (1:5000; Sigma-Aldrich) and signal detection was again visualized.

Phase Contrast Microscopy:

The effect of PAX2 knock-down on cell growth was analyzed by phase contrast microscopy as described in Example 1.

MTT Cytotoxicity Assay:

DU145, PC3 and LNCaP cells (1×10$^5$) were transfected with 0.5 µg of the PAX2 siRNA pool or control siRNA pool using Codebreaker transfection reagent according to the manufacturer's protocol (Promega). Next, cell suspensions were diluted and seeded onto a 96-well plate at 1-5×10$^3$ cells per well and allowed to grow for 2-, 4- or 6 days. After culture, cell viability was determined by measuring the conversion of 3-[4,5-dimethylthiazol-2yl]-2,5 diphenyl tetrazolium bromide, MTT (Promega), to a colored formazan product. Absorbance was read at 540 nm on a scanning multiwell spectrophotometer.

Pan-Caspase Detection:

Detection of caspase activity in the prostate cancer cell lines was performed s described in Example 1.

Quantitative Real-time RT-PCR:

Quantitative real-time RT-PCR was performed as described in Example 1 in order to verify gene expression after PAX2 siRNA treatment in PC3, DU145 and LNCaP cell lines. The primer pairs for GAPDH (control gene), BAX, BID and BAD are:

```
Sense (5'-3')
GAPDH
                                          SEQ ID NO: 55
5'-CCACCCATGGCAAATTCCATGGCA-3'

BAD
                                          SEQ ID NO: 57
5'-CTCAGGCCTATGCAAAAAGAGGA-3'

BID
                                          SEQ ID NO: 59
5'-AACCTACGCACCTACGTGAGGAG-3'

BAX
                                          SEQ ID NO: 61
5'-GACACCTGAGCTGACCTTGG-3'

Antisense (5'-3')
GAPDH
                                          SEQ ID NO: 56
5'-TCTAGACGGCAGGTCAGGTCAACC-3'

BAD
                                          SEQ ID NO: 58
5'-GCCCTCCCTCCAAAGGAGAC-3'

BID
                                          SEQ ID NO: 60
5'-CGTTCAGTCCATCCCATTTCTG-3'

BAX
                                          SEQ ID NO: 62
5'-GAGGAAGTCCAGTGTCCAGC-3'
```

Reactions were performed in MicroAmp Optical 96-well Reaction Plate (PE Biosystems). Forty cycles of PCR were performed under standard conditions using an annealing temperature of 60° C. Quantification was determined by the cycle number where exponential amplification began (threshold value) and averaged from the values obtained from the triplicate repeats. There was an inverse relationship between message level and threshold value. In addition, GAPDH was used as a housekeeping gene to normalize the initial content of total cDNA. Gene expression was calculated as the relative expression ratio between the pro-apoptotic genes and GAPDH. All reactions were carried out in triplicate.

Figure 6:
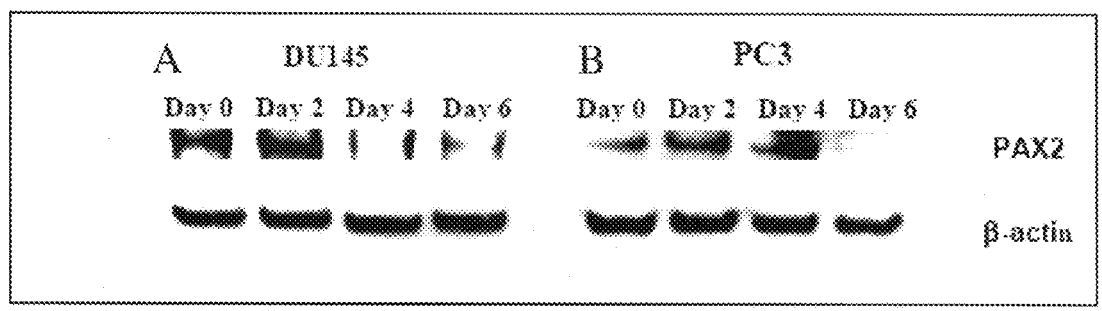
FIG. 6 show silencing of paired box homeotic gene 2 (PAX2) protein expression following PAX2 siRNA treatment.

Results siRNA Inhibition of PAX2 Protein:

In order to confirm that the siRNA effective targeted the PAX2 mRNA, Western Analysis was performed to monitor PAX2 protein expression levels over a six day treatment period. Cells were given a single round of transfection with the pool of PAX2 siRNA. The results confirmed specific targeting of PAX2 mRNA by showing knock-down of PAX2 protein by day four in DU145 (FIG. 6, panel A) and by day six in PC3 (FIG. 6, panel B).

Figure 7:
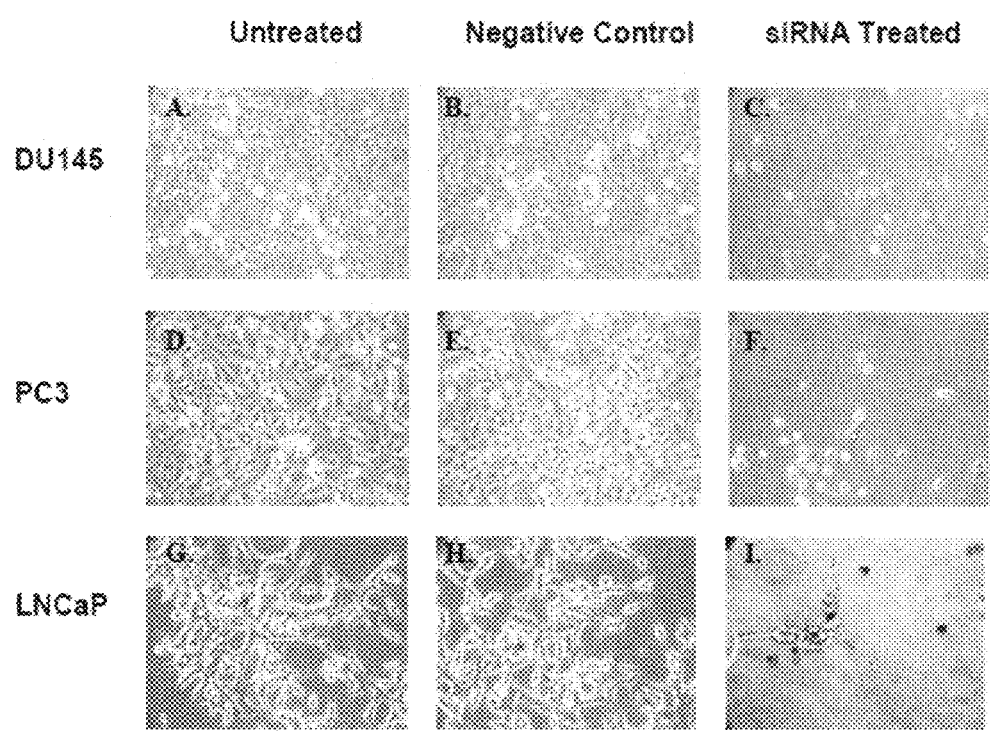
FIG. 7 shows analysis of prostate cancer cells growth after treatment with PAX2 siRNA.

Knock-down of PAX2 inhibit Prostate Cancer Cell Growth:

Cells were analyzed following a six day treatment period with media only, negative control non-specific siRNA or PAX2 siRNA (FIG. 7). DU145 (panel A), PC3 (panel D) and LNCaP (panel G) cells all reached at least 90% confluency in the culture dishes containing media only. Treatment of DU145 (panel B), PC3 (panel E) and LNCaP (panel H) with negative control non-specific siRNA had no effect on cell growth, and cells again reached confluency after six days. However, treatment with PAX2 siRNA resulted in a significant decrease in cell number. DU145 cells were approximately 15% confluent (panel C) and PC3 cells were only 10% confluent (panel F). LNCaP cell were 5% confluent following siRNA treatment.

Figure 8:
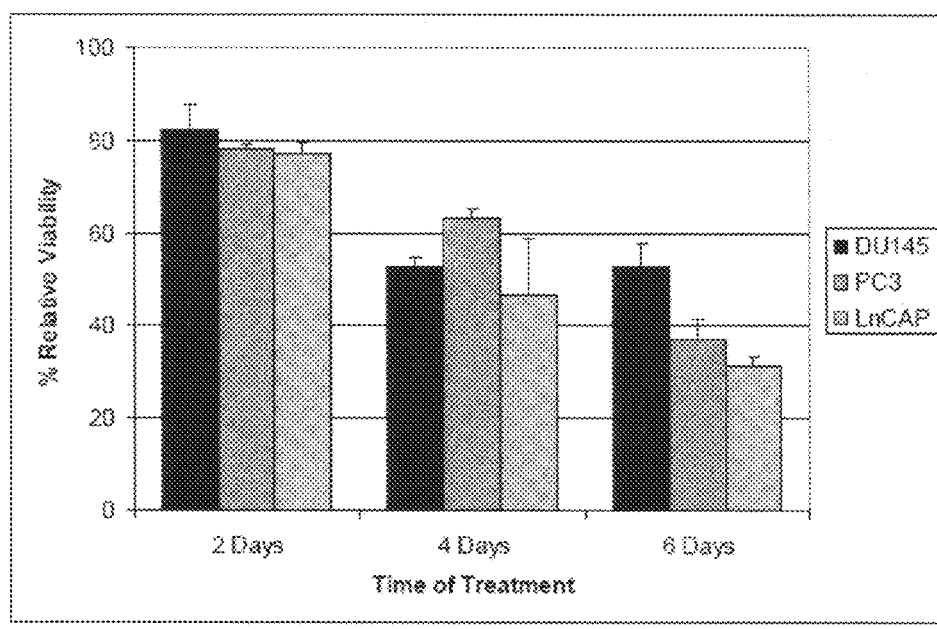
FIG. 8 shows analysis of cell death following siRNA silencing of PAX2. Results represent mean±s.d., n=9.

Cytotoxicity Assays:

Cell viability was measured after two-, four-, and six-day exposure times, and is expressed as a ratio of the 570-630 nm absorbance of treated cells divided by that of the untreated control cells (FIG. 8). Relative cell viability following 2 days of treatment was 77% in LNCaP, 82% in DU145 and 78% in PC3. After four days, relative cell viability was 46% in LNCaP, 53% in DU145 and 63% in PC3. After six days of treatment, relative cell viability decreased to 31% in LNCaP, 37% in PC3, and was 53% in DU145. As negative controls, cell viability was measured in after a six day treatment period with negative control non-specific siRNA or transfection reagent alone. For both conditions, there was no statistically significant change in cell viability compared to normal growth media.

Figure 9:
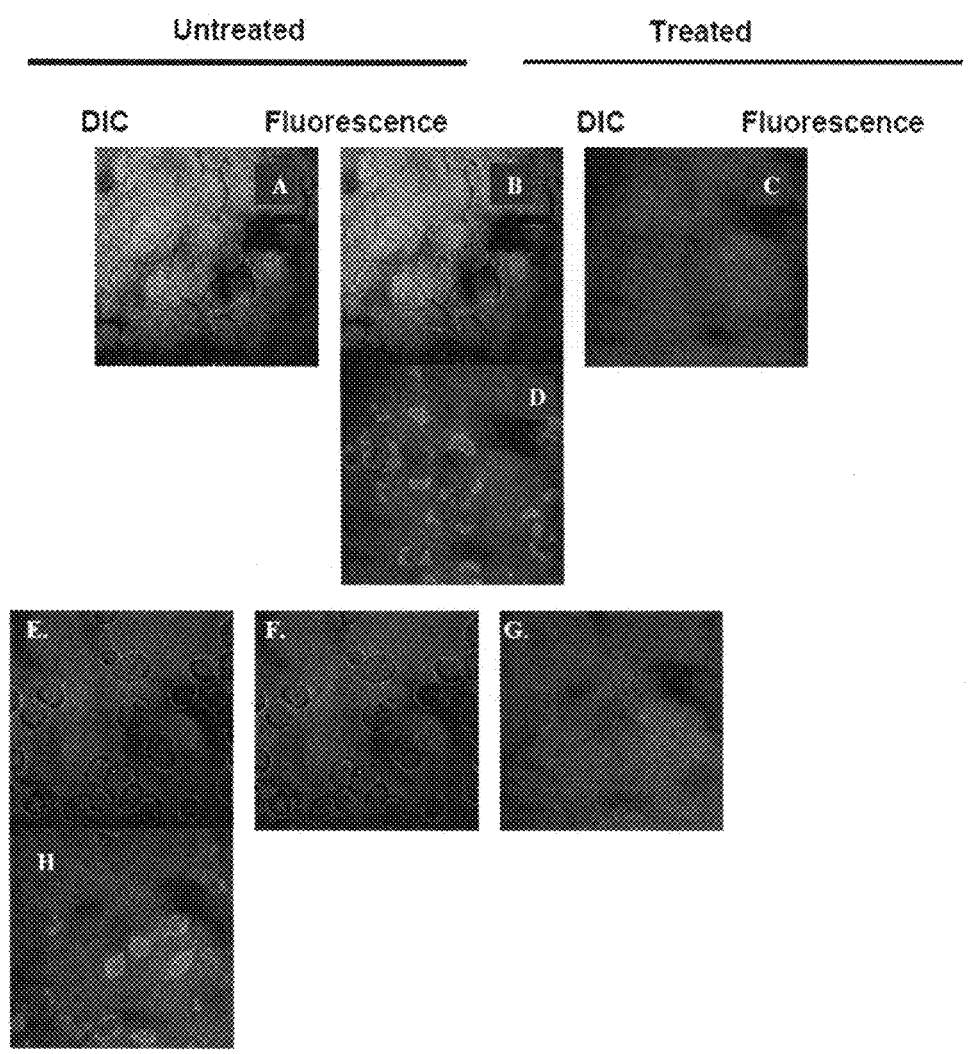
FIG. 9 shows analysis of caspase activity.
Figure 9:
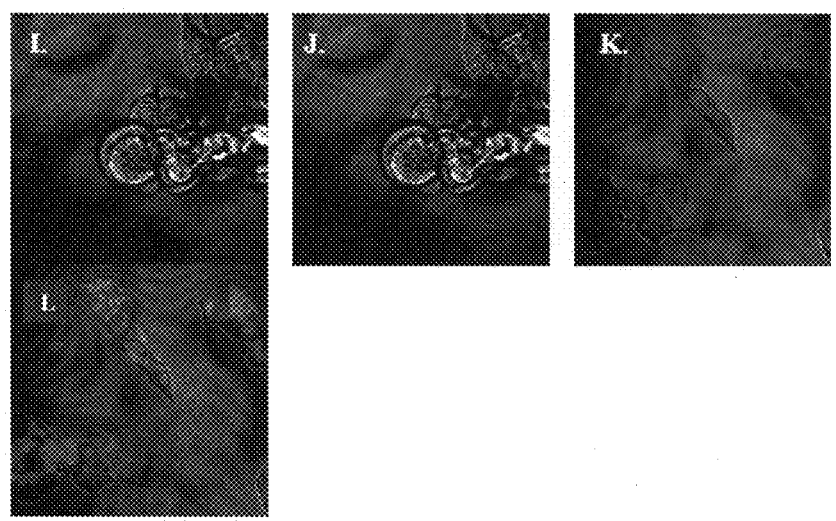

Pan-Caspase Detection:

Caspase activity was detected by confocal laser microscopic analysis. DU145, PC3 and LNCaP cells were treated with PAX2 siRNA and activity was monitored based on the binding of FAM-labeled peptide to caspases in cells actively undergoing apoptosis which will fluoresce green. Analysis of cells with media only under DIC shows the presence of viable DU145 (A), PC3 (E) and LNCaP (I) cells at 0 hours (FIG. 9). Excitation by the confocal laser at 488 nm produced no detectable green staining which indicates no caspase activity in untreated DU145 (B), PC3 (F) or LNCaP (J). Following four days of treatment with PAX2 siRNA, DU145 (C), PC3 (G) and LNCaP (K) cells were again visible under DIC. Under fluorescence, the treated DU145 (D), PC3 (H) and LNCaP (L) cells presented green staining indicating caspase activity.

Figure 10A:
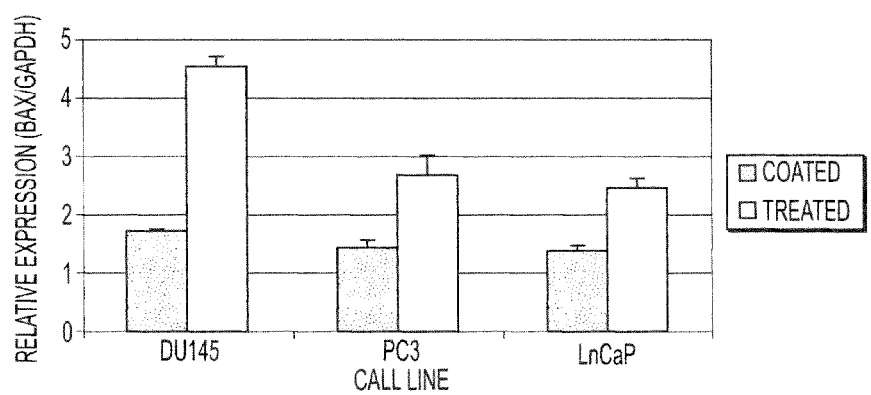
FIG. 10 shows analysis of apoptotic factors following PAX2 siRNA treatment.
Figure 10B:
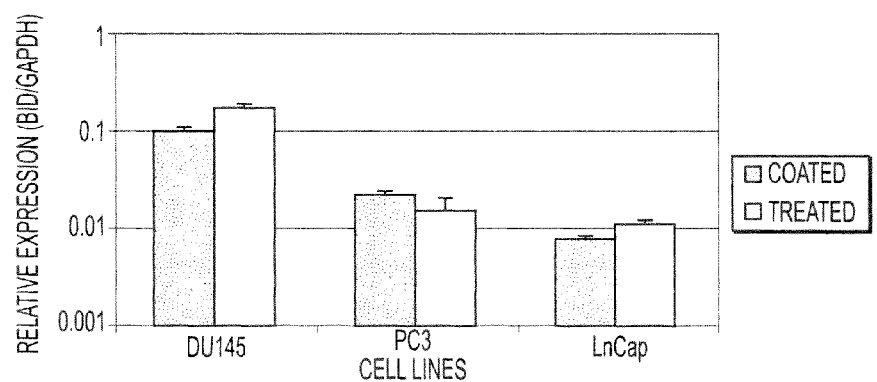
Figure 10C:
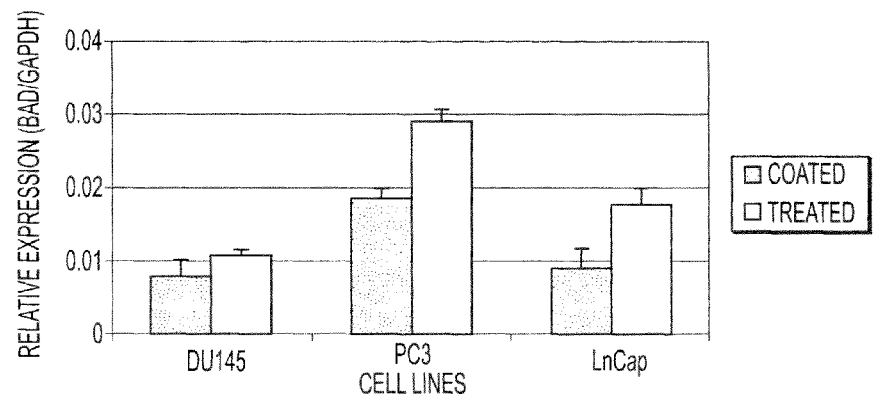

Effect of PAX2 Inhibition on Pro-apoptotic Factors:

DU145, PC3 and LNCaP cells were treated with siRNA against PAX2 for six days and expression of pro-apoptotic genes dependent and independent of p53 transcription regulation were measured to monitor cell death pathways. For BAX, there was a 1.81-fold increase in LNCaP, a 2.73-fold increase in DU145, and a 1.87-fold increase in PC3 (FIG. 10, panel A). Expression levels of BID increased by 1.38-fold in LNCaP and 1.77-fold in DU145 (FIG. 10, panel B). However, BID expression levels decreased by 1.44-fold in PC3 following treatment (FIG. 10, panel C). Analysis of BAD revealed a 2.0-fold increase in expression in LNCaP, a 1.38-fold increase in DU145, and a 1.58-fold increase in PC3.

These results demonstrate dependency of prostate cancer cell survival on PAX2 expression. Following p53 activation as a result of PAX2 knock-down in the p53-expressing cell line LNCaP, the p53-mutated line DU145, and the p53-null line PC3, caspase activity was detected in all three lines, indicating of the initiation of programmed cell death. BAX expression was upregulated in all three cell lines independent of p53 status. The expression of pro-apoptotic factor BAD was also increased in all three lines following PAX2 inhibition. Following treatment with PAX2 siRNA, BID expression was increased in LNCaP and DU145, but actually decreased in PC3. These results indicate that cell death observed in prostate cancer is influenced by but is not dependent on p53 expression. The initiation of apoptosis in prostate cancer cells through different cell death pathways irrespective of p53 status indicates that PAX2 inhibits other tumor suppressors.

EXAMPLE 3

Figure 11:
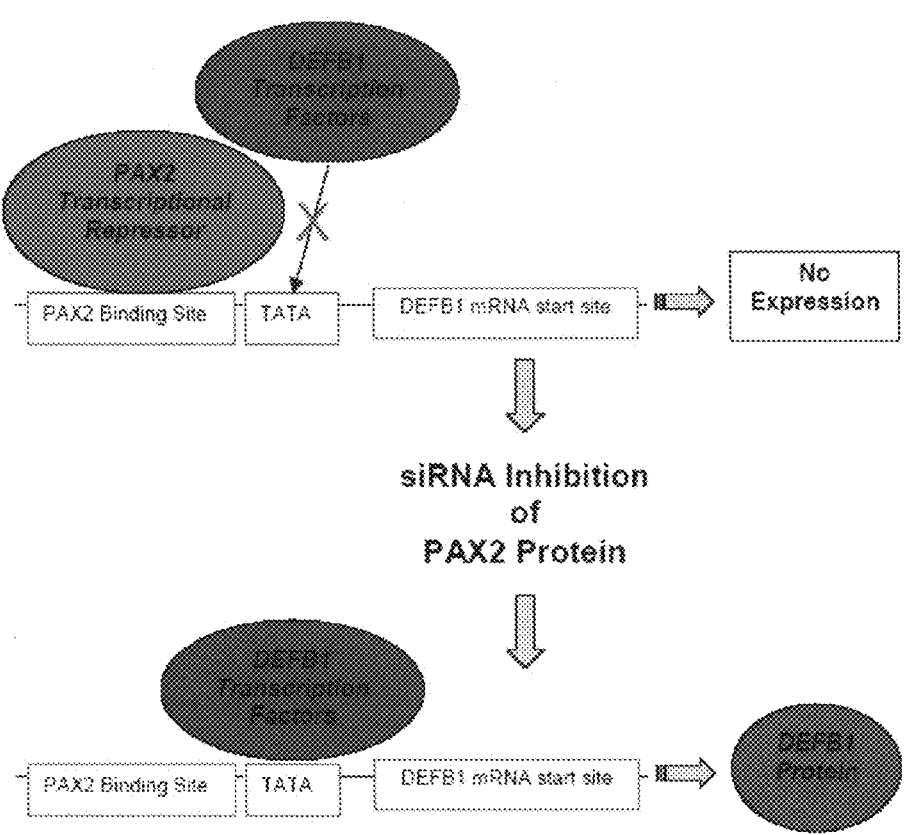
FIG. 11 shows model of PAX2 binding to DNA recognition sequence.

Inhibition of PAX2 Oncogene Results in DEFB1-Mediated Death of Prostate Cancer Cells The identification of tumor-specific molecules that serve as targets for the development of new cancer drugs is considered to be a major goal in cancer research. Example 1 demonstrated that there is a high frequency of DEFB1 expression loss in prostate cancer, and that induction of DEFB1 expression results in rapid apoptosis in androgen receptor negative-stage prostate cancer. These data show that DEFB1 plays a role in prostate tumor suppression. In addition, given that it is a naturally occurring component of the immune system of normal prostate epithelium, DEFB1 is expected to be a viable therapeutic agent with little to no side effects. Example 2 demonstrated that inhibition of PAX2 expression results in prostate cancer cell death independent of p53. These data indicate that there is an addition pro-apoptotic factor or tumor suppressor that is inhibited by PAX2. In addition, the data show that the oncogenic factor PAX2, which is over-expressed in prostate cancer, is a transcriptional repressor of DEFB1. The purpose of this study is to determine if loss of DEFB1 expression is due to aberrant expression of the PAX2 oncogene, and whether inhibiting PAX2 results in expression of DEFB1 and DEFB1-mediated cell death (FIG. 11).

Materials and Methods

RNA Isolation and Quantitative RT-PCR:

RNA isolation and quantitative RT-PCR of DEFB1 were performed as described in Example 1.

Figure 12:
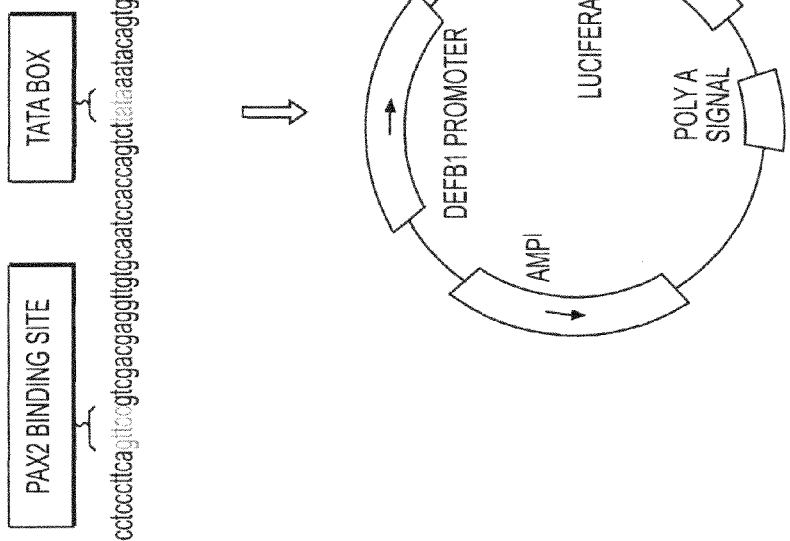
FIG. 12 illustrates the DEFB1 reporter construct.

Generation of the DEFB1 Reporter Construct:

The pGL3 luciferase reporter plasmid was used to monitor DEFB1 reporter activity. Here, a region 160 bases upstream of the DEFB1 transcription initiation site and included the DEFB1 TATA box. The region also included the CCTTG (SEQ ID NO: 1) sequence which is necessary for PAX2 binding. The PCR primers were designed to contain Kpn1 and Nhe1 restriction sites. The DEFB1 promoter PCR products were restriction digested Kpn I and NheI and ligated into a similarly restriction digested pGL3 plasmid (FIG. 12). The constructs were transfected into *E. coli* and individual clones were selected and expanded. Plasmids were isolated and sequence integrity of the DEFB1/pGL3 construct was verified by automated sequencing.

Luciferase Reporter Assay:

Here, 1 µg of the DEFB1 reporter construct or the control pGL3 plasmid was transfected into $1 \times 10^6$ DU145 cells. Next, $0.5 \times 103$ cells were seeded onto each well of a 96-well plate and allowed to grow overnight. Then fresh medium was added containing PAX2 siRNA or media only and the cells were incubated for 48 hours. Luciferase was detected by the BrightGlo kit according to the manufacturer's protocol (Promega) and the plates were read on a Veritas automated 96-well luminometer. Promoter activity was expressed as relative luminescence.

Analysis of Membrane Permeability:

Acridine orange (AO)/ethidium bromide (EtBr) dual staining was performed to identify changes in cell membrane integrity, as well as apoptotic cells by staining the condensed chromatin. AO stains viable cells as well as early apoptotic cells, whereas EtBr stains late stage apoptotic cells that have lost membrane permeability. Briefly, cells were seeded into 2 chamber culture slides (BD Falcon, USA). Cells transfected with empty pIND plasmid/pvgRXR or pIND DEFB1/pvgRXR were induced for 24 or 48 h with media containing 10 µM Ponasterone A. Control cells were provided fresh media at 24 and 48 h. In order to determine the effect of PAX2 inhibition on membrane integrity, separate culture slides containing DU145, PC3 and LNCaP were treated with PAX2 siRNA and incubated for 4 days. Following this, cells were washed once with PBS and stained with 2 ml of a mixture (1:1) of AO (Sigma, USA) and EtBr (Promega, USA) (5 ug/ml) solution for 5 min. Following staining, the cells were again washed with PBS. Fluorescence was viewed by a Zeiss LSM 5 Pascal Vario 2 Laser Scanning Confocal Microscope (Carl Zeiss Jena, Germany). The excitation color wheel contain B5505-530 (green) and LP560 (red) filter blocks which allowed for the separation of emitted green light from AO into the green channel and red light from EtBr into the red channel. The laser power output and gain control settings within each individual experiment were identical between control and DEFB1 induced cells. The excitation was provided by a Kr/Ar mixed gas laser at wavelengths of 543 nm for AO and 488 nm for EtBr. Slides were analyzed under 40× magnification and digital images were stored as uncompressed TIFF files and exported into Photoshop CS software (Adobe Systems, San Jose, Calif.) for image processing and hard copy presentation.

ChIP Analysis of PAX2:

Chromatin immunoprecipitation (ChIP) allows the identification of binding sites for DNA-binding proteins based upon in vivo occupancy of a promoter by a transcription factor and enrichment of transcription factor bound chromatin by immunoprecipitation. A modification of the protocol described by the Farnham laboratory was used; also on line at http://mcardle.oncology.wisc.edu/farnham/). The DU145 and PC3 cell lines over-expresses the PAX2 protein, but does not express DEFB1. Cells were incubated with PBS containing 1.0% formaldehyde for 10 minutes to crosslink proteins to DNA. Samples were then sonicated to yield DNA with an average length of 600 bp. Sonicated chromatin precleared with Protein A Dynabeads was incubated with PAX2-specific antibody or "no antibody" control [isotype-matched control antibodies]. Washed immunoprecipitates were then collected. After reversal of the crosslinks, DNA was analyzed by PCR using promoter-specific primers to determine whether DEFB1 is represented in the PAX2-immunoprecipitated samples. Primers were designed to amplify the 160 bp region immediately upstream of the DEFB1 mRNA start site which contained the DEFB1 TATA box and the functional CCTTG (SEQ ID NO: 1) PAX2 recognition site. For these studies, positive controls included PCR of an aliquot of the input chromatin (prior to immunoprecipitation, but crosslinks reversed). All steps were performed in the presence of protease inhibitors.

Figure 13:
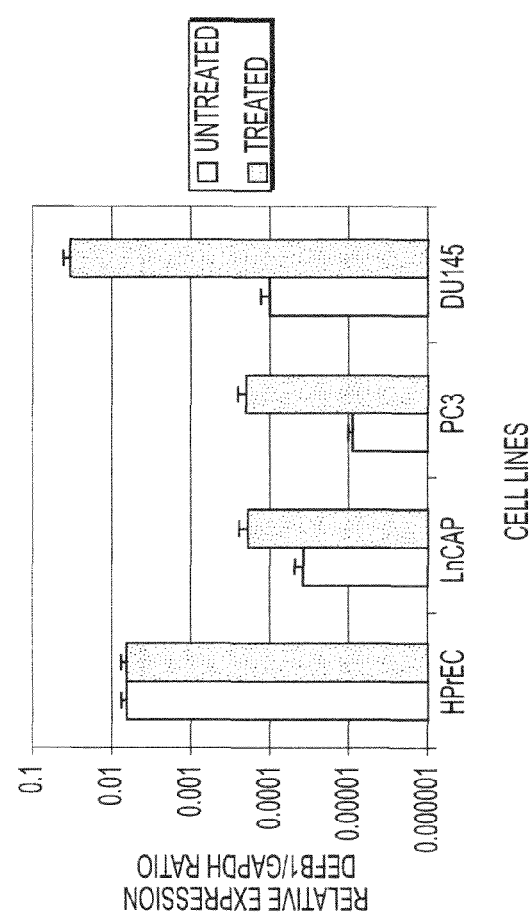
FIG. 13 shows inhibition of PAX2 results in DEFB1 Expression.
Figure 14:
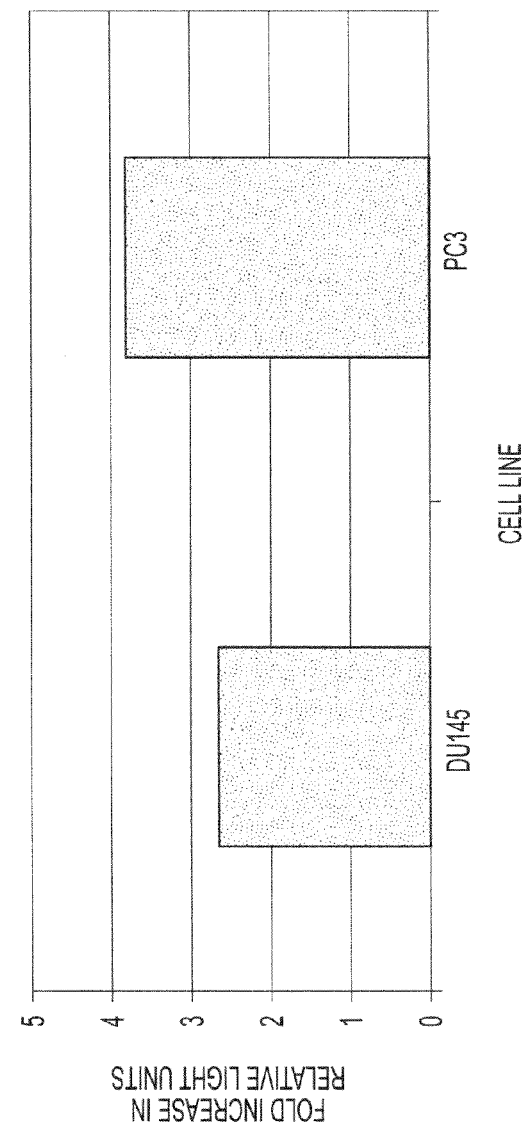
FIG. 14 shows that inhibition of PAX2 results in increased DEFB1 promoter activity.

Results siRNA Inhibition of PAX2 Increases DEFB1 Expression:

QRT-PCR analysis of DEFB1 expression before siRNA treatment revealed relative expression levels of 0.00097 in DU145, 0.00001 in PC3, and 0.00004 LNCaP (FIG. 13). Following siRNA knock-down of PAX2, relative expression was 0.03294 (338-fold increase) in DU145, 0.00020 (22.2-fold increase) in PC3 and 0.00019 (4.92-fold increase) in LNCaP. As a negative control, the human prostate epithelial cell line (hPrEC) which is PAX2 null, revealed expression levels at 0.00687 before treatment and 0.00661 following siRNA treatment confirming no statistical change in DEFB1 expression.

siRNA Inhibition of PAX2 Increases DEFB1 Promoter Activity:

FIG. 14 shows that inhibition of PAX2 results in increased DEFB1 promoter activity. PC3 promoter/pGL3 and DU145 promoter/pGL3 construct were generated and were transfected into PC3 and DU145 cells, respectively. Promoter activity was compared before and after PAX2 inhibition by siRNA treatment. DEFB1 promoter activity increased 2.65-fold in DU145 and 3.78 fold in PC3 following treatment.

Figure 15:
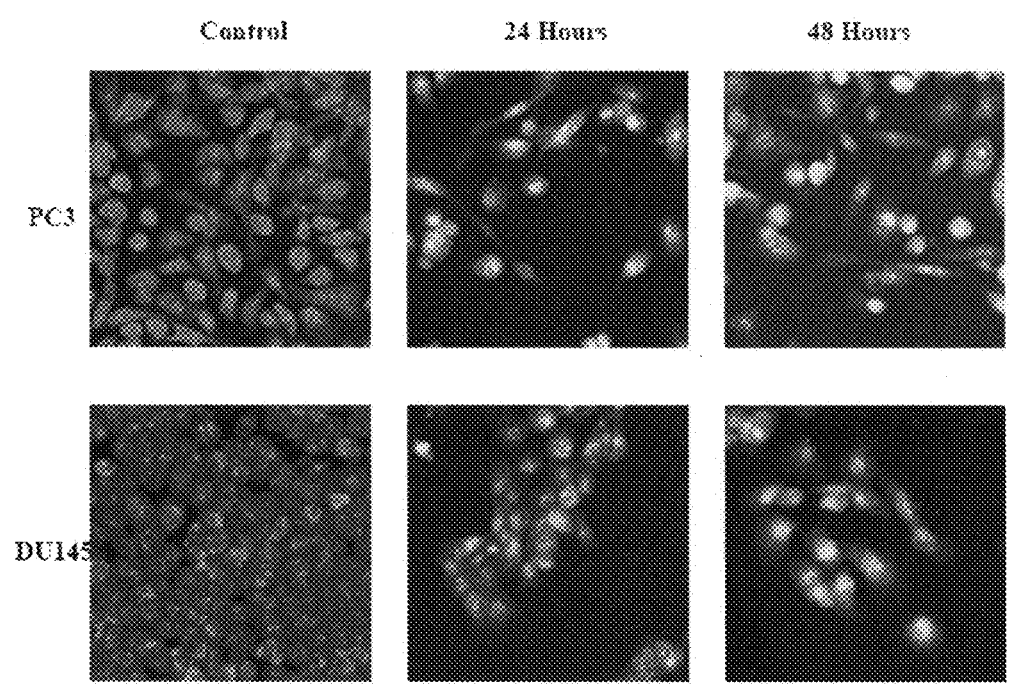
FIG. 15 shows that DEFB1 expression causes loss of membrane integrity.

DEFB1 Causes Cell Membrane Permeability:

Membrane integrity was monitored by confocal analysis. As shown in FIG. 15, intact cells stain green due to AO which is membrane permeable. In addition, cells with compromised plasma membranes would stain red by EtBr which is membrane impermeable. Here, uninduced DU145 (A) and PC3 (D) cells stained positively with AO and emitted green color, but did not stain with EtBr. However, DEFB1 induction in both DU145 (B) and PC3 (E) resulted in the accumulation of EtBr in the cytoplasm at 24 hours indicated by the red staining. By 48 hours, DU145 (C) and PC3 (F) possessed condensed nuclei and appeared yellow, which was due to the presence of both green and red staining resulting from the accumulation of AO and EtBr, respectively.

Figure 16:
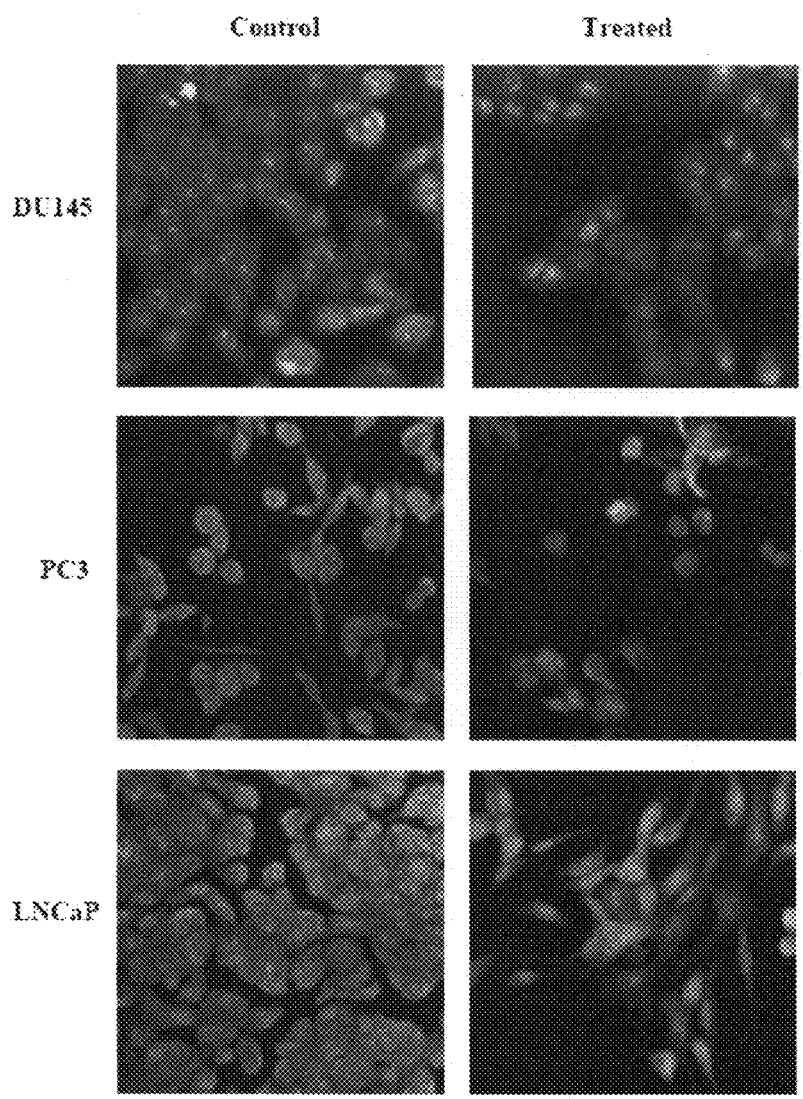
FIG. 16 shows that PAX2 inhibition results in loss of membrane integrity.

Inhibition of PAX2 Results in Membrane Permeability:

Cells were treated with PAX2 siRNA for 4 days and membrane integrity was monitored again by confocal analysis. As shown in FIG. 16, both DU145 and PC3 possessed condensed nuclei and appeared yellow. However, LNCaP cells' cytoplasm and nuclei remained green following siRNA treatment. Also red staining at the cell periphery indicates the maintenance of cell membrane integrity. These findings indicate that the inhibition of PAX2 results in specifically DEFB1-mediated cell death in DU1145 and PC3, but not LNCaP cells. Death observed in LNCaP is due to the transactivation of the existing wild-type p53 in LNCap following PAX2 inhibition.

Figure 17:
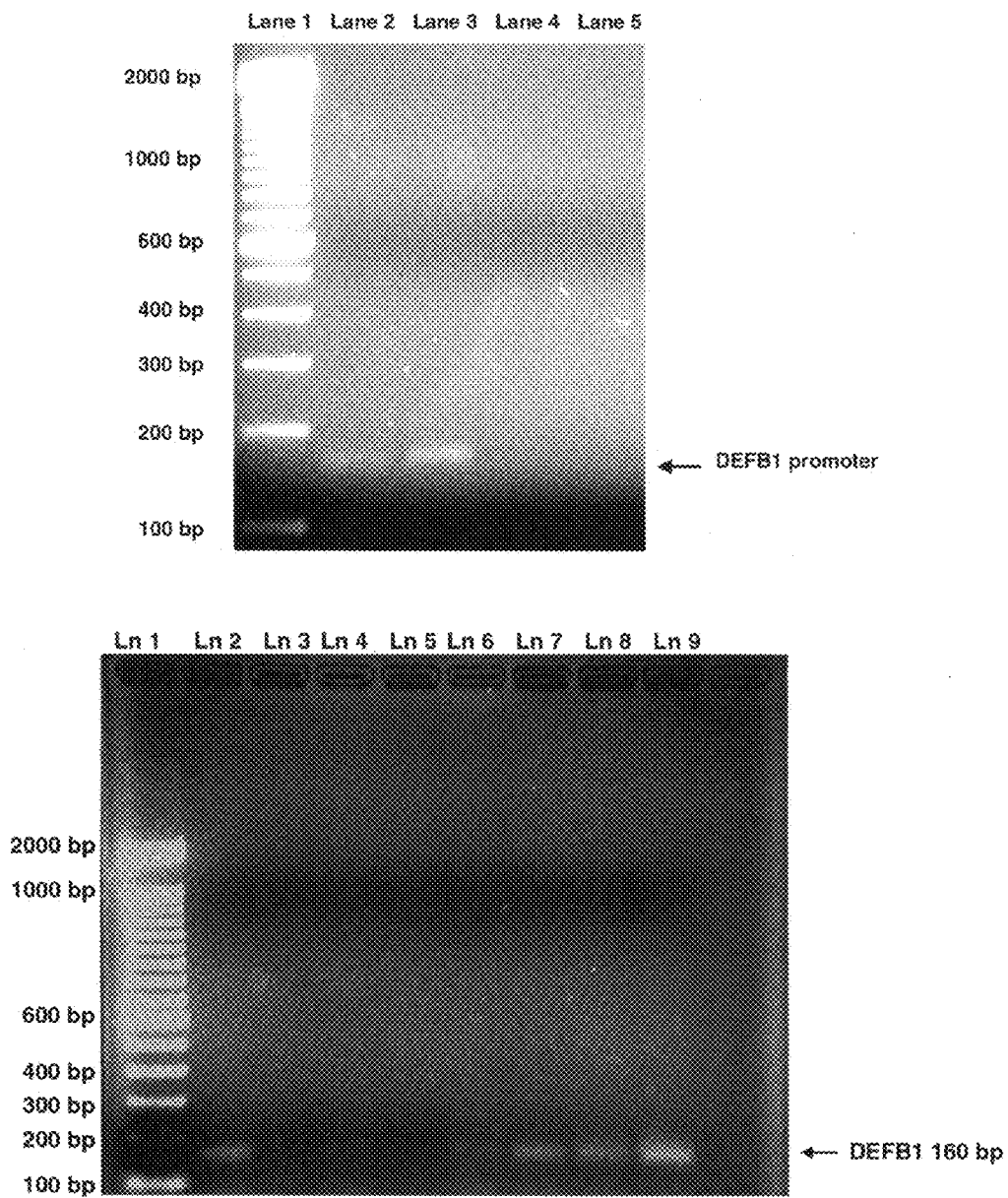
FIGS. 17A and 17B show ChIP analysis of PAX2 binding to DEFB1 promoter.

PAX2 Binds to the DEFB1 Promoter:

ChIP analysis was performed on DU145 and PC3 cells to determine if the PAX2 transcriptional repressor is bound to the DEFB1 promoter (FIG. 17). Lane 1 contains a 100 bp molecular weight marker. Lane 2 is a positive control representing 160 bp region of the DEFB1 promoter amplified from DU145 before cross-linking and immunoprecipitation. Lane 3 is a negative control representing PCR performed without DNA. Lanes 4 and 5 are negative controls representing PCR from immunoprecipitations performed with IgG from cross-linked DU145 and PC3, respectively. PCR amplification of 25 pg of DNA (lane 6 and 8) and 50 pg of DNA (lane 7 and 9) immunoprecipitated with anti-PAX2 antibody after crosslinking show 160 bp promoter fragment in DU145 and PC3, respectively.

Figure 18:
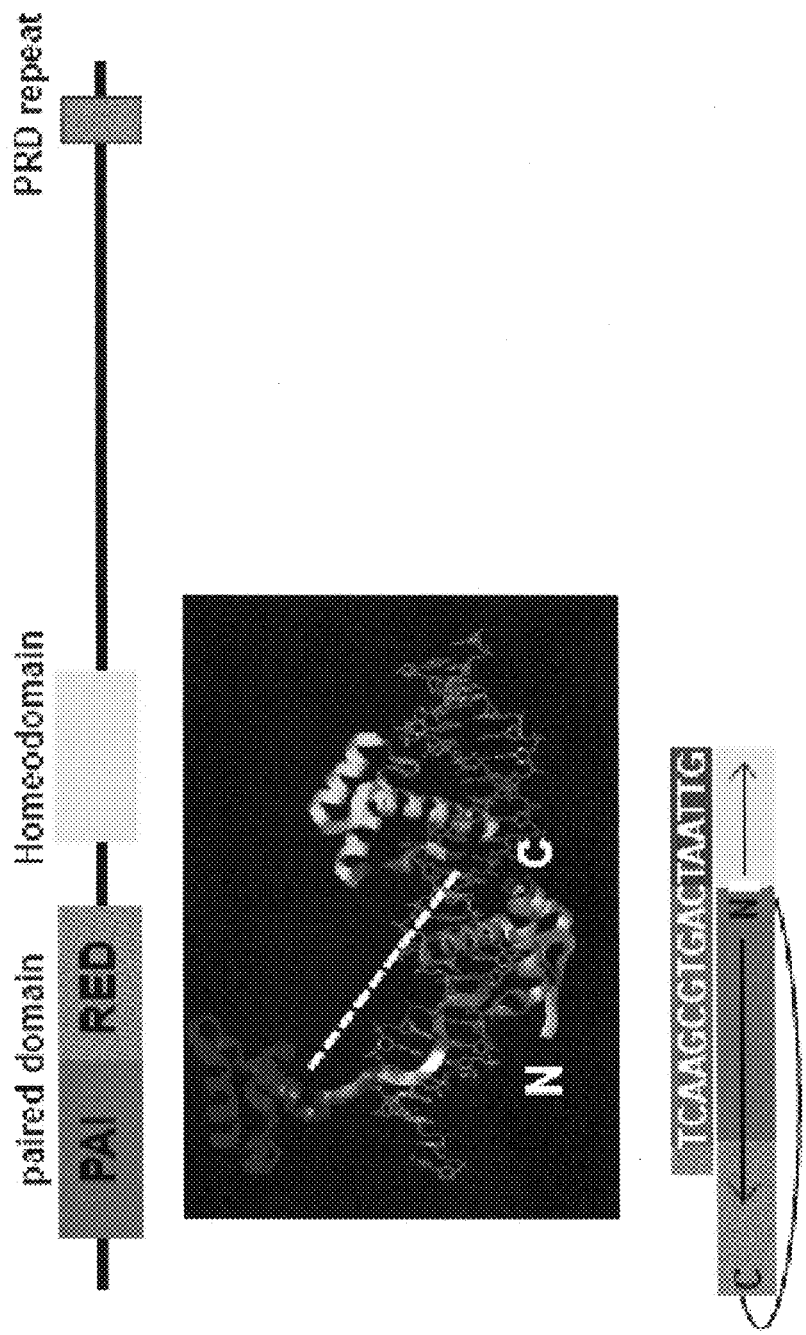
FIG. 18 shows predicted structure of the PrdPD and PrdHD with DNA.

FIG. 18 shows predicted structure of the PrdPD and PrdHD with DNA. The coordinates of the structures of the PrdPD bound to DNA (Xu et al., 1995) and the PrdHD bound to DNA (Wilson et al., 1995) were used to construct a model of the two domains as they bound to a PH0 site. The individual binding sites are abutted next to each other with a specific orientation as indicated. The RED domain is oriented based on the PrdPD crystal structure.

Figure 19:
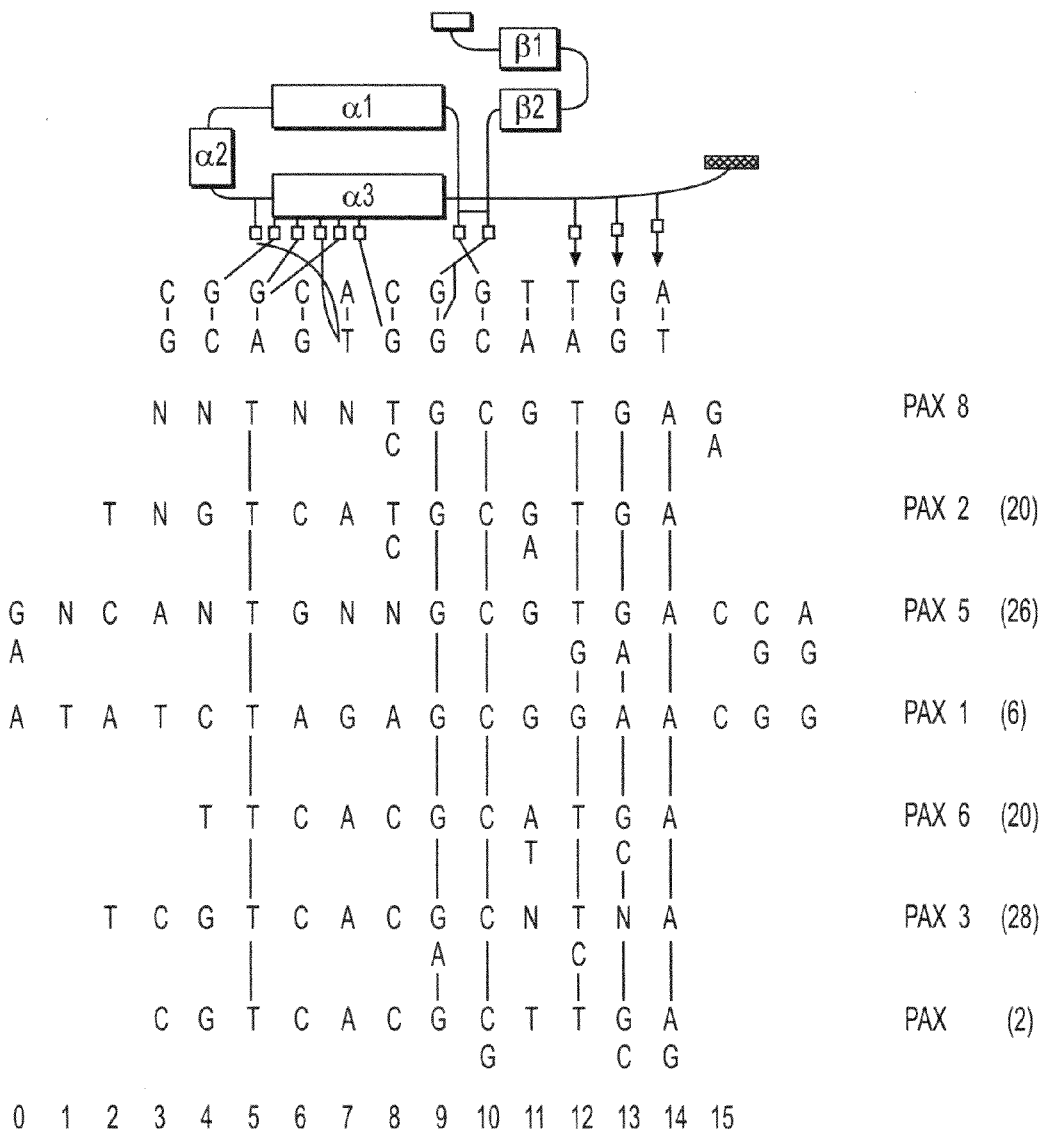
FIG. 19 shows comparison of consensus sequences of different paired domains. At the top of the Figure is drawn a schematic representation of protein±DNA contacts described in the crystallographic analysis of the Prd-paired-domain±DNA complex. Empty boxes indicate a-helices, shaded boxes indicates b-sheets and a thick line indicate a b-turn. Contacting amino acids are shown by single-letter code. Only direct amino acid±base contacts are shown. Empty circles indicate major groove contacts while red arrows indicate minor groove contacts. This scheme is aligned to all known consensus sequences for paired-domain proteins (top strands only are shown). Vertical lines between consensus sequences indicate conserved base-pairs. Numbering of the positions is shown at the bottom of the Figure.

FIG. 19 shows comparison of consensus sequences of different paired domains. At the top of the Figure is drawn a schematic representation of protein±DNA contacts described in the crystallographic analysis of the Prd-paired-domain±DNA complex. Empty boxes indicate a-helices, shaded boxes indicates b-sheets and a thick line indicate a b-turn. Contacting amino acids are shown by single-letter code. Only direct amino acid±base contacts are shown. Empty circles indicate major groove contacts while red arrows indicate minor groove contacts. This scheme is aligned to all known consensus sequences for paired-domain proteins (top strands only are shown). Vertical lines between consensus sequences indicate conserved base-pairs. Numbering of the positions is shown at the bottom of the Figure.

These results demonstrate that the oncogenic factor PAX2 suppresses DEFB1 expression. The suppression occurs at the transcriptional level. Furthermore, computational analysis of the DEFB1 promoter revealed the presence of a CCTTG (SEQ ID NO: 1) DNA binding site for the PAX2 transcriptional repressor next to the DEFB1 TATA box (FIG. 1). One of the hallmarks of defensin cytotoxicity is the disruption of membrane integrity. These results show that ectopic expression of DEFB1 in prostate cancer cells results in a loss of membrane potential due to compromised cell membranes. The same phenomenon is observed after inhibiting PAX2 protein expression. Therefore, suppression of PAX2 expression or function, results in the re-establishment of DEFB1 expression and subsequently DEFB1-mediated cell death. Also, the present results establish the utility of DEFB1 as a directed therapy for prostate cancer treatment, and potentially other cancer treatments, through innate immunity.

EXAMPLE 4

Effect of DEFB1 Expression in Implanted Tumor Cells

The anti-tumoral ability of DEFB1 is evaluated by injecting tumor cells that overexpress DEFB1 into nude mice.

DEFB1 is cloned into pBI-EGFP vector, which has a bidirectional tetracycline responsible promoter. Tet-Off Cell lines are generated by transfecting pTet-Off into DU145, PC3 and LNCaP cells and selecting with G418. The pBI-EGFP-DEFB1 plasmid is co-transfected with pTK-Hyg into the Tet-off cell lines and selected with hygromycin. Only single-cell suspensions with a viability of >90% are used. Each animal receives approximately 500,000 cells administered subcutaneously into the right flank of female nude mice. There are two groups, a control group injected with vector only clones and a group injected with the DEFB1 over-expressing clones. 35 mice are in each group as determined by a statistician. Animals are weighed twice weekly, tumor growth monitored by calipers and tumor volumes determined using the following formula: volume=0.5×(width)2×length. All animals are sacrificed by CO2 overdose when tumor size reaches 2 mm3 or 6 months following implantation; tumors are excised, weighed and stored in neutral buffered formalin for pathological examination. Differences in tumor growth between the groups are descriptively characterized through summary statistics and graphical displays. Statistical significance is evaluated with either the t-test or non-parametric equivalent.

EXAMPLE 5

Effect of PAX2 siRNA on Implanted Tumor Cells

Hairpin PAX2 siRNA template oligonucleotides utilized in the in vitro studies are utilized to examine the effect of the up-regulation of DEFB1 expression in vivo. The sense and antisense strand (see Table 3) are annealed and cloned into pSilencer 2.1 U6 hygro siRNA expression vector (Ambion) under the control of the human U6 RNA pol III promoter. The cloned plasmid is sequenced, verified and transfected into PC3, Du145, and LNCap cell lines. Scrambled shRNA is cloned and used as a negative control in this study. Hygromycin resistant colonies are selected, cells are introduced into the mice subcutaneously and tumor growth is monitored as described above.

EXAMPLE 6

Effect of Small Molecule Inhibitors of PAX2 Binding on Implanted Tumor Cells The DNA recognition sequence for PAX2 binding resides in the DEFB1 promoter between nucleotides −75 and −71 (+1 refers to the transcriptional start site). Short oligonucleotides complementary to the PAX2 DNA—binding domain are provided. Examples of such oligonucleotides include the 20-mer and 40-mer oligonucleotides containing the CCTTG (SEQ ID NO: 1) recognition sequence provided below. These lengths were randomly selected, and other lengths are expected to be effective as blockers of binding. As a negative control, oligonicleotides with a scrambled sequence (CTCTG)-(SEQ ID NO: 22) were designed to verify specificity. The oligonucleotides are transfected into the prostate cancer cells and the HPrEC cells with lipofectamine reagent or Codebreaker transfection reagent (Promega, Inc). In order to confirm DNA-protein interactions, double stranded oligonucleotides will be labeled with [$^{32}$P] dCTP and electrophoretic mobility shift assays are performed. In addition, DEFB1 expression is monitored by QRT-PCR and Western analysis following treatment with oligonucleotides. Finally, cell death is detected by MTT assay and flow cytometry as previously described.

```
Recognition Sequence #1:
                                        (SEQ ID NO: 18)
CTCCCTTCAGTTCCGTCGAC Recognition Sequence #2:
                                        (SEQ ID NO: 19)
CTCCCTTCACCTTGGTCGAC Scramble Sequence #1:
                                        (SEQ ID NO: 23)
CTCCCTTCACTCTGGTCGAC Recognition Sequence #3:
                                        (SEQ ID NO: 20)
ACTGTGGCACCTCCCTTCAGTTCCGTCGACGAGGTTGTGC Recognition Sequence #4:
                                        (SEQ ID NO: 21)
ACTGTGGCACCTCCCTTCACCTTGGTCGACGAGGTTGTGC Scramble Sequence #2:
                                        (SEQ ID NO: 24)
ACTGTGGCACCTCCCTTCACTCTGGTCGACGAGGTTGTGC
```

Further examples of oligonucleotides of the invention include:

```
Recognition Sequence #1:
                                        (SEQ ID NO: 25)
5'-AGAAGTTCACCCTTGACTGT-3'

Recognition Sequence #2:
                                        (SEQ ID NO: 26)
5'-AGAAGTTCACGTTCCACTGT-3'

Scramble Sequence #1:
                                        (SEQ ID NO: 27)
5'-AGAAGTTCACGCTCTACTGT-3'

Recognition Sequence #3:
                                        (SEQ ID NO: 28)
5'-TTAGCGATTAGAAGTTCACCCTTGACTGTGGCACCTCCC-3'

Recognition Sequence #4:
                                        (SEQ ID NO: 29)
5'-GTTAGCGATTAGAAGTTCACGTTCCACTGTGGCACCTCCC-3'

Scramble Sequence #2:
                                        (SEQ ID NO: 30)
5'-GTTAGCGATTAGAAGTTCACGCTCTACTGTGGCACCTCCC-3'
```

This set of alternative inhibitory oligonucleotides represents the recognition sequence for the PAX2 binding domain and homeobox. These include actual sequences from the DEFB1 promoter.

The PAX2 gene is required for the growth and survival of various cancer cells including prostate. In addition, the inhibition of PAX2 expression results in cell death mediated by the innate immunity component DEFB1. Suppression of DEFB1 expression and activity is accomplished by binding of the PAX2 protein to a CCTTG (SEQ ID NO: 1) recognition site in the DEFB1 promoter. Therefore, this pathway provides a viable therapeutic target for the treatment of prostate cancer. In this method, the sequences bind to the PAX2 DNA binding site and block PAX2 binding to the DEFB1 promoter thus allowing DEFB1 expression and activity. The oligonucleotide sequences and experiment described above are examples of and demonstrate a model for the design of additional PAX2 inhibitor drugs.

Given that the CCTTG (SEQ ID NO: 1) sequence exists in interleukin-3, interleukin-4, the insulin receptor and others, PAX2 regulates their expression and activity as well. Therefore the PAX2 inhibitors disclosed herein have utility in a number of other diseases including those directed related to inflammation including prostatitis and benign prostatic hypertrophy (BPH).

EXAMPLE 7

Loss of DEFB1 Expression Results in Increased Tumorigenesis

Generation of Loss of Function Mice:

The Cre/loxP system has been useful in elucidating the molecular mechanisms underlying prostate carcinogenesis. Here a DEFB1 Cre conditional KO is used for inducible disruption within the prostate. The DEFB1 Cre conditional KO involves the generation of a targeting vector containing loxP sites flanking DEFB1 coding exons, targeted ES cells with this vector and the generation of germline chimeric mice from these targeted ES cells. Heterozygotes are mated to prostate-specific Cre transgenics and heterozygous intercross is used to generate prostate-specific DEFB1 KO mice. Four genotoxic chemical compounds have been found to induce prostate carcinomas in rodents: N-methyl-N-nitrosourea (MNU), N-nitrosobis 2-oxopropyl amine (BOP), 3,2X-dimethyl-4-amino-biphenyl (MAB) and 2-amino-1-methyl-6-phenylimidazow 4,5-bxpyridine (PhIP). DEFB1-transgenic mice are treated with these carcinogenic compounds via intra-gastric administration or i.v. injection for prostate adenoma and adenocarcinoma induction studies. Prostate samples are studied for differences in tumor growth and changes gene expression though histological, immunohistological, mRNA and protein analyses.

Generation of GOF Mice:

For PAX2 inducible GOF mice, PAX2 GOF (bi-transgenic) and wild-type (mono-transgenic) littermates are administered doxycycline (Dox) from 5 weeks of age to induce prostate-specific PAX2 expression. Briefly, PROBASIN-rtTA mono-transgenic mice (prostate cell-specific expression of tet-dependent rtTA inducer) are crossed to our PAX2 transgenic responder lines. For, induction, bi-transgenic mice are fed Dox via the drinking water (500 mg/L freshly prepared twice a week). Initial experiments verify low background levels, good inducibility and cell-type specific expression of PAX2 and the EGFP reporter using transgenic founder line in bi-transgenic mice. Regarding experimental group sizes, 5-7 age- and sex-matched individuals in each group (wild-type and GOF) allow for statistical significance. For all animals in this study, prostate tissues are collected initially at weekly intervals for analysis and comparison, to determine carcinogenic time parameters.

PCR Genotyping, RT-PCR and qPCR:

PROBASIN-rtTA transgenic mice are genotyped using the following PCR primers and conditions: PROBASIN5 (forward) 5'-ACTGCCCATTGCCCAAACAC-3' (SEQ ID NO: 31); RTTA3 (reverse) 5'-AAAATCTTGCCAGCTTTCCCC-3' (SEQ ID NO: 32); 95° C. denaturation for 5 min, followed by 30 cycles of 95° C. for 30 sec, 57° C. for 30 sec, 72° C. for 30 sec, followed by a 5 min extension at 72° C., yielding a 600 bp product. PAX2 inducible transgenic mice are genotyped using the following PCR primers and conditions: PAX2 For 5'-GTCGGTTACGGAGCGGACCGGAG-3' (SEQ ID NO: 33); Rev5'IRES 5'-TAACATATAGACAAACGCACACCG-3' (SEQ ID NO: 34); 95° C. denaturation for 5 min, followed by 34 cycles of 95° C. for 30 sec, 63° C. for 30 sec. 72° C. for 30 sec, followed by a 5 min extension at 72° C., yielding a 460 bp product.

Immortomouse hemizygotes are be genotyped using the following PCR primers and conditions: Immol1, 5'-GCGCT-TGTGTC GCCATTGTATTC-3' (SEQ ID NO: 35); Immol2, 5'-GTCACACCACAGAAGTAAGGTTCC-3' (SEQ ID NO: 36); 94° C. 30 sec, 58° C. 1 min, 72° C. 1 min 30 sec, 30 cycles to yield a ~1 kb transgene band. For genotyping PAX2 knockout mice, the following PCR primers and conditions are used: PAX2 For 5'-GTCGGTTACGGAGCGGACCGGAG-3' (SEQ ID NO: 37); PAX2Rev 5'-CACAGAGCATTGGC-GATCTCGATGC-3' (SEQ ID NO: 38); 94° C. 1 min, 65° C. 1 min, 72° C. 30 sec, 36 cycles to yield a 280 bp band.

DEFB1 Peptide Animal Studies:

Six-week-old male athymic (nude) mice purchased from Charles River Laboratories are injected sub-cutaneously over the scapula with $10^6$ viable PC3 cells. One week after injection, the animals are randomly allocated to one of three groups—group I: control; group II: intraperitoneal injections of DEFB1, 100 µg/day, 5 days a week, for weeks 2-14; group III: intraperitoneal injections of DEFB1, 100 mg/day, 5 days a week, for weeks 8-14. Animals are maintained in sterile housing, four animals to a cage, and observed on a daily basis. At 10-day intervals, the tumors are measured by using calipers, and the volumes of the tumors are calculated by using $V=(L \times W2)/2$.

EXAMPLE 8

Targeting PAX2 Expression for the Chemoprevention of Intraepithelial Neoplasia and Cancer Cancer chemoprevention is defined as the prevention of cancer or treatment at the pre-cancer state or even earlier. The long period of progression to invasive cancer is a major scientific opportunity but also an economic obstacle to showing the clinical benefit of candidate chemopreventive drugs. Therefore, an important component of chemopreventive agent development research in recent years has been to identify earlier (than cancer) end points or biomarkers that accurately predict an agent's clinical benefit or cancer incidence—reducing effect. In many cancers, IEN is an early end point such as in prostate cancer. Given that the PAX2/DEFB1 pathway is deregulated during IEN and perhaps at even an earlier histopathological state makes it a powerful predictive biomarker and an excellent target for chemoprevention of cancer. Shown are a number of compounds that suppress PAX2 and increases DEFB1 expression that may have utility as chemoprevention agents for prostate cancer.

Figure 20:
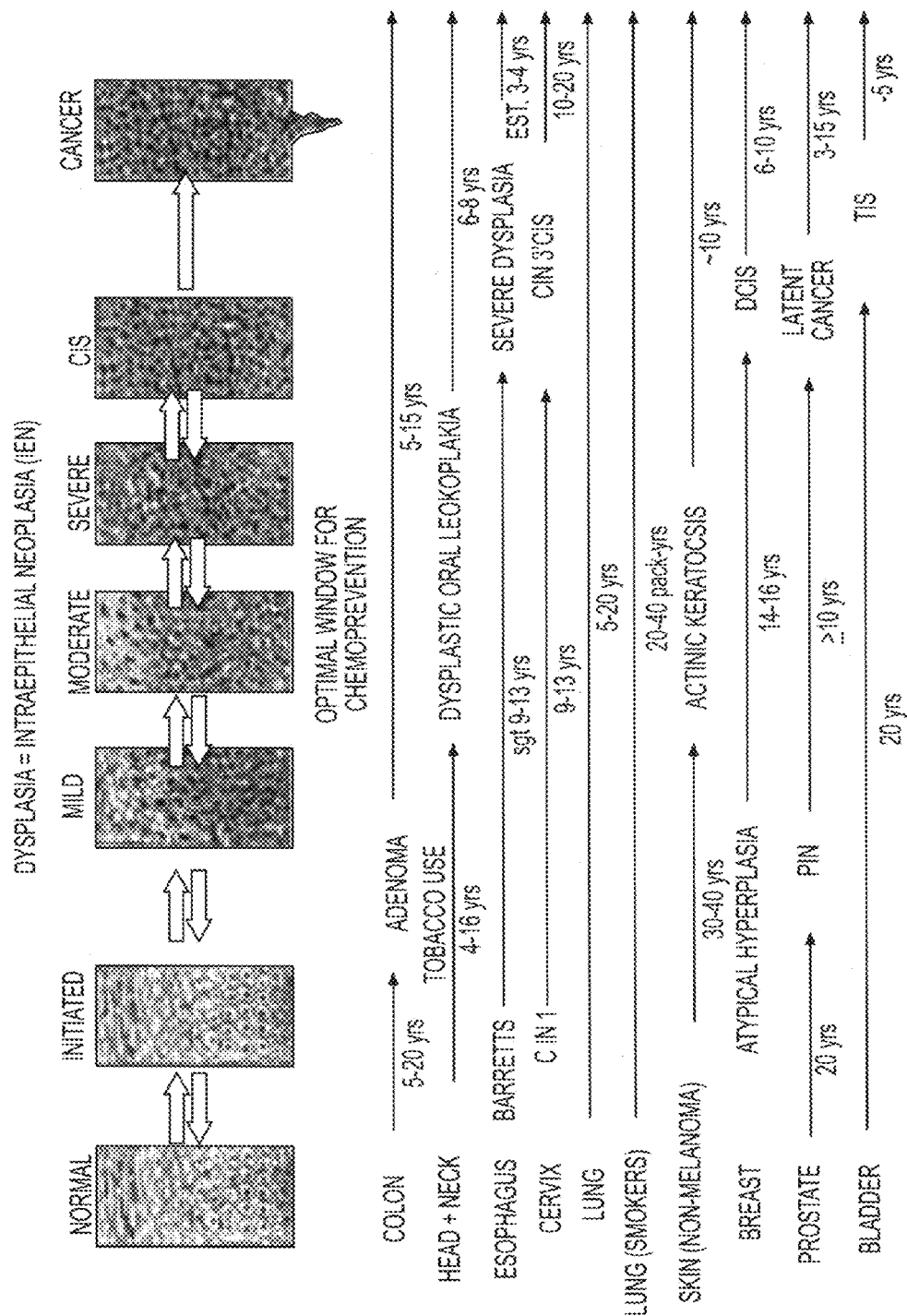
FIG. 20 shows targeting PAX2 as a chemopreventive strategy.

As shown in Table 1, the PAX2 gene is expressed in a number of cancers. In addition, several cancers have been shown to have aberrant PAX2 expression (FIG. 20). Angiotensin II (AngII) is a major regulator of blood pressure and cardiovascular homeostasis and is recognized as a potent mitogen. AngII mediates its biological effects through binding to two subtypes of receptors, Angiotensin Type I receptor (AT1R) and Angiotensin Type II receptor (AT2R) which belong to the super-family of G-protein-coupled receptors but have different tissue distribution and intracellular signaling pathways. In addition to its effects on blood pressure, AngII has been shown to play a role in various pathological situations involving tissue remodeling, such as wound healing, cardiac hypertrophy and development. In fact, recent studies have revealed local expression of several components of the Renin-Angiotensin System (RAS) in various cancer cells and tissues including the prostate. Upregulation of AT1R provides a considerable advantage to cancer cells that have learn to evade apoptosis and growth regulatory elements. To date a number of cancers have been shown to aberrantly express PAX2. Chemoprevention via target PAX2 expression may have a significant impact on cancer related deaths Materials and Methods Cell Culture:

The cell lines DU145, LnCap and PC3 were cultured as described in Example 1. The hPrEC cells were cultured in prostate epithelium basal media (Cambrex Bio Science, Inc., Walkersville, Md.) and maintained at 37° C. and 5% CO2.

Reagents and Treatments:

Cells were treated with 5 or 10 uM of AngII, 5 uM of the ATR1 antagonist Los, 5 uM of the ATR2 antagonist PD123319, 25 uM of the MEK inhibitor U0126, 20 uM of the MEK/ERK inhibitor PD98059 or 250 µM of the AMP kinase inducer AICAR.

Western Analysis:

Western blot was performed as described in Example 2. Blots were then probed with primary antibody (anti-PAX2,-phospho-PAX2, -JNK, -phospho-JNK, -ERK1/2, or -phospho-ERK1/2) (Zymed, San Francisco, Calif.) at 1:1000-2000 dilutions. After washing, the membranes were incubated with anti-rabbit antibody conjugated to horseradish peroxidase (HRP) (dilution 1:5000; Sigma), and signal detection was visualized using chemilluminescence reagents (Pierce) on an Alpha Innotech Fluorchem 8900. As a control, blots were stripped and re-probed with mouse anti-β-actin primary antibody (1:5000; Sigma-Aldrich) and HRP-conjugated anti-mouse secondary antibody (1:5000; Sigma-Aldrich), and signal detection was again visualized.

QRT-PCR Analysis:

Quantitative real-time RT-PCR was performed as described in Example 1 to verify changes in gene expression following PAX2 knockdown in PC3 and DU145 prostate cancer cell lines and the hPrEC normal prostate epithelial cells. Forty cycles of PCR were performed under standard conditions using an annealing temperature of 60° C. Quantification was determined by the cycle number where exponential amplification began (threshold value) and averaged from the values obtained from the triplicate repeats. There was an inverse relationship between message level and threshold value. In addition, GAPDH was used as a housekeeping gene to normalize the initial content of total cDNA. Relative expression was calculated as the ratio between each genes and GAPDH. All reactions, were carried out in triplicate.

Thymidine Incorporation:

Proliferation of cells was determined by [$^3$H] thymidine ribotide ([3H] TdR) incorporation into DNA. 0.5×106 cells/well of suspension DU145 cells were plated in their appropriate media. Cells were incubated for 72 h with or without the presence of AngII at the indicated concentrations. Cells were exposed to 37 kBq/ml [methyl-3H] thymidine in the same medium for 6 h. The adherent cells were fixed by 5% trichloroacetic acid and lysed in SDS/NaOH lysis buffer overnight. Radioactivity was measured by Beckman LS3801 liquid scintillation counter (Canada). Suspension cell culture was harvested by cell harvester (Packard instrument Co., Meriden, Conn.), and radioactivity was measured by 1450 microbeta liquid scintillation counter (PerkinElmer Life Sciences).

Results

Figure 21:
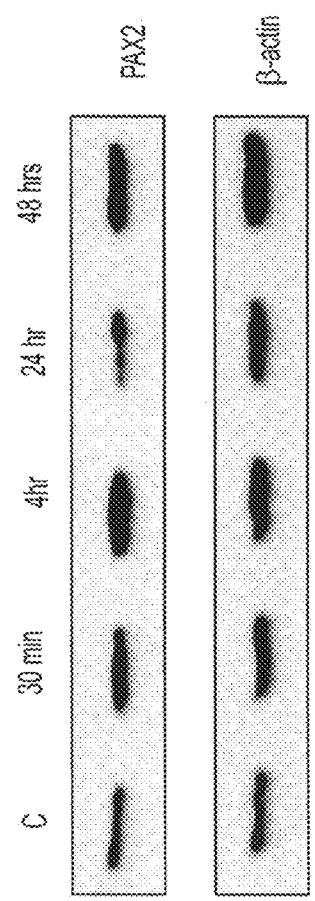
FIG. 21 shows effect of angiotensin II (Ang II) on PAX2 expression in DU145 Cells.
Figure 22A:
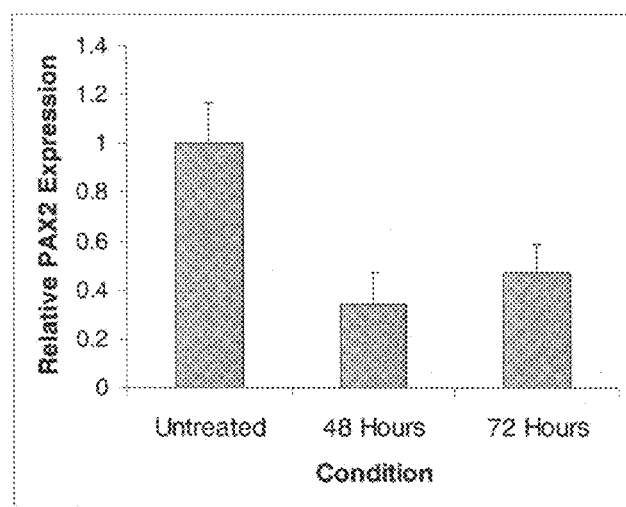
FIG. 22A shows effect of Losartan (Los) on PAX2 expression in DU145.
Figure 22B:
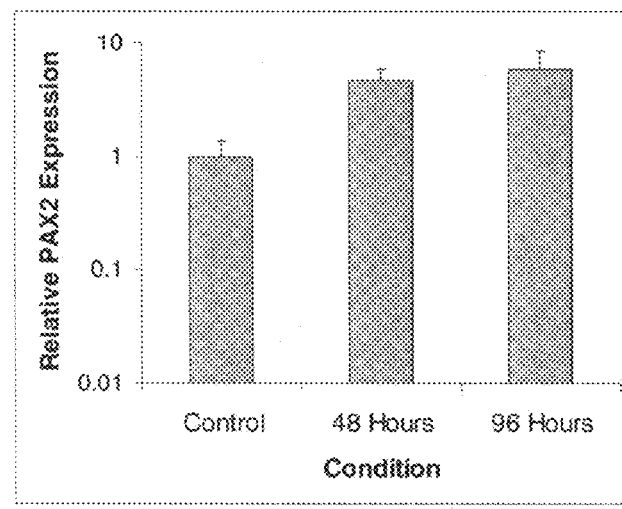

To investigate the effect of AngII on PAX2 expression in DU145 prostate cancer cells, PAX2 expression was examined following treatment with AngII over a 30 min to 48 hour period. As shown in FIG. 21, PAX2 expression progressively increased over time following AngII treatment. Blocking RAS signaling by treating DU145 with Los significantly reduced PAX2 expression. Here, PAX2 expression was 37% after 48 hours and was 50% after 72 hours of Los treatment compared to untreated control DU145 cells (FIG. 22A). It is known that the AT2R receptor oppose the action of the AT1R. Therefore, the effect of blocking the AT2R receptor on PAX2 expression was examined. Treatment of DU145 with the AT2R blocker PD123319 resulted in a 7-fold increase in PAX2 expression after 48 hours and an 8-fold increase after 96 hours of treatment (FIG. 22B). Collectively, these findings demonstrate that PAX2 expression is regulated by the ATR1 receptor.

Figure 23:
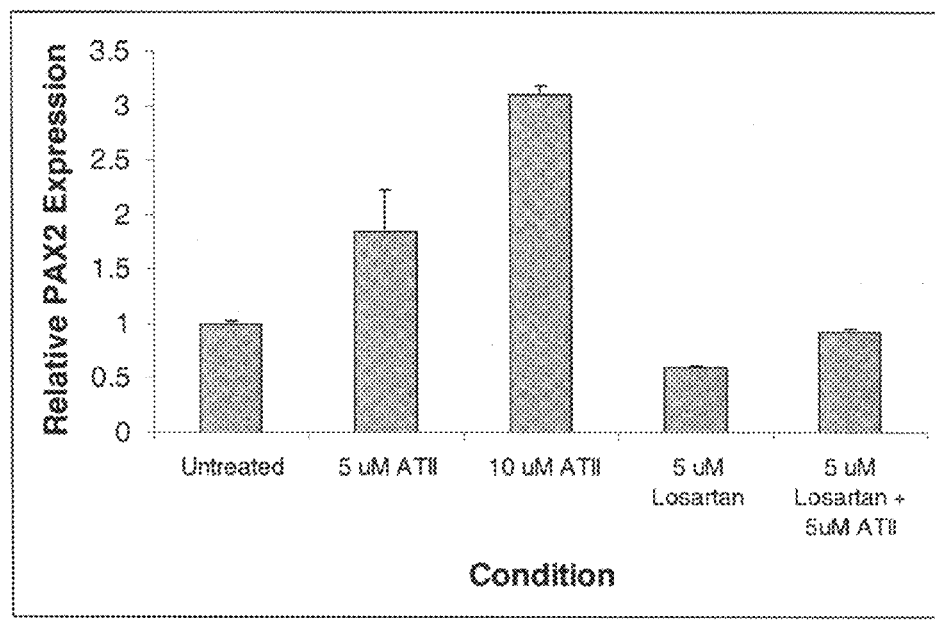
FIG. 23 shows Los blocks AngII effect on PAX2 expression in DU145.

It is known that AngII directly affects the proliferation of prostate cancer cells through AT1R—mediated activation of MAPK and STAT3 phosphorylation. Treatment of DU145 with AngII resulted in a two- to three-fold increase in proliferation rate (FIG. 23). However, treatment with Los decreased proliferated rates by 50%. In addition, blocking the AT1R receptor by pre-treating with Los for 30 min suppressed the effect of AngII on proliferation.

Figure 24:
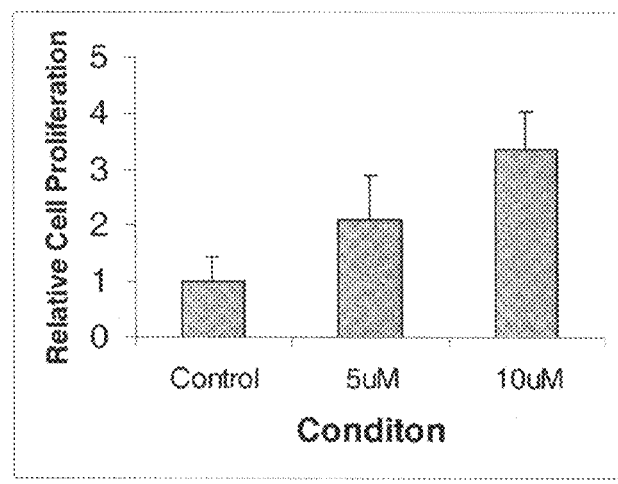
FIG. 24 shows AngII increases DU145 cell proliferation.
Figure 25A:
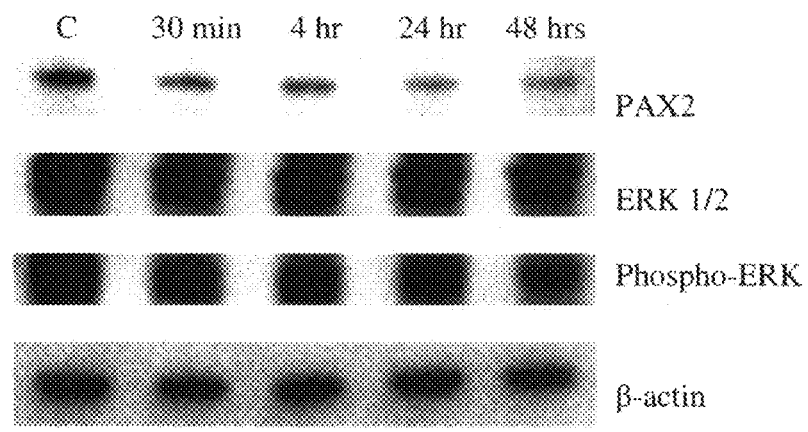
FIGS. 25A, 25B and 25C show effect of Los and MAP Kinase inhibitors on PAX2 expression in DU145 cells.
Figure 25B:
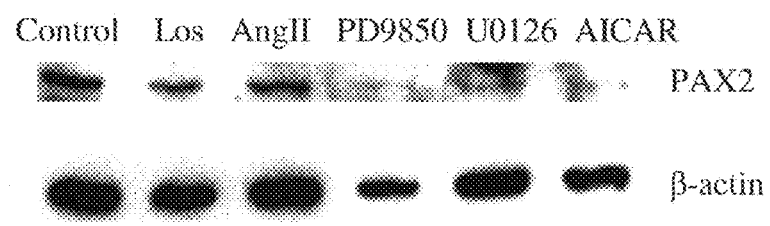
Figure 25C:
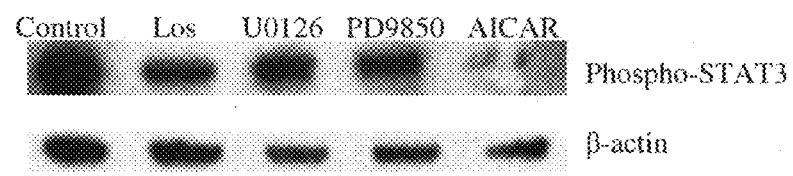

To further examine the role of the AT1R signaling in the regulation of PAX2 expression and activation, the effect of blocking various components of the MAP kinase signaling pathway on PAX2 expression was examined. Here, DU145 cells treated with the MEK inhibitor U0126 resulted in a significant reduction of PAX2 expression (FIG. 24). Furthermore, treatment with MEK/ERK inhibitor PD98059 also resulted in decreased PAX2. Treatment of DU145 cells with Los had no effect on ERK protein levels, but reduced the amount of phospho-ERK (FIG. 25A). However, treatment of DU145 with Los resulted in a significant reduction of PAX2 expression. Similar results were observed with U0126 and PD98059 (FIG. 25B). It is also known that PAX2 expression is regulated by STAT3 which is a down-stream target of ERK. Treatment of DU145 with Los, U0126, and PD98059 reduced phospho-STAT3 protein levels (FIG. 25C). These results demonstrate that PAX2 is regulated via AT1R in prostate cancer cells.

Figure 26A:
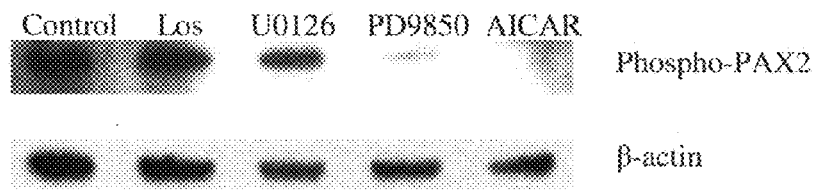
FIGS. 26A and 26B show effect of Los and MEK kinase inhibitors on PAX2 activation in DU145 cells
Figure 26B:
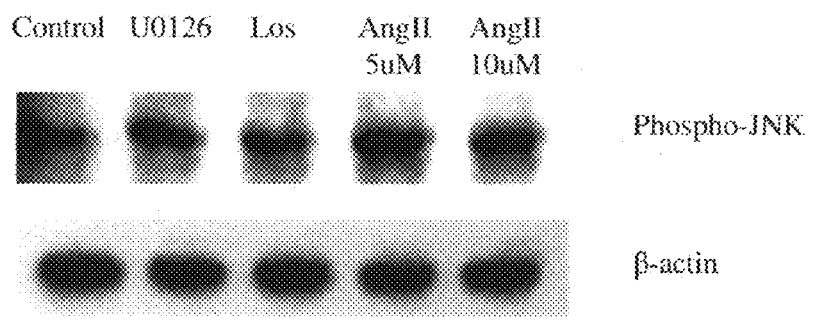

In addition, the effect of AT1R signaling on PAX2 activation by JNK was examined. Treatment of DU145 with Los, U0126, and PD98059 all resulted in a significant decrease or suppression of phospho-PAX2 protein levels (FIG. 26A). However, Los and U0126 did not decrease phospho-JNK protein levels (FIG. 26B). Therefore, the decrease in phospho-PAX2 appears to be due to decreased PAX2 levels, but not decreased phosphorylation.

5-Aminoimidazole-4-carboxamide-1-β-4-ribofuranoside (AICAR) is widely used as an AMP-kinase activator, which regulates energy homeostasis and response to metabolic stress. Recent reports have indicated anti-proliferative and pro-apoptotic action of activated AMPK using pharmacological agents or AMPK overexpression. AMPK activation has been shown to induce apoptosis in human gastric cancer cells, lung cancer cells, prostate cancer, pancreatic cells, and hepatic carcinoma cells and enhance oxidative stress induced apoptosis in mouse neuroblastoma cells, by various mechanisms that include inhibition of fatty acid synthase pathway and induction of stress kinases and caspase 3. In addition, treatment of PC3 prostate cancer cells increased expression of p21, p27, and p53 proteins and inhibition of PI3K-Akt pathway. All of these pathways are directly or indirectly regulated by PAX2. Treatment of prostate cancer cells with AICAR resulted in the suppression of PAX2 pression expression (FIG. 25B) as well as its activated form phosphor-PAX2 (FIG. 26A). In addition, phospho-STAT3 which regulated PAX2 expression was also suppressed (FIG. 25C).

Figure 27:
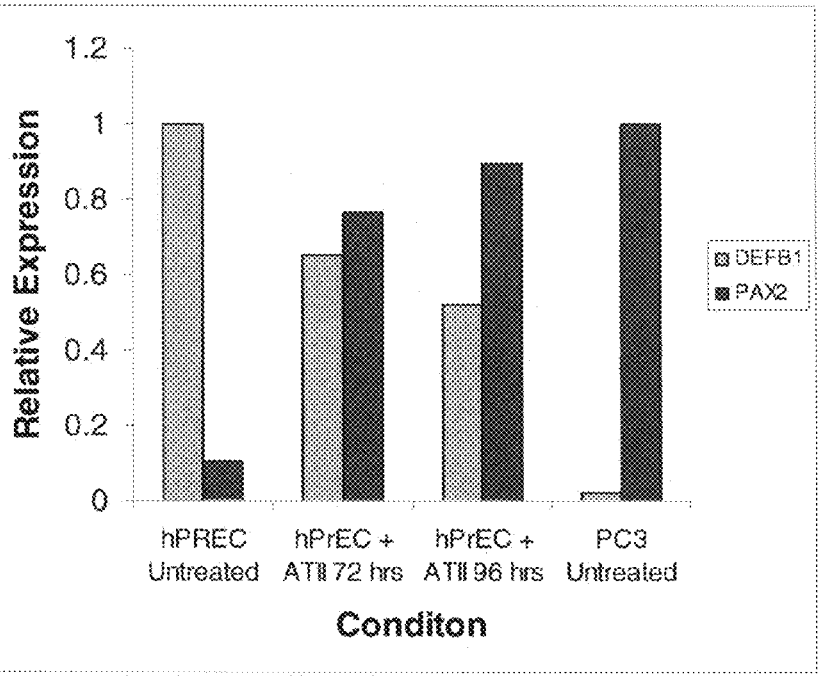
FIG. 27 shows AngII increases PAX2 and decreases DEFB1 expression in hPrEC cells.

Finally, it was hypothesized that aberrant RAS signaling which leads to upregulation and overexpression of PAX2 suppresses the expression of the DEFB1 tumor suppressor gene. To investigate this, the normal prostate epithelial primary culture hPrEC was treated with AngII and examined both PAX2 and DEFB1 expression levels. An inverse relationship between DEFB1 and PAX2 expression was discovered in normal prostate cells versus prostate cancer cells. As shown in FIG. 27, untreated hPrEC exhibited 10% relative PAX2 expression compared to expression in PC3 prostate cancer cells. Conversely, untreated PAX2 exhibited only 2% relative DEFB1 expression compared to expression in hPrEC. Following 72 hours of treatment with 10 uM of AngII, there was a 35% decrease in DEFB1 expression compared to untreated hPrEC, and by 96 hours there was a 50% decrease in DEFB1 expression compared to untreated hPrEC cells. However, there was 66% increase in PAX2 expression at 72 hours, and by 96 hours there was a 79% increase in PAX2 expression compared to untreated hPrEC cells. Furthermore, the increase in PAX2 expression in hPrEC after 72 hours was 77% of PAX2 levels observed in PC3 prostate cancer cells. After 96 hours of AngII treatment PAX2 expression was 89% of PAX2 expression in PC3. These results demonstrate that deregulated RAS signaling suppresses DEFB1 expression via the upregulation of PAX2 expression in prostate cells.

Figure 28:
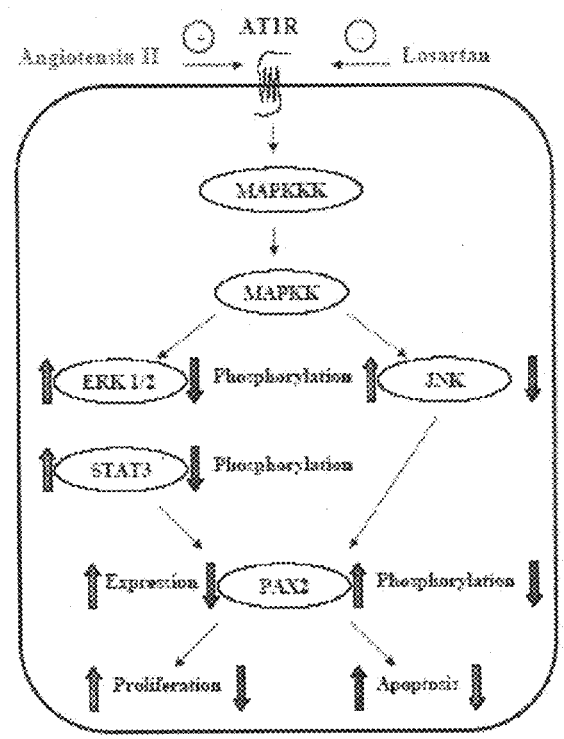
FIG. 28 shows schematic of AngII signaling and PAX2 prostate cancer.
Figure 29:
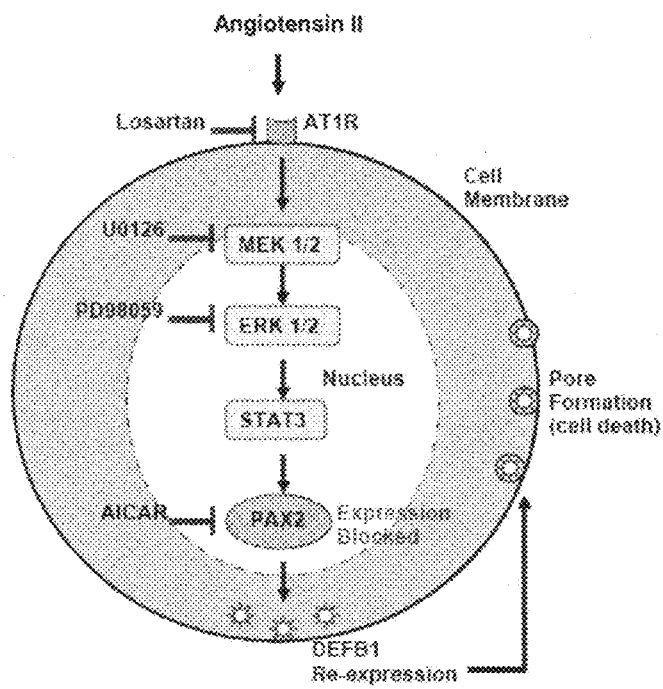
FIG. 29 shows schematic of blocking PAX2 expression as a therapy for prostate cancer.

Inhibition of apoptosis is a critical pathophysiological factor that contributes to the development of cancer. Despite significant advances in cancer therapeutics, little progress has been made in the treatment of advanced disease. Given that carcinogenesis is a multiyear, multistep, multipath disease of progression, chemoprevention through the use of drug or other agents to inhibit, delay, or reverse this process has been recognized as a very promising area of cancer research. Successful drug treatment for the chemoprevention of prostate cancer requires the use of therapeutics with specific effects on target cells while maintaining minimal clinical effects on the host with the overall goal of suppressing cancer development. Therefore, understanding the mechanisms in early stage carcinogenesis is critical in determining the efficacy of a specific treatment. The significance of aberrant PAX2 expression and its abrogation of apoptosis, with subsequent contribution to tumor formation, suggest that it may be a suitable target for prostate cancer treatment. PAX2 was regulated by the AT1R in prostate cancer (FIG. 28). In this, deregulated RAS signaling resulted in increased PAX2 oncogene expression, and a decrease in the expression of DEFB1 tumor suppressor. Therefore, the use of AT1R antagonists decreases PAX2 expression and results in increased prostate cancer cell death via re-expression of DEFB1 (FIG. 29). These results offer a novel finding that targeting PAX2 expression via the Renin-Angiotensin signaling pathway, the AMP Kinase pathway, or other methods involving the inactivation of the PAX2 protein (i.e. anti-PAX2 antibody vaccination) may be a viable target for cancer prevention (Table 4).

TABLE 4

Compounds Utilized to Inhibit PAX2 Expression for Chemoprevention

|  | NAME | Drug Class |
| --- | --- | --- |
| Drug 1 | Losartan | Angiotensin Type 1 Receptor blocker |
| Drug 2 | PD123319 | Angiotensin Type 2 Receptor blocker |
| Drug 3 | U0126 | MEK inhibitor |
| Drug 4 | PD98059 | MEK/ERK inhibitor |
| Drug 5 | AICAR | AMP kinase inducer |
|  | Target | Drug Function |
| Drug A | Anti-PAX2 Antibody | PAX2 Vaccine |
| Drug B | Angiotensinogen | Renin-AngII pathway inhibitor |
| Drug C | Angiotensin Converting Enzyme | Renin-AngII pathway inhibitor |

This study demonstrates that the upregulation of the PAX2 oncogene in prostate cancer is due to deregulated RAS signaling. PAX2 expression is regulated by the ERK 1/2 signaling pathway which is mediated by the Angiotensin type I receptor. In addition, blocking the AT1R with Losartan (Los) suppresses PAX2 expression. In addition, AICAR which is an AMPK activator has also shown promise as a potential PAX2 inhibitor. Collectively, these studies strongly implicate these classes of drugs as potential suppressors of PAX2 expression and may ultimately serve as novels chemoprevention agents.

EXAMPLE 9

PAX2-DEFB1 Expression Level as a Grading Tool for Prostate Tissue and Predictor of Prostate Cancer Development Materials and Methods
QRT-PCR Analysis:
Prostate sections were collected from patients that underwent radical prostatectomies. Following pathological examination, laser capture microdisection was performed to isolate areas of Normal, Proliferative Intraepithelial Neoplasia (PIN) and Cancerous tissue. QRT-PCR was performed as previously described to assess expression. DEFB1 and PAX2 expression in each region and GAPDH was used as an internal control.

Blood Collection and RNA Isolation:
For QRT-PCR, blood (2.5 ml) from each individual was colleted into a PAXgene™ Blood RNA tube (QIAGEN) following the manufacturer's protocol. Whole blood was thoroughly mixed with PAXgene stabilization reagent and stored at room temperature for 6 hours prior to RNA extraction. Total RNA was then extracted using the PAXgene™ Blood RNA kit according to the manufacturer's directions (QIAGEN). In order to remove contaminating genomic DNA, total RNA samples absorbed to the PAXgene™ Blood RNA System spin column was incubated with DNase I (QIAGEN) at 25° C. for 20 min to remove genomic DNA. Total RNA was eluted, quantitated, and QRT-PCR is performed as previously mentioned to compare PAX2 and DEFB1 expression ratios.

Figure 30:
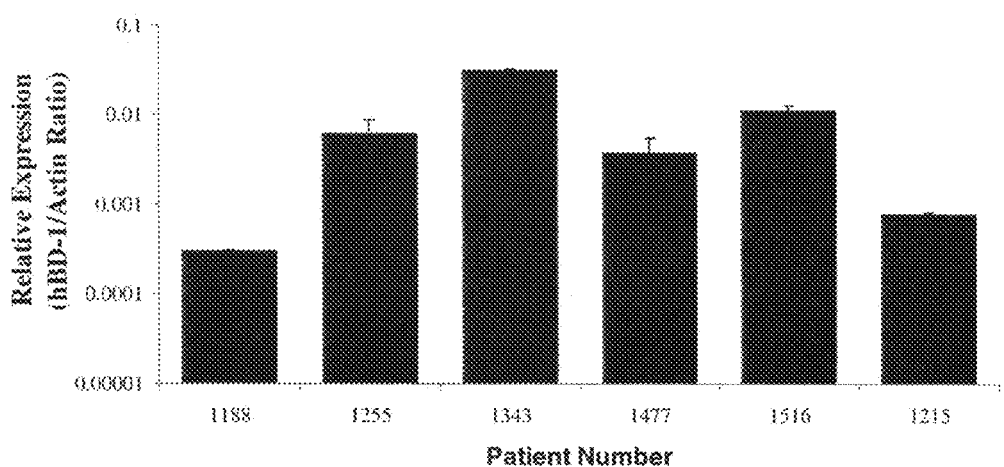
FIG. 30 shows comparison of DEFB1 and PAX2 expression with Gleason Score.

Results
QRT-PCR analysis of LCM normal tissue demonstrated that patients with relative DEFB1 expression levels greater than 0.005 have a lower Gleason Score compared to those with expression levels lower than 0.005 (FIG. 30). Thus, there is an inverse relationship between DEFB1 expression and Gleason score. Conversely, there was a positive correlation between PAX2 expression and Gleason score in malignant prostate tissue and PIN (FIG. 30, panel B).

Figure 31A:
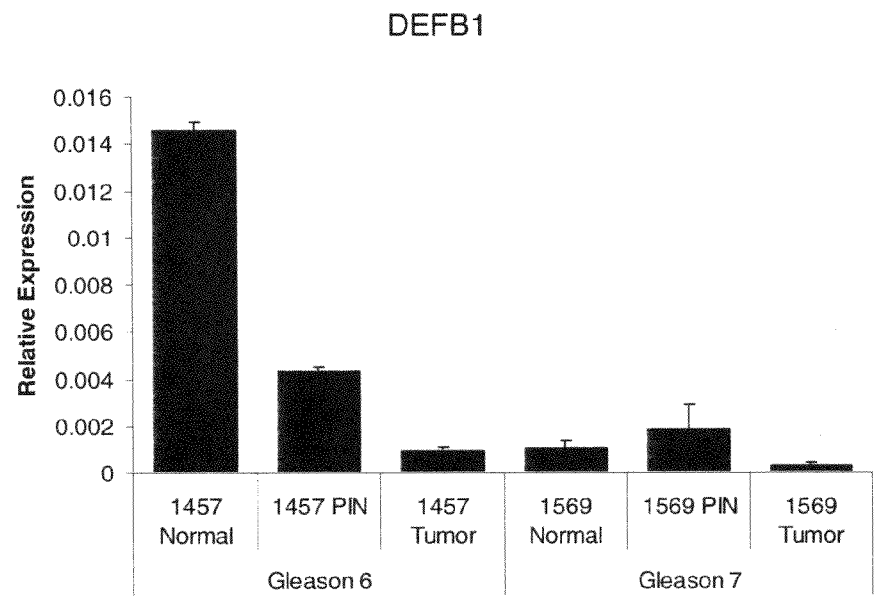
FIGS. 31A and 31B show PAX2-DEFB1 ratio as a predictive factor for prostate cancer development.
Figure 31B:
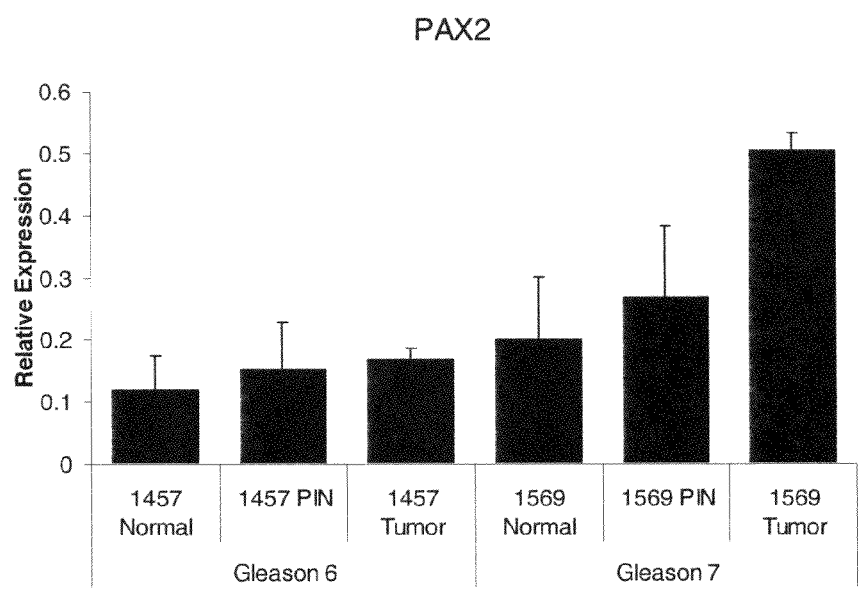
Figure 32:
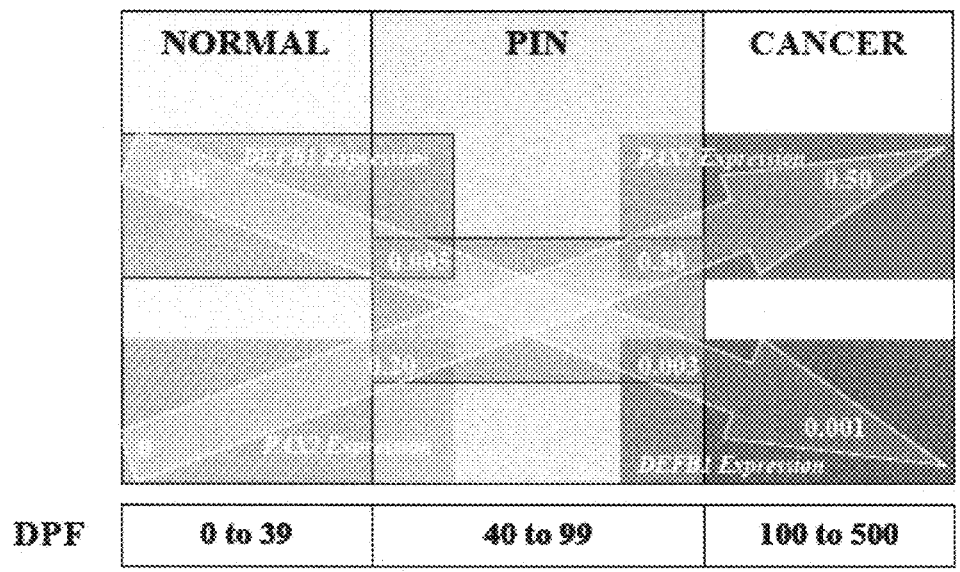
FIG. 32 shows the Donald Predictive Factor (DPF) is based on the relative PAX2-DEFB1 expression ratio.

The PAX2 and DEFB1 expression levels in normal, PIN and cancerous tissues from separate patients were calculated and compared (FIGS. 31A and 31B). Overall, PAX2 expression levels relative to GAPDH internal control ranged between 0 and 0.2 in normal (benign) tissue, 0.2 and 0.3 in PIN, and between 0.3 and 0.5 in cancerous (malignant) tissue (FIG. 32). For DEFB1 there was an inverse relationship compared to PAX2. Here, DEFB1 expression levels relative to GAPDH internal control ranged between 0.06 and 0.005 in normal (benign) tissue, 0.005 and 0.003 in PIN, and between 0.003 and 0.001 in cancerous (malignant) tissue. Therefore, disclosed is a predictive scale, designated as Donld Predictive Factor (DPF), which utilizes the PAX2-DEFB1 expression ratio as a prognosticator of benign, precancerous (PIN) and malignant prostate tissue. Tissues with PAX2-DEFB1 ratios between 0 and 39 based on the DPF will represent normal (pathologically benign). Tissue with a PAX2-DEFB1 ratio between 40 and 99 will represent PIN (pre-cancerous) based on the DPF scale. Finally, tissue with a PAX2-DEFB1 ratio between 100 and 500 will be malignant (low to high grade cancer).

There currently is a critical need for predictive biomarkers for prostate cancer development. It is known that the onset of prostate cancer occurs long before the disease is detectable by current screening methods such as the PSA test or the digital rectal exam. It is thought that a reliable test which could monitor the progression and early onset of prostate cancer would greatly reduce the mortality rate through more effective disease management. Disclosed herein is a predictive index to allow physicians to know well in advance the pathological state of the prostate. The DPF measures the decrease in the PAX2-DEFB1 expression ratio associated with prostate disease progression. This powerful measure can not only predict the likelihood of a patient developing prostate cancer, but also may pinpoint the early onset of pre-malignant cancer. Ultimately, this tool can allow physicians to segregate which patients have more aggressive disease from those which do not.

The identification of cancer-specific markers has been utilized to help identify circulating tumor cells (CTCs). There is also emerging evidence which demonstrates that detection of tumor cells disseminated in peripheral blood can provide clinically important data for tumor staging, prognostication, and identification of surrogate markers for early assessment of the effectiveness of adjuvant therapy. Furthermore, by comparing gene expression profiling of all circulating cells, one can examine the expression of the DEFB1 and PAX2 genes which play a role in "immunosurveillance" and "cancer survival", respectively as a prognosticator for the early detection of prostate cancer.

EXAMPLE 10

Functional Analysis of the Host Defense Peptide Human Beta Defensin-1: New Insight into its Potential Role in Cancer Materials and Methods Cell Culture:

The prostate cancer cell lines were cultured as described in Example 1. The hPrEC primary culture was obtained from Cambrex Bio Science, Inc. (Walkersville, Md.) and cells were grown in prostate epithelium basal media.

Tissue Samples and Laser Capture Microdissection:

Prostate tissues were obtained from patients who provided informed consent prior to undergoing radical prostatectomy. Samples were acquired through the Hollings Cancer Center tumor bank in accordance with an Institutional Review Board-approved protocol. This included guidelines for the processing, sectioning, histological characterization, RNA purification and PCR amplification of samples. Prostate specimens received from the surgeons and pathologists were immediately frozen in OCT compound. Each OCT block was cut to produce serial sections which were stained and examined. Areas containing benign cells, prostatic intraepithelial neoplasia (PIN), and cancer were identified and used to guide our selection of regions from unstained slides using the Arcturus PixCell II System (Sunnyvale, Calif.). Caps containing captured material were exposed to 20 µl of lysate from the Arcturus Pico Pure RNA Isolation Kit and processed immediately. RNA quantity and quality was evaluated using sets of primers that produce 5' amplicons. The sets include those for the ribosomal protein L32 (the 3' amplicon and the 5' amplicon are 298 bases apart), for the glucose phosphate isomerase (391 bases apart), and for the glucose phosphate isomerase (842 bases apart). Ratios of 0.95 to 0.80 were routinely obtained for these primer sets using samples from a variety of prepared tissues. Additional tumor and normal samples were grossly dissected by pathologists, snap frozen in liquid nitrogen and evaluated for hBD-1 and cMYC expression.

Cloning of hBD-1 Gene:

hBD-1 cDNA was generated from RNA by reverse transcription-PCR using primers generated from the published hBD-1 sequence (accession no. U50930) (Ganz, 2004). The PCR primers were designed to contain ClaI and KpnI restriction sites. hBD-1 PCR products were restriction digested with ClaI and KpnI and ligated into a TA cloning vector. The TA/hBD1 vector was then transfected into the XL-1 Blue strain of $E.\ coli$ by heat shock and individual clones were selected and expanded. Plasmids were isolated by Cell Culture DNA Midiprep (Qiagen, Valencia, Calif.) and sequence integrity verified by automated sequencing. The hBD-1 gene fragment was then ligated into the pTRE2 digested with ClaI and KpnI, which served as an intermediate vector for orientation purposes. The pTRE2/hBD-1 construct was digested with ApaI and KpnI to excise the hBD-1 insert. The insert was ligated into pIND vector of the Ecdysone Inducible Expression System (Invitrogen, Carlsbad, Calif.) also double digested with ApaI and KpnI. The construct was transfected into $E.\ coli$ and individual clones were selected and expanded. Plasmids were isolated and sequence integrity of pIND/hBD-1 was again verified by automated sequencing.

Transfection:

Cells ($1 \times 10^6$) were seeded onto 100-mm Petri dishes and grown overnight. Next, the cells were co-transfected using Lipofectamine 2000 (Invitrogen) with 1 µg of pvgRXR plasmid, which expresses the heterodimeric ecdysone receptor, and 1 µg of the pIND/hBD-1 vector construct or pIND/β-galactosidase (β-gal) control vector in Opti-MEM media (Life Technologies, Inc.). Transfection efficiency was determined by inducing β-gal expression with Ponasterone A (PonA) and staining cells with a β-galactosidase detection kit (Invitrogen). Assessment of transfection efficiency by counting positive staining (blue) colonies which demonstrated that 60-85% of cells expressed β-galactosidase for the cell lines.

Immunocytochemistry:

In order to verify hBD-1 protein expression, DU145 and hPrEC cells were seeded onto 2-chamber culture slides (BD Falcon, USA) at $1.5\text{-}2 \times 10^4$ cells per chamber. DU145 cells transfected with pvgRXR alone (control) or with the hBD-1 plasmid were induced for 18 h with media containing 10 µM PonA, while untransfected cells received fresh growth media. Following induction, cells were washed in 1×PBS and fixed for 1 h at room temperature with 4% paraformaldehyde. Cells were then washed six times with 1×PBS and blocked in 1×PBS supplemented with 2% BSA, 0.8% normal goat serum (Vector Laboratories, Inc., Burlingame, Calif.) and 0.4% Triton-X 100 for 1 h at room temperature. Next, cells were incubated overnight in primary rabbit anti-human BD-1 polyclonal antibody (PeproTech Inc., Rocky Hill, N.J.) diluted 1:1000 in blocking solution. Following this, cells were washed six times with blocking solution and incubated for 1 h at room temperature in Alexa Fluor 488 goat anti-rabbit IgG (H+L) secondary antibody at a dilution of 1:1000 in blocking solution. After washing cells with blocking solution six times, coverslips were mounted with Gel Mount (Biomeda, Foster City, Calif.). Finally, cells were viewed under differential interference contrast (DIC) and under laser excitation at 488 nm. The fluorescent signal was analyzed by confocal microscopy (Zeiss LSM 5 Pascal) using a 63× DIC oil lens with a Vario 2 RGB Laser Scanning Module. The digital images were exported into Photoshop CS Software (Adobe Systems) for image processing and hard copy presentation.

RNA Isolation and Quantitative RT-PCR:

QRT-PCR was performed as previously described (Gibson et al., 2007). Briefly, total RNA (0.5 µg per reaction) from tissue sections were reverse transcribed into cDNA utilizing random primers (Promega). Two-step QRT-PCR was performed on cDNA generated using the MultiScribe Reverse Transcriptase from the TaqMan Reverse Transcription System and the SYBR Green PCR Master Mix (Applied Biosystems, Foster City, Calif.). The primer pairs for hBD-1 and c-MYC were generated from the published sequences (Table 5). Forty cycles of PCR were performed under standard conditions using an annealing temperature of 56.4° C. for hBD-1 and c-MYC and 55° C. for PAX2. In addition, β-actin (Table 5) was amplified as a housekeeping gene to normalize the initial content of total cDNA. Gene expression in benign prostate tissue samples was calculated as the expression ratio compared to β-actin. Levels of hBD-1 expression in malignant prostate tissue, hPREC prostate primary culture, and prostate cancer cell lines before and after induction were calculated relative to the average level of hBD-1 expression in hPrEC cells. As a negative control, QRT-PCR reactions without cDNA template were also performed. All reactions were run a minimum of three times.

TABLE 5

Sequences of QRT-PCR primers

| | Sense (5'-3') | Antisense (5'-3') |
|---|---|---|
| β-Actin | CCTGGCACCCAGCACAAT (SEQ ID NO: 51) | GCCGATCCACACGGAGTACT (SEQ ID NO: 52) |
| hBD-1 | TCAGCAGTGGAGGGCAATG (SEQ ID NO: 65) | CCTCTGTAACAGGTGCCTTG AAT (SEQ ID NO: 66) |
| cMYC | ACAGCAAACCTCCTCACAG CC (SEQ ID NO: 67) | TGGAGACGTGGCACCTCTTG (SEQ ID NO: 68) |

MTT Cell Viability Assay:

To examine the effects of hBD-1 on cell growth, metabolic 3-[4,5-dimethylthiazol-2yl]-2,5-diphenyl tetrazolium bromide (MTT) assay was performed. DU145, LNCaP, PC3 and PC3/AR+ cells co-transfected with pvgRXR plasmid and pIND/hBD-1 construct or control pvgRXR plasmid were seeded onto a 96-well plate at 1-5×10³ cells per well. Twenty-four hours after seeding, fresh growth medium was added containing 10 µM Pon A daily to induce hBD-1 expression for 24, 48 and 72 h after which the MTT assay was performed according to the manufacturer's instructions (Promega). Reactions were performed three times in triplicate.

Analysis of Membrane Integrity:

Acridine orange (AO)/ethidium bromide (EtBr) dual staining was performed to identify changes in cell membrane integrity, as well as apoptotic cells by staining the condensed chromatin. AO stains viable cells and early apoptotic cells, whereas EtBr stains late stage apoptotic cells that have compromised membranes. Briefly, PC3, DU145 and LNCaP cells were seeded into 2-chamber culture slides (BD Falcon). Cells transfected with empty plasmid or hBD-1 plasmid were induced for 24 or 48 h with media containing 10 µM Pon A, while control cells received fresh growth media at each time point. After induction, cells were washed once with PBS and stained with 2 ml of a mixture (1:1) of AO (Sigma, St. Louis, Mo.) and EtBr (Promega) (5 µg/ml) solution for 5 min and were again washed with PBS.

Fluorescence was viewed by a Zeiss LSM 5 Pascal Vario 2 Laser Scanning Confocal Microscope (Carl Zeiss). The excitation color wheel contains BS505-530 (green) and LP560 (red) filter blocks which allowed for the separation of emitted green light from AO into the green channel and red light from EtBr into the red channel. The laser power output and gain control settings within each individual experiment were identical between control and hBD-1 induced cells. The excitation was provided by a Kr/Ar mixed gas laser at wavelengths of 543 nm for AO and 488 nm for EtBr. Slides were analyzed under 40× magnification and digital images were stored as uncompressed TIFF files and exported into Photoshop CS software (Adobe Systems) for image processing and hard copy presentation.

Flow Cytometry:

PC3 and DU145 cells transfected with the hBD-1 expression system were grown in 60-mm dishes and induced for 12, 24, and 48 h with 10 µM Pon A. The cells were harvested and analyzed by flow cytometry as described in Example 1.

Caspase Detection:

Detection of caspase activity in the prostate cancer cell lines was performeds described in Example 1.

siRNA Silencing of PAX2:

SiRNA knock-down and verification was performed as described in Example 2.

Figure 33A:
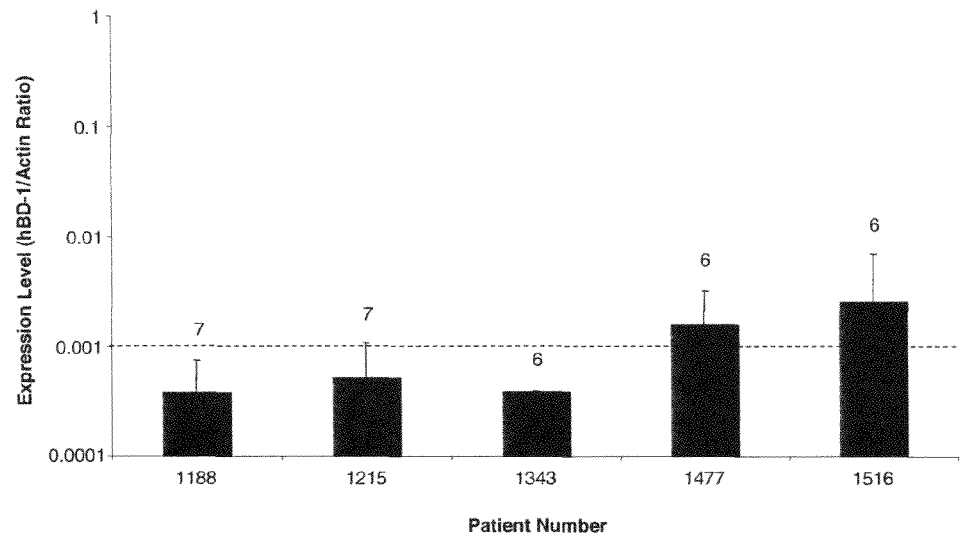
FIGS. 33A and 33B show analysis of hBD-1 expression in human prostate tissue.
Figure 33B:
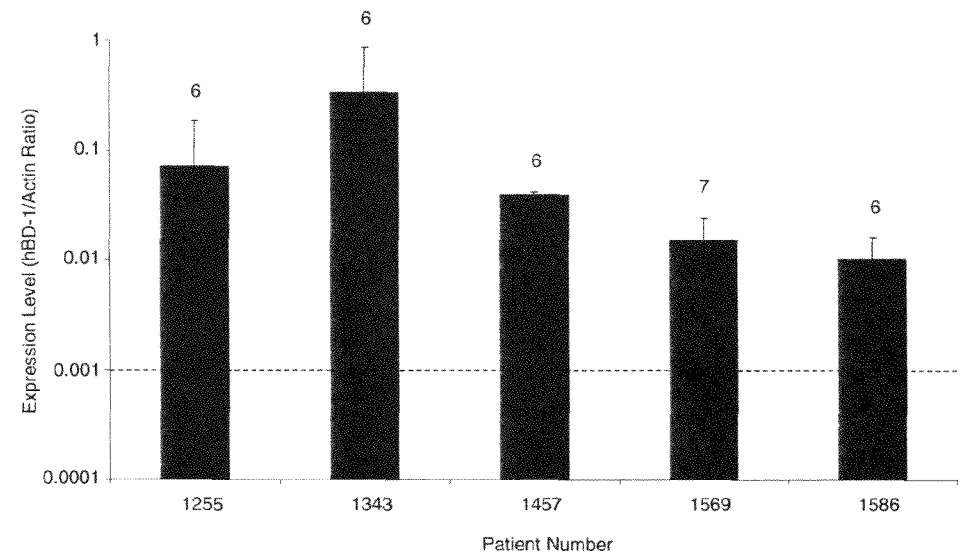
Figure 34A:
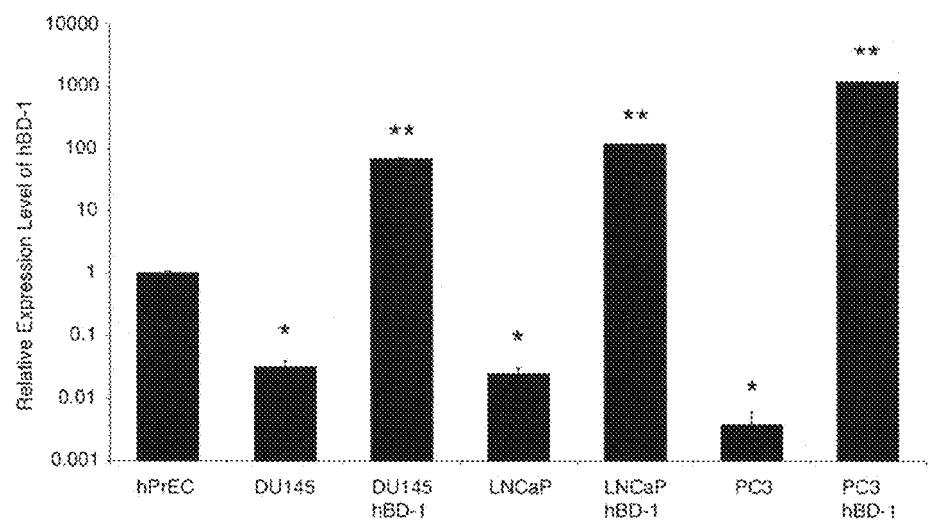
FIGS. 34A and 34B show analysis of hBD-1 expression in prostate cell lines.

Results hBD-1 Expression in Prostate Tissue:

82% of prostate cancer frozen tissue sections analyzed exhibited little or no expression of hBD-1 (Donald et al., 2003). To compare hBD-1 expression levels, QRTPCR analysis was performed on normal prostate tissue obtained by gross dissection or LCM of normal prostate tissue adjacent to malignant regions which were randomly chosen. Here, hBD-1 was detected in all of the gross dissected normal clinical samples with a range of expression that represents approximately a 6.6-fold difference in expression levels (FIG. 33A). LCM captured normal tissue samples expressed hBD-1 at levels in a range that represents a 32-fold difference in expression (FIG. 33B). Matching sample numbers to corresponding patient profiles revealed that in most cases, the hBD-1 expression level was higher in patient samples with a Gleason score of 6 than in patient samples with a Gleason score of 7. In addition, a comparison of hBD-1 expression levels in tissue obtained by gross dissection and LCM from the same patient, #1343, demonstrated an 854-fold difference in expression between the two isolation techniques. Therefore, these results indicate that LCM provides a more sensitive technique to assess hBD-1 expression in prostate tissue.

hBD-1 Expression in Prostate Cell Lines:

To verify upregulation of hBD-1 in the prostate cancer cell lines after transfection with the hBD-1 expression system, QRTPCR was performed. In addition, no template negative controls were also performed, and amplification products were verified by gel electrophoresis. Here, hBD-1 expression was significantly lower in the prostate cancer cell lines compared to hPrEC cells. Following a 24 h induction period, relative expression levels of hBD-1 significantly increased in DU145, PC3 and LNCaP as compared to the cell lines prior to hBD-1 induction (FIG. 34A).

Figure 34B:
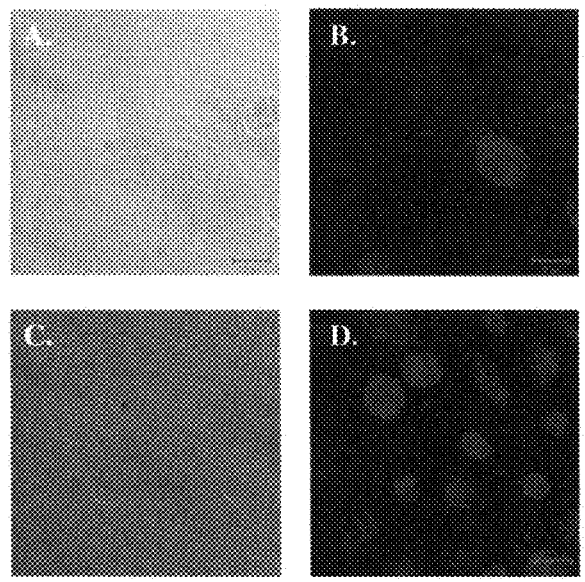

Next, protein expression of hBD-1 in was verified DU145 cells transfected with the hBD-1 expression system after induction with Pon A by immunocytochemistry. As a positive control, hBD-1 expressing hPrEC prostate epithelial cells were also examined. Cells were stained with primary antibody against hBD-1 and protein expression was monitored based on the green fluorescence of the secondary antibody (FIG. 34B). Analysis of cells under DIC verify the presence of hPrEC cells and DU145 cells induced for hBD-1 expression at 18 h. Excitation by the confocal laser at 488 nm produced revealed green fluorescence indicating the presence of hBD-1 protein in hPrEC as a positive control. However, there was no detectable green fluorescence in control DU145 cells and empty plasmid induced DU145 cells demonstrating no hBD-1 expression. Confocal analysis of DU145 cells induced for hBD-1 expression revealed green fluorescence indicating the presence of hBD-1 protein following induction with Pon A.

Figure 35:
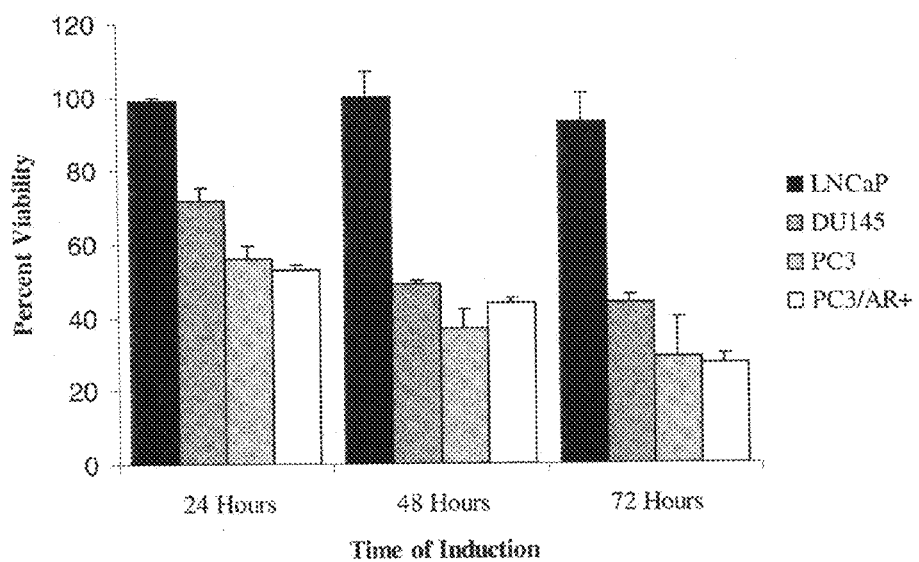
FIG. 35 shows analysis of hBD-1 cytotoxicity in prostate cancer cells. Each bar represents the mean±S.E.M. of three independent experiments performed in triplicate.

Expression of hBD-1 Results in Decreased Cell Viability:

MTT assay was performed to assess the effect of hBD-1 expression on relative cell viability in DU145, PC3, PC3/AR+ and LNCaP prostate cancer cell lines. MTT analysis with empty vector exhibited no statistical significant change in cell viability. Twenty-four hours following hBD-1 induction, relative cell viability was 72% in DU145 and 56% in PC3 cells, and after 48 h cell viability was reduced to 49% in DU145 and 37% in PC3 cells (FIG. 35). Following 72 h of hBD-1 induction, relative cell viability decreased further to 44% in DU145 and 29% PC3 cells. Conversely, there was no significant effect on the viability of LNCaP cells. In order to assess whether the resistance to hBD-1 cytotoxicity observed in LNCaP was due to the presence of the androgen receptor (AR), the hBD-1 cytotoxicity in PC3 cells was examined with ectopic AR expression (PC3/AR+). Here, there was no difference between PC3/AR+ and PC3 cells. Therefore, the data indicates that that hBD-1 is cytotoxic specifically to late-stage prostate cancer cells.

In order to determine whether the effects of hBD-1 on PC3 and DU145 were cytostatic or cytotoxic, FACS analysis was performed to measure cell death. Under normal growth conditions, more than 90% of PC3 and DU145 cultures were viable and non-apoptotic (lower left quadrant) and did not stain with annexin V or PI. After inducing hBD-1 expression in PC3 cells, the number of cells undergoing early apoptosis and late apoptosis/necrosis (lower and upper right quadrants, respectively) totaled 10% at 12 h, 20% at 24 h, and 44% at 48 h (FIG. 4B). For DU145 cells, the number of cells undergoing early apoptosis and late apoptosis/necrosis totaled 12% after 12 h, 34% at 24 h, and 59% after 48 h of induction (FIG. 4A). No increase in apoptosis was observed in cells containing empty plasmid following induction with Pon A. Annexin V and propidium iodide uptake studies have demonstrated that hBD-1 has cytotoxic activity against DU145 and PC3 prostate cancer cells and results indicate apoptosis as a mechanism of cell death.

hBD-1 causes alterations in membrane integrity and caspase activation: It was investigated whether the cell death observed in prostate cancer cells after hBD-1 induction is caspase-mediated apoptosis. To better understand the cellular mechanisms involved in hBD-1 expression, confocal laser microscopic analysis was performed (FIG. 5) on DU145 and LNCaP cells induced for hBD-1 expression. Pan-caspase activation was monitored based on the binding and cleavage of green fluorescing FAM-VAD-FMK to caspases in cells actively undergoing apoptosis. Analysis of cells under DIC showed the presence of viable control DU145 (panel A) and LNCaP (panel E) cells at 0 h. Excitation by the confocal laser at 488 nm produced no detectable green staining which indicates no caspase activity in DU145 (panel B) or LNCaP (panel F) control cells. Following induction for 24 h, DU145 (panel C) and LNCaP (panel G) cells were again visible under DIC. Confocal analysis under fluorescence revealed green staining in DU145 (panel D) cells indicating pan-caspase activity after the induction of hBD-1 expression. However, there was no green staining in LNCaP (panel H) cells induced for hBD-1 expression. Therefore, cell death observed following induction of hBD-1 is caspase-mediated apoptosis.

The proposed mechanism of antimicrobial activity of defensin peptides is the disruption of the microbial membrane due to pore formation (Papo and Shai, 2005). In order to determine if hBD-1 expression altered membrane integrity EtBr uptake was examined by confocal analysis. Intact cells were stained green due to AO which is membrane permeable, while only cells with compromised plasma membranes stained red due to incorporation of membrane impermeable EtBr. Control DU145 and PC3 cells stained positively with AO and emitted green color, but did not stain with EtBr. However, hBD-1 induction in both DU145 and PC3 resulted in the accumulation of EtBr in the cytoplasm at 24 as indicated by the red staining. By 48 h, DU145 and PC3 possessed condensed nuclei and appeared yellow due to the colocalization of green and red staining from AO and EtBr, respectively. Conversely, there were no observable alterations to membrane integrity in LNCaP cells after 48 h of induction as indicated by positive green fluorescence with AO, but lack of red EtBr fluorescence. This finding indicates that alterations to membrane integrity and permeabiization in response to hBD-1 expression differ between early- and late-stage prostate cancer cells.

Figure 36A:
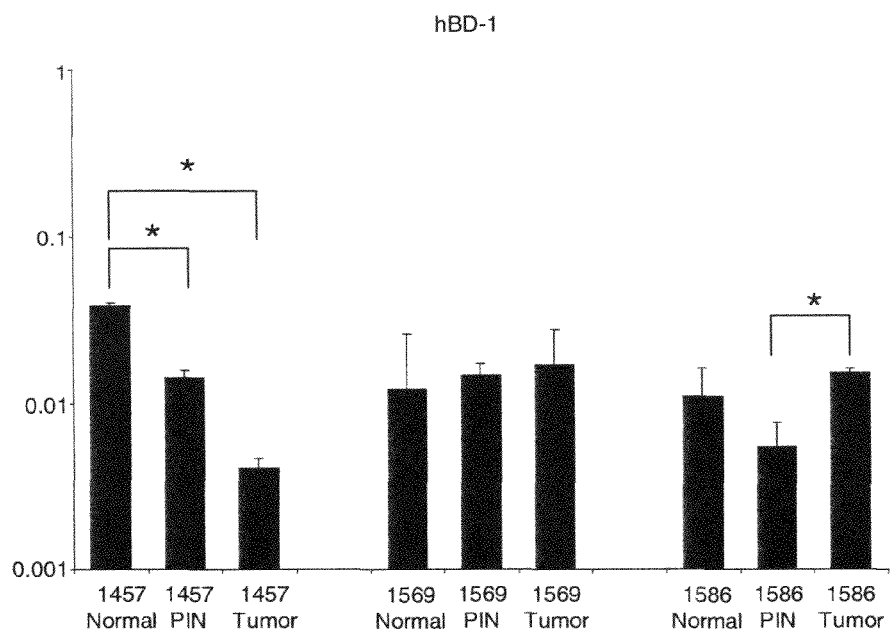
FIGS. 36A and 36B show QRT-PCR analysis of hBD-1 and cMYC expression in LCM human prostate tissue sections of normal, PIN and tumor. Expression for each gene is presented as expression ratios compared to β-actin.
Figure 36B:
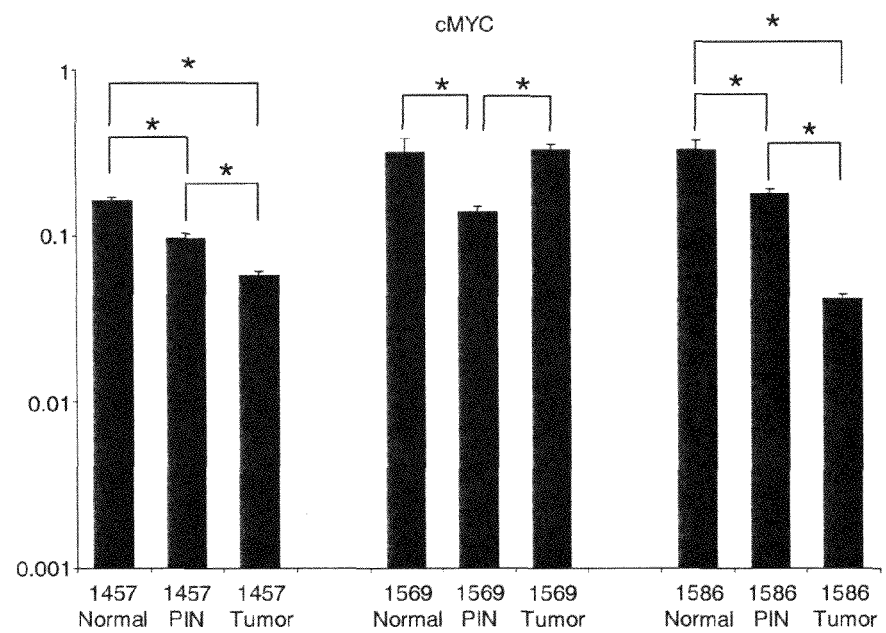

Comparison of hBD-1 and cMYC Expression Levels:

QRT-PCR analysis was performed on LCM prostate tissue sections from three patients (FIG. 34). In patient #1457, hBD-1 expression exhibited a 2.7-fold decrease from normal to PIN, a 3.5-fold decrease from PIN to tumor and a 9.3-fold decrease from normal to tumor (FIG. 36A). Likewise, cMYC expression followed a similar expression pattern in patient #1457 where expression decreased by 1.7-fold from normal to PIN, 1.7-fold from PIN to tumor and 2.8-fold from normal to tumor (FIG. 36B). In addition, there was a statistically significant decrease in cMYC expression in the other two patients. Patient #1569 had a 2.3-fold decrease from normal to PIN, while in patient #1586 there was a 1.8-fold decrease from normal to PIN, a 4.3-fold decrease from PIN to tumor and a 7.9-fold decrease from normal to tumor.

Figure 37:
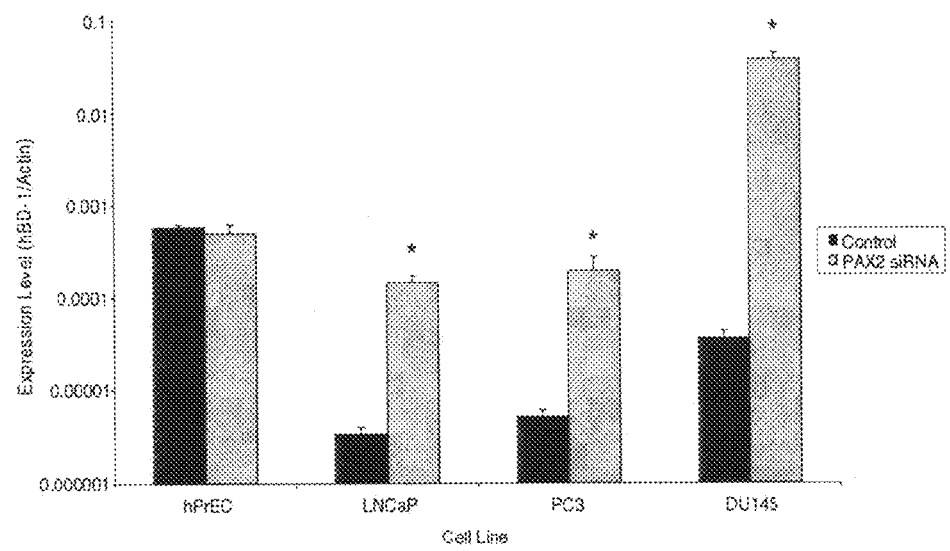
FIG. 37 shows QRT-PCR analysis of hBD 1 expression following PAX2 knockdown with siRNA. hBD-1 expression levels are presented as expression ratios compared to β-actin. An asterisk represents statistically higher expression levels compared to the cell line before PAX2 siRNA treatment (Student's t-test, p<0.05).

Induction of hBD-1 Expression Following PAX2 Inhibition:

To further examine the role of PAX2 in regulating hBD-1 expression, siRNA was utilized to knockdown PAX2 expression and QRT-PCR performed to monitor hBD-1 expression. Treatment of hPrEC cells with PAX2 siRNA exhibited no effect on hBD-1 expression (FIG. 37). However, PAX2 knockdown resulted in a 42-fold increase in LNCaP, a 37-fold increase in PC3 and a 1026-fold increase in DU145 expression of hBD-1 compared to untreated cells. As a negative control, cells were treated with non-specific siRNA which had no significant effect on hBD-1 expression.

EXAMPLE 11

Inhibition of PAX2 Expression Results in Alternate Cell Death Pathways in Prostate Cancer Cells Differing in PB53 Status Materials and Methods Cell Lines:

The cancer cell lines PC3, DU145 and LNCaP, which all differ in p53 mutational status (Table 6), were cultured as described in Example 1. The prostate epithelial cell line HPrEC was obtained from Cambrex Bio Science, Inc., (Walkersville, Md.) and were cultured in prostate epithelium basal media. Cells were maintained at 37° C. in 5% CO2.

TABLE 6 p53 gene mutation in prostate cancer cell lines

| Nucleotide change | Amino acid change | Gene status | Reference |
|---|---|---|---|
| CCT-CTT | Pro-Leu | Gain/loss-of-function | Tepper et al. 2005; Bodhoven et al. 2003 |
| GTT-TTT Deleted a C, GCC-GC | Val-Phe Frame-shift | No activity | Isaacs et al. 1991 |
| No deletion, wild-type | — | Normal function | Carroll et al. 1993 | siRNA Silencing of PAX2:

siRNA silencing of PAX2 was performed s described in Example 2.

Western Analysis:

Western blot was performed as described in Example 2. Blots were then probed with rabbit anti-PAX2 primary antibody (Zymed, San Francisco, Calif.) at a 1:1000 dilution. After washing, the membranes were incubated with anti-rabbit antibody conjugated to horseradish peroxidase (HRP) (dilution 1:5000; Sigma), and signal detection was visualized using chemiluminescence reagents (Pierce) on an Alpha Innotech Fluorchem 8900. As a control, blots were stripped and reprobed with mouse anti-β-actin primary antibody (1:5000; Sigma-Aldrich) and HRP-conjugated anti-mouse secondary antibody (1:5000; Sigma-Aldrich), and signal detection was again visualized.

Phase Contrast Microscopy:

The effect of PAX2 knockdown on cell number was analyzed by phase contrast microscopy as described in Example 1.

MTT Cytotoxicity Assay:

MTT cytotoxicity assay was performed as described in Example 1.

Pan-Caspase Detection:

Detection of caspase activity in the prostate cancer cell lines was performed as described in Example 1.

Quantitative Real-Time RT-PCR:

To verify changes in gene expression following PAX2 knockdown in PC3, DU145 and LNCaP cell lines, quantitative real-time RT-PCR was performed as described in Example 1. The primer pairs for BAX, BID, BCL-2, AKT and BAD were generated from the published sequences (Table 7). Reactions were performed in MicroAmp Optical 96-well Reaction Plate (PE Biosystems). Forty cycles of PCR were performed under standard conditions using an annealing temperature of 60° C. Quantification was determined by the cycle number where exponential amplification began (threshold value) and averaged from the values obtained from the triplicate repeats. There was an inverse relationship between message level and threshold value. In addition, GAPDH was used as a housekeeping gene to normalize the initial content of total cDNA. Relative expression was calculated as the ratio between each genes and GAPDH. All reactions were carried out in triplicate.

TABLE 10

Quantitative RT-PCR primers

| | Sense (5'-3') | Antisense (5'-3') |
|---|---|---|
| GAPDH | CCACCCATGGCAAATTCCAT GGCA (SEQ ID NO: 55) | TCTAGACGGCAGGTCAGGTC AACC (SEQ ID NO: 56) |
| BAD | CTCAGGCCTATGCAAAAAGA GGA (SEQ ID NO: 57) | GCCCTCCCTCCAAAGGAGAC (SEQ ID NO: 58) |
| BID | AACCTACGCACCTACGTGAG GAG (SEQ ID NO: 59) | CGTTCAGTCCATCCCATTTC TG (SEQ ID NO: 60) |
| BAX | GACACCTGAGCTGACCTTGG (SEQ ID NO: 61) | GAGGAAGTCCAGTGTCCAGC (SEQ ID NO: 62) |
| BCL-2 | TATGATACCCGGGAGATCGT GATC (SEQ ID NO: 69) | GTGCAGATGCCGGTTCAGGT ACTC (SEQ ID NO: 70) |
| AKT | TCAGCCCTGGACTACCTGCA (SEQ ID NO: 71) | GAGGTCCCGGTACACCACGT (SEQ ID NO: 72) |

Membrane Permeability Assay:

Membrane permeability assay was performed s described in Example 3.

Results

Analysis of PAX2 Protein Expression in Prostate Cells:

PAX2 protein expression was examined by Western analysis in HPrEC prostate primary culture and in LNCaP, DU145 and PC3 prostate cancer cell lines. Here, PAX2 protein was detected in all of the prostate cancer cell lines (FIG. 38A). However, no PAX2 protein was detectable in HPrEC. Blots were stripped and re-probed for β-actin as internal control to ensure equal loading. PAX2 protein expression was also monitored after selective targeting and inhibition by PAX2 specific siRNA in DU145, PC3 and LNCaP prostate cancer cell lines. Cells were given a single round of transfection with the pool of PAX2 siRNA over a 6-day treatment period. PAX2 protein was expressed in control cells treated with media only. Specific targeting of PAX2 mRNA was confirmed by observing knockdown of PAX2 protein in all three cell lines (FIG. 38B).

Figure 39:
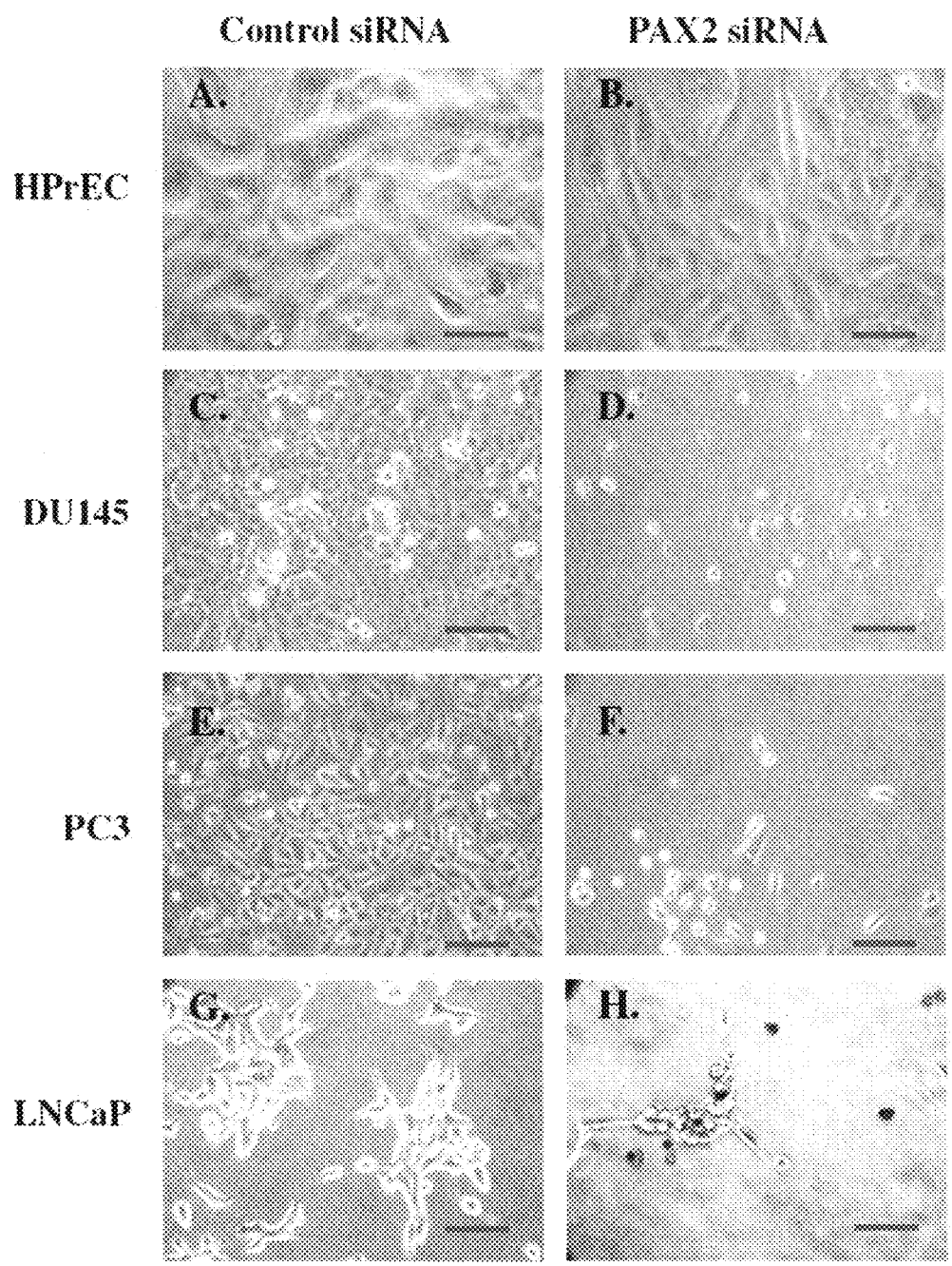
FIG. 39 shows analysis of prostate cancer cells growth after treatment with PAX2 siRNA. Bar=20 µm.

Effect of PAX2 Knockdown on Prostate Cancer Cell Growth:

The effect of PAX2 siRNA on cell number and cell viability was analyzed using light microscopy and MTT analysis. To examine the effect of PAX2 siRNA on cell number, PC3, DU145 and LNCaP cell lines were transfected with media only, non-specific siRNA or PAX2 siRNA over a period of 6 days. Each of the cell lines reached a confluency of 80-90% in 60 mm culture dishes containing media only. Treatment of HPrEC, DU145, PC3 and LNCaP cells with non-specific siRNA appeared to have little to no effect on cell growth compared to cell treated with media only (FIG. 39, panels A, C and E, respectively). Treatment of the PAX2-null cell line HPrEC with PAX2 siRNA appeared to have no significant effect on cell growth (FIG. 39, panel B). However, treatment of the prostate cancer cell lines DU145, PC3 and LNCaP with PAX2 siRNA resulted in a significant decrease in cell number (FIG. 39, panels D, F and H, respectively).

Figure 40:
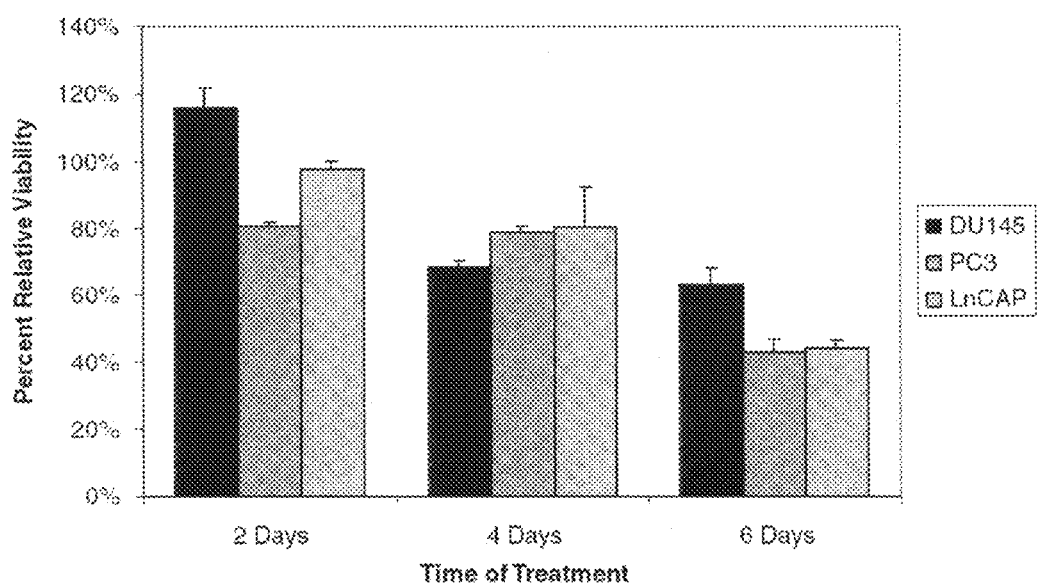
FIG. 40 shows analysis of cell death following siRNA silencing of PAX2. Results represent mean±SD, n=9.

Effect of PAX2 Knockdown on Prostate Cancer Cell Viability:

Cell viability was measured after 2-, 4-, and 6-day exposure times. Percent viability was calculated as the ratio of the 570-630 nm absorbance of cell treated with PAX2 siRNA divided by untreated control cells. As negative controls, cell viability was measured after each treatment period with negative control non-specific siRNA or transfection with reagent alone. Relative cell viability was calculated by dividing percent viability following PAX2 siRNA treatment by percent viability following treatment with non-specific siRNA (FIG. 40). After 2 days of treatment, relative viability was 116% in DU145, 81% in PC3 and 98% in LNCaP. After 4 days of treatment, relative cell viability decreased to 69% in DU145, 79% in PC3, and 80% in LNCaP. Finally, by 6 days relative viability was 63% in DU145, 43% in PC3 and 44% in LNCaP. In addition, cell viability was also measured following treatment with transfection reagent alone. Here, each cell line exhibited no significant decrease in cell viability.

Figure 41:
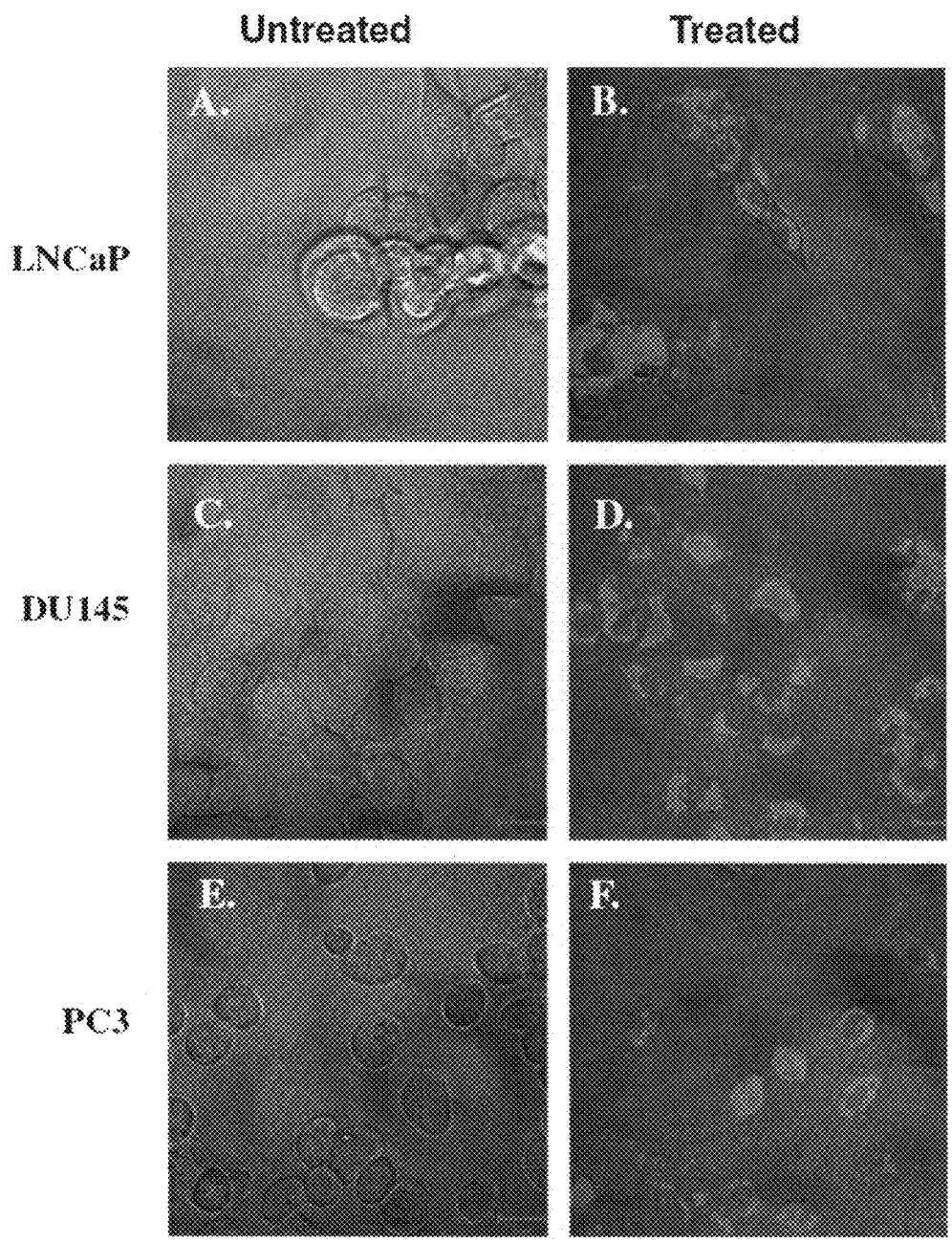
FIG. 41 shows analysis of caspase activity. Bar=20 μm.

Detection of Pan-Caspase Activity:

Caspase activity was detected by confocal laser microscopic analysis. LNCaP, DU145 and PC3 cells were treated with PAX2 siRNA and activity was monitored based on the binding of FAM-labeled peptide to caspases in cells actively undergoing apoptosis which will fluoresce green. Analysis of cells with media only shows the presence of viable LNCaP, DU 145 and PC3 cells, respectively. Excitation by the confocal laser at 488 nm produced no detectable green staining which indicates no caspase activity in the untreated cells (FIG. 41, panels A, C and E, respectively). Following 4 days of treatment with PAX2 siRNA, LNCaP, DU145 and PC3 cells under fluorescence presented green staining indicating caspase activity (FIG. 41, panels B, D and F, respectively).

Figure 42A:
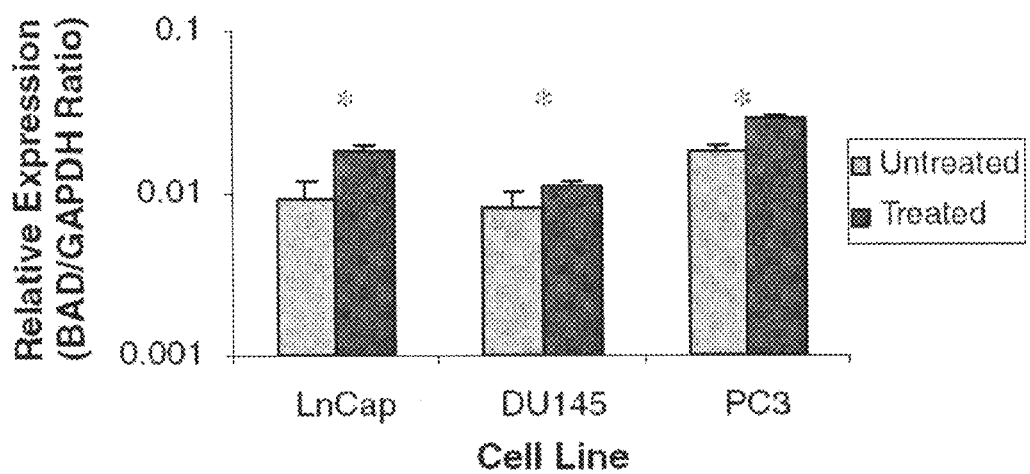
FIGS. 42A-42C show analysis of apoptotic factors following PAX2 siRNA treatment. Results represent mean±SD, n=9. Asterisks represents statistical differences (p<0.05).
Figure 42B:
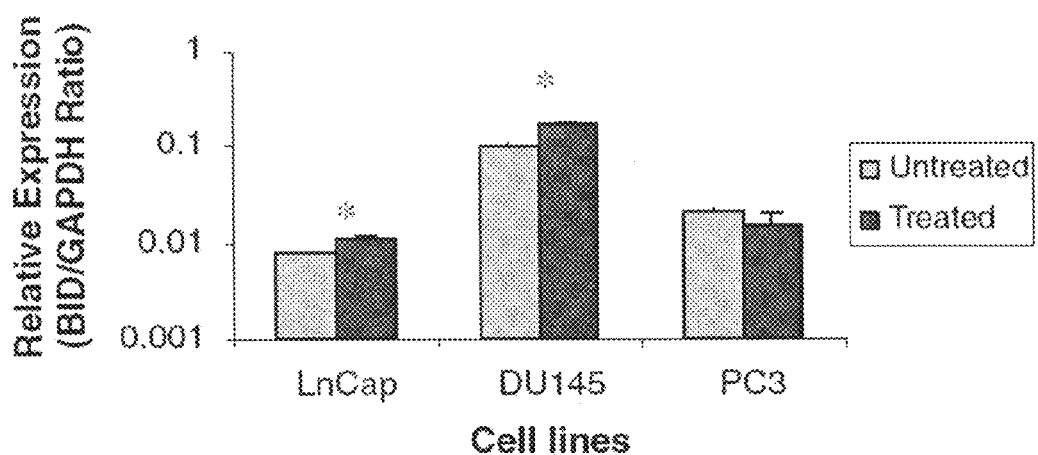
Figure 42C:
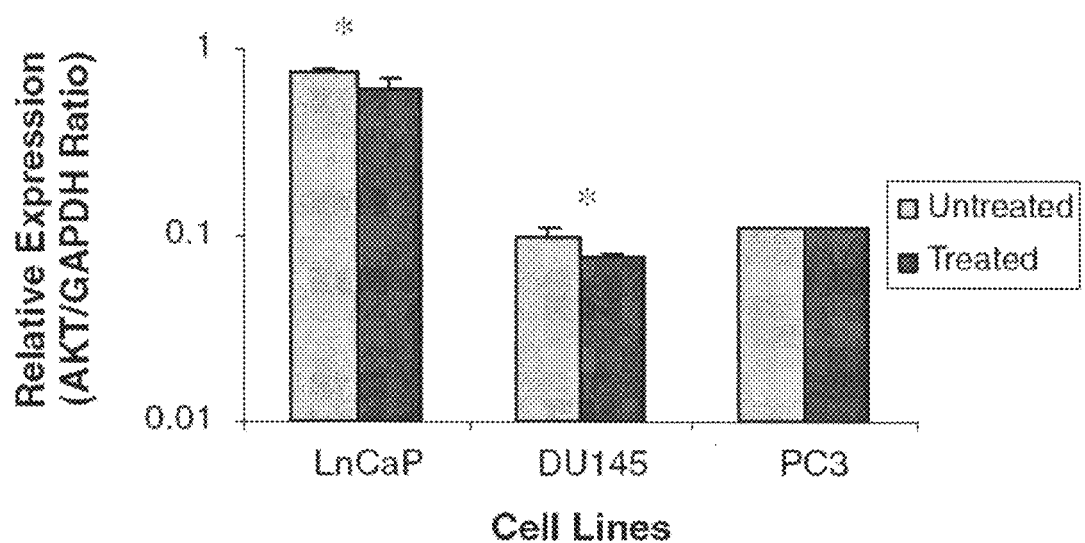

Effect of PAX2 Inhibition on Apoptotic Factors:

LNCaP, DU145 and PC3 cells were treated with siRNA against PAX2 for 4 days and expression of both pro- and anti-apoptotic factors were measured by QRTPCR. Following PAX2 knockdown, analysis of BAD revealed a 2-fold in LNCaP, 1.58-fold in DU145 and 1.375 in PC3 (FIG. 42A). Expression levels of BID increased by 1.38-fold in LNCaP and a 1.78-fold increase in DU145, but there was no statistically significant difference in BID observed in PC3 after suppressing PAX2 expression (FIG. 42B). Analysis of the anti-apoptotic factor AKT revealed a 1.25-fold decrease in expression in LNCaP and a 1.28-fold decrease in DU145 following treatment, but no change was observed in PC3 (FIG. 42C).

Analysis of Membrane Integrity and Necrosis:

Membrane integrity was monitored by confocal analysis in LNCaP, DU145 and PC3 cells. Here, intact cells stained green due to AO which is membrane permeable, while cells with compromised plasma membranes would stained red due to incorporation of membrane impermeable EtBr into the cytoplasm, and yellow due to co-localization of AO and EtBr in the nuclei. Untreated LNCaP, DU145 and PC3 cells stained positively with AO and emitted green color, but did not stain with EtBr. Following PAX2 knockdown, there were no observable alterations to membrane integrity in LNCaP cells as indicated by positive green fluorescence with AO and absence of red EtBr fluorescence. These finding further indicate that LNCaP cells can be undergoing apoptotic, but not necrotic cell death following PAX2 knockdown. Conversely, PAX2 knockdown in DU145 and PC3 resulted in the accumulation of EtBr in the cytoplasm as indicated by the red staining. In addition, both DU145 and PC3 possessed condensed nuclei which appeared yellow due to the co-localization of green and red staining from AO and EtBr, respectively. These results indicate that DU145 and PC3 are undergoing an alternate cell death pathway involving necrotic cell death compared to LNCaP.

EXAMPLE 12

PAX2 and DEFB-1 Expression in Breast Cancer Cell Lines and Mammary Tissues with Ductal or Lobular Intraepithelial Neoplasia PAX2 and DEFB-1 expression will be determined in breast biopsy samples of ductal or lobular intraepithelial neoplasia, and in the following breast cancer cell lines:

BT-20: Isolated from a primary invasive ductal carcinoma; cell express E-cadherin, ER, EGFR and uPA.

BT-474: Isolated from a primary invasive ductal carcinoma; cell express E-cadherin, ER, PR, and have amplified HER2/neu.

Hs578T: Isolated from a primary invasive ductal carcinoma; a cell line was also established from normal adjacent tissue, termed Hs578Bst.

MCF-7: Established from a pleural effusion. The cells express ER and are the most common example of estrogen-responsive breast cancer cells.

MDA-MB-231: Established from a pleural effusion. The cells are ER-negative, E-cadherin negative and highly invasive in in vitro assays.

MDA-MB-361: Established from a brain metastasis. The cells express ER, PR, EGFR and HER2/neu.

MDA-MB-435: Established from a pleural effusion. The cells are ER-negative, E-cadherin negative, and are highly invasive and metastatic in immunodeficient mice.

MDA-MB-468: Established from a pleural effusion. The cells have amplified EGFR and are ER-negative.

SK-BR-3: Established from a pleural effusion. The cells have amplified HER/2neu, express EGFR and are ER-negative.

T-47D: established from a pleural effusion. The cells retain expression of E-cadherin, ER and PR.

ZR-75-1: Established from ascites fluid. The cells express ER, E-cadherin, HER2/neu and VEGF.

The PAX2-to-DEFB-1 expression ratio will be determined using the methods described in Example 9.

EXAMPLE 13

Expression of DEFB1 in Breast Cancer Cells

DEFB1 will be expressed in breast cancer cells using methods described in Example 1. The cell viability and caspase activity will be determined as described in Example 1.

EXAMPLE 14

Inhibition of PAX2 Expression in Breast Cancer Cells

PAX2 expression in breast cancer cells will be inhibited using the siRNA described in Example 2. The expression levels of pro-apoptotic genes such as BAX, BID and BAD, the cell viability and caspase activity will be determined as described in Example 2.

EXAMPLE 15

Effect of DEFB1 Expression on Tumor Growth in vivo

The anti-tumoral ability of DEFB1 will be evaluated by injecting breast cancer cells that overexpress DEFB1 into nude mice. Breast cancer cells will be transfected with an expression vector carrying the DEFB1 gene. Cells expressing the exogenous DEFB1 gene will be selected and cloned. Only single-cell suspensions with a viability of >90% are used. Each animal receives approximately 500,000 cells administered subcutaneously into the right flank of female nude mice. There are two groups, a control group injected with vector only clones and a group injected with the DEFB1 over-expressing clones. 35 mice are in each group as determined by a statistician. Animals are weighed twice weekly, tumor growth monitored by calipers and tumor volumes determined using the following formula: volume=$0.5 \times (\text{width})^2 \times \text{length}$. All animals are sacrificed by CO2 overdose when tumor size reaches 2 mm3 or 6 months following implantation; tumors are excised, weighed and stored in neutral buffered formalin for pathological examination. Differences in tumor growth between the groups are descriptively characterized through summary statistics and graphical displays. Statistical significance is evaluated with either the t-test or non-parametric equivalent.

EXAMPLE 16

Effect of PAX2 siRNA on Tumor Growth in vivo

Hairpin PAX2 siRNA template oligonucleotides utilized in the in vitro studies are utilized to examine the effect of the up-regulation of DEFB1 expression in vivo. The sense and antisense strand (see Table 3) are annealed and cloned into pSilencer 2.1 U6 hygro siRNA expression vector (Ambion) under the control of the human U6 RNA pol III promoter. The cloned plasmid is sequenced, verified and transfected into breast cancer cell lines. Scrambled shRNA is cloned and used as a negative control in this study. Hygromycin resistant colonies are selected, cells are introduced into the mice subcutaneously and tumor growth is monitored as described above.

EXAMPLE 17

Effect of Small Molecule Inhibitors of PAX2 Binding on Breast Cancer Cells

The alternative inhibitory oligonucleotides described in Example 6 will be transfected into the breast cancer cells with lipofectamine reagent or Codebreaker transfection reagent (Promega, Inc). In order to confirm DNA-protein interactions, double stranded oligonucleotides will be labeled with [32P] dCTP and electrophoretic mobility shift assays are performed DEFB1 expression will be monitored by QRT-PCR and Western analysis following treatment with oligonucleotides. Finally, cell death will be detected by MTT assay and flow cytometry as previously described.

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims. The claims are intended to cover the claimed components and steps in any sequence which is effective to meet the objectives there intended, unless the context specifically indicates the contrary.

What is claimed is:

1. A method for treating a breast condition in a subject, comprising:
   (a) determining the PAX2-to-DEFB1 expression ratio in a diseased breast tissue from said subject;
   (b) determining the ER/PR status of said diseased breast tissue from said subject; and
   (c) based on the results of (a) and (b), administering to a breast tissue of said subject, a first composition comprising an effective amount of an antagonist of STAT3.

2. The method of claim 1, wherein said breast condition is breast cancer or MIN.

3. The method of claim 1, wherein said antagonist is conjugated to an antibody, a receptor or a ligand to target tumor tissue in said subject.

4. The method of claim 1, wherein said antagonist is a small molecule.

5. The method of claim 1, wherein step (c) further comprises administering a second composition comprising an anti-hormonal agent.

6. The method of claim 5, wherein the anti-hormonal agent is tamoxifen.

7. The method of claim 1, wherein step (c) further comprises administering a second composition comprising an anti-ERBB-2 agent.

8. The method of claim 7, wherein the anti-ERBB-2 agent is trastuzumab.

9. The method of claim 1, wherein step (c) further comprises administering a second composition comprising an anti-Her-2 agent.

10. The method of claim 9, wherein the anti-Her-2 agent is trastuzumab.

11. The method of claim 1, wherein step (c) further comprises administering a second composition comprising an anti-AIB-1/SRC-3 agent.

* * * * *

SEQUENCE LISTING

```
<160> NUMBER OF SEQ ID NOS: 72

<210> SEQ ID NO 1
<211> LENGTH: 5
<212> TYPE: DNA
<213> ORGANISM: Homo sapiens

<400> SEQUENCE: 1 ccttg                                                                    5

<210> SEQ ID NO 2
<211> LENGTH: 5
<212> TYPE: DNA
<213> ORGANISM: Homo sapiens

<400> SEQUENCE: 2 caagg                                                                    5

<210> SEQ ID NO 3
<211> LENGTH: 21
<212> TYPE: RNA
<213> ORGANISM: Homo sapiens

<400> SEQUENCE: 3
auagacucga cuugacuucu u                                                 21

<210> SEQ ID NO 4
<211> LENGTH: 21
<212> TYPE: RNA
<213> ORGANISM: Homo sapiens
```

<400> SEQUENCE: 4
aucuucauca cguuccucu u                    21

<210> SEQ ID NO 5
<211> LENGTH: 21
<212> TYPE: RNA
<213> ORGANISM: Homo sapiens

<400> SEQUENCE: 5
guauucagca aucuuguccu u                   21

<210> SEQ ID NO 6
<211> LENGTH: 21
<212> TYPE: RNA
<213> ORGANISM: Homo sapiens

<400> SEQUENCE: 6
gauuugaugu gcucugaugu u                   21

<210> SEQ ID NO 7
<211> LENGTH: 21
<212> TYPE: RNA
<213> ORGANISM: Homo sapiens

<400> SEQUENCE: 7
gaagucaagu cgagucuauu u                   21

<210> SEQ ID NO 8
<211> LENGTH: 21
<212> TYPE: RNA
<213> ORGANISM: Homo sapiens

<400> SEQUENCE: 8
gaggaaacgu gaugaagauu u                   21

<210> SEQ ID NO 9
<211> LENGTH: 21
<212> TYPE: RNA
<213> ORGANISM: Homo sapiens

<400> SEQUENCE: 9
ggacaagauu gcugaauacu u                   21

<210> SEQ ID NO 10
<211> LENGTH: 21
<212> TYPE: RNA
<213> ORGANISM: Homo sapiens

<400> SEQUENCE: 10
caucagagca caucaaaucu u                   21

<210> SEQ ID NO 11
<211> LENGTH: 20
<212> TYPE: DNA
<213> ORGANISM: Homo sapiens

<400> SEQUENCE: 11
acccgactat gttcgcctgg                     20

<210> SEQ ID NO 12
<211> LENGTH: 21
<212> TYPE: DNA
<213> ORGANISM: Homo sapiens

<400> SEQUENCE: 12
aagctctgga tcgagtcttt g                                              21

<210> SEQ ID NO 13
<211> LENGTH: 20
<212> TYPE: DNA
<213> ORGANISM: Homo sapiens

<400> SEQUENCE: 13
atgtgtcagg cacacagacg                                                20

<210> SEQ ID NO 14
<211> LENGTH: 21
<212> TYPE: RNA
<213> ORGANISM: Homo sapiens

<400> SEQUENCE: 14
gucgagucua ucugcauccu u                                              21

<210> SEQ ID NO 15
<211> LENGTH: 21
<212> TYPE: RNA
<213> ORGANISM: Homo sapiens

<400> SEQUENCE: 15
ggaugcagau agacucgacu u                                              21

<210> SEQ ID NO 16
<211> LENGTH: 19
<212> TYPE: DNA
<213> ORGANISM: Homo sapiens

<400> SEQUENCE: 16
aagttcaccc ttgactgtg                                                 19

<210> SEQ ID NO 17
<211> LENGTH: 5
<212> TYPE: DNA
<213> ORGANISM: Homo sapiens

<400> SEQUENCE: 17 ccttg                                                                 5

<210> SEQ ID NO 18
<211> LENGTH: 20
<212> TYPE: DNA
<213> ORGANISM: Homo sapiens

<400> SEQUENCE: 18
ctcccttcag ttccgtcgac                                                20

<210> SEQ ID NO 19
<211> LENGTH: 20
<212> TYPE: DNA
<213> ORGANISM: Homo sapiens

<400> SEQUENCE: 19
ctcccttcac cttggtcgac                                                20

<210> SEQ ID NO 20
<211> LENGTH: 40
<212> TYPE: DNA
<213> ORGANISM: Homo sapiens

```
<400> SEQUENCE: 20
actgtggcac ctcccttcag ttccgtcgac gaggttgtgc                              40

<210> SEQ ID NO 21
<211> LENGTH: 40
<212> TYPE: DNA
<213> ORGANISM: Homo sapiens

<400> SEQUENCE: 21
actgtggcac ctcccttcac cttggtcgac gaggttgtgc                              40

<210> SEQ ID NO 22
<211> LENGTH: 5
<212> TYPE: DNA
<213> ORGANISM: Homo sapiens

<400> SEQUENCE: 22 ctctg                                                                     5

<210> SEQ ID NO 23
<211> LENGTH: 20
<212> TYPE: DNA
<213> ORGANISM: Homo sapiens

<400> SEQUENCE: 23
ctcccttcac tctggtcgac                                                    20

<210> SEQ ID NO 24
<211> LENGTH: 40
<212> TYPE: DNA
<213> ORGANISM: Homo sapiens

<400> SEQUENCE: 24
actgtggcac ctcccttcac tctggtcgac gaggttgtgc                              40

<210> SEQ ID NO 25
<211> LENGTH: 20
<212> TYPE: DNA
<213> ORGANISM: Homo sapiens

<400> SEQUENCE: 25
agaagttcac ccttgactgt                                                    20

<210> SEQ ID NO 26
<211> LENGTH: 20
<212> TYPE: DNA
<213> ORGANISM: Homo sapiens

<400> SEQUENCE: 26
agaagttcac gttccactgt                                                    20

<210> SEQ ID NO 27
<211> LENGTH: 20
<212> TYPE: DNA
<213> ORGANISM: Homo sapiens

<400> SEQUENCE: 27
agaagttcac gctctactgt                                                    20

<210> SEQ ID NO 28
<211> LENGTH: 39
<212> TYPE: DNA
<213> ORGANISM: Homo sapiens
```

```
<400> SEQUENCE: 28
ttagcgatta gaagttcacc cttgactgtg gcacctccc                              39

<210> SEQ ID NO 29
<211> LENGTH: 40
<212> TYPE: DNA
<213> ORGANISM: Homo sapiens

<400> SEQUENCE: 29
gttagcgatt agaagttcac gttccactgt ggcacctccc                             40

<210> SEQ ID NO 30
<211> LENGTH: 40
<212> TYPE: DNA
<213> ORGANISM: Homo sapiens

<400> SEQUENCE: 30
gttagcgatt agaagttcac gctctactgt ggcacctccc                             40

<210> SEQ ID NO 31
<211> LENGTH: 20
<212> TYPE: DNA
<213> ORGANISM: Homo sapiens

<400> SEQUENCE: 31
actgcccatt gcccaaacac                                                   20

<210> SEQ ID NO 32
<211> LENGTH: 21
<212> TYPE: DNA
<213> ORGANISM: Homo sapiens

<400> SEQUENCE: 32
aaaatcttgc cagctttccc c                                                 21

<210> SEQ ID NO 33
<211> LENGTH: 23
<212> TYPE: DNA
<213> ORGANISM: Homo sapiens

<400> SEQUENCE: 33
gtcggttacg gagcggaccg gag                                               23

<210> SEQ ID NO 34
<211> LENGTH: 24
<212> TYPE: DNA
<213> ORGANISM: Homo sapiens

<400> SEQUENCE: 34
taacatatag acaaacgcac accg                                              24

<210> SEQ ID NO 35
<211> LENGTH: 23
<212> TYPE: DNA
<213> ORGANISM: Homo sapiens

<400> SEQUENCE: 35
gcgcttgtgt cgccattgta ttc                                               23

<210> SEQ ID NO 36
<211> LENGTH: 24
<212> TYPE: DNA
<213> ORGANISM: Homo sapiens
```

<400> SEQUENCE: 36
gtcacaccac agaagtaagg ttcc                                          24

<210> SEQ ID NO 37
<211> LENGTH: 23
<212> TYPE: DNA
<213> ORGANISM: Homo sapiens

<400> SEQUENCE: 37
gtcggttacg gagcggaccg gag                                           23

<210> SEQ ID NO 38
<211> LENGTH: 25
<212> TYPE: DNA
<213> ORGANISM: Homo sapiens

<400> SEQUENCE: 38
cacagagcat tggcgatctc gatgc                                         25

<210> SEQ ID NO 39
<211> LENGTH: 135
<212> TYPE: PRT
<213> ORGANISM: Homo sapiens

<400> SEQUENCE: 39

Met Asp Met His Cys Lys Ala Asp Pro Phe Ser Ala Met His Arg His
1               5                   10                  15

Gly Gly Val Asn Gln Leu Gly Gly Val Phe Val Asn Gly Arg Pro Leu
            20                  25                  30

Pro Asp Val Val Arg Gln Arg Ile Val Glu Leu Ala His Gln Gly Val
        35                  40                  45

Arg Pro Cys Asp Ile Ser Arg Gln Leu Arg Val Ser His Gly Cys Val
    50                  55                  60

Ser Lys Ile Leu Gly Arg Tyr Tyr Glu Thr Gly Ser Ile Lys Pro Gly
65                  70                  75                  80

Val Ile Gly Gly Ser Lys Pro Lys Val Ala Thr Pro Lys Val Val Asp
                85                  90                  95

Lys Ile Ala Glu Tyr Lys Arg Gln Asn Pro Thr Met Phe Ala Trp Glu
            100                 105                 110

Ile Arg Asp Arg Leu Leu Ala Glu Gly Ile Cys Asp Asn Asp Thr Val
        115                 120                 125

Pro Ser Val Ser Ser Ile Asn
    130                 135

<210> SEQ ID NO 40
<211> LENGTH: 7331
<212> TYPE: DNA
<213> ORGANISM: Homo sapiens
<220> FEATURE:
<221> NAME/KEY: misc_feature
<222> LOCATION: (1)..(7331)
<223> OTHER INFORMATION: n= a, c, g, or t

<400> SEQUENCE: 40
ttcccccttt ccangagggc ctaatccgtt gcgcgcgcgc acgcggacac acacacacac     60
acacacacac acacacacac acacacggcc cccatagcca ccgcaactct cagcagcagn    120
ncctagctcc tctgacccga ggccccaaga cggcgggcac aggaacccct ggacgtcct     180 ggctccaggc tggacgtagg cggaggtggc aggagtggac aaacccaggc gggtcccacg    240

```
acgccccttt cctcgggtct ctccttgttt cagccagccg ctctcgcccc tggtcccctc    300
ttccctgcgt tagggtcctt tgtctccagc cacctcgcag cctgtccccg cctcggcggc    360
cctgcccttt gggcctccca gatctctctg gcgggtcccc ctgccttacc agctcccggc    420
tgtggcgcgc tcttcgcctg ctcctcacat ncacacagct gctgggagag gaggaaggaa    480
aggcggncgc gccgcggatg gatccgagac ggtagatttg gtgccggctc gcaaactctg    540
ggaaacttaa ngccggttct tccgcccctc tncaactatg nccagcgcgg cccggtcgcg    600
cgcgctcacc ccgcggggac cctttccttt tcctgtattt cggctgcggc tgtttcgctt    660
cctctggtct cccagccttt ggagtggctt ccctggccct gcactccgtt cccttcggc     720 cgccccggc tgtcgcctgc ccccaccctc cgcaggtccc acggtcgcgg cggcgatgac     780
tgtggaggta acgccgggga cgtcctgggt cagcctgcac cgtctccctc gaccacagcc    840
cgatgaggcc gcgggctccg ggccggctgc taagagagtt aatcattact tcgccagcga    900
cactcagcct cccttccga ctctctcgcc cggcctaggg gaggagggga ggggacagct     960
ggccaggtgg ggacttcggc ttcgcacaaa ccagcctctt caggcctccc agagacaggt   1020
ggtggcttct cagttccctc ggcaactctc taaggtcctc tttcttcccc tcctgtctct   1080
ccctccttcg agcctcctcc cagccaggcc tctccccacc gtctcctgtc cgctctggct   1140
ttgactgatt aactgcaggt cctgggagaa ccaactttct ttgtttggaa ccggaccgga   1200
cgggatttcc ttccctaggt ctccgccaat gggccagctc ctcccgacgg ttttggcgga   1260
ctggctgaag aggaccgcgc ctgaggccac aattaacccg gctgttggtg gtggtggttg   1320
gggggtgggc agtgaggaat ttaaccgatc ctctagcagc tgcgctggtg cagttgggag   1380 ggggtgcag gaagtgggaa tggaggagtg gcaggaggta tagacagagg gaagaacgat    1440
aaacctggac aggtgtggca tagccaatag aagggggaaac aaaataaaac aggaaggcgg   1500
cgcggggagg aatccccagt aacctttata ggattgaagt tgggtggaaa acgccacctc   1560
ctgccctacc ttagcactca gatccctcct ttacctcttt gtgaaagggt aagagttcag   1620
aaagctggcc atttactcca taatctacta gagaaatgtc tgggtttgca aaatgcctat   1680
tgattagctc catggagtag acaagacagg cgtaattatc cccatttac aggtgagaaa    1740 actgagtctc aaagaagcaa agggactgtg tatgtagtgg ctgtcacttt ttcctgtagg   1800
ctgtggggtg agtggcccct ttagctgtgc agaggtccat gggtatctag ggaggcggta   1860
caggctgtgt ccaggtctga gccagaagta ccagggcctc acggggctcc tagcccttt    1920 agcttgttct ctgttggaca ggaccttcac tcttactctc tagacctgct ggctgggttt   1980
ctcccagctt cgctattttt tcagttccct agtagagtgg cccatgggcg gtagccacct   2040
ggctggcccg tgccactaag aggcagcttt ggtggccaag tggcttgcat tgttgttgct   2100
cctcaaaggg cctgtgaagg gctgggcagg tcgcaaagac ctcttgtgag gggaaagcta   2160
gattaaaggg ggtaaggatc ctggaggata aaggccaagc acgtgcgcct ggactccaca   2220
ggaccaacag accgagcggg cggggccngc tgggagtcag gccccccggg cttcacgcag   2280
ggagcccaaa tattgggaac aaaagcagga aagaagagt gagagcagga gggagggagg    2340
gagcgaggaa gcagaaatta gggggtctta gatgaaaaaa aaaagaaagt agctttaggg   2400
ggaatgtgct gtggagtgtg aaattgcagc ccatggtgct ccatattgta ccagaagctc   2460
ttccaaaaaa aaaaaaaaa accatcctcc aacgtgacca gagggccagg caggggaag     2520 ggcggggaga gaatggggag gaggaggggg aaaggccggg caggagccgg tcaggccttt   2580
ctgcggaagg ggctggggtg taagtttcgg ctccctggga tctgacagcc gagggtatgc   2640
```

```
gccctggggt gcgccgggac ccagagggcg agtgagcctc ggttggtcgg ctctggagtt      2700
cggttgtcag aagaactttt attttctctt ttggtggtga cttctaaaag tgggaataat      2760
ccagaaatga agctcagctg cggagctgca gctctgttct ccctctctcc cctgcctttc      2820
tgcttctctt cccttcggac tacttttctc cccttggttc taaatagctt tttccctct       2880 gaactttaat gcatttaatt tggtccgcgc tgtggggagc atttcctggg gagatgcatt      2940
taatttcgga atttctaatc ccctccctca gaccccggtc ctagctcccc tagccgctcc      3000
ccgggaagtg gaaggaggaa ggcaggtccc ggccacgggg gaggggcgcg gctgggatgc      3060
tcccgcggcc ccctccgtct caccaaggct cagccgcctt cccaagctac tggaggccgg      3120
gcgcctgggc cccgggtcag ggccctgcan gaagaagaga ggcaaccccc gctttctgcc      3180
ttttcttcgc ctgggcaaga aaacgctggg ccagggaact ggaaccggaa aacaggaga       3240 aagggttnt ggaaggcanc gggagcgggt ggcagncggg gcancgggca ntggactagg       3300
tctacaccgg cacttcactt ttgcacaaca tgcccagaaa cgcatttgag agccctggag      3360
tcgcgcttgg cttggcttgg ggcgccggtg cgtgggtaca ctcgaggtcg gggtgcctat      3420
ccgccacccc gacacctaca cccagtgcag agcaggcgcg gcccagccag acaaccaggc      3480
cggcagtagc tcggcctgga gggcggaggc aaggttgggg gccgccaggc gcctgggcaa      3540
gcctggcagg gaagggagcc gagaaggcaa aggagccgag atccacaagg aagattnntt      3600
gggcagatca gatgcacaga ggcggctaat gaagcaaatc ccgagatggg tttcagagca      3660
actccccaaa agtttatttt gcctttaaat ttccgcaggg aggcgggctc cttgtttgaa      3720
gtgtaaatgc ccctaggttg gggggtggaa gggccgcttt gaaaacacca gagagaaaag      3780
gttcatttag aggcggacgg gaaaagcaac caacccctgac aggtcggagc ccgggtagtg     3840
tttggggttg ggtngttttc tttctttctc tttcttttcc cctttcctct tctttcttcc      3900
cttttgtgnn ttttnnttgt ttttttttntn ttnttttttnt ttaantggct ttcttgcttc    3960
cccccacccc tctactagac tctatagaag aaagagaaca gaaaaggggg agtcagagga      4020
gcggccagtg actggatgaa ggccagcccct tcatcctgga gccccaggag aaggcagagc     4080
tttggagaaa aggggttcct aatctccagg gagcattact ctttgactct ctagacccag      4140
gaatgggctg gacgctaatg gggaagcggc caggaacccg gcctggcgga agagtgagtg      4200
tccagctagt gcagtgctgg gaagacgatc ccaggagcag gggggactct caggggctac      4260
ctgggaatgg gactatcaga agggtcttta ctcctcanaa ggtgcatgtg aaggacaggt      4320
gtgtgaggac aacttccagc acacttggcg cattaagtcc ccttctctac aaaatggaaa      4380
atccttctcg cccaacatgt gaaaatgctt gttgtgggca cccacatttc atggtacttg      4440
taacatagga catgtctagc tggttctaga aaaatctgtg tctgtgtgga aggggggggg      4500
tttactcaca gctttcttcc ttcaatagtt cacacacccc gagacaaatt cctggatgac      4560
caacttggag agacctgggg caaaggttac tttagttctg agctcctcta aataaggacc      4620
ctttctcaac gttcctttca ccccagttct gggttaatta cttccagtta gtgcgtgttc      4680
gtggggttgt gaggccaaag caaacccggg agcgccatct gcaggcctca agaggaagag      4740
actgacctta gaggctaggc cctgcgtctt caacctctag cccaagggaa ccaacctgcc      4800
tagccaccca agggaagtgg gatagggggct gggaggggca ggcggtgagg agtgttttcc     4860
tcccagactt taccccgcag gtggattaag cttattgggc tctggaggat acaggaggga     4920
gggcaaatgc caggatccca gcggaccag gccccacagg agtgagaggc tcagaacctc       4980
gtcccgctga gcctggcctg agctcctcct gaggaataag ggcatcccaa aaacccgggt     5040
```

```
acaagacgcc cagtagtagt agttaggctg agtcaggcag gtgcatctct ccccatggta    5100
tctgccgccc aggctccggc cagagggagg ggagcgcgag tccgcggcgc ttccgcgggg    5160
cgcccggaac tgcagacggg ggctggagga atctcggatt cgggctgcaa gagcgctgcg    5220
caagcttcgc cgagccgccc tttcgcagac ccagggaagc ggggggaggg agcgaaggag    5280
ggagagagag ttaaaacatc agcttgaaag tgcccaagat gattttatta agaccgaggg    5340
gaaaattatt ttcatgaaag attctccccg gaatatttct tgtacttaac ccagttagga    5400
agacaaaggg cttctttctg cctggtgcgg tgcgagcgga ccccagcgag caagggagct    5460
agtgccaaag agaactgcgg aggctccggc aggagtgggg acgtcccgt ggttgcgcct     5520
cctgcgctcg ccccggatcc accgagctag cagcgggcgg cgctcagccg cgtccgcagc    5580
ctcctcttct ccccagccgg ggagagccag cctcgtctcc cacatcctct gccgccagcg    5640
acctgcagct ccgcactgtt tccctcccct gtacccctt cccagtcacc cgagggttca     5700
gaaaccaagt cccccggctc tcccgccatc cgctgggtcc caccgaggca ggtgggtact    5760
cgccggaggt cttcagctcg attctgaacc aagcgttctg gactgcccag acccggtggg    5820
caaggggact ggggaggccc tgcgcacagt cgcgtggaac gggaggggac aagacaaact    5880
gctggacact tttccgtgga atgagaagtg gggggtgcgt gggtgggaag gtacctccgg    5940
agggaaaggc caaagggaag gaccagaaag agaggaagga agagccggga aggaacggaa    6000
gggaactcag agccgagggt ggtggggttg ggctaggga tgcgcactgg gcccggggcc     6060
gcgcggccca gcggggcact ggccagtgga tggcagggct gggcgagtta gaactgagag    6120
cccggcttca cagcgcagcg cgctccgagg ccctctgtcg ttacctgaat attcattaga    6180
ctgaccgctc tttatcctta tctaacgttt atcttatcgg cgagtttcgt ttctcagtgt    6240
agttttaatc ccgggctccc attccccctc ccccggtccg ctcccctccc tcctcttcc     6300
ttcgccggct gctccctccc tcctccctc ccatttctcc ctcccctgcc ctccccttgc     6360
cggcaccgga gtgacaggct cggggccctc ctcgccgaag ctcggggctc cagcgctggc    6420
gaatcacaga gtggtggaat ctattgcctt tgtctgacaa gtcatccatc tcccggcgcg    6480
gggaggggga ggaggtctgg aggggctttt gcagctttta gagagacaca caccgggagc    6540
cgaggctcca gtctccggcc gagtcttcta gcagccgcaa cccacctggg gccagcccag    6600
agctgccagc gccgctcggc tccctccctc cctcccggcc cttcggccgc ggcggcgtgc    6660
gcctgccttt tccggggggcg ggggcctggc ccgcgcgctc ccctcccgca ggcgccacct   6720
cggacatccc cgggattgct acttctctgc caacttcgcc aactcgccag cacttggaga    6780
ggcccggctc ccctcccggc gccctctgac cgcccccgcc ccgcgcgctc tccgaccacc    6840
gcctctcgga tgaacaggtt ccaggggagc tgagcgagtc gcctcccccg cccagcttca    6900
gccctggctg cagctgcagc gcgagccatg cgcccccagt gcaccccggc ccggcccacc    6960
gccccggggc cattctgctg accgcccagc cccgagcccc gacagtggca agttgcggct    7020
actgcggttg caagctccgg ccaacccgga ggagcccag cggggagcgc agtgttgcgc     7080
ccccgcccc cgcgcgcgcc gcagcagccg ggcgttcact catcctccct cccccaccgt     7140
ccctcccttt tctcctcaag tcctgaagtt gagtttgaga ggcgacacgg cggcggcggc    7200
cgcgctgctc ccgctcctct gcctcccat ggatatgcac tgcaaagcag acccccttctc   7260
cgcgatgcac cgtgagtacc cgcgcccggc tcctgtcccg gctcgggctc tccgtcccaa    7320
ccctgtccag t                                                         7331
```

<210> SEQ ID NO 41

```
<211> LENGTH: 416
<212> TYPE: PRT
<213> ORGANISM: Homo sapiens

<400> SEQUENCE: 41

Met Asp Met His Cys Lys Ala Asp Pro Phe Ser Ala Met His Pro Gly
1               5                   10                  15

His Gly Gly Val Asn Gln Leu Gly Gly Val Phe Val Asn Gly Arg Pro
            20                  25                  30

Leu Pro Asp Val Val Arg Gln Arg Ile Val Glu Leu Ala His Gln Gly
        35                  40                  45

Val Arg Pro Cys Asp Ile Ser Arg Gln Leu Arg Val Ser His Gly Cys
    50                  55                  60

Val Ser Lys Ile Leu Gly Arg Tyr Tyr Glu Thr Gly Ser Ile Lys Pro
65                  70                  75                  80

Gly Val Ile Gly Gly Ser Lys Pro Lys Val Ala Thr Pro Lys Val Val
                85                  90                  95

Asp Lys Ile Ala Glu Tyr Lys Arg Gln Asn Pro Thr Met Phe Ala Trp
            100                 105                 110

Glu Ile Arg Asp Arg Leu Leu Ala Glu Gly Ile Cys Asp Asn Asp Thr
        115                 120                 125

Val Pro Ser Val Ser Ser Ile Asn Arg Ile Ile Arg Thr Lys Val Gln
    130                 135                 140

Gln Pro Phe His Pro Thr Pro Asp Gly Ala Gly Thr Gly Val Thr Ala
145                 150                 155                 160

Pro Gly His Thr Ile Val Pro Ser Thr Ala Ser Pro Val Ser Ser
                165                 170                 175

Ala Ser Asn Asp Pro Val Gly Ser Tyr Ser Ile Asn Gly Ile Leu Gly
            180                 185                 190

Ile Pro Arg Ser Asn Gly Glu Lys Arg Lys Arg Asp Glu Val Glu Val
        195                 200                 205

Tyr Thr Asp Pro Ala His Ile Arg Gly Gly Gly Leu His Leu Val
210                 215                 220

Trp Thr Leu Arg Asp Val Ser Glu Gly Ser Val Pro Asn Gly Asp Ser
225                 230                 235                 240

Gln Ser Gly Val Asp Ser Leu Arg Lys His Leu Arg Ala Asp Thr Phe
            245                 250                 255

Thr Gln Gln Gln Leu Glu Ala Leu Asp Arg Val Phe Glu Arg Pro Ser
        260                 265                 270

Tyr Pro Asp Val Phe Gln Ala Ser Glu His Ile Lys Ser Glu Gln Gly
    275                 280                 285

Asn Glu Tyr Ser Leu Pro Ala Leu Thr Pro Gly Leu Asp Glu Val Lys
290                 295                 300

Ser Ser Leu Ser Ala Ser Thr Asn Pro Glu Leu Gly Ser Asn Val Ser
305                 310                 315                 320

Gly Thr Gln Thr Tyr Pro Val Val Thr Gly Arg Asp Met Ala Ser Thr
            325                 330                 335

Thr Leu Pro Gly Tyr Pro Pro His Val Pro Pro Thr Gly Gln Gly Ser
        340                 345                 350

Tyr Pro Thr Ser Thr Leu Ala Gly Met Val Pro Gly Ser Glu Phe Ser
    355                 360                 365

Gly Asn Pro Tyr Ser His Pro Gln Tyr Thr Ala Tyr Asn Glu Ala Trp
370                 375                 380

Arg Phe Ser Asn Pro Ala Leu Leu Ser Ser Pro Tyr Tyr Tyr Ser Ala
385                 390                 395                 400
```

Ala Pro Arg Ser Ala Pro Ala Ala Ala Ala Ala Tyr Asp Arg His
          405                 410                 415

<210> SEQ ID NO 42
<211> LENGTH: 4276
<212> TYPE: DNA
<213> ORGANISM: Homo sapiens

<400> SEQUENCE: 42

| | | | | | |
|---|---|---|---|---|---|
| aggctccagt | ctccggccga | gtcttctcgc | agccgcaacc | cacctggggc | cagcccagag | 60 |
| ctgccagcgc | cgctcggctc | cctccctccc | tcccggccct | tcggccgcgg | cggcgtgcgc | 120 |
| ctgccttttc | cggggggcggg | ggcctggccc | gcgcgctccc | ctcccgcagg | cgccacctcg | 180 |
| gacatccccg | ggattgctac | ttctctgcca | acttcgccaa | ctcgccagca | cttggagagg | 240 |
| cccggctccc | ctcccggcgc | cctctgaccg | ccccgcccc | gcgcgctctc | cgaccaccgc | 300 |
| ctctcggatg | accaggttcc | aggggagctg | agcgagtcgc | ctcccccgcc | cagcttcagc | 360 |
| cctggctgca | gctgcagcgc | gagccatgcg | ccccagtgc | accccggccc | ggcccaccgc | 420 |
| cccggggcca | ttctgctgac | cgcccagccc | cgagccccga | cagtggcaag | ttgcggctac | 480 |
| tgcagttgca | agctccggcc | aacccggagg | agccccagcg | gggagcgcag | tgttgcgccc | 540 |
| cccgcccccg | cgcgcccgc | agcagccggg | cgttcactca | tcctccctcc | ccaccgtcc | 600 |
| ctcccttttc | tcctcaagtc | ctgaagttga | gtttgagagg | cgacacggcg | gcggcggccg | 660 |
| cgctgctccc | gctcctctgc | ctccccatgg | atatgcactg | caaagcagac | cccttctccg | 720 |
| cgatgcaccc | agggcacggg | ggtgtgaacc | agctcggggg | ggtgtttgtg | aacggccggc | 780 |
| ccctacccga | cgtggtgagg | cagcgcatcg | tggagctggc | ccaccagggt | gtgcggccct | 840 |
| gtgacatctc | ccggcagctg | cgggtcagcc | acggctgtgt | cagcaaaatc | ctgggcaggt | 900 |
| actacgagac | cggcagcatc | aagcgggtg | tgatcggtgg | ctccaagccc | aaagtggcga | 960 |
| cgcccaaagt | ggtggacaag | attgctgaat | acaaacgaca | gaacccgact | atgttcgcct | 1020 |
| gggagattcg | agaccggctc | ctggccgagg | gcatctgtga | caatgacaca | gtgcccagcg | 1080 |
| tctcttccat | caacagaatc | atccggacca | aagttcagca | gccttttccac | ccaacgccgg | 1140 |
| atggggctgg | gacaggagtg | accgcccctg | gccacaccat | tgttcccagc | acggcctccc | 1200 |
| ctcctgtttc | cagcgcctcc | aatgaccccag | tgggatccta | ctccatcaat | gggatcctgg | 1260 |
| ggattcctcg | ctccaatggt | gagaagagga | aacgtgatga | agttgaggta | tacactgatc | 1320 |
| ctgcccacat | tagaggaggt | ggaggttttgc | atctggtctg | gactttaaga | gatgtgtctg | 1380 |
| agggctcagt | ccccaatgga | gattcccaga | gtggtgtgga | cagtttgcgg | aagcacttgc | 1440 |
| gagctgacac | cttcacccag | cagcagctgg | aagctttgga | tcgggtcttt | gagcgtcctt | 1500 |
| cctaccctga | cgtcttccag | gcatcagagc | acatcaaatc | agaacagggg | aacgagtact | 1560 |
| ccctcccagc | cctgacccct | gggcttgatg | aagtcaagtc | gagtctatct | gcatccacca | 1620 |
| accctgagct | gggcagcaac | gtgtcaggca | cacagacata | cccagttgtg | actggtcgtg | 1680 |
| acatggcgag | caccactctg | cctggttacc | cccctcacgt | gcccccacact | ggccagggaa | 1740 |
| gctaccccac | ctccacccctg | gcaggaatgg | tgcctgggag | cgagttctcc | ggcaacccgt | 1800 |
| acagccaccc | ccagtacacg | gcctacaacg | aggcttggag | attcagcaac | cccgccttac | 1860 |
| taagttcccc | ttattattat | agtgccgccc | cccggtccgc | cctgccgct | gctgccgctg | 1920 |
| cctatgaccg | ccactagtta | ccgcggggac | cacatcaagc | ttcaggccga | cagcttcggc | 1980 |
| ctccacatcg | tccccgtctg | accccacccc | ggagggaggg | aggaccgacg | cgacgcgatg | 2040 |

```
cctccggcc accgccccag cctcacccca tcccacgacc cccgcaaccc ttcacatcac    2100 cccctcgaa ggtcggacag gacgggtgga gccgtgggcg ggaccctcag gcccgggccc    2160
gccgccccca gccccgcctg ccgcccctcc ccgcctgcct ggactgcgcg gcgccgtgag    2220
ggggattcgg cccagctcgt cccggcctcc accaagccag ccccgaagcc cgccagccac    2280
cctgccggac tcgggcgcga cctgctggcg cgcgccggat gtttctgtga cacacaatca    2340
gcgcggaccg cagcgcggcc cagccccggg caccgcctc ggacgctcgg gcgccaggag     2400
gcttcgctgg aggggctggg ccaaggagat taagaagaaa cgactttct gcaggaggaa     2460 gagcccgctg ccgaatccct gggaaaaatt cttttccccc agtgccagcc ggactgccct    2520
cgccttccgg gtgtgccctg tcccagaaga tggaatgggg gtgtgggggt ccggctctag    2580
gaacgggctt tggggggcgtc aggtctttcc aaggttggga cccaaggatc gggggggccca  2640 gcagcccgca ccgatcgagc cggactctcg gctcttcact gctcctcctg gcctgcctag    2700
ttccccaggg cccggcacct cctgctgcga gacccggctc tcagccctgc cttgcccta    2760 cctcagcgtc tcttccacct gctggcctcc cagtttcccc tcctgccagt ccttcgcctg    2820
tcccttgacg ccctgcatcc tcctcccctga ctcgcagccc catcggacgc tctcccggga   2880
ccgccgcagg accagtttcc atagactgcg gactgggggtc ttcctccagc agttacttga   2940 tgcccctcc cccgacacag actctcaatc tgccggtggt aagaaccggt tctgagctgg     3000
cgtctgagct gctgcgggt ggaagtgggg ggctgcccac tccactcctc ccatcccctc     3060
ccagcctcct cctccggcag gaactgaaca gaaccacaaa aagtctacat ttatttaata    3120
tgatggtctt tgcaaaaagg aacaaaacaa cacaaagcc caccaggctg ctgctttgtg     3180
gaaagacggt gtgtgtcgtg tgaaggcgaa acccggtgta cataaccccct ccccctccgc   3240 cccgccccgc ccggccccgt agagtccctg tcgcccgccg gccctgcctg tagatacgcc    3300
ccgctgtctg tgctgtgaga gtcgccgctc gctgggggggg aagggggggga cacagctaca  3360 cgcccattaa agcacagcac gtcctggggg aggggggcat ttttatgtt acaaaaaaaa     3420 attacgaaag aaaagaaatc tctatgcaaa atgacgaaca tggtcctgtg gactcctctg    3480
gcctgttttg ttggctcttt ctctgtaatt ccgtgtttc gctttttcct ccctgccct      3540 ctctccctct gccctctct cctctcgct tctctcccc tctgtctctg tctctctccg       3600
tctctgtcgc tcttgtctgt ctgtctctgc tcttttcctcg gcctctctcc ccagacctgg   3660
cccggccgcc ctgtctccgc aggctagatc cgaggtggca gctccagccc ccgggctcgc    3720 ccctcgcgg gcgtgcccg cgcgcccgg gcggccgaag gccgggccgc ccgtcccgc        3780 cccgtagttg ctcttttcggt agtggcgatg cgccctgcat gtctcctcac ccgtggatcg   3840
tgacgactcg aaataacaga aacaaagtca ataaagtgaa aataaataaa atccttgaa     3900 caaatccgaa aaggcttgga gtcctcgccc agatctctct ccctgcgag ccctttttat     3960 ttgagaagga aaaagagaaa agagaatcgt ttaagggaac ccggcgccca gccaggctcc    4020
agtggcccga acggggcggc gagggcggcg agggcgccga ggtccggccc atcccagtcc    4080
tgtggggctg gccgggcaga gaccccggac ccaggcccag gcctaacctg ctaaatgtcc    4140
ccggacggtt ctggtctcct cggccacttt cagtgcgtcg gttcgttttg attcttttc     4200 ttttgtgcac ataagaaata aataataata ataaataaag aataaatttt tgtatgtcaa    4260
aaaaaaaaaa aaaaaa                                                    4276
```

<210> SEQ ID NO 43
<211> LENGTH: 393
<212> TYPE: PRT

<213> ORGANISM: Homo sapiens

<400> SEQUENCE: 43

Met Asp Met His Cys Lys Ala Asp Pro Phe Ser Ala Met His Pro Gly
1               5                   10                  15

His Gly Gly Val Asn Gln Leu Gly Gly Val Phe Val Asn Gly Arg Pro
            20                  25                  30

Leu Pro Asp Val Val Arg Gln Arg Ile Val Glu Leu Ala His Gln Gly
        35                  40                  45

Val Arg Pro Cys Asp Ile Ser Arg Gln Leu Arg Val Ser His Gly Cys
50                  55                  60

Val Ser Lys Ile Leu Gly Arg Tyr Tyr Glu Thr Gly Ser Ile Lys Pro
65                  70                  75                  80

Gly Val Ile Gly Gly Ser Lys Pro Lys Val Ala Thr Pro Lys Val Val
                85                  90                  95

Asp Lys Ile Ala Glu Tyr Lys Arg Gln Asn Pro Thr Met Phe Ala Trp
            100                 105                 110

Glu Ile Arg Asp Arg Leu Leu Ala Glu Gly Ile Cys Asp Asn Asp Thr
        115                 120                 125

Val Pro Ser Val Ser Ser Ile Asn Arg Ile Ile Arg Thr Lys Val Gln
130                 135                 140

Gln Pro Phe His Pro Thr Pro Asp Gly Ala Gly Thr Gly Val Thr Ala
145                 150                 155                 160

Pro Gly His Thr Ile Val Pro Ser Thr Ala Ser Pro Pro Val Ser Ser
                165                 170                 175

Ala Ser Asn Asp Pro Val Gly Ser Tyr Ser Ile Asn Gly Ile Leu Gly
            180                 185                 190

Ile Pro Arg Ser Asn Gly Glu Lys Arg Lys Arg Asp Glu Asp Val Ser
        195                 200                 205

Glu Gly Ser Val Pro Asn Gly Asp Ser Gln Ser Gly Val Asp Ser Leu
210                 215                 220

Arg Lys His Leu Arg Ala Asp Thr Phe Thr Gln Gln Gln Leu Glu Ala
225                 230                 235                 240

Leu Asp Arg Val Phe Glu Arg Pro Ser Tyr Pro Asp Val Phe Gln Ala
                245                 250                 255

Ser Glu His Ile Lys Ser Glu Gln Gly Asn Glu Tyr Ser Leu Pro Ala
            260                 265                 270

Leu Thr Pro Gly Leu Asp Glu Val Lys Ser Ser Leu Ser Ala Ser Thr
        275                 280                 285

Asn Pro Glu Leu Gly Ser Asn Val Ser Gly Thr Gln Thr Tyr Pro Val
290                 295                 300

Val Thr Gly Arg Asp Met Ala Ser Thr Thr Leu Pro Gly Tyr Pro Pro
305                 310                 315                 320

His Val Pro Pro Thr Gly Gln Gly Ser Tyr Pro Thr Ser Thr Leu Ala
                325                 330                 335

Gly Met Val Pro Gly Ser Glu Phe Ser Gly Asn Pro Tyr Ser His Pro
            340                 345                 350

Gln Tyr Thr Ala Tyr Asn Glu Ala Trp Arg Phe Ser Asn Pro Ala Leu
        355                 360                 365

Leu Ser Ser Pro Tyr Tyr Tyr Ser Ala Ala Pro Arg Ser Ala Pro Ala
370                 375                 380

Ala Ala Ala Ala Ala Tyr Asp Arg His
385                 390

<210> SEQ ID NO 44
<211> LENGTH: 4207
<212> TYPE: DNA
<213> ORGANISM: Homo sapiens

<400> SEQUENCE: 44

| | | | | | |
|---|---|---|---|---|---|
| aggctccagt | ctccggccga | gtcttctcgc | agccgcaacc | cacctggggc | cagcccagag | 60 |
| ctgccagcgc | cgctcggctc | cctccctccc | tccggccct | tcggccgcgg | cggcgtgcgc | 120 |
| ctgccttttc | cggggcggg | ggcctggccc | gcgcgctccc | ctcccgcagg | cgccacctcg | 180 |
| gacatccccg | ggattgctac | ttctctgcca | acttcgccaa | ctcgccagca | cttggagagg | 240 |
| cccggctccc | ctcccggcgc | cctctgaccg | ccccgcccc | gcgcgctctc | cgaccaccgc | 300 |
| ctctcggatg | accaggttcc | agggagctg | agcgagtcgc | ctccccgcc | cagcttcagc | 360 |
| cctggctgca | gctgcagcgc | gagccatgcg | ccccagtgc | accccggccc | ggcccaccgc | 420 |
| cccggggcca | ttctgctgac | cgcccagccc | cgagccccga | cagtggcaag | ttgcggctac | 480 |
| tgcagttgca | agctccggcc | aacccggagg | agccccagcg | gggagcgcag | tgttgcgccc | 540 |
| cccgcccccg | cgcgcccccgc | agcagccggg | cgttcactca | tcctccctcc | cccaccgtcc | 600 |
| ctcccttttc | tcctcaagtc | ctgaagttga | gtttgagagg | cgacacgcg | gcggcggccg | 660 |
| cgctgctccc | gctcctctgc | ctcccatgg | atatgcactg | caaagcagac | cccttctccg | 720 |
| cgatgcaccc | agggcacggg | ggtgtgaacc | agctcggggg | ggtgtttgtg | aacgccggc | 780 |
| ccctacccga | cgtggtgagg | cagcgcatcg | tggagctggc | ccaccagggt | gtgcggccct | 840 |
| gtgacatctc | ccggcagctg | cgggtcagcc | acggctgtgt | cagcaaaatc | ctgggcaggt | 900 |
| actacgagac | cggcagcatc | aagccgggtg | tgatcggtgg | ctccaagccc | aaagtggcga | 960 |
| cgcccaaagt | ggtggacaag | attgctgaat | acaaacgaca | gaacccgact | atgttcgcct | 1020 |
| gggagattcg | agaccggctc | ctggccgagg | gcatctgtga | caatgacaca | gtgcccagcg | 1080 |
| tctcttccat | caacagaatc | atccggacca | aagttcagca | gcctttccac | ccaacgccgg | 1140 |
| atggggctgg | acaggagtg | accgcccctg | gccacaccat | tgttcccagc | acggcctccc | 1200 |
| ctcctgtttc | cagcgcctcc | aatgaccag | tgggatccta | ctccatcaat | gggatcctgg | 1260 |
| ggattcctcg | ctccaatggt | gagaagagga | aacgtgatga | agatgtgtct | gagggctcag | 1320 |
| tccccaatgg | agattcccag | agtggtgtgg | acagtttgcg | gaagcacttg | cgagctgaca | 1380 |
| ccttcacccca | gcagcagctg | gaagctttgg | atcgggtctt | tgagcgtcct | tcctaccctg | 1440 |
| acgtcttcca | ggcatcagag | cacatcaaat | cagaacaggg | gaacgagtac | tccctcccag | 1500 |
| ccctgacccc | tgggcttgat | gaagtcaagt | cgagtctatc | tgcatccacc | aaccctgagc | 1560 |
| tgggcagcaa | cgtgtcaggc | acacagacat | acccagttgt | gactggtcgt | gacatggcga | 1620 |
| gcaccactct | gcctggttac | cccctcacg | tgcccccac | tggccaggga | agctacccca | 1680 |
| cctccaccct | ggcaggaatg | gtgcctggga | gcgagttctc | cggcaacccg | tacagccacc | 1740 |
| cccagtacac | ggcctacaac | gaggcttgga | gattcagcaa | ccccgcctta | ctaagttccc | 1800 |
| cttattatta | tagtgccgcc | cccggtccg | ccctgccgc | tgctgccgct | gcctatgacc | 1860 |
| gccactagtt | accgcgggga | ccacatcaag | cttcaggccg | acagcttcgg | cctccacatc | 1920 |
| gtccccgtct | gaccccaccc | cggagggagg | gaggaccgac | gcgacgcgat | gcctcccggc | 1980 |
| caccgccca | gcctcacccc | atcccacgac | ccccgcaacc | cttcacatca | cccccctcga | 2040 |
| aggtcggaca | ggacgggtgg | agccgtgggc | gggaccctca | ggcccgggcc | cgccgccccc | 2100 |
| agccccgcct | gccgccccctc | cccgcctgcc | tggactgcgc | ggcgccgtga | gggggattcg | 2160 |
| gcccagctcg | tcccggcctc | caccaagcca | gccccgaagc | ccgccagcca | ccctgccgga | 2220 |

```
ctcgggcgcg acctgctggc gcgcgccgga tgtttctgtg acacacaatc agcgcggacc    2280
gcagcgcggc ccagccccgg gcacccgcct cggacgctcg ggcgccagga ggcttcgctg    2340
gaggggctgg gccaaggaga ttaagaagaa aacgactttc tgcaggagga agagcccgct    2400
gccgaatccc tgggaaaaat tcttttcccc cagtgccagc cggactgccc tcgccttccg    2460
ggtgtgccct gtcccagaag atggaatggg ggtgtggggg tccggctcta ggaacgggct    2520
ttgggggcgt caggtctttc caaggttggg acccaaggat cgggggggccc agcagcccgc    2580 accgatcgag ccggactctc ggctcttcac tgctcctcct ggcctgccta gttcccagg    2640 gcccggcacc tcctgctgcg agacccggct ctcagccctg ccttgcccct acctcagcgt    2700
ctcttccacc tgctggcctc ccagtttccc ctcctgccag tccttcgcct gtcccttgac    2760
gccctgcatc ctcctccctg actcgcagcc ccatcggacg ctctcccggg accgccgcag    2820
gaccagtttc catagactgc ggactggggt cttcctccag cagttacttg atgcccctc    2880 ccccgacaca gactctcaat ctgccggtgg taagaaccgg ttctgagctg cgtctgagc    2940 tgctgcgggg tggaagtggg gggctgccca ctccactcct cccatcccct cccagcctcc    3000
tcctccggca ggaactgaac agaaccacaa aaagtctaca tttatttaat atgatggtct    3060
ttgcaaaaag gaacaaaaca acacaaaagc ccaccaggct gctgctttgt ggaaagacgg    3120
tgtgtgtcgt gtgaaggcga aacccggtgt acataacccc tcccccctccg ccccgccccg    3180 cccggccccg tagagtccct gtcgcccgcc ggccctgcct gtagatacgc cccgctgtct    3240
gtgctgtgag agtcgccgct cgctgggggg gaaggggggg acacagctac acgcccatta    3300
aagcacagca cgtcctgggg gagggggggca ttttttatgt tacaaaaaaa aattacgaaa    3360
gaaaagaaat ctctatgcaa aatgacgaac atggtcctgt ggactcctct ggcctgtttt    3420
gttggctctt tctctgtaat tccgtgtttt cgcttttttcc tccctgcccc tctctccctc    3480 tgccctctc tcctctccgc ttctctcccc ctctgtctct gtctctctcc gtctctgtcg    3540
ctcttgtctg tctgtctctg ctctttcctc ggcctctctc cccagacctg gccggccgc    3600 cctgtctccg caggctagat ccgaggtggc agctccagcc cccgggctcg ccccctcgcg    3660
ggcgtgcccc gcgcgccccg ggcggccgaa ggccgggccg cccccgtcccg ccccgtagtt    3720 gctcttttcgg tagtggcgat gcgccctgca tgtctcctca cccgtggatc gtgacgactc    3780
gaaataacag aaacaaagtc aataaagtga aaataaataa aaatccttga acaaatccga    3840
aaaggcttgg agtcctcgcc cagatctctc tccccctgcga gcccttttta tttgagaagg    3900
aaaaagagaa aagagaatcg tttaagggaa cccggcgccc agccaggctc cagtggcccg    3960
aacggggcgg cgagggcggc gagggcgccg aggtccggcc catcccagtc ctgtggggct    4020
ggccgggcag agacccgga cccaggccca ggcctaacct gctaaatgtc cccggacggt    4080
tctggtctcc tcggccactt tcagtgcgtc ggttcgtttt gattcttttt cttttgtgca    4140
cataagaaat aaataataat aataaataaa gaataaaatt ttgtatgtca aaaaaaaaa    4200 aaaaaaa                                                             4207
```

<210> SEQ ID NO 45
<211> LENGTH: 396
<212> TYPE: PRT
<213> ORGANISM: Homo sapiens

<400> SEQUENCE: 45

```
Met Asp Met His Cys Lys Ala Asp Pro Phe Ser Ala Met His Pro Gly
 1               5                  10                  15
```

-continued

His Gly Gly Val Asn Gln Leu Gly Gly Val Phe Val Asn Gly Arg Pro
            20                  25                  30

Leu Pro Asp Val Val Arg Gln Arg Ile Val Glu Leu Ala His Gln Gly
        35                  40                  45

Val Arg Pro Cys Asp Ile Ser Arg Gln Leu Arg Val Ser His Gly Cys
 50                  55                  60

Val Ser Lys Ile Leu Gly Arg Tyr Tyr Glu Thr Gly Ser Ile Lys Pro
 65                  70                  75                  80

Gly Val Ile Gly Gly Ser Lys Pro Lys Val Ala Thr Pro Lys Val Val
                85                  90                  95

Asp Lys Ile Ala Glu Tyr Lys Arg Gln Asn Pro Thr Met Phe Ala Trp
            100                 105                 110

Glu Ile Arg Asp Arg Leu Leu Ala Glu Gly Ile Cys Asp Asn Asp Thr
        115                 120                 125

Val Pro Ser Val Ser Ser Ile Asn Arg Ile Ile Arg Thr Lys Val Gln
130                 135                 140

Gln Pro Phe His Pro Thr Pro Asp Gly Ala Gly Thr Gly Val Thr Ala
145                 150                 155                 160

Pro Gly His Thr Ile Val Pro Ser Thr Ala Ser Pro Pro Val Ser Ser
                165                 170                 175

Ala Ser Asn Asp Pro Val Gly Ser Tyr Ser Ile Asn Gly Ile Leu Gly
            180                 185                 190

Ile Pro Arg Ser Asn Gly Glu Lys Arg Lys Arg Asp Glu Asp Val Ser
        195                 200                 205

Glu Gly Ser Val Pro Asn Gly Asp Ser Gln Ser Gly Val Asp Ser Leu
210                 215                 220

Arg Lys His Leu Arg Ala Asp Thr Phe Thr Gln Gln Gln Leu Glu Ala
225                 230                 235                 240

Leu Asp Arg Val Phe Glu Arg Pro Ser Tyr Pro Asp Val Phe Gln Ala
                245                 250                 255

Ser Glu His Ile Lys Ser Glu Gln Gly Asn Glu Tyr Ser Leu Pro Ala
            260                 265                 270

Leu Thr Pro Gly Leu Asp Glu Val Lys Ser Ser Leu Ser Ala Ser Thr
        275                 280                 285

Asn Pro Glu Leu Gly Ser Asn Val Ser Gly Thr Gln Thr Tyr Pro Val
290                 295                 300

Val Thr Gly Arg Asp Met Ala Ser Thr Thr Leu Pro Gly Tyr Pro Pro
305                 310                 315                 320

His Val Pro Pro Thr Gly Gln Gly Ser Tyr Pro Thr Ser Thr Leu Ala
                325                 330                 335

Gly Met Val Pro Glu Ala Ala Val Gly Pro Ser Ser Ser Leu Met Ser
            340                 345                 350

Lys Pro Gly Arg Lys Leu Ala Glu Val Pro Pro Cys Val Gln Pro Thr
        355                 360                 365

Gly Ala Ser Ser Pro Ala Thr Arg Thr Ala Thr Pro Ser Thr Arg Pro
370                 375                 380

Thr Thr Arg Leu Gly Asp Ser Ala Thr Pro Pro Tyr
385                 390                 395

<210> SEQ ID NO 46
<211> LENGTH: 4290
<212> TYPE: DNA
<213> ORGANISM: Homo sapiens

<400> SEQUENCE: 46

| | |
|---|---|
| aggctccagt ctccggccga gtcttctcgc agccgcaacc cacctggggc cagcccagag | 60 |
| ctgccagcgc cgctcggctc cctccctccc tcccggccct tcggccgcgg cggcgtgcgc | 120 |
| ctgccttttc cggggggcggg ggcctggccc gcgcgctccc ctcccgcagg cgccacctcg | 180 |
| gacatccccg ggattgctac ttctctgcca acttcgccaa ctcgcagca cttggagagg | 240 |
| cccggctccc ctcccggcgc cctctgaccg ccccgcccc gcgcgctctc cgaccaccgc | 300 |
| ctctcggatg accaggttcc aggggagctg agcgagtcgc ctccccgcc cagcttcagc | 360 |
| cctggctgca gctgcagcgc gagccatgcg cccccagtgc accccggccc ggcccaccgc | 420 |
| cccggggcca ttctgctgac cgcccagccc cgagccccga cagtggcaag ttgcggctac | 480 |
| tgcagttgca agctccggcc aacccggagg agcccagcg gggagcgcag tgttgcgccc | 540 |
| cccgcccccg cgcgccccgc agcagccggg cgttcactca tcctccctcc cccaccgtcc | 600 |
| ctcccttttc tcctcaagtc ctgaagttga gtttgagagg cgacacggcg gcggcggccg | 660 |
| cgctgctccc gctcctctgc ctccccatgg atatgcactg caaagcagac cccttctccg | 720 |
| cgatgcaccc agggcacggg ggtgtgaacc agctcggggg ggtgtttgtg aacggccggc | 780 |
| ccctacccga cgtggtgagg cagcgcatcg tggagctggc ccaccagggt gtgcggccct | 840 |
| gtgacatctc ccggcagctg cgggtcagcc acggctgtgt cagcaaaatc ctgggcaggt | 900 |
| actacgagac cggcagcatc aagccgggtg tgatcggtgg ctccaagccc aaagtggcga | 960 |
| cgcccaaagt ggtggacaag attgctgaat acaaacgaca gaacccgact atgttcgcct | 1020 |
| gggagattcg agaccggctc ctggccgagg gcatctgtga caatgacaca gtgcccagcg | 1080 |
| tctcttccat caacagaatc atccggacca agttcagca gcctttccac ccaacgccgg | 1140 |
| atggggctgg gacaggagtg accgcccctg gccacaccat tgttcccagc acggcctccc | 1200 |
| ctcctgtttc cagcgcctcc aatgaccag tgggatccta ctccatcaat gggatcctgg | 1260 |
| ggattcctcg ctccaatggt gagaagagga acgtgatga agatgtgtct gagggctcag | 1320 |
| tccccaatgg agattcccag agtggtgtgg acagtttgcg gaagcacttg cgagctgaca | 1380 |
| ccttcacccca gcagcagctg gaagcttttg atcgggtctt tgagcgtcct tcctaccctg | 1440 |
| acgtcttcca ggcatcagag cacatcaaat cagaacaggg gaacgagtac tccctcccag | 1500 |
| ccctgacccc tgggcttgat gaagtcaagt cgagtctatc tgcatccacc aaccctgagc | 1560 |
| tgggcagcaa cgtgtcaggc acacagacat acccagttgt gactggtcgt gacatggcga | 1620 |
| gcaccactct gcctggttac ccccctcacg tgccccccac tggccaggga agctaccccc | 1680 |
| cctccacccct ggcaggaatg gtgcctgagg ctgcagttgg tccctcatcc tccctcatga | 1740 |
| gcaagccggg gaggaagctt gcagaagtgc ccccttgtgt gcaacccact ggagcgagtt | 1800 |
| ctccggcaac ccgtacagcc accccagta cacggcctac aacgaggctt ggagattcag | 1860 |
| caaccccgcc ttactaagtt ccccttatta ttatagtgcc gcccccggt ccgcccctgc | 1920 |
| cgctgctgcc gctgcctatg accgccacta gttaccgcgg ggaccacatc aagcttcagg | 1980 |
| ccgacagctt cggcctccac atcgtccccg tctgacccca cccggaggg agggaggacc | 2040 |
| gacgcgacgc gatgcctccc ggccaccgcc ccagcctcac cccatcccac gaccccgca | 2100 |
| acccttcaca tcacccccct cgaaggtcgg acaggacggg tggagccgtg gcgggaccc | 2160 |
| tcaggcccgg gccgccgcc cccagcccg cctgccgccc ctcccgcct gcctggactg | 2220 |
| cgcggcgccg tgaggggat tcggcccagc tcgtcccggc ctccaccaag ccagcccga | 2280 |
| agcccgccag ccaccctgcc ggactcgggc gcgacctgct ggcgcgcgcc ggatgttcct | 2340 |
| gtgacacaca atcagcgcgg accgcagcgc ggcccagccc cgggcacccg cctcggacgc | 2400 |

```
tcgggcgcca ggaggcttcg ctggaggggc tgggccaagg agattaagaa gaaaacgact   2460
ttctgcagga ggaagagccc gctgccgaat ccctgggaaa aattctttc ccccagtgcc    2520 agccggactg ccctcgcctt ccgggtgtgc cctgtcccag aagatggaat ggggtgtgg    2580 gggtccggct ctaggaacgg gctttggggg cgtcaggtct ttccaaggtt gggacccaag   2640
gatcgggggg cccagcagcc cgcaccgatc gagccggact ctcggctctt cactgctcct   2700
cctggcctgc ctagttcccc agggcccggc acctcctgct gcgagacccg gctctcagcc   2760
ctgccttgcc cctacctcag cgtctcttcc acctgctggc ctcccagttt ccctcctgc    2820 cagtccttcg cctgtccctt gacgcccctgc atcctcctcc ctgactcgca gccccatcgg   2880
acgctctccc gggaccgccg caggaccagt ttccatagac tgcggactgg ggtcttcctc   2940
cagcagttac ttgatgcccc ctcccccgac acagactctc aatctgccgg tggtaagaac   3000
cggttctgag ctggcgtctg agctgctgcg gggtggaagt gggggctgc ccactccact    3060 cctcccatcc cctcccagcc tcctcctccg gcaggaactg aacagaacca caaaaagtct   3120
acatttattt aatatgatgg tctttgcaaa aaggaacaaa acaacacaaa agcccaccag   3180
gctgctgctt tgtggaaaga cggtgtgtgt cgtgtgaagg cgaaacccgg tgtacataac   3240 ccctcccct ccgccccgcc ccgcccggcc ccgtagagtc cctgtcgccc gccggccctg    3300
cctgtagata cgccccgctg tctgtgctgt gagagtcgcc gctcgctggg ggggaagggg   3360
gggacacagc tacacgccca ttaaagcaca gcacgtcctg ggggagggg gcatttttta    3420 tgttacaaaa aaaaattacg aaagaaaaga aatctctatg caaaatgacg aacatggtcc   3480
tgtggactcc tctggcctgt tttgttggct cttctctgt aattccgtgt tttcgcttt      3540 tcctccctgc ccctctctcc ctctgccct ctctcctctc cgcttctctc ccctctgtc     3600 tctgtctctc tccgtctctg tcgctcttgt ctgtctgtct ctgctctttc ctcggcctct   3660
ctccccagac ctggcccggc cgccctgtct ccgcaggcta gatccgaggt ggcagctcca   3720 gccccgggc tcgccccctc gcgggcgtgc cccgcgcgcc ccgggcggcc gaaggccggg    3780 ccgcccgtc ccgccccgta gttgctcttt cggtagtggc gatgcgccct gcatgtctcc    3840
tcacccgtgg atcgtgacga ctcgaaataa cagaaacaaa gtcaataaag tgaaaataaa   3900
taaaaatcct tgaacaaatc cgaaaaggct tggagtcctc gcccagatct ctctcccctg   3960
cgagcccttt ttatttgaga aggaaaaaga gaaaagagaa tcgtttaagg gaacccggcg   4020
cccagccagg ctccagtggc ccgaacgggg cggcgagggc ggcgagggcg ccgaggtccg   4080
gcccatccca gtcctgtggg gctggccggg cagagacccc ggacccaggc ccaggcctaa   4140
cctgctaaat gtccccggac ggttctggtc tcctcggcca ctttcagtgc gtcggttcgt   4200
tttgattctt tttcttttgt gcacataaga aataaataat aataataaat aaagaataaa   4260
attttgtatg tcaaaaaaaa aaaaaaaaa                                     4290
```

<210> SEQ ID NO 47
<211> LENGTH: 408
<212> TYPE: PRT
<213> ORGANISM: Homo sapiens

<400> SEQUENCE: 47

Met Asp Met His Cys Lys Ala Asp Pro Phe Ser Ala Met His Pro Gly
1               5                   10                  15

His Gly Gly Val Asn Gln Leu Gly Gly Val Phe Val Asn Gly Arg Pro
            20                  25                  30

Leu Pro Asp Val Val Arg Gln Arg Ile Val Glu Leu Ala His Gln Gly
        35                  40                  45

```
Val Arg Pro Cys Asp Ile Ser Arg Gln Leu Arg Val Ser His Gly Cys
 50                  55                  60
Val Ser Lys Ile Leu Gly Arg Tyr Tyr Glu Thr Gly Ser Ile Lys Pro
 65                  70                  75                  80
Gly Val Ile Gly Gly Ser Lys Pro Lys Val Ala Thr Pro Lys Val Val
                 85                  90                  95
Asp Lys Ile Ala Glu Tyr Lys Arg Gln Asn Pro Thr Met Phe Ala Trp
                 100                 105                 110
Glu Ile Arg Asp Arg Leu Leu Ala Glu Gly Ile Cys Asp Asn Asp Thr
            115                 120                 125
Val Pro Ser Val Ser Ser Ile Asn Arg Ile Ile Arg Thr Lys Val Gln
     130                 135                 140
Gln Pro Phe His Pro Thr Pro Asp Gly Ala Gly Thr Gly Val Thr Ala
 145                 150                 155                 160
Pro Gly His Thr Ile Val Pro Ser Thr Ala Ser Pro Pro Val Ser Ser
                 165                 170                 175
Ala Ser Asn Asp Pro Val Gly Ser Tyr Ser Ile Asn Gly Ile Leu Gly
                 180                 185                 190
Ile Pro Arg Ser Asn Gly Glu Lys Arg Lys Arg Asp Glu Asp Val Ser
            195                 200                 205
Glu Gly Ser Val Pro Asn Gly Asp Ser Gln Ser Gly Val Asp Ser Leu
     210                 215                 220
Arg Lys His Leu Arg Ala Asp Thr Phe Thr Gln Gln Gln Leu Glu Ala
 225                 230                 235                 240
Leu Asp Arg Val Phe Glu Arg Pro Ser Tyr Pro Asp Val Phe Gln Ala
                 245                 250                 255
Ser Glu His Ile Lys Ser Glu Gln Gly Asn Glu Tyr Ser Leu Pro Ala
                 260                 265                 270
Leu Thr Pro Gly Leu Asp Glu Val Lys Ser Ser Leu Ser Ala Ser Thr
            275                 280                 285
Asn Pro Glu Leu Gly Ser Asn Val Ser Gly Thr Gln Thr Tyr Pro Val
     290                 295                 300
Val Thr Gly Arg Asp Met Ala Ser Thr Thr Leu Pro Gly Tyr Pro Pro
 305                 310                 315                 320
His Val Pro Pro Thr Gly Gln Gly Ser Tyr Pro Thr Ser Thr Leu Ala
                 325                 330                 335
Gly Met Val Pro Gly Ser Glu Phe Ser Gly Asn Pro Tyr Ser His Pro
                 340                 345                 350
Gln Tyr Thr Ala Tyr Asn Glu Ala Trp Arg Phe Ser Asn Pro Ala Leu
            355                 360                 365
Leu Met Pro Pro Pro Gly Pro Pro Leu Pro Leu Pro Leu Pro Met
     370                 375                 380
Thr Ala Thr Ser Tyr Arg Gly Asp His Ile Lys Leu Gln Ala Asp Ser
 385                 390                 395                 400
Phe Gly Leu His Ile Val Pro Val
                 405
```

<210> SEQ ID NO 48
<211> LENGTH: 4188
<212> TYPE: DNA
<213> ORGANISM: Homo sapiens

<400> SEQUENCE: 48
aggctccagt ctccggccga gtcttctcgc agccgcaacc cacctggggc cagcccagag    60

```
ctgccagcgc cgctcggctc cctccctccc tcccggccct tcggccgcgg cggcgtgcgc    120
ctgccttttc cggggggcggg ggcctggccc gcgcgctccc ctcccgcagg cgccacctcg    180
gacatccccg ggattgctac ttctctgcca acttcgccaa ctcgccagca cttggagagg    240
cccggctccc ctcccggcgc cctctgaccg ccccgcccc gcgcgctctc cgaccaccgc    300
ctctcggatg accaggttcc aggggagctg agcgagtcgc ctcccccgcc cagcttcagc    360
cctggctgca gctgcagcgc gagccatgcg ccccagtgc accccggccc ggcccaccgc    420
cccggggcca ttctgctgac cgcccagccc cgagcccga cagtggcaag ttgcggctac    480
tgcagttgca agctccggcc aacccggagg agccccagcg gggagcgcag tgttgcgccc    540
cccgccccg cgcgccccgc agcagccggg cgttcactca tcctccctcc cccaccgtcc    600
ctcccttttc tcctcaagtc ctgaagttga gtttgagagg cgacacgcg gcggcggccg    660
cgctgctccc gctcctctgc ctcccatgg atatgcactg caaagcagac cccttctccg    720
cgatgcaccc agggcacggg ggtgtgaacc agctcggggg ggtgtttgtg aacggccggc    780
ccctacccga cgtggtgagg cagcgcatcg tggagctggc ccaccagggt gtgcggccct    840
gtgacatctc ccggcagctg cgggtcagcc acggctgtgt cagcaaaatc ctgggcaggt    900
actacgagac cggcagcatc aagccgggtg tgatcggtgg ctccaagccc aaagtggcga    960
cgcccaaagt ggtggacaag attgctgaat acaaacgaca gaacccgact atgttcgcct    1020
gggagattcg agaccggctc ctggccgagg gcatctgtga caatgacaca gtgcccagcg    1080
tctcttccat caacagaatc atccggacca aagttcagca gcctttccac ccaacgccgg    1140
atggggctgg gacaggagtg accgcccctg gccacaccat tgttcccagc acggcctccc    1200
ctcctgtttc cagcgcctcc aatgacccag tgggatccta ctccatcaat gggatcctgg    1260
ggattcctcg ctccaatggt gagaagagga acgtgatga agatgtgtct gagggctcag    1320
tccccaatgg agattcccag agtggtgtgg acagtttgcg gaagcacttg cgagctgaca    1380
ccttcaccca gcagcagctg gaagctttgg atcgggtctt tgagcgtcct tcctaccctg    1440
acgtcttcca ggcatcagag cacatcaaat cagaacaggg gaacgagtac tccctcccag    1500
ccctgacccc tgggcttgat gaagtcaagt cgagtctatc tgcatccacc aaccctgagc    1560
tgggcagcaa cgtgtcaggc acacagacat acccagttgt gactggtcgt gacatggcga    1620
gcaccactct gcctggttac ccccctcacg tgccccccac tggccaggga agctacccca    1680
cctccaccct ggcaggaatg gtgcctggga gcgagttctc cggcaacccg tacagccacc    1740
cccagtacac ggcctacaac gaggcttgga gattcagcaa cccccgcctta ctaatgccgc    1800
cccccggtcc gccctgccg ctgctgccgc tgcctatgac cgccactagt taccgcgggg    1860
accacatcaa gcttcaggcc gacagcttcg gcctccacat cgtccccgtc tgaccccacc    1920
ccggagggag ggaggaccga cgcgacgcga tgcctcccgg ccaccgcccc agcctcaccc    1980
catcccacga cccccgcaac ccttcacatc accccccctcg aaggtcggac aggacgggtg    2040
gagccgtggg cgggaccctc aggcccgggc ccgccgcccc cagccccgcc tgccgcccct    2100
ccccgcctgc ctggactgcg cggcgccgtg agggggattc ggcccagctc gtcccggcct    2160
ccaccaagcc agccccgaag cccgccagcc accctgccgg actcgggcgc gacctgctgg    2220
cgcgcgccgg atgtttctgt gacacacaat cagcgcggac cgcagcgcgg cccagccccg    2280
ggcacccgcc tcggacgctc gggcgccagg aggcttcgct ggaggggctg ggccaaggag    2340
attaagaaga aaacgacttt ctgcaggagg aagagcccgc tgccgaatcc ctgggaaaaa    2400
ttcttttccc ccagtgccag ccggactgcc ctcgccttcc gggtgtgccc tgtcccagaa    2460
```

```
gatggaatgg gggtgtgggg gtccggctct aggaacgggc tttggggggcg tcaggtctttt    2520 ccaaggttgg gacccaagga tcgggggggcc cagcagcccg caccgatcga gccggactct    2580
cggctcttca ctgctcctcc tggcctgcct agttccccag ggcccggcac ctcctgctgc    2640
gagacccggc tctcagccct gccttgcccc tacctcagcg tctcttccac ctgctggcct    2700
cccagtttcc cctcctgcca gtccttcgcc tgtcccttga cgccctgcat cctcctccct    2760
gactcgcagc cccatcggac gctctcccgg gaccgccgca ggaccagttt ccatagactg    2820
cggactgggg tcttcctcca gcagttactt gatgccccct cccccgacac agactctcaa    2880
tctgccggtg gtaagaaccg gttctgagct ggcgtctgag ctgctgcggg gtggaagtgg    2940
ggggctgccc actccactcc tcccatcccc tcccagcctc ctcctccggc aggaactgaa    3000
cagaaccaca aaaagtctac atttatttaa tatgatggtc tttgcaaaaa ggaacaaaac    3060
aacacaaaag cccaccaggc tgctgctttg tggaaagacg gtgtgtgtcg tgtgaaggcg    3120
aaacccggtg tacataaccc ctccccctcc gccccgcccc gccggcccc gtagagtccc    3180 tgtcgcccgc cggccctgcc tgtagatacg ccccgctgtc tgtgctgtga gagtcgccgc    3240
tcgctggggg ggaaggggggg gacacagcta cacgcccatt aaagcacagc acgtcctggg    3300
ggaggggggc attttttatg ttacaaaaaa aaattacgaa agaaaagaaa tctctatgca    3360
aaatgacgaa catggtcctg tggactcctc tggcctgttt tgttggctct ttctctgtaa    3420
ttccgtgttt tcgcttttttc ctccctgccc ctctctccct ctgccctct ctcctctccg    3480 cttctctccc cctctgtctc tgtctctctc cgtctctgtc gctcttgtct gtctgtctct    3540
gctctttcct cggcctctct ccccagacct ggcccggccg ccctgtctcc gcaggctaga    3600
tccgaggtgg cagctccagc cccgggctc gccccctcgc gggcgtgccc cgcgcgcccc    3660
gggcggccga aggccgggcc gccccgtccc gccccgtagt tgctctttcg gtagtggcga    3720
tgcgccctgc atgtctcctc acccgtggat cgtgacgact cgaaataaca gaaacaaagt    3780
caataaagtg aaaataaata aaaatccttg aacaaatccg aaaaggcttg gagtcctcgc    3840
ccagatctct ctccccctgcg agcccttttt atttgagaag gaaaaagaga aagagaatc    3900 gtttaaggga acccggcgcc cagccaggct ccagtggccc gaacggggcg gcgagggcgg    3960
cgagggcgcc gaggtccggc ccatcccagt cctgtggggc tggccgggca gagaccccgg    4020
acccaggccc aggcctaacc tgctaaatgt ccccggacgg ttctggtctc ctcggccact    4080
ttcagtgcgt cggttcgttt tgattctttt tcttttgtgc acataagaaa taaataataa    4140
taataaataa agaataaaat tttgtatgtc aaaaaaaaaa aaaaaaaa              4188

<210> SEQ ID NO 49
<211> LENGTH: 431
<212> TYPE: PRT
<213> ORGANISM: Homo sapiens

<400> SEQUENCE: 49

Met Asp Met His Cys Lys Ala Asp Pro Phe Ser Ala Met His Pro Gly
1               5                   10                  15

His Gly Gly Val Asn Gln Leu Gly Gly Val Phe Val Asn Gly Arg Pro
            20                  25                  30

Leu Pro Asp Val Val Arg Gln Arg Ile Val Glu Leu Ala His Gln Gly
        35                  40                  45

Val Arg Pro Cys Asp Ile Ser Arg Gln Leu Arg Val Ser His Gly Cys
    50                  55                  60

Val Ser Lys Ile Leu Gly Arg Tyr Tyr Glu Thr Gly Ser Ile Lys Pro
65                  70                  75                  80
```

-continued

```
Gly Val Ile Gly Gly Ser Lys Pro Lys Val Ala Thr Pro Lys Val Val
                 85                  90                  95

Asp Lys Ile Ala Glu Tyr Lys Arg Gln Asn Pro Thr Met Phe Ala Trp
            100                 105                 110

Glu Ile Arg Asp Arg Leu Leu Ala Glu Gly Ile Cys Asp Asn Asp Thr
        115                 120                 125

Val Pro Ser Val Ser Ser Ile Asn Arg Ile Ile Arg Thr Lys Val Gln
130                 135                 140

Gln Pro Phe His Pro Thr Pro Asp Gly Ala Gly Thr Gly Val Thr Ala
145                 150                 155                 160

Pro Gly His Thr Ile Val Pro Ser Thr Ala Ser Pro Val Ser Ser
                165                 170                 175

Ala Ser Asn Asp Pro Val Gly Ser Tyr Ser Ile Asn Gly Ile Leu Gly
            180                 185                 190

Ile Pro Arg Ser Asn Gly Glu Lys Arg Lys Arg Asp Glu Val Glu Val
        195                 200                 205

Tyr Thr Asp Pro Ala His Ile Arg Gly Gly Gly Leu His Leu Val
    210                 215                 220

Trp Thr Leu Arg Asp Val Ser Glu Gly Ser Val Pro Asn Gly Asp Ser
225                 230                 235                 240

Gln Ser Gly Val Asp Ser Leu Arg Lys His Leu Arg Ala Asp Thr Phe
                245                 250                 255

Thr Gln Gln Gln Leu Glu Ala Leu Asp Arg Val Phe Glu Arg Pro Ser
            260                 265                 270

Tyr Pro Asp Val Phe Gln Ala Ser Glu His Ile Lys Ser Glu Gln Gly
        275                 280                 285

Asn Glu Tyr Ser Leu Pro Ala Leu Thr Pro Gly Leu Asp Glu Val Lys
    290                 295                 300

Ser Ser Leu Ser Ala Ser Thr Asn Pro Glu Leu Gly Ser Asn Val Ser
305                 310                 315                 320

Gly Thr Gln Thr Tyr Pro Val Val Thr Gly Arg Asp Met Ala Ser Thr
                325                 330                 335

Thr Leu Pro Gly Tyr Pro Pro His Val Pro Pro Thr Gly Gln Gly Ser
            340                 345                 350

Tyr Pro Thr Ser Thr Leu Ala Gly Met Val Pro Gly Ser Glu Phe Ser
        355                 360                 365

Gly Asn Pro Tyr Ser His Pro Gln Tyr Thr Ala Tyr Asn Glu Ala Trp
    370                 375                 380

Arg Phe Ser Asn Pro Ala Leu Leu Met Pro Pro Pro Gly Pro Pro Leu
385                 390                 395                 400

Pro Leu Leu Pro Leu Pro Met Thr Ala Thr Ser Tyr Arg Gly Asp His
                405                 410                 415

Ile Lys Leu Gln Ala Asp Ser Phe Gly Leu His Ile Val Pro Val
            420                 425                 430
```

<210> SEQ ID NO 50
<211> LENGTH: 4257
<212> TYPE: DNA
<213> ORGANISM: Homo sapiens

<400> SEQUENCE: 50

```
aggctccagt ctccggccga gtcttctcgc agccgcaacc cacctggggc cagcccagag      60
ctgccagcgc cgctcggctc cctccctccc tccggccct tcggccgcgg cggcgtgcgc     120
ctgccttttc cggggcggg ggcctggccc gcgcgctccc ctcccgcagg cgccacctcg     180
```

```
gacatccccg ggattgctac ttctctgcca acttcgccaa ctcgccagca cttggagagg    240
cccggctccc ctcccggcgc cctctgaccg ccccogcccc gcgcgctctc cgaccaccgc    300
ctctcggatg accaggttcc aggggagctg agcgagtcgc ctcccccgcc cagcttcagc    360
cctggctgca gctgcagcgc gagccatgcg cccccagtgc accccggccc ggcccaccgc    420
cccggggcca ttctgctgac cgcccagccc cgagccccga cagtggcaag ttgcggctac    480
tgcagttgca agctccggcc aacccggagg agccccagcg gggagcgcag tgttgcgccc    540
cccgcccccg cgcgcccgc agcagccggg cgttcactca tcctccctcc cccaccgtcc    600 ctccctttc tcctcaagtc ctgaagttga gtttgagagg cgacacggcg gcggcggccg    660
cgctgctccc gctcctctgc ctcccatgg atatgcactg caaagcagac ccttctccg    720 cgatgcaccc agggcacggg ggtgtgaacc agctcggggg ggtgtttgtg aacggccggc    780
ccctacccga cgtggtgagg cagcgcatcg tggagctggc ccaccagggt gtgcggccct    840
gtgacatctc ccggcagctg cgggtcagcc acggctgtgt cagcaaaatc ctgggcaggt    900
actacgagac cggcagcatc aagccgggtg tgatcggtgg ctccaagccc aaagtggcga    960
cgcccaaagt ggtggacaag attgctgaat acaaacgaca gaacccgact atgttcgcct    1020
gggagattcg agaccggctc ctggccgagg gcatctgtga caatgacaca gtgcccagcg    1080
tctcttccat caacagaatc atccggacca aagttcagca gccttccac ccaacgccgg    1140 atggggctgg gacaggagtg accgcccctg gccacaccat tgttcccagc acggcctccc    1200
ctcctgtttc cagcgcctcc aatgacccag tgggatccta ctccatcaat gggatcctgg    1260
ggattcctcg ctccaatggt gagaagagga acgtgatga agttgaggta tacactgatc    1320
ctgcccacat tagaggaggt ggaggtttgc atctggtctg gactttaaga gatgtgtctg    1380
agggctcagt ccccaatgga gattcccaga gtggtgtgga cagtttgcgg aagcacttgc    1440
gagctgacac cttcacccag cagcagctgg aagctttgga tcgggtcttt gagcgtcctt    1500
cctaccctga cgtcttccag gcatcagagc acatcaaatc agaacagggg aacgagtact    1560
ccctcccagc cctgacccct gggcttgatg aagtcaagtc gagtctatct gcatccacca    1620
accctgagct gggcagcaac gtgtcaggca cacagacata cccagttgtg actggtcgtg    1680
acatggcgag caccactctg cctggttacc cccctcacgt gccccccact ggccagggaa    1740
gctaccccac ctccaccctg gcaggaatgg tgcctgggag cgagttctcc ggcaacccgt    1800
acagccaccc ccagtacacg gcctacaacg aggcttggag attcagcaac cccgccttac    1860
taatgccgcc ccccggtccg cccctgccgc tgctgccgct gcctatgacc gccactagtt    1920
accgcgggga ccacatcaag cttcaggccg acagcttcgg cctccacatc gtccccgtct    1980
gaccccaccc cggagggagg gaggaccgac gcgacgcgat gcctcccggc caccgcccca    2040
gcctcacccc atcccacgac ccccgcaacc cttcacatca ccccccctcga aggtcggaca    2100 ggacgggtgg agccgtgggc gggaccctca ggccgggcc cgccgccccc agcccgcct    2160 gccgccctc cccgcctgcc tggactgcgc ggcgccgtga gggggattcg gcccagctcg    2220
tcccggcctc caccaagcca gcccgaagc ccgccagcca cctgccgga ctcgggcgcg    2280 acctgctggc gcgcgccgga tgtttctgtg acacacaatc agcgcggacc gcagcgcggc    2340 ccagcccgg gcacccgcct cggacgctcg ggcgccagga ggcttcgctg gaggggctgg    2400
gccaaggaga ttaagaagaa acgactttc tgcaggagga gagcccgct gccgaatccc    2460 tgggaaaaat tcttttcccc cagtgccagc cggactgccc tcgccttccg ggtgtgcct    2520 gtcccagaag atggaatggg ggtgtggggg tccggctcta ggaacgggct ttgggggcgt    2580
```

-continued

```
caggtctttc caaggttggg acccaaggat cggggggccc agcagcccgc accgatcgag      2640
ccggactctc ggctcttcac tgctcctcct ggcctgccta gttccccagg gcccggcacc      2700
tcctgctgcg agacccggct ctcagccctg ccttgcccct acctcagcgt ctcttccacc      2760
tgctggcctc ccagtttccc ctcctgccag tccttcgcct gtcccttgac gccctgcatc      2820
ctcctccctg actcgcagcc ccatcggacg ctctcccggg accgccgcag gaccagtttc      2880
catagactgc ggactggggt cttcctccag cagttacttg atgccccctc ccccgacaca      2940
gactctcaat ctgccggtgg taagaaccgg ttctgagctg cgtctgagc tgctgcgggg       3000 tggaagtggg gggctgccca ctccactcct cccatcccct cccagcctcc tcctccggca      3060
ggaactgaac agaaccacaa aaagtctaca tttatttaat atgatggtct ttgcaaaaag      3120
gaacaaaaca acacaaaagc ccaccaggct gctgctttgt ggaaagacgg tgtgtgtcgt      3180
gtgaaggcga aacccggtgt acataacccc tcccctccg ccccgccccg cccggccccg       3240
tagagtccct gtcgcccgcc ggccctgcct gtagatacgc cccgctgtct gtgctgtgag      3300
agtcgccgct cgctgggggg aagggggggg acacagctac acgcccatta agcacagca       3360 cgtcctgggg gagggggca ttttttatgt tacaaaaaaa aattacgaaa gaaagaaat        3420 ctctatgcaa aatgacgaac atggtcctgt ggactcctct ggcctgtttt gttggctctt      3480
tctctgtaat tccgtgtttt cgcttttttcc tccctgcccc tctctccctc tgcccctctc     3540
tcctctccgc ttctctcccc ctctgtctct gtctctctcc gtctctgtcg ctcttgtctg      3600
tctgtctctg ctctttcctc ggcctctctc cccagacctg gccgccgc cctgtctccg        3660 caggctagat ccgaggtggc agctccagcc cccgggctcg ccccctcgcg ggcgtgcccc      3720
gcgcgccccg ggcggccgaa ggccgggccg ccccgtcccg ccccgtagtt gctctttcgg      3780
tagtggcgat gcgccctgca tgtctcctca cccgtggatc gtgacgactc gaaataacag      3840
aaacaaagtc aataaagtga aaataaataa aaatccttga acaaatccga aaaggcttgg      3900
agtcctcgcc cagatctctc tcccctgcga gcccttttta tttgagaagg aaaaagagaa      3960
aagagaatcg tttaagggaa cccggcgccc agccaggctc cagtgcccg aacggggcgg       4020 cgagggcggc gagggcgccg aggtccggcc catcccagtc ctgtggggct ggccgggcag      4080
agaccccgga cccaggccca ggcctaacct gctaaatgtc cccggacggt tctggtctcc      4140
tcggccactt tcagtgcgtc ggttcgtttt gattcttttt cttttgtgca cataagaaat      4200
aaataataat aataaataaa gaataaaatt ttgtatgtca aaaaaaaaa aaaaaaa         4257
```

<210> SEQ ID NO 51
<211> LENGTH: 18
<212> TYPE: DNA
<213> ORGANISM: Homo sapiens

<400> SEQUENCE: 51

```
cctggcaccc agcacaat                                                     18
```

<210> SEQ ID NO 52
<211> LENGTH: 20
<212> TYPE: DNA
<213> ORGANISM: Homo sapiens

<400> SEQUENCE: 52

```
gccgatccac acggagtact                                                   20
```

<210> SEQ ID NO 53
<211> LENGTH: 32

<212> TYPE: DNA
<213> ORGANISM: Homo sapiens

<400> SEQUENCE: 53
gttgcctgcc agtcgccatg agaacttcct ac        32

<210> SEQ ID NO 54
<211> LENGTH: 32
<212> TYPE: DNA
<213> ORGANISM: Homo sapiens

<400> SEQUENCE: 54
tggccttccc tctgtaacag gtgccttgaa tt        32

<210> SEQ ID NO 55
<211> LENGTH: 24
<212> TYPE: DNA
<213> ORGANISM: Homo sapiens

<400> SEQUENCE: 55
ccacccatgg caaattccat ggca        24

<210> SEQ ID NO 56
<211> LENGTH: 24
<212> TYPE: DNA
<213> ORGANISM: Homo sapiens

<400> SEQUENCE: 56
tctagacggc aggtcaggtc aacc        24

<210> SEQ ID NO 57
<211> LENGTH: 23
<212> TYPE: DNA
<213> ORGANISM: Homo sapiens

<400> SEQUENCE: 57
ctcaggccta tgcaaaaaga gga        23

<210> SEQ ID NO 58
<211> LENGTH: 20
<212> TYPE: DNA
<213> ORGANISM: Homo sapiens

<400> SEQUENCE: 58
gccctccctc caaaggagac        20

<210> SEQ ID NO 59
<211> LENGTH: 23
<212> TYPE: DNA
<213> ORGANISM: Homo sapiens

<400> SEQUENCE: 59
aacctacgca cctacgtgag gag        23

<210> SEQ ID NO 60
<211> LENGTH: 22
<212> TYPE: DNA
<213> ORGANISM: Homo sapiens

<400> SEQUENCE: 60
cgttcagtcc atcccatttc tg        22

<210> SEQ ID NO 61
<211> LENGTH: 20

<212> TYPE: DNA
<213> ORGANISM: Homo sapiens

<400> SEQUENCE: 61
gacacctgag ctgaccttgg					20

<210> SEQ ID NO 62
<211> LENGTH: 20
<212> TYPE: DNA
<213> ORGANISM: Homo sapiens

<400> SEQUENCE: 62
gaggaagtcc agtgtccagc					20

<210> SEQ ID NO 63
<211> LENGTH: 68
<212> TYPE: PRT
<213> ORGANISM: Homo sapiens

<400> SEQUENCE: 63

Met Arg Thr Ser Tyr Leu Leu Leu Phe Thr Leu Cys Leu Leu Leu Ser
1               5                   10                  15

Glu Met Ala Ser Gly Gly Asn Phe Leu Thr Gly Leu Gly His Arg Ser
            20                  25                  30

Asp His Tyr Asn Cys Val Ser Ser Gly Gly Gln Cys Leu Tyr Ser Ala
        35                  40                  45

Cys Pro Ile Phe Thr Lys Ile Gln Gly Thr Cys Tyr Arg Gly Lys Ala
    50                  55                  60

Lys Cys Cys Lys
65

<210> SEQ ID NO 64
<211> LENGTH: 914
<212> TYPE: DNA
<213> ORGANISM: Homo sapiens
<220> FEATURE:
<221> NAME/KEY: misc_feature
<222> LOCATION: (1)..(914)
<223> OTHER INFORMATION: n= a, c, g, or t

<400> SEQUENCE: 64
ctgcagggtg ggcccaggct gggccnagac cctcaccctc caagggccac actgggggct     60
cactttctga ggagtgccct ttggaaacgt cccaggaaca cgtctagtgg aaaagagaa     120 aagttggtcc atcgaggaga gtgttctgca taagggagga gatgagaagg tagccttggc    180
cagaggaaga aacttcatta caaccagctc tccttctsca agggaagagg gtgaagtttg    240
agtttgtctt gcaggaagac aatcaaacta aagaggccaa caccagctta gagccgagcg    300
gccccctgct cagagcttcc ctgtggctct cctccatgtg atccagaagg agggactcca    360
gtgtgaactg cctgttccag aaaccccatc agaactgcct aacctagaaa accaaacagg    420
aggagctggc accagggctc caggctgaaa gctaaatcca gcggcagcca gatggagaca    480
atgtgccatg tgactgctga ctgctcaggg caaatgacac caggggttag cgattagaag    540
ttcacccttg actgtggcac ctcccttcag ttccgtcgac gaggttgtgc aatccaccag    600
tcttataaat acagtgacgc tccagcctct ggaagcctct gtcagctcag cctcaaagg    660 agccagcctc tccccagttc ctgaaatcct gagtgttgcc tgccagtcgc catgagaact    720
tcctaccttc tgctgtttac tctctgctta cttttgtctg agatggcctc aggtaagctc    780
tggtacctgc tagagtttcc catccccagg gctggggaca atggggctga tgtgagtctc    840

```
ggatggctgc ctccgtgtcc caagggacga ggaacaagca gcaggaaagc atcccgtggt    900
tgagtggcct gcag                                                      914
```

<210> SEQ ID NO 65
<211> LENGTH: 19
<212> TYPE: DNA
<213> ORGANISM: Homo sapiens

<400> SEQUENCE: 65

```
tcagcagtgg agggcaatg                                                  19
```

<210> SEQ ID NO 66
<211> LENGTH: 23
<212> TYPE: DNA
<213> ORGANISM: Homo sapiens

<400> SEQUENCE: 66

```
cctctgtaac aggtgccttg aat                                             23
```

<210> SEQ ID NO 67
<211> LENGTH: 21
<212> TYPE: DNA
<213> ORGANISM: Homo sapiens

<400> SEQUENCE: 67

```
acagcaaacc tcctcacagc c                                               21
```

<210> SEQ ID NO 68
<211> LENGTH: 20
<212> TYPE: DNA
<213> ORGANISM: Homo sapiens

<400> SEQUENCE: 68

```
tggagacgtg gcacctcttg                                                 20
```

<210> SEQ ID NO 69
<211> LENGTH: 24
<212> TYPE: DNA
<213> ORGANISM: Homo sapiens

<400> SEQUENCE: 69

```
tatgataccc gggagatcgt gatc                                            24
```

<210> SEQ ID NO 70
<211> LENGTH: 24
<212> TYPE: DNA
<213> ORGANISM: Homo sapiens

<400> SEQUENCE: 70

```
gtgcagatgc cggttcaggt actc                                            24
```

<210> SEQ ID NO 71
<211> LENGTH: 20
<212> TYPE: DNA
<213> ORGANISM: Homo sapiens

<400> SEQUENCE: 71

```
tcagccctgg actacctgca                                                 20
```

<210> SEQ ID NO 72
<211> LENGTH: 20
<212> TYPE: DNA
<213> ORGANISM: Homo sapiens

```
<400> SEQUENCE: 72
gaggtcccgg tacaccacgt                                              20
```